(12) United States Patent
Lee et al.

(10) Patent No.: US 10,640,490 B2
(45) Date of Patent: *May 5, 2020

(54) DIAMINOPYRIMIDINE DERIVATIVES AND PROCESSES FOR THE PREPARATION THEREOF

(71) Applicant: Yuhan Corporation, Seoul (KR)

(72) Inventors: Hyun-Joo Lee, Seoul (KR); Dong-Hoon Kim, Suwon-si (KR); Tae-Kyun Kim, Yongin-si (KR); Young-Ae Yoon, Seoul (KR); Jae-Young Sim, Yongin-si (KR); Myung-Hun Cha, Hwaseong-si (KR); Eun-Jung Jung, Seoul (KR); Kyoung-Kyu Ahn, Suwon-si (KR); Tai-Au Lee, Seoul (KR)

(73) Assignee: Yuhan Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/813,741

(22) Filed: Nov. 15, 2017

(65) Prior Publication Data
US 2018/0072705 A1  Mar. 15, 2018

Related U.S. Application Data

(62) Division of application No. 14/001,475, filed as application No. PCT/KR2012/001423 on Feb. 24, 2012, now Pat. No. 9,850,227.

(30) Foreign Application Priority Data

Feb. 25, 2011 (KR) .......... 10-2011-0016981

(51) Int. Cl.
| | | |
|---|---|---|
| *A01N 43/00* | (2006.01) | |
| *A01N 43/46* | (2006.01) | |
| *A61K 31/55* | (2006.01) | |
| *C07D 403/04* | (2006.01) | |
| *C07D 401/04* | (2006.01) | |
| *C07D 413/04* | (2006.01) | |
| *C07D 413/14* | (2006.01) | |
| *C07D 417/04* | (2006.01) | |

(52) U.S. Cl.
CPC .......... *C07D 403/04* (2013.01); *C07D 401/04* (2013.01); *C07D 413/04* (2013.01); *C07D 413/14* (2013.01); *C07D 417/04* (2013.01)

(58) Field of Classification Search
CPC .......... A01N 43/00; A01N 43/46; A61K 31/55
USPC ...................................................... 514/217
See application file for complete search history.

(56) References Cited

U.S. PATENT DOCUMENTS

| | | |
|---|---|---|
| 4,962,115 A | 10/1990 | Van Daele |
| 5,185,335 A | 2/1993 | Van Daele et al. |
| 5,262,418 A | 11/1993 | Van Daele et al. |
| 5,510,353 A | 4/1996 | Giger et al. |
| 5,744,489 A | 4/1998 | Greenwood |
| 5,750,531 A | 5/1998 | Lee et al. |
| 6,342,503 B1 | 1/2002 | Aldrich et al. |
| 6,352,993 B1 | 3/2002 | Lee et al. |
| 2006/0057972 A1 | 3/2006 | Wikel et al. |
| 2006/0128726 A1 | 6/2006 | Wang et al. |
| 2006/0188453 A1 | 8/2006 | Marquais-Bienewald et al. |
| 2008/0207690 A1 | 8/2008 | Noguchi et al. |
| 2008/0293942 A1 | 11/2008 | Cousins |

FOREIGN PATENT DOCUMENTS

| | | |
|---|---|---|
| EP | 0 243 959 A1 | 4/1987 |
| EP | 0 445 862 B1 | 4/2000 |
| WO | 2006-057972 A1 | 6/2006 |

OTHER PUBLICATIONS

Michel Langlois and Rodolphe Fischmeister, "5-HT4 Receptor Ligands: Applications and New Prospects," Journal of Medicinal Chemistry, American Chemical Society, vol. 46, No. 3, Jan. 30, 2003, pp. 319-344.
Ivashchenko et al., "Synthesis and Study of 2,4-Diamino- and 2-Amino-4-(1H-Pyrazol-1-YI)Pyrimidine Derivatives", Chemistry of Heterocyclic Compounds, vol. 16, No. 3, pp. 309-312, (1980). XP002725604.
Yamanaka et al., "Studies on Pyrimidine Derivatives. XIII. Reaction of 4-Alkoxy-pyrimidine 1-Oxides with Phenyl Isocyanate and Phenyl Isothiocyanate", Chem. Pharm. Bull., vol. 27, No. 11, pp. 2642-2646, (1979). XP002725603.
The Supplementary European Search Report for European Application No. EP 12 74 9916, two pages, search completed on Jun. 12, 2014.

(Continued)

*Primary Examiner* — Layla Soroush
(74) *Attorney, Agent, or Firm* — Vorys, Sater, Seymour & Pease LLP; Min Suhn Koh

(57) ABSTRACT

The present invention provides a diaminopyrimidine derivative or its pharmaceutically acceptable salt, a process for the preparation thereof, a pharmaceutical composition comprising the same, and a use thereof. The diaminopyrimidine derivative or its pharmaceutically acceptable salt functions as a 5-HT$_4$ receptor agonist, and therefore can be usefully applied for preventing or treating dysfunction in gastrointestinal motility, one of the gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony.

3 Claims, No Drawings

(56) References Cited

OTHER PUBLICATIONS

Arvanitis et al., "Non-Peptide Corticotropin-Releasing Hormone Antagonists: Syntheses and Structure-Activity Relationships of 2-Anilinopyrimidines and -triazines", Journal of Medicinal Chemistry, 1999, vol. 42, No. 5, p. 805-818.
Om et al., "A Convenient Method for the Synthesis of 2-[(2-Benzimidazolyl)Amino]-6-Methyl-4-Pyrimidinols", Current Science, 1978, vol. 47, No. 1, p. 15-17.
Chemical Abstract, RN 946245-74-5, 1 page, (2007).
Chemical Abstract, RN 946245-42-7, 1 page, (2007).
Chemical Abstract, RN 946221-62-1, 1 page, (2007).
Chemical Abstract, RN 1115306-26-7, 1 page, (2009).
Chemical Abstract, RN 923139-86-0, 1 page, (2007).
Chemical Abstract, RN 946268-08-2, 1 page, (2007).
Chemical Abstract, RN 946268-05-9, 1 page, (2007).
Chemical Abstract, RN 946245-09-6, 1 page, (2007).
Chemical Abstract, RN 946245-06-3, 1 page, (2007).
Sweetser et al., "Do corticotropin releasing factor-1 receptors influence colonic transit and bowel function in women with irritable bowel syndrome?" Am J Physiol Gastrointest Liver Physiol, vol. 296, pp. G1299-G1306, (2009).
Camilleri et al., "Current and novel therapeutic options for irritable bowel syndrome management", Digestive and Liver Disease, vol. 41, pp. 854-862, (2009).

DIAMINOPYRIMIDINE DERIVATIVES AND PROCESSES FOR THE PREPARATION THEREOF

TECHNICAL FIELD

The present invention relates to a novel 5-$HT_4$ receptor agonist, more specifically a novel diaminopyrimidine derivative or its pharmaceutically acceptable salt having an activity as a 5-$HT_4$ receptor agonist, a process for the preparation thereof, a pharmaceutical composition comprising the same, and a use thereof.

BACKGROUND ART

Serotonin (5-hydroxytryptamine, 5-HT), one of the neurotransmitters, is broadly distributed throughout human body including both the central nervous system and the peripheral nervous system. Approximately 95% of the human body's total serotonin is found in the gastrointestinal tract, while about 5% thereof is found in the brain. Serotonin receptors are located in intestinal nerves, enterochromaffin cells, intestinal smooth muscle, immune tissues, etc. Serotonin receptor subtypes include 5-$HT_1$, 5-$HT_2$, 5-$HT_3$, 5-$HT_4$, 5-$HT_5$, 5-$HT_6$, and 5-$HT_7$. Interactions between these various receptors and serotonin are linked to various physiological functions. Therefore, various researches have been performed for developing therapeutic agents that are capable of interacting with a specific serotonin subtype as a target. The researches include identification of 5-$HT_4$ receptors and active agents interacting therewith (Langlois and Fischmeister, J. Med. Chem. 2003, 46, 319-344).

It has been found by the previous literatures that 5-$HT_4$ receptor agonists are useful for treating an abnormal gastrointestinal motility, i.e., dysfunction in gastrointestinal motility. The abnormal gastrointestinal motility may result in various disorders, for example irritable bowel syndrome (IBS), constipation, dyspepsia, delayed gastric emptying, gastroesophageal reflux disease (GERD), gastroparesis, post-operative ileus, intestinal pseudo-obstruction, drug-induced delayed transit, etc.

Representative 5-$HT_4$ receptor agonists disclosed in prior arts include tegaserod (an aminoguanidine derivative, U.S. Pat. No. 5,510,353), prucalopride (a benzofuran carboxamide derivative, EP0445862), cisapride (a benzamide derivative, U.S. Pat. No. 4,962,115), mosapride (EP0243959), etc. These compounds are known as an agent stimulating gastrointestinal motility.

DETAILED DESCRIPTION OF THE INVENTION

Technical Problem

The present inventors found that a certain diaminopyrimidine derivative functions as a 5-$HT_4$ receptor agonist, and therefore can be usefully applied for preventing or treating dysfunction in gastrointestinal motility.

Therefore, the present invention provides the above diaminopyrimidine derivative or its pharmaceutically acceptable salt, a process for the preparation thereof, a pharmaceutical composition comprising the same, and a use thereof.

Technical Solution

According to an aspect of the present invention, there is provided a use of a diaminopyrimidine derivative or its pharmaceutically acceptable salt for the manufacture of a medicament for preventing or treating a dysfunction in gastrointestinal motility According to another aspect of the present invention, there is provided a pharmaceutical composition for preventing or treating a dysfunction in gastrointestinal motility comprising a diaminopyrimidine derivative or its pharmaceutically acceptable salt as an active ingredient.

According to still another aspect of the present invention, there is provided a diaminopyrimidine derivative or its pharmaceutically acceptable salt.

According to still another aspect of the present invention, there is provided a process for preparing the diaminopyrimidine derivative or its pharmaceutically acceptable salt.

Advantageous Effects

The compound of the present invention, i.e., the diaminopyrimidine derivative or its pharmaceutically acceptable salt, functions as a 5-$HT_4$ receptor agonist, and therefore can be usefully applied for preventing or treating dysfunction in gastrointestinal motility, one of the gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony.

BEST MODE FOR CARRYING OUT THE INVENTION

As used herein, the term "alkyl" refers to a straight or branched aliphatic hydrocarbon radical. For example, $C_1$-$C_6$ alkyl means a straight or branched aliphatic hydrocarbon having 1 to 6 carbon atoms, such as methyl, ethyl, propyl, n-butyl, n-pentyl, n-hexyl, isopropyl, isobutyl, sec-butyl, tert-butyl, neopentyl, and isopentyl.

The term "alkoxy or alkyloxy" refers to a radical formed by substituting the hydrogen atom of a hydroxyl group with an alkyl. For example, $C_1$-$C_6$ alkoxy includes methoxy, ethoxy, propoxy, n-butoxy, n-pentyloxy, isopropoxy, sec-butoxy, tert-butoxy, neopentyloxy, and isopentyloxy.

The term "alkenyl" refers to a straight or branched aliphatic hydrocarbon radical having one or more double bond(s). For example, $C_2$-$C_6$ alkenyl includes ethenyl, propenyl, butenyl, pentenyl, and hexenyl.

The term "alkynyl" refers to a straight or branched aliphatic hydrocarbon radical having one or more triple bond(s). For example, $C_2$-$C_6$ alkynyl includes ethynyl, propynyl, butynyl, pentynyl, and hexynyl.

The present invention provides a use of a compound of Formula 1 or its pharmaceutically acceptable salt for the manufacture of a medicament for preventing or treating a dysfunction in gastrointestinal motility:

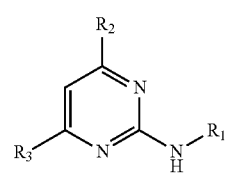

<Formula 1> wherein,

R₁ is a phenyl group substituted with one or more substituents selected from the group consisting of hydroxy, amino, halogen, cyano, nitro, hydroxycarbonyl, $C_{1-5}$ alkyl (where the $C_{1-5}$ alkyl is optionally substituted with halogen or amino), $C_{2-6}$ alkenyl, $C_{2-6}$ alkynyl, $C_{1-5}$ alkoxy (where the $C_{1-5}$ alkoxy is optionally substituted with halogen), $C_{1-5}$ alkylthio, mono- or di-$C_{1-5}$ alkylamino, $C_{1-5}$ alkylsulfonylamino, $C_{1-5}$ alkylcarbonylamino, $C_{1-5}$ alkoxycarbonyl, aminosulfonyl, aminocarbonyl, $C_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzimidazolonyl, benzoxazolonyl, benzofuranyl, benzothiophenyl, benzo[d][1,3]dioxolyl, dihydrobenzo[1,4]dioxinyl, indolyl, indolinyl, benzimidazolyl, benzoxazolyl, benzothiazolyl, and indazolyl, wherein the heteroaryl group may be optionally substituted with one or more substituents selected from the group consisting of amino, di-$C_{1-5}$ alkylamino, cyano, nitro, halogen, $C_{1-5}$ alkyl (where the $C_{1-5}$ alkyl is optionally substituted with halogen), $C_{1-5}$ alkoxy (where the $C_{1-5}$ alkoxy is optionally substituted with halogen), acetyl, and $C_{1-5}$ alkylsulfonyl, R₂ is a nitrogen-containing cyclic group selected from the group consisting of the following Formulas A to D (where * in Formulas A to D represents the position attached to the compound of Formula 1),

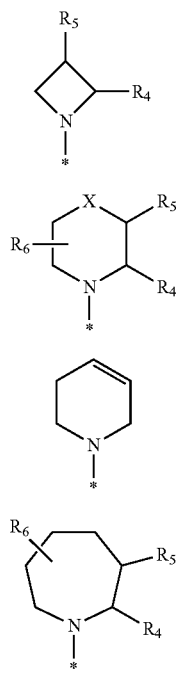

R₃ is a $C_{1-5}$ alkyl group optionally substituted with phenyl; or a $C_{2-6}$ alkenyl group optionally substituted with phenyl or $C_{3-6}$ cycloalkyl, R₄ is hydrogen; a $C_{1-5}$ alkyl group optionally substituted with a substituent selected from the group consisting of hydroxy, $C_{1-5}$ alkoxy, benzylamino (where the benzylamino is optionally substituted with halogen), phenylamino, $C_{1-5}$ alkylamino, $C_{3-6}$ cycloalkylamino, pyrrolidinyl, and hydroxy-$C_{1-5}$ alkylamino; a $C_{1-5}$ alkoxycarbonyl group; a hydroxycarbonyl group; an aminocarbonyl group; a formyl group; or an oxo(=O) group, R₅ is hydrogen; a hydroxyl group; a $C_{1-5}$ alkoxy group; a phenoxy group; a benzyloxy group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the following Formulas E to I (where * in Formulas E to I represents the position attached to one of the compounds of Formulas A to D),

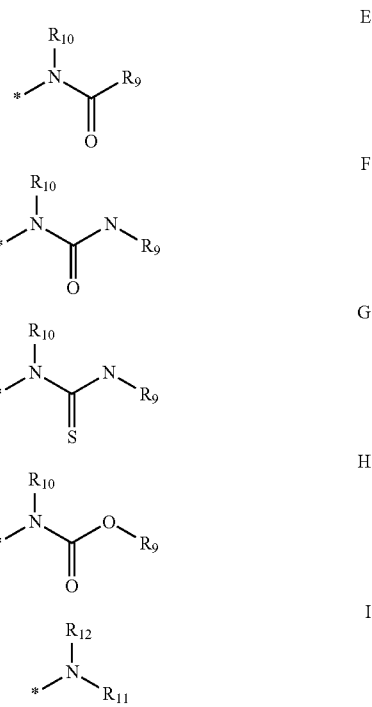

R₆ is hydrogen; a hydroxyl group; or a $C_{1-5}$ alkyl group optionally substituted with hydroxy, X is —CH(R₇)—; —C(=O)—; —N(R₈)—; —O—; or —S—, R₇ is hydrogen; a hydroxyl group; an aminocarbonyl group; a phenyl group; or a $C_{1-5}$ alkyl group optionally substituted with piperidinyl or hydroxy, R₄ and R₅, R₅ and R₆, R₄ and R₆, or R₅ and R₇ may be jointed each other to form a pentagonal or hexagonal ring, R₈ is hydrogen; a $C_{1-5}$ alkyl group; a $C_{1-5}$ alkoxycarbonyl group; a phenyl group optionally substituted with $C_{1-5}$ alkoxy or halogen, R₉ is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with C$_{1-5}$ alkoxycarbonyl; a C$_{1-10}$ alkenyl group optionally substituted with phenyl; a trifluoromethyl group; a trifluoroethyl group; or a phenyl group optionally substituted with halogen, R$_{10}$ is hydrogen; or a C$_{1-5}$ alkyl group, R$_{11}$ and R$_{12}$ are, independently each other, hydrogen; a C$_{1-10}$ alkyl group optionally substituted with a substituent selected from the group consisting of amino, C$_{1-5}$ alkoxycarbonylamino, hydroxy, C$_{1-5}$ alkylthio, C$_{3-10}$ cycloalkyl, phenyl (where the phenyl is optionally substituted with one or more substituents selected from the group consisting of hydroxy, C$_{1-5}$ alkyl, mono- or di-C$_{1-5}$ alkylamino, trifluoromethyl, halogen, C$_{1-5}$ alkoxy, and C$_{1-5}$ alkylcarbonyloxy), thiophenyl, pyrrolyl, furanyl (where the furanyl is optionally substituted with mono- or di-C$_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, C$_{1-5}$ alkyl, or C$_{1-5}$ alkylcarbonyl; an azetidinyl group optionally substituted with C$_{1-5}$ alkoxycarbonyl; a C$_{1-5}$ alkylsulfonyl group; a phenylsulfonyl group (where the phenyl moiety is optionally substituted with halogen); or a C$_{3-10}$ cycloalkyl group.

In the use for the manufacture of a medicament for preventing or treating a dysfunction in gastrointestinal motility according to the present invention, the dysfunction in gastrointestinal motility includes gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony. The constipation includes chronic constipation, chronic idiopathic constipation (CIC), opioid-induced constipation (OIC), etc. And also, the dyspepsia includes functional dyspepsia.

In the use for the manufacture of a medicament for preventing or treating a dysfunction in gastrointestinal motility according to the present invention, the compound or its salt may be the compound of Formula 1 or its pharmaceutically acceptable salt wherein, R$_1$ is a phenyl group substituted with one or more substituents selected from the group consisting of hydroxy, amino, halogen, cyano, nitro, hydroxycarbonyl, C$_{1-5}$ alkyl (where the C$_{1-5}$ alkyl is optionally substituted with halogen or amino), C$_{2-6}$ alkenyl, C$_{2-6}$ alkynyl, C$_{1-5}$ alkoxy (where the C$_{1-5}$ alkoxy is optionally substituted with halogen), C$_{1-5}$ alkylthio, mono- or di-C$_{1-5}$ alkylamino, C$_{1-5}$ alkylsulfonylamino, C$_{1-5}$ alkylcarbonylamino, C$_{1-5}$ alkoxycarbonyl, aminosulfonyl, aminocarbonyl, C$_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzimidazolonyl, benzoxazolonyl, benzofuranyl, benzothiophenyl, benzo[d][1,3]dioxolyl, dihydrobenzo[1,4]dioxinyl, indolyl, indolinyl, benzimidazolyl, benzoxazolyl, benzothiazolyl, and indazolyl, wherein the heteroaryl group may be optionally substituted with one or more substituents selected from the group consisting of amino, di-C$_{1-5}$ alkylamino, cyano, nitro, halogen, C$_{1-5}$ alkyl (where the C$_{1-5}$ alkyl is optionally substituted with halogen), C$_{1-5}$ alkoxy (where the C$_{1-5}$ alkoxy is optionally substituted with halogen), acetyl, and C$_{1-5}$ alkylsulfonyl, R$_2$ is the nitrogen-containing cyclic group of Formula B, R$_3$ is a C$_{1-5}$ alkyl group, R$_4$ is hydrogen; a C$_{1-5}$ alkyl group optionally substituted with a substituent selected from the group consisting of hydroxy, C$_{1-5}$ alkoxy, benzylamino (where the benzylamino is optionally substituted with halogen), phenylamino, C$_{1-5}$ alkylamino, C$_{3-6}$ cycloalkylamino, pyrrolidinyl, and hydroxy-C$_{1-5}$ alkylamino; a C$_{1-5}$ alkoxycarbonyl group; or an aminocarbonyl group, R$_5$ is hydrogen; a hydroxyl group; a C$_{1-5}$ alkoxy group; a phenoxy group; a benzyloxy group; a C$_{1-5}$ alkyl group optionally substituted with a substituent selected from the group consisting of amino, C$_{1-5}$ alkoxycarbonylamino, and mono- or di-C$_{1-5}$ alkylamino; or a group selected from the group consisting of the Formulas E to I, R$_6$, R$_7$, and R$_{10}$ are hydrogen, X is —CH(R$_7$)—; —N(R$_8$)—; or —O—, R$_4$ and R$_5$ may be jointed each other to form a pentagonal or hexagonal ring, R$_8$ is hydrogen; or a C$_{1-5}$ alkyl group, R$_9$ is a C$_{1-10}$ alkyl group optionally substituted with a substituent selected from the group consisting of hydroxy, halogen, C$_{1-5}$ alkoxy, amino, C$_{1-5}$ alkoxycarbonylamino, benzyloxycarbonylamino, mono- or di-C$_{1-5}$ alkylamino, C$_{1-5}$ alkoxy-C$_{1-5}$ alkyloxy, phenoxy, benzyloxy, phenyl (where the phenyl is optionally substituted with one or more substituents selected from the group consisting of halogen, amino, C$_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), C$_{3-6}$ cycloalkyl, acetyl, and benzoyl; a C$_{3-6}$ cycloalkyl group; a piperidinyl group optionally substituted with C$_{1-5}$ alkoxycarbonyl; a C$_{1-10}$ alkenyl group optionally substituted with phenyl; a trifluoromethyl group; a trifluoroethyl group; or a phenyl group optionally substituted with halogen, R$_{11}$ and R$_{12}$ are, independently each other, hydrogen; a C$_{1-10}$ alkyl group optionally substituted with a substituent selected from the group consisting of amino, C$_{1-5}$ alkoxycarbonylamino, hydroxy, C$_{1-5}$ alkylthio, C$_{3-10}$ cycloalkyl, phenyl (where the phenyl is optionally substituted with one or more substituents selected from the group consisting of hydroxy, C$_{1-5}$ alkyl, mono- or di-C$_{1-5}$ alkylamino, trifluoromethyl, halogen, C$_{1-5}$ alkoxy, and C$_{1-5}$ alkylcarbonyloxy), thiophenyl, pyrrolyl, furanyl (where the furanyl is optionally substituted with mono- or di-C$_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, C$_{1-5}$ alkyl, or C$_{1-5}$ alkylcarbonyl; an azetidinyl group optionally substituted with C$_{1-5}$ alkoxycarbonyl; a C$_{1-5}$ alkylsulfonyl group; a phenylsulfonyl group (where the phenyl moiety is optionally substituted with halogen); or a C$_{3-10}$ cycloalkyl group.

The present invention also provides a pharmaceutical composition for preventing or treating a dysfunction in gastrointestinal motility comprising a therapeutically effective amount of a compound of Formula 1 or its pharmaceutically acceptable salt; and a pharmaceutically acceptable carrier:

<Formula 1>

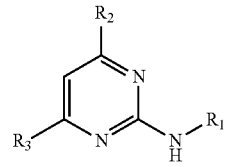

wherein,

R$_1$ is a phenyl group substituted with one or more substituents selected from the group consisting of hydroxy, amino, halogen, cyano, nitro, hydroxycarbonyl, C$_{1-5}$ alkyl (where the C$_{1-5}$ alkyl is optionally substituted with halogen or amino), C$_{2-6}$ alkenyl, C$_{2-6}$ alkynyl, C$_{1-5}$ alkoxy (where the C$_{1-5}$ alkoxy is optionally substituted with halogen), C$_{1-5}$ alkylthio, mono- or di-C$_{1-5}$ alkylamino, C$_{1-5}$ alkylsulfonylamino, C$_{1-5}$ alkylcarbonylamino, C$_{1-5}$ alkoxycarbonyl, aminosulfonyl, aminocarbonyl, C$_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzimidazolonyl, benzoxazolonyl, benzofuranyl, benzothiophenyl, benzo[d][1,3]dioxolyl, dihydrobenzo[1,4]dioxinyl, indolyl, indolinyl, benzimidazolyl, benzoxazolyl, benzothiazolyl, and indazolyl, wherein the heteroaryl group may be optionally substituted with one or more substituents selected from the group consisting of amino, di-C$_{1-5}$ alkylamino, cyano, nitro, halogen, C$_{1-5}$ alkyl (where the C$_{1-5}$ alkyl is optionally substituted with halogen), C$_{1-5}$ alkoxy (where the C$_{1-5}$ alkoxy is optionally substituted with halogen), acetyl, and C$_{1-5}$ alkylsulfonyl, R$_2$ is a nitrogen-containing cyclic group selected from the group consisting of the following Formulas A to D (where * in Formulas A to D represents the position attached to the compound of Formula 1),

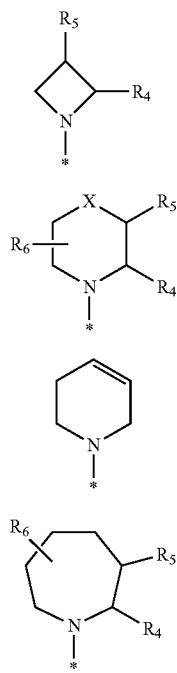

R$_3$ is a C$_{1-5}$ alkyl group optionally substituted with phenyl; or a C$_{2-6}$ alkenyl group optionally substituted with phenyl or C$_{3-6}$ cycloalkyl, R$_4$ is hydrogen; a C$_{1-5}$ alkyl group optionally substituted with a substituent selected from the group consisting of hydroxy, C$_{1-5}$ alkoxy, benzylamino (where the benzylamino is optionally substituted with halogen), phenylamino, C$_{1-5}$ alkylamino, C$_{3-6}$ cycloalkylamino, pyrrolidinyl, and hydroxy-C$_{1-5}$ alkylamino; a C$_{1-5}$ alkoxycarbonyl group; a hydroxycarbonyl group; an aminocarbonyl group; a formyl group; or an oxo(=O) group, R$_5$ is hydrogen; a hydroxyl group; a C$_{1-5}$ alkoxy group; a phenoxy group; a benzyloxy group; a C$_{1-5}$ alkyl group optionally substituted with a substituent selected from the group consisting of amino, C$_{1-5}$ alkoxycarbonylamino, and mono- or di-C$_{1-5}$ alkylamino; or a group selected from the group consisting of the following Formulas E to I (where * in Formulas E to I represents the position attached to one of the compounds of Formulas A to D),

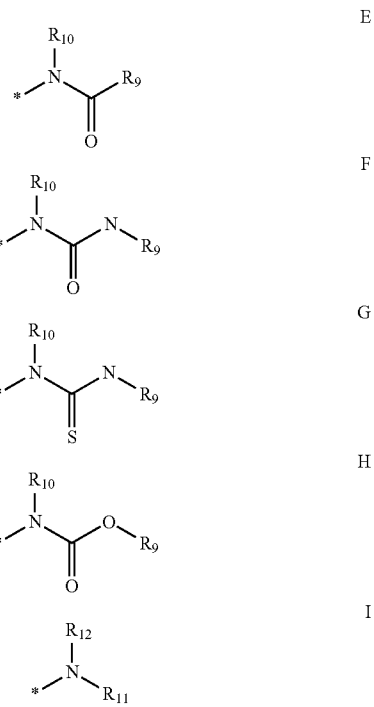

R$_6$ is hydrogen; a hydroxyl group; or a C$_{1-5}$ alkyl group optionally substituted with hydroxy, X is —CH(R$_7$)—; —C(=O)—; —N(R$_8$)—; —O—; or —S—, R$_7$ is hydrogen; a hydroxyl group; an aminocarbonyl group; a phenyl group; or a C$_{1-5}$ alkyl group optionally substituted with piperidinyl or hydroxy, R$_4$ and R$_5$, R$_5$ and R$_6$, R$_4$ and R$_6$, or R$_5$ and R$_7$ may be jointed each other to form a pentagonal or hexagonal ring, R$_8$ is hydrogen; a C$_{1-5}$ alkyl group; a C$_{1-5}$ alkoxycarbonyl group; a phenyl group optionally substituted with C$_{1-5}$ alkoxy or halogen, R$_9$ is a C$_{1-10}$ alkyl group optionally substituted with a substituent selected from the group consisting of hydroxy, halogen, C$_{1-5}$ alkoxy, amino, C$_{1-5}$ alkoxycarbonylamino, benzyloxycarbonylamino, mono- or di-C$_{1-5}$ alkylamino, C$_{1-5}$ alkoxy-C$_{1-5}$ alkyloxy, phenoxy, benzyloxy, phenyl (where the phenyl is optionally substituted with one or more substituents selected from the group consisting of halogen, amino, C$_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), C$_{3-6}$ cycloalkyl, acetyl, and benzoyl; a C$_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, $R_{10}$ is hydrogen; or a $C_{1-5}$ alkyl group, $R_{11}$ and $R_{12}$ are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-10}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-10}$ cycloalkyl group.

In the pharmaceutical composition according to the present invention, the dysfunction in gastrointestinal motility includes gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony. The constipation includes chronic constipation, chronic idiopathic constipation (CIC), opioid-induced constipation (OIC), etc. And also, the dyspepsia includes functional dyspepsia.

In the pharmaceutical composition according to the present invention, the compound or its salt may be the compound of Formula 1 or its pharmaceutically acceptable salt wherein, $R_1$ is a phenyl group substituted with one or more substituents selected from the group consisting of hydroxy, amino, halogen, cyano, nitro, hydroxycarbonyl, $C_{1-5}$ alkyl (where the $C_{1-5}$ alkyl is optionally substituted with halogen or amino), $C_{2-6}$ alkenyl, $C_{2-6}$ alkynyl, $C_{1-5}$ alkoxy (where the $C_{1-5}$ alkoxy is optionally substituted with halogen), $C_{1-5}$ alkylthio, mono- or di-$C_{1-5}$ alkylamino, alkylsulfonylamino, $C_{1-5}$ alkylcarbonylamino, $C_{1-5}$ alkoxycarbonyl, aminosulfonyl, aminocarbonyl, $C_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzimidazolonyl, benzoxazolonyl, benzofuranyl, benzothiophenyl, benzo[d][1,3]dioxolyl, dihydrobenzo[1,4]dioxinyl, indolyl, indolinyl, benzimidazolyl, benzoxazolyl, benzothiazolyl, and indazolyl, wherein the heteroaryl group may be optionally substituted with one or more substituents selected from the group consisting of amino, di-$C_{1-5}$ alkylamino, cyano, nitro, halogen, $C_{1-5}$ alkyl (where the $C_{1-5}$ alkyl is optionally substituted with halogen), $C_{1-5}$ alkoxy (where the $C_{1-5}$ alkoxy is optionally substituted with halogen), acetyl, and $C_{1-5}$ alkylsulfonyl, $R_2$ is the nitrogen-containing cyclic group of Formula B, $R_3$ is a $C_{1-5}$ alkyl group, $R_4$ is hydrogen; a $C_{1-5}$ alkyl group optionally substituted with a substituent selected from the group consisting of hydroxy, $C_{1-5}$ alkoxy, benzylamino (where the benzylamino is optionally substituted with halogen), phenylamino, $C_{1-5}$ alkylamino, $C_{3-6}$ cycloalkylamino, pyrrolidinyl, and hydroxy-$C_{1-5}$ alkylamino; a $C_{1-5}$ alkoxycarbonyl group; or an aminocarbonyl group, $R_5$ is hydrogen; a hydroxyl group; a $C_{1-5}$ alkoxy group; a phenoxy group; a benzyloxy group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the Formulas E to I, $R_6$, $R_7$, and $R_{10}$ are hydrogen, X is —CH($R_7$)—; —N($R_8$)—; or —O—, $R_4$ and $R_5$ may be jointed each other to form a pentagonal or hexagonal ring, $R_8$ is hydrogen; or a $C_{1-5}$ alkyl group, $R_9$ is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, $R_{11}$ and $R_{12}$ are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-10}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-10}$ cycloalkyl group.

The pharmaceutical composition of the present invention may comprise a pharmaceutically acceptable carrier, such as diluents, disintegrants, sweeteners, lubricants, or flavoring agents. The pharmaceutical composition may be formulated to an oral dosage form such as tablets, capsules, powders, granules, suspensions, emulsions, or syrups; or a parenteral dosage form such as injection. The dosage form may be various forms, e.g., dosage forms for single administration or for multiple administrations.

The pharmaceutical composition of the present invention may comprise, for example, a diluent (e.g., lactose, corn starch, etc); a lubricant (e.g., magnesium stearate); an emulsifying agent; a suspending agent; a stabilizer; and/or an isotonic agent. If necessary, the composition further comprises sweeteners and/or flavoring agents.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular blood-stream by local bolus injection.

The compound of Formula 1 or its pharmaceutically acceptable salt may be administered in a therapeutically effective amount ranging from about 0.001 mg/kg to about 10 mg/kg per day to a subject patient. Of course, the dosage may be changed according to the patient's age, weight, susceptibility, symptom, or activity of the compound.

The present invention also provides a method for treating a dysfunction in gastrointestinal motility, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony, in a patient, which comprises administering a therapeutically effective amount of the compound of Formula 1 or its pharmaceutically acceptable salt to the patient in need thereof. The constipation includes chronic constipation, chronic idiopathic constipation (CIC), opioid-induced constipation (OIC), etc. And also, the dyspepsia includes functional dyspepsia.

The present invention also provides a compound of Formula 1 or its pharmaceutically acceptable salt:

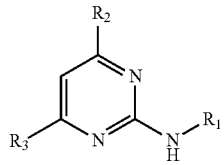

<Formula 1> wherein, $R_1$ is a phenyl group substituted with one or more substituents selected from the group consisting of hydroxy, amino, halogen, cyano, nitro, hydroxycarbonyl, $C_{1-3}$ alkyl (where the $C_{1-3}$ alkyl is optionally substituted with halogen or amino), $C_{2-6}$ alkenyl, $C_{2-6}$ alkynyl, $C_{1-5}$ alkoxy (where the $C_{1-5}$ alkoxy is optionally substituted with halogen), $C_{1-5}$ alkylthio, mono- or di-$C_{1-5}$ alkylamino, $C_{1-5}$ alkylsulfonylamino, $C_{1-5}$ alkylcarbonylamino, $C_{1-5}$ alkoxycarbonyl, aminosulfonyl, aminocarbonyl, $C_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzimidazolonyl, benzoxazolonyl, benzofuranyl, benzothiophenyl, benzo[d][1,3]dioxolyl, dihydrobenzo[1,4]dioxinyl, indolyl, indolinyl, benzimidazol-4-yl, benzimidazol-5-yl, benzimidazol-6-yl, benzimidazol-7-yl, benzoxazolyl, benzothiazolyl, and indazolyl, wherein the heteroaryl group may be optionally substituted with one or more substituents selected from the group consisting of amino, di-$C_{1-5}$ alkylamino, cyano, nitro, halogen, $C_{1-5}$ alkyl (where the $C_{1-5}$ alkyl is optionally substituted with halogen), $C_{1-5}$ alkoxy (where the $C_{1-5}$ alkoxy is optionally substituted with halogen), acetyl, and $C_{1-5}$ alkylsulfonyl, $R_2$ is a nitrogen-containing cyclic group selected from the group consisting of the following Formulas A to D (where * in Formulas A to D represents the position attached to the compound of Formula 1),

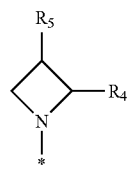

A

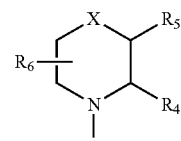

B

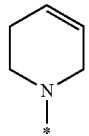

C

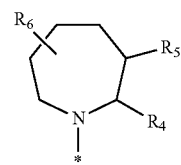

D $R_3$ is a $C_{1-5}$ alkyl group optionally substituted with phenyl; or a $C_{2-6}$ alkenyl group optionally substituted with phenyl or $C_{3-6}$ cycloalkyl, $R_4$ is hydrogen; a $C_{1-5}$ alkyl group optionally substituted with a substituent selected from the group consisting of hydroxy, $C_{1-5}$ alkoxy, benzylamino (where the benzylamino is optionally substituted with halogen), phenylamino, $C_{1-5}$ alkylamino, $C_{3-6}$ cycloalkylamino, pyrrolidinyl, and hydroxy-$C_{1-5}$ alkylamino; a $C_{1-5}$ alkoxycarbonyl group; a hydroxycarbonyl group, an aminocarbonyl group; a formyl group; or an oxo(=O) group, $R_5$ is hydrogen; a hydroxyl group; a $C_{1-5}$ alkoxy group; a phenoxy group; a benzyloxy group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the following Formulas E to I (where * in Formulas E to I represents the position attached to one of the compounds of Formulas A to D),

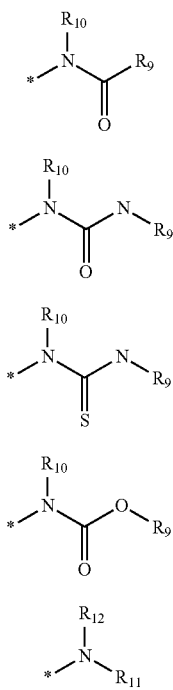

R<sub>6</sub> is hydrogen; a hydroxyl group; or a $C_{1-5}$ alkyl group optionally substituted with hydroxy, X is —CH(R$_7$)—; —C(=O)—; —N(R$_8$)—; —O—; or —S—, R$_7$ is hydrogen; a hydroxyl group; an aminocarbonyl group; a phenyl group; or a $C_{1-5}$ alkyl group optionally substituted with piperidinyl or hydroxy, R$_4$ and R$_5$, R$_5$ and R$_6$, R$_4$ and R$_6$, or R$_5$ and R$_7$ may be jointed each other to form a pentagonal or hexagonal ring, R$_8$ is hydrogen; a $C_{1-5}$ alkyl group; a $C_{1-5}$ alkoxycarbonyl group; a phenyl group optionally substituted with $C_{1-5}$ alkoxy or halogen, R$_9$ is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, R$_{10}$ is hydrogen; or a $C_{1-5}$ alkyl group, R$_{11}$ and R$_{12}$ are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-10}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-10}$ cycloalkyl group.

Preferably, the compound or its salt may be the compound of Formula 1 or its pharmaceutically acceptable salt wherein, R$_1$ is a phenyl group substituted with one or more substituents selected from the group consisting of hydroxy, amino, halogen, cyano, nitro, hydroxycarbonyl, $C_{1-3}$ alkyl (where the $C_{1-3}$ alkyl is optionally substituted with halogen or amino), $C_{2-6}$ alkenyl, $C_{2-6}$ alkynyl, $C_{1-5}$ alkoxy (where the $C_{1-5}$ alkoxy is optionally substituted with halogen), $C_{1-5}$ alkylthio, mono- or di-$C_{1-5}$ alkylamino, $C_{1-5}$ alkylsulfonylamino, $C_{1-5}$ alkylcarbonylamino, $C_{1-5}$ alkoxycarbonyl, aminosulfonyl, aminocarbonyl, $C_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzimidazolonyl, benzoxazolonyl, benzofuranyl, benzothiophenyl, benzo[d][1,3]dioxolyl, dihydrobenzo[1,4]dioxinyl, indolyl, indolinyl, benzimidazol-4-yl, benzimidazol-5-yl, benzimidazol-6-yl, benzimidazol-7-yl, benzoxazolyl, benzothiazolyl, and indazolyl, wherein the heteroaryl group may be optionally substituted with one or more substituents selected from the group consisting of amino, di-$C_{1-5}$ alkylamino, cyano, nitro, halogen, $C_{1-5}$ alkyl (where the $C_{1-5}$ alkyl is optionally substituted with halogen), $C_{1-5}$ alkoxy (where the $C_{1-5}$ alkoxy is optionally substituted with halogen), acetyl, and $C_{1-5}$ alkylsulfonyl, R$_2$ is the nitrogen-containing cyclic group of Formula B, R$_3$ is a $C_{2-5}$ alkyl group, R$_4$ is hydrogen; a $C_{1-5}$ alkyl group optionally substituted with a substituent selected from the group consisting of hydroxy, alkoxy, benzylamino (where the benzylamino is optionally substituted with halogen), phenylamino, $C_{1-5}$ alkylamino, $C_{3-6}$ cycloalkylamino, pyrrolidinyl, and hydroxy-$C_{1-5}$ alkylamino; a $C_{1-5}$ alkoxycarbonyl group; or an aminocarbonyl group, R$_5$ is hydrogen; a hydroxyl group; a $C_{1-5}$ alkoxy group; a phenoxy group; a benzyloxy group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the Formulas E to I, R$_6$, R$_7$, and R$_{10}$ are hydrogen, X is —CH(R$_7$)—; —N(R$_8$)—; or —O—, R$_4$ and R$_5$ may be jointed each other to form a pentagonal or hexagonal ring, R$_8$ is hydrogen; or a $C_{1-5}$ alkyl group, R$_9$ is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, $R_{11}$ and $R_{12}$ are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-10}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-10}$ cycloalkyl group.

The compound of Formula 1 or its pharmaceutically acceptable salt may have substituents containing asymmetric carbon and therefore be in the form of racemic mixture (RS) or in forms of optical isomers, such as (R) or (S) isomer. The compound of Formula 1 or its pharmaceutically acceptable salt comprises both racemic mixture (RS) and optical isomers such as (R) or (S) isomer. And also, the compound of Formula 1 or its pharmaceutically acceptable salt may be in the form of cis- or trans-geometrical isomer, according to substituents having e.g., the double bond therein. The compound of Formula 1 or its pharmaceutically acceptable salt comprises both cis- and trans-geometrical isomers. And also, the compound of Formula 1 or its pharmaceutically acceptable salt may be in the form of one or more diastereomic isomer(s) or a mixture thereof. The compound of Formula 1 or its pharmaceutically acceptable salt comprises both diastereomic isomer(s) and a mixture thereof.

The compound of Formula 1 of the present invention may be in a pharmaceutically acceptable salt form. The salt may be an acid addition salt form, which includes e.g., salts derived from an inorganic acid such as hydrochloric acid, hydrobromic acid, sulfuric acid, sulfonic acid, sulfamic acid, phosphoric acid, or nitric acid; and salts derived from an organic acid such as acetic acid, propionic acid, succinic acid, glycolic acid, stearic acid, citric acid, maleic acid, malonic acid, methanesulfonic acid, ethanesulfonic acid, tartaric acid, hydroxymaleic acid, phenylacetic acid, glutamic acid, benzoic acid, salicylic acid, 2-acetoxybenzoic acid, fumaric acid, toluenesulfonic acid, benzenesulfonic acid, oxalic acid or trifluoroacetic acid. The salt may be prepared by reacting a compound of Formula 1 in the form of free base with a salt-forming inorganic or organic acid in stoichiometric amount or excessive amount, in a suitable solvent or a mixture of two or more solvents.

In the use, the pharmaceutical composition, the treatment method, and the compound according to the present invention, more preferable compounds include a compound (or its pharmaceutically acceptable salt) selected from the group consisting of:

N-(4-fluorophenyl)-4-(piperidin-1-yl)-6-propylpyrimidin-2-amine;
N-(4-fluorophenyl)-4-morpholino-6-propylpyrimidin-2-amine;
4-(azepan-1-yl)-N-(4-fluorophenyl)-6-propylpyrimidin-2-amine;
N-(4-fluorophenyl)-4-(2-methylpiperidin-1-yl)-6-propylpyrimidin-2-amine;
N-(4-fluorophenyl)-4-(3-methylpiperidin-1-yl)-6-propylpyrimidin-2-amine;
N-(4-fluorophenyl)-4-propyl-6-thiomorpholinopyrimidin-2-amine;
4-(2,5-dimethylpiperazin-1-yl)-N-(4-fluorophenyl)-6-propylpyrimidin-2-amine;
4-(5,6-dihydropyridin-1(2H)-yl)-N-(4-fluorophenyl)-6-propylpyrimidin-2-amine;
N-(4-fluorophenyl)-4-(decahydroquinolin-1(2H)-yl)-6-propylpyrimidin-2-amine;
N-(4-fluorophenyl)-4-[decahydroisoquinolin-1(2H)-yl]-6-propylpyrimidin-2-amine;
N-(4-fluorophenyl)-4-(4-phenylpiperidin-1-yl)-6-propylpyrimidin-2-amine;
N-(4-fluorophenyl)-4-(piperazin-1-yl)-6-propylpyrimidin-2-amine;
4-(2-ethylpiperidin-1-yl)-N-(4-fluorophenyl)-6-propylpyrimidin-2-amine;
2-{1-[2-(4-fluorophenylamino)-6-propylpyrimidin-4-yl]piperidin-2-yl}ethanol;
ethyl 1-[2-(4-fluorophenylamino)-6-propylpyrimidin-4-yl]piperidin-2-carboxylate;
1-[2-(4-fluorophenylamino)-6-propylpyrimidin-4-yl]piperidin-4-carboxamide;
{1-[2-(4-fluorophenylamino)-6-propylpyrimidin-4-yl]piperidin-4-yl}methanol;
1-[2-(4-fluorophenylamino)-6-propylpyrimidin-4-yl]piperidin-4-one;
4-butyl-N-(4-fluorophenyl)-6-(piperidin-1-yl)pyrimidin-2-amine;
4-butyl-6-(2-ethylpiperidin-1-yl)-N-(4-fluorophenyl)pyrimidin-2-amine;
2-{1-[6-butyl-2-(4-fluorophenylamino)pyrimidin-4-yl]piperidin-2-yl}ethanol;
4-butyl-N-(4-fluorophenyl)-6-morpholinopyrimidin-2-amine;
2-{1-[2-(4-chloro-3-nitrophenylamino)-6-propylpyrimidin-4-yl]piperidin-2-yl}ethanol;
2-(1-{2-[3-(methylthio)phenylamino]-6-propylpyrimidin-4-yl}piperidin-2-yl)ethanol;
4-(2,6-dimethylmorpholino)-N-(4-fluorophenyl)-6-propylpyrimidin-2-amine;
8-[2-(4-fluorophenylamino)-6-propylpyrimidin-4-yl]-8-azabicyclo[3.2.1]octan-3-ol;
N-{1-[2-(4-fluorophenylamino)-6-propylpyrimidin-4-yl]piperidin-3-yl}acetamide;
N-(4-fluorophenyl)-4-{4-[3-(piperidin-4-yl)propyl]piperidin-1-yl}-6-propylpyrimidin-2-amine;
4-[3-(benzyloxy)piperidin-1-yl]-N-(4-fluorophenyl)-6-propylpyrimidin-2-amine;
4-(3-oxa-8-azabicyclo[3.2.1]octan-8-yl)-N-(4-fluorophenyl)-6-propylpyrimidin-2-amine;
N-[4-(piperidin-1-yl)-6-propylpyrimidin-2-yl]-1H-indol-5-amine;
N-(3-chloro-4-methylphenyl)-4-(piperidin-1-yl)-6-propylpyrimidin-2-amine;
N-[4-(piperidin-1-yl)-6-propylpyrimidin-2-yl]quinolin-6-amine;

4-(piperidin-1-yl)-6-propyl-N-[3-(trifluoromethyl)phenyl]pyrimidin-2-amine;
N-[4-(piperidin-1-yl)-6-propylpyrimidin-2-yl]-2-(trifluoromethyl)-1H-benzo[d]imidazol-5-amine;
N-[3-(methylthio)phenyl]-4-(piperidin-1-yl)-6-propylpyrimidin-2-amine;
N-(5-methoxy-2-methylphenyl)-4-(piperidin-1-yl)-6-propylpyrimidin-2-amine;
N-(5-chloro-2-methylphenyl)-4-(piperidin-1-yl)-6-propylpyrimidin-2-amine;
N-(4-fluoro-3-nitrophenyl)-4-(piperidin-1-yl)-6-propylpyrimidin-2-amine;
N-(4-methoxyphenyl)-4-(piperidin-1-yl)-6-propylpyrimidin-2-amine;
N-(3-methoxyphenyl)-4-(piperidin-1-yl)-6-propylpyrimidin-2-amine;
N-(3-chlorophenyl)-4-(piperidin-1-yl)-6-propylpyrimidin-2-amine;
N-(3-nitrophenyl)-4-(piperidin-1-yl)-6-propylpyrimidin-2-amine;
N-(4-chloro-3-nitrophenyl)-4-(piperidin-1-yl)-6-propylpyrimidin-2-amine;
3-[4-(piperidin-1-yl)-6-propylpyrimidin-2-ylamino]benzonitrile;
N-(4-methyl-3-nitrophenyl)-4-(piperidin-1-yl)-6-propylpyrimidin-2-amine;
4-(4-ethylpiperazin-1-yl)-N-(4-fluorophenyl)-6-methylpyrimidin-2-amine;
N-(4-fluorophenyl)-4-[4-(4-methoxyphenyl)piperazin-1-yl]-6-methylpyrimidin-2-amine;
N-(4-fluorophenyl)-4-[4-(4-fluorophenyl)piperazin-1-yl]-6-methylpyrimidin-2-amine;
N-(4-fluorophenyl)-4-methyl-6-(morpholin-4-yl)pyrimidin-2-amine;
1-[2-(4-fluorophenylamino)-6-methylpyrimidin-4-yl]piperidin-4-one;
N-(4-fluorophenyl)-4-methyl-6-(piperidin-1-yl)pyrimidin-2-amine;
4-(azetidin-1-yl)-N-(4-fluorophenyl)-6-methylpyrimidin-2-amine;
1-[2-(4-fluorophenylamino)-6-methylpyrimidin-4-yl]piperidin-3-ol;
1-[2-(4-fluorophenylamino)-6-methylpyrimidin-4-yl]piperidin-4-ol;
N-(4-fluorophenyl)-4-methyl-6-(2-methylpiperidin-1-yl)pyrimidin-2-amine;
N-(4-fluorophenyl)-4-methyl-6-(3-methylpiperidin-1-yl)pyrimidin-2-amine;
4-(3,5-cis-dimethylpiperidin-1-yl)-N-(4-fluorophenyl)-6-methylpyrimidin-2-amine;
4-(azepan-1-yl)-N-(4-fluorophenyl)-6-methylpyrimidin-2-amine;
4-(2-ethylpiperidin-1-yl)-N-(4-fluorophenyl)-6-methylpyrimidin-2-amine;
4-((2R,6S)-2,6-dimethylpiperidin-1-yl)-N-(4-fluorophenyl)-6-methylpyrimidin-2-amine;
N-(4-fluorophenyl)-4-methyl-6-(4-phenylpiperidin-1-yl)pyrimidin-2-amine;
N-(4-fluorophenyl)-4-methyl-6-(piperazin-1-yl)pyrimidin-2-amine;
N-(4-fluorophenyl)-4-methyl-6-(4-methylpiperazin-1-yl)pyrimidin-2-amine;
4-(2,5-dimethylpiperazin-1-yl)-N-(4-fluorophenyl)-6-methylpyrimidin-2-amine;
4-(3,5-dimethylpiperazin-1-yl)-N-(4-fluorophenyl)-6-methylpyrimidin-2-amine;
N-(4-fluorophenyl)-4-methyl-6-(octahydroquinolin-1(2H)-yl)pyrimidin-2-amine;
N-(4-fluorophenyl)-4-methyl-6-(octahydroisoquinolin-2(1H)-yl)pyrimidin-2-amine;
4-(5,6-dihydropyridin-1(2H)-yl)-N-(4-fluorophenyl)-6-methylpyrimidin-2-amine;
2-{1-[2-(4-fluorophenylamino)-6-methylpyrimidin-4-yl]piperidin-2-yl}ethanol;
2-{1-[2-(4-fluorophenylamino)-6-methylpyrimidin-4-yl]piperidin-2-yl}methanol;
N-[4-(octahydroquinolin-1(2H)-yl)-6-propylpyrimidin-2-yl]-1H-indol-6-amine;
2-{1-[2-(1H-indol-6-ylamino)-6-propylpyrimidin-4-yl]piperidin-2-yl}ethanol;
N-[4-(piperidin-1-yl)-6-propylpyrimidin-2-yl]-1H-indol-6-amine;
N-(4-morpholino-6-propylpyrimidin-2-yl)-1H-indol-6-amine;
N-[4-(2-ethylpiperidin-1-yl)-6-propylpyrimidin-2-yl]-1H-indol-6-amine;
(R)-3-[4-(3-ethylmorpholino)-6-propylpyrimidin-2-ylamino]benzonitrile;
(R)-tert-butyl 4-[2-(3-cyanophenylamino)-6-propylpyrimidin-4-yl]-3-methylpiperazin-1-carboxylate;
(R)-3-[4-(2-methylpiperazin-1-yl)-6-propylpyrimidin-2-ylamino]benzonitrile;
4-morpholino-N-(3-nitrophenyl)-6-propylpyrimidin-2-amine;
N-(4-fluoro-3-nitrophenyl)-4-morpholino-6-propylpyrimidin-2-amine;
N-(4-chloro-3-nitrophenyl)-4-morpholino-6-propylpyrimidin-2-amine;
N-(3-methoxyphenyl)-4-morpholino-6-propylpyrimidin-2-amine;
N-(4-methoxyphenyl)-4-morpholino-6-propylpyrimidin-2-amine;
N-[3-(methylthio)phenyl]-4-morpholino-6-propylpyrimidin-2-amine;
N-(3-chlorophenyl)-4-morpholino-6-propylpyrimidin-2-amine;
N-(3-chloro-4-methylphenyl)-4-morpholino-6-propylpyrimidin-2-amine;
4-morpholino-6-propyl-N-[3-(trifluoromethyl)phenyl]pyrimidin-2-amine;
N-(4-morpholino-6-propylpyrimidin-2-yl)-1H-indol-5-amine;
N-(4-morpholino-6-propylpyrimidin-2-yl)-2-(trifluoromethyl)-1H-benzo[d]imidazol-6-amine;
N-(4-morpholino-6-propylpyrimidin-2-yl)quinolin-6-amine;
3-(4-morpholino-6-propylpyrimidin-2-ylamino)benzonitrile;
N-(5-methoxy-2-methylphenyl)-4-morpholino-6-propylpyrimidin-2-amine;
N-(5-chloro-2-methylphenyl)-4-morpholino-6-propylpyrimidin-2-amine;
N-(4-morpholino-6-propylpyrimidin-2-yl)quinolin-3-amine;
4-(2-ethylpiperidin-1-yl)-N-(3-nitrophenyl)-6-propylpyrimidin-2-amine;
4-(2-ethylpiperidin-1-yl)-N-(4-fluoro-3-nitrophenyl)-6-propylpyrimidin-2-amine;
N-(4-chloro-3-nitrophenyl)-4-(2-ethylpiperidin-1-yl)-6-propylpyrimidin-2-amine;
4-(2-ethylpiperidin-1-yl)-N-(3-methoxyphenyl)-6-propylpyrimidin-2-amine;

4-(2-ethylpiperidin-1-yl)-N-(4-methoxyphenyl)-6-propylpyrimidin-2-amine;
4-(2-ethylpiperidin-1-yl)-N-[3-(methylthio)phenyl]-6-propylpyrimidin-2-amine;
N-(3-chlorophenyl)-4-(2-ethylpiperidin-1-yl)-6-propylpyrimidin-2-amine;
N-(3-chloro-4-methylphenyl)-4-(2-ethylpiperidin-1-yl)-6-propylpyrimidin-2-amine;
4-(2-ethylpiperidin-1-yl)-6-propyl-N-[3-(trifluoromethyl)phenyl]pyrimidin-2-amine;
N-[4-(2-ethylpiperidin-1-yl)-6-propylpyrimidin-2-yl]-1-H-indol-5-amine;
N-[4-(2-ethylpiperidin-1-yl)-6-propylpyrimidin-2-yl]-2-(trifluoromethyl)-1-H-benzo[d]imidazol-6-amine;
N-[4-(2-ethylpiperidin-1-yl)-6-propylpyrimidin-2-yl]quinolin-6-amine;
3-[4-(2-ethylpiperidin-1-yl)-6-propylpyrimidin-2-ylamino]benzonitrile;
4-(2-ethylpiperidin-1-yl)-N-(5-methoxy-2-methylphenyl)-6-propylpyrimidin-2-amine;
N-(5-chloro-2-methylphenyl)-4-(2-ethylpiperidin-1-yl)-6-propylpyrimidin-2-amine;
N-[4-(2-ethylpiperidin-1-yl)-6-propylpyrimidin-2-yl]quinolin-3-amine;
(R)—N-(4-chloro-3-nitrophenyl)-4-(2-methylpiperazin-1-yl)-6-propylpyrimidin-2-amine;
(R)—N-[4-(2-methylpiperazin-1-yl)-6-propylpyrimidin-2-yl]-1-H-indol-6-amine;
(R)—N-(2-methylpiperazin-1-yl)-6-propyl-N-[3-(trifluoromethyl)phenyl]pyrimidin-2-amine;
(R)—N-(2-methylpiperazin-1-yl)-N-(3-nitrophenyl)-6-propylpyrimidin-2-amine;
(R)—N-(4-fluoro-3-nitrophenyl)-4-(2-methylpiperazin-1-yl)-6-propylpyrimidin-2-amine;
(R)—N-(4-methyl-3-nitrophenyl)-4-(2-methylpiperazin-1-yl)-6-propylpyrimidin-2-amine;
(R)-4-fluoro-N$^1$-[4-(2-methylpiperazin-1-yl)-6-propylpyrimidin-2-yl]benzene-1,3-diamine;
(R)—N$^1$-[4-(2-methylpiperazin-1-yl)-6-propylpyrimidin-2-yl]-3-(trifluoromethyl)benzene-1,4-diamine;
(R)-2-fluoro-5-[4-(2-methylpiperazin-1-yl)-6-propylpyrimidin-2-ylamino]benzonitrile;
(R)-2-methyl-5-[4-(2-methylpiperazin-1-yl)-6-propylpyrimidin-2-ylamino]benzonitrile;
(R)-2-amino-5-[4-(2-methylpiperazin-1-yl)-6-propylpyrimidin-2-ylamino]benzonitrile;
(R)—N-[4-(2-methylpiperazin-1-yl)-6-propylpyrimidin-2-yl]-3-nitrobenzene-1,4-diamine;
(R)-3-amino-5-[4-(2-methylpiperazin-1-yl)-6-propylpyrimidin-2-ylamino]benzonitrile;
(R)-3-[4-(2-methylpiperazin-1-yl)-6-propylpyrimidin-2-ylamino]benzamide;
3-{4-[2-(2-hydroxyethyl)piperidin-1-yl]-6-propylpyrimidin-2-ylamino}benzonitrile;
2-{1-[2-(1-ethyl-1H-indol-6-ylamino)-6-propylpyrimidin-4-yl]piperidin-2-yl}ethanol;
2-{1-[2-(1H-indol-5-ylamino)-6-propylpyrimidin-4-yl]piperidin-2-yl}ethanol;
2-(1-{6-propyl-2-[2-(trifluoromethyl)-1H-benzo[d]imidazol-6-ylamino]pyrimidin-4-yl}piperidin-2-yl)ethanol;
2-{1-[2-(4-methoxyphenylamino)-6-propylpyrimidin-4-yl]piperidin-2-yl}ethanol;
2-{1-[2-(3-methoxyphenylamino)-6-propylpyrimidin-4-yl]piperidin-2-yl}ethanol;
2-{1-[2-(5-methoxy-2-methylphenylamino)-6-propylpyrimidin-4-yl]piperidin-2-yl}ethanol;
2-{1-[2-(3-chloro-4-methylphenylamino)-6-propylpyrimidin-4-yl]piperidin-2-yl}ethanol;
2-{1-[2-(3-nitrophenylamino)-6-propylpyrimidin-4-yl]piperidin-2-yl}ethanol;
2-{1-[2-(4-fluoro-3-nitrophenylamino)-6-propylpyrimidin-4-yl]piperidin-2-yl}ethanol;
2-{1-[2-(2,3-dimethylbenzofuran-5-ylamino)-6-propylpyrimidin-4-yl]piperidin-2-yl}ethanol;
2-{1-[6-propyl-2-(quinolin-6-ylamino)pyrimidin-4-yl]piperidin-2-yl}ethanol;
2-{1-[2-(3-chlorophenylamino)-6-propylpyrimidin-4-yl]piperidin-2-yl}ethanol;
7-{4-[2-(2-hydroxyethyl)piperidin-1-yl]-6-propylpyrimidin-2-ylamino}-4-methyl-2H-chromen-2-one;
2-{1-[6-propyl-2-(3-trifluoromethylphenylamino)pyrimidin-4-yl]piperidin-2-yl}ethanol;
2-{1-[6-propyl-2-(quinolin-3-ylamino)pyrimidin-4-yl]piperidin-2-yl}ethanol;
(S)-5-[4-(3-aminopiperidin-1-yl)-6-propylpyrimidin-2-ylamino]-2-methylbenzonitrile;
(S)-4-(3-aminopiperidin-1-yl)-N-(3-nitrophenyl)-6-propylpyrimidin-2-amine;
(S)-3-[4-(3-aminopiperidin-1-yl)-6-propylpyrimidin-2-ylamino]benzonitrile;
(R)-5-[4-(3-aminopiperidin-1-yl)-6-propylpyrimidin-2-ylamino]-2-methylbenzonitrile;
(S)-5-{4-[3-(butylamino)piperidin-1-yl]-6-propylpyrimidin-2-ylamino}-2-methylbenzonitrile;
(S)-5-{4-[3-(pentylamino)piperidin-1-yl]-6-propylpyrimidin-2-ylamino}-2-methylbenzonitrile;
(S)-5-{4-[3-(isobutylamino)piperidin-1-yl]-6-propylpyrimidin-2-ylamino}-2-methylbenzonitrile;
(S)-5-{4-[3-(isopentylamino)piperidin-1-yl]-6-propylpyrimidin-2-ylamino}-2-methylbenzonitrile;
(S)-2-methyl-5-{4-[3-(neopentylamino)piperidin-1-yl]-6-propylpyrimidin-2-ylamino}benzonitrile;
(S)-5-(4-{3-[(1H-pyrrol-2-yl)methylamino]piperidin-1-yl}-6-propylpyrimidin-2-ylamino)-2-methylbenzonitrile;
(S)-2-methyl-5-(4-propyl-6-{3-[(thiophen-2-ylmethyl)amino]piperidin-1-yl}pyrimidin-2-ylamino)benzonitrile;
(S)-5-(4-{3-[(4,5-dimethylfuran-2-ylmethyl)amino]piperidin-1-yl}-6-propylpyrimidin-2-ylamino)-2-methylbenzonitrile;
(S)-2-methyl-5-{4-[3-(3-methylthiopropylamino)piperidin-1-yl]-6-propylpyrimidin-2-ylamino}benzonitrile;
(S)-5-{4-[3-(cyclopropylmethylamino)piperidin-1-yl]-6-propylpyrimidin-2-ylamino}-2-methylbenzonitrile;
(S)-5-{4-[3-(4-hydroxybenzylamino)piperidin-1-yl]-6-propylpyrimidin-2-ylamino}-2-methylbenzonitrile;
(S)-5-[4-(3-diethylaminopiperidin-1-yl)-6-propylpyrimidin-2-ylamino]-2-methylbenzonitrile;
(S)-5-(4-{3-[bis(cyclopropylmethyl)amino]piperidin-1-yl}-6-propylpyrimidin-2-ylamino)-2-methylbenzonitrile;
(R)-5-(4-{3-[bis(cyclopropylmethyl)amino]piperidin-1-yl}-6-propylpyrimidin-2-ylamino)-2-methylbenzonitrile;
4-ethyl-N-(4-fluorophenyl)-6-(piperidin-1-yl)pyrimidin-2-amine;
4-ethyl-N-(4-fluorophenyl)-6-(octahydroquinolin-1(2H)-yl)pyrimidin-2-amine;
4-ethyl-6-(2-ethylpiperidin-1-yl)-N-(4-fluorophenyl)pyrimidin-2-amine;
2-{1-[6-ethyl-2-(4-fluorophenylamino)pyrimidin-4-yl]piperidin-2-yl}ethanol;
4-ethyl-N-(4-fluorophenyl)-6-morpholinopyrimidin-2-amine;
2-{1-[2-(4-methyl-3-nitrophenylamino)-6-propylpyrimidin-4-yl]piperidin-2-yl}ethanol;

2-{1-[2-(4-amino-3-trifluoromethylphenylamino)-6-propylpyrimidin-4-yl]piperidin-2-yl}ethanol;
2-{1-[2-(4-amino-3-nitrophenylamino)-6-propylpyrimidin-4-yl]piperidin-2-yl}ethanol;
5-{4-[2-(2-hydroxyethyl)piperidin-1-yl]-6-propylpyrimidin-2-ylamino}-2-methylbenzonitrile;
2-fluoro-5-{4-[2-(2-hydroxyethyl)piperidin-1-yl]-6-propylpyrimidin-2-ylamino}benzonitrile;
2-amino-5-{4-[2-(2-hydroxyethyl)piperidin-1-yl]-6-propylpyrimidin-2-ylamino}benzonitrile;
2-{1-[2-(3-amino-4-methylphenylamino)-6-propylpyrimidin-4-yl]piperidin-2-yl}ethanol;
2-{1-[2-(3-amino-4-fluorophenylamino)-6-propylpyrimidin-4-yl]piperidin-2-yl}ethanol;
2-{1-[2-(3-amino-4-chlorophenylamino)-6-propylpyrimidin-4-yl]piperidin-2-yl}ethanol;
2-{1-[2-(indolin-6-ylamino)-6-propylpyrimidin-4-yl]piperidin-2-yl}ethanol;
(S)-2-{1-[2-(4-chloro-3-nitrophenylamino)-6-propylpyrimidin-4-yl]piperidin-2-yl}ethanol;
(S)-2-{1-[2-(4-amino-3-nitrophenylamino)-6-propylpyrimidin-4-yl]piperidin-2-yl}ethanol;
(R)-2-{1-[2-(4-amino-3-nitrophenylamino)-6-propylpyrimidin-4-yl]piperidin-2-yl}ethanol;
3-[4-(octahydroquinolin-1(2H)-yl)-6-propylpyrimidin-2-ylamino]benzonitrile;
N-(3-nitrophenyl)-4-(octahydroquinolin-1(2H)-yl)-6-propylpyrimidin-2-amine;
N-(4-fluoro-3-nitrophenyl)-4-(octahydroquinolin-1(2H)-yl)-6-propylpyrimidin-2-amine;
N-(4-chloro-3-nitrophenyl)-4-(octahydroquinolin-1(2H)-yl)-6-propylpyrimidin-2-amine;
N-(3-methoxyphenyl)-4-(octahydroquinolin-1(2H)-yl)-6-propylpyrimidin-2-amine;
N-(5-methoxy-2-methylphenyl)-4-(octahydroquinolin-1(2H)-yl)-6-propylpyrimidin-2-amine;
N-(4-methoxyphenyl)-4-(octahydroquinolin-1(2H)-yl)-6-propylpyrimidin-2-amine;
4-(octahydroquinolin-1(2H)-yl)-6-propyl-N-(3-trifluoromethylphenyl)pyrimidin-2-amine;
N-(3-chlorophenyl)-4-(octahydroquinolin-1(2H)-yl)-6-propylpyrimidin-2-amine;
N-(5-chloro-2-methylphenyl)-4-(octahydroquinolin-1(2H)-yl)-6-propylpyrimidin-2-amine;
N-(3-chloro-4-methylphenyl)-4-(octahydroquinolin-1(2H)-yl)-6-propylpyrimidin-2-amine;
N-(3-methylthiophenyl)-4-(octahydroquinolin-1(2H)-yl)-6-propylpyrimidin-2-amine;
N-[4-(octahydroquinolin-1(2H)-yl)-6-propylpyrimidin-2-yl]-1H-indol-5-amine;
N-[4-(octahydroquinolin-1(2H)-yl)-6-propylpyrimidin-2-yl]-2-(trifluoromethyl)-1H-benzo[d]imidazol-5-amine;
N-[4-(octahydroquinolin-1(2H)-yl)-6-propylpyrimidin-2-yl]quinolin-6-amine;
4-methyl-7-[4-(octahydroquinolin-1(2H)-yl)-6-propylpyrimidin-2-amino]-2H-chromen-2-one;
N-[4-(octahydroquinolin-1(2H)-yl)-6-propylpyrimidin-2-yl]quinolin-3-amine;
(R)-5-{4-[3-(ethylamino)piperidin-1-yl]-6-propylpyrimidin-2-ylamino}-2-methylbenzonitrile;
(R)-5-{4-[3-(propylamino)piperidin-1-yl]-6-propylpyrimidin-2-ylamino}-2-methylbenzonitrile;
(R)-5-{4-[3-(butylamino)piperidin-1-yl]-6-propylpyrimidin-2-ylamino}-2-methylbenzonitrile;
(R)-2-methyl-5-{4-[3-(pentylamino)piperidin-1-yl]-6-propylpyrimidin-2-ylamino}benzonitrile;
(R)-5-{4-[3-(isobutylamino)piperidin-1-yl]-6-propylpyrimidin-2-ylamino}-2-methylbenzonitrile;
(R)-5-{4-[3-(isopentylamino)piperidin-1-yl]-6-propylpyrimidin-2-ylamino}-2-methylbenzonitrile;
(R)-2-methyl-5-{4-[3-(neopentylamino)piperidin-1-yl]-6-propylpyrimidin-2-ylamino}benzonitrile;
(R)-5-{4-[3-(isopropylamino)piperidin-1-yl]-6-propylpyrimidin-2-ylamino}-2-methylbenzonitrile;
(R)-5-(4-{3-[(1H-pyrrol-2-yl)methylamino]piperidin-1-yl}-6-propylpyrimidin-2-ylamino)-2-methylbenzonitrile;
(R)-2-methyl-5-(4-propyl-6-{3-[(thiophen-2-ylmethyl)amino]piperidin-1-yl}pyrimidin-2-ylamino)benzonitrile;
(R)-5-(4-{3-[(4,5-dimethylfuran-2-ylmethyl)amino]piperidin-1-yl}-6-propylpyrimidin-2-ylamino)-2-methylbenzonitrile;
(R)-2-methyl-5-{4-[3-(3-methylthiopropylamino)piperidin-1-yl]-6-propylpyrimidin-2-ylamino}benzonitrile;
(R)-5-{4-[3-(cyclopropylmethylamino)piperidin-1-yl]-6-propylpyrimidin-2-ylamino}-2-methylbenzonitrile;
(R)-5-{4-[3-(cyclopentylmethylamino)piperidin-1-yl]-6-propylpyrimidin-2-ylamino}-2-methylbenzonitrile;
(R)-5-{4-[3-(4-hydroxybenzylamino)piperidin-1-yl]-6-propylpyrimidin-2-ylamino}-2-methylbenzonitrile;
(R)—N-{1-[2-(3-cyano-4-methylphenylamino)-6-propylpyrimidin-4-yl]piperidin-3-yl}acetamide;
(R)-3-[4-(3-aminopiperidin-1-yl)-6-propylpyrimidin-2-ylamino]benzonitrile;
(R)-5-[4-(3-aminopiperidin-1-yl)-6-propylpyrimidin-2-ylamino]-2-fluorobenzonitrile;
(R)-3-{4-[3-(propylamino)piperidin-1-yl]-6-propylpyrimidin-2-ylamino}benzonitrile;
(R)-3-{4-[3-(cyclopropylmethylamino)piperidin-1-yl]-6-propylpyrimidin-2-ylamino}benzonitrile;
(R)-2-fluoro-5-{4-[3-(propylamino)piperidin-1-yl]-6-propylpyrimidin-2-ylamino}benzonitrile;
(R)-5-{4-[3-(cyclopropylmethylamino)piperidin-1-yl]-6-propylpyrimidin-2-ylamino}-2-fluorobenzonitrile;
(R)—N¹-{4-[3-(cyclopropylmethylamino)piperidin-1-yl]-6-propylpyrimidin-2-yl}-4-fluorobenzene-1,3-diamine;
(R)—N¹-{4-[3-(cyclopropylmethylamino)piperidin-1-yl]-6-propylpyrimidin-2-yl}-3-nitrobenzene-1,4-diamine;
(R)-3-amino-5-{4-[3-(cyclopropylmethylamino)piperidin-1-yl]-6-propylpyrimidin-2-ylamino}benzonitrile;
(R)—N¹-{4-[3-(cyclopropylmethylamino)piperidin-1-yl]-6-propylpyrimidin-2-yl}-3-(trifluoromethyl)benzene-1,4-diamine;
(R)—N¹-{4-[3-(cyclopropylmethylamino)piperidin-1-yl]-6-propylpyrimidin-2-yl}-5-(trifluoromethyl)benzene-1,3-diamine;
(R)—N-{1-[2-(4-amino-3-nitrophenylamino)-6-butylpyrimidin-4-yl]piperidin-3-yl}acetamide;
(R)—N-{1-[6-butyl-2-(4-methyl-3-nitrophenylamino)pyrimidin-4-yl]piperidin-3-yl}acetamide;
(R)—N-{1-[6-butyl-2-(4-fluoro-3-nitrophenylamino)pyrimidin-4-yl]piperidin-3-yl}acetamide;
(R)—N-{1-[6-butyl-2-(4-chloro-3-nitrophenylamino)pyrimidin-4-yl]piperidin-3-yl}acetamide;
(R)—N-{1-[2-(3-amino-5-cyanophenylamino)-6-butylpyrimidin-4-yl]piperidin-3-yl}acetamide;
(R)—N-{1-[2-(3-amino-5-trifluoromethylphenylamino)-6-butylpyrimidin-4-yl]piperidin-3-yl}acetamide;
(R)—N-{1-[2-(4-amino-3-trifluoromethylphenylamino)-6-butylpyrimidin-4-yl]piperidin-3-yl}acetamide;
(R)—N-{1-[6-butyl-2-(4-fluoro-3-trifluoromethylphenylamino)pyrimidin-4-yl]piperidin-3-yl}acetamide;
(R)—N-{1-[6-butyl-2-(3-cyano-4-fluorophenylamino)pyrimidin-4-yl]piperidin-3-yl}acetamide;

(R)—N-{1-[2-(3-amino-4-fluorophenylamino)-6-butylpyrimidin-4-yl]piperidin-3-yl}acetamide;
(R)—N-{1-[2-(3-amino-4-chlorophenylamino)-6-butylpyrimidin-4-yl]piperidin-3-yl}acetamide;
(R)—N-{1-[2-(4-amino-3-cyanophenylamino)-6-butylpyrimidin-4-yl]piperidin-3-yl}acetamide;
(R)—N-{1-[2-(3-cyano-4-methylphenylamino)-6-propylpyrimidin-4-yl]piperidin-3-yl}-2-hydroxyacetamide;
(R)—N-{1-[2-(3-cyanophenylamino)-6-propylpyrimidin-4-yl]piperidin-3-yl}-2-hydroxyacetamide;
(R)—N-{1-[2-(3-cyano-4-fluorophenylamino)-6-propylpyrimidin-4-yl]piperidin-3-yl}-2-hydroxyacetamide;
(R)—N-(1-{2-[3-amino-5-(trifluoromethyl)phenylamino]-6-propylpyrimidin-4-yl}piperidin-3-yl)-2-hydroxyacetamide;
(R)—N-(1-{2-[4-amino-3-(trifluoromethyl)phenylamino]-6-propylpyrimidin-4-yl}piperidin-3-yl)-2-hydroxyacetamide;
(R)—N-(1-{2-[4-fluoro-3-(trifluoromethyl)phenylamino]-6-propylpyrimidin-4-yl}piperidin-3-yl)-2-hydroxyacetamide;
(R)—N-{1-[2-(3-amino-4-fluorophenylamino)-6-propylpyrimidin-4-yl]piperidin-3-yl}-2-hydroxyacetamide;
(R)—N-{1-[2-(3-amino-4-chlorophenylamino)-6-propylpyrimidin-4-yl]piperidin-3-yl}-2-hydroxyacetamide;
(R)—N-{1-[2-(3-amino-4-methylphenylamino)-6-propylpyrimidin-4-yl]piperidin-3-yl}-2-hydroxyacetamide;
(R)—N-{1-[2-(3-chloro-4-methylphenylamino)-6-propylpyrimidin-4-yl]piperidin-3-yl}-2-hydroxyacetamide;
(R)-2-hydroxy-N-(1-{2-[4-methyl-3-(trifluoromethyl)phenylamino]-6-propylpyrimidin-4-yl}piperidin-4-yl)acetamide;
(R)—N-{1-[2-(3-amino-5-cyanophenylamino)-6-propylpyrimidin-4-yl]piperidin-3-yl}-2-hydroxyacetamide;
(R)—N$^1$-[4-(3-aminopiperidin-1-yl)-6-propylpyrimidin-2-yl]-5-(trifluoromethyl)benzene-1,3-diamine;
(R)—N$^1$-[4-(3-aminopiperidin-1-yl)-6-propylpyrimidin-2-yl]-3-(trifluoromethyl)benzene-1,4-diamine;
(R)-4-(3-aminopiperidin-1-yl)-N-(3-fluoro-4-methylphenyl)-6-propylpyrimidin-2-amine;
(R)—N$^1$-[4-(3-aminopiperidin-1-yl)-6-propylpyrimidin-2-yl]-4-fluorobenzene-1,3-diamine;
(R)-3-amino-5-{[4-(3-aminopiperidin-1-yl)-6-propylpyrimidin-2-ylamino}benzonitrile;
(R)-2-amino-5-{[4-(3-aminopiperidin-1-yl)-6-propylpyrimidin-2-yl]amino}benzonitrile;
(R)—N$^1$-[4-(3-aminopiperidin-1-yl)-6-propylpyrimidin-2-yl]-4-chlorobenzene-1,3-diamine;
(R)-4-(3-aminopiperidin-1-yl)-N-[4-methyl-3-(trifluoromethyl)phenyl]-6-propylpyrimidin-2-amine;
(R)—N-[4-(3-aminopiperidin-1-yl)-6-propylpyrimidin-2-yl]-1-H-indol-6-amine;
(R)-4-(3-aminopiperidin-1-yl)-N-(4-methyl-3-nitrophenyl)-6-propylpyrimidin-2-amine;
(R)—N$^1$-[4-(3-aminopiperidin-1-yl)-6-propylpyrimidin-2-yl]-3-nitrobenzene-1,4-diamine;
(R)—N-{1-[2-(3-cyano-4-fluorophenylamino)-6-propylpyrimidin-4-yl]piperidin-3-yl}acetamide;
(R)-5-[4-(3-diethylaminopiperidin-1-yl)-6-propylpyrimidin-2-ylamino]-2-methylbenzonitrile;
(R)-5-[4-(3-diethylaminopiperidin-1-yl)-6-propylpyrimidin-2-ylamino]-2-fluorobenzonitrile;
(R)-5-[4-(3-ethylaminopiperidin-1-yl)-6-propylpyrimidin-2-ylamino]-2-fluorobenzonitrile;
(R)—N-{1-[6-butyl-2-(3-cyanophenylamino)pyrimidin-4-yl]piperidin-3-yl}acetamide;
(R)—N-{1-[2-(3-cyanophenylamino)-6-propylpyrimidin-4-yl]piperidin-3-yl}acetamide;
(R)—N-{1-[2-(3-amino-5-cyanophenylamino)-6-propylpyrimidin-4-yl]piperidin-3-yl}acetamide;
N-{1-[2-(4-amino-3-nitrophenylamino)-6-propylpyrimidin-4-yl]piperidin-3-yl}acetamide;
N-{1-[2-(3-amino-4-fluorophenylamino)-6-propylpyrimidin-4-yl]piperidin-3-yl}acetamide;
(R)—N-{1-[2-(4-fluoro-3-trifluoromethylphenylamino)-6-propylpyrimidin-4-yl]piperidin-3-yl}acetamide;
(R)—N-(1-{2-[3-amino-5-(trifluoromethyl)phenylamino]-6-propylpyrimidin-4-yl}piperidin-3-yl)acetamide;
(R)—N-(1-{2-[4-amino-3-(trifluoromethyl)phenylamino]-6-propylpyrimidin-4-yl}piperidin-3-yl)acetamide;
(R)-5-[4-(3-ethylaminopiperidin-1-yl)-6-propylpyrimidin-2-ylamino]-2-methylbenzonitrile;
(R)-2-fluoro-5-[4-(3-methylaminopiperidin-1-yl)-6-propylpyrimidin-2-ylamino]benzonitrile;
(R)-2-methyl-5-[4-(3-methylaminopiperidin-1-yl)-6-propylpyrimidin-2-ylamino]benzonitrile;
(R)—N$^1$-[4-(3-methylaminopiperidin-1-yl)-6-propylpyrimidin-2-yl]-5-(trifluoromethyl)benzene-1,3-diamine;
(R)—N$^1$-[4-(3-methylaminopiperidin-1-yl)-6-propylpyrimidin-2-yl]-3-(trifluoromethyl)benzene-1,4-diamine;
(R)-3-amino-5-[4-(3-methylaminopiperidin-1-yl)-6-propylpyrimidin-2-ylamino]benzonitrile;
(R)-(4-fluoro-3-trifluoromethylphenyl)-[4-(3-methylaminopiperidin-1-yl)-6-propylpyrimidin-2-yl]amine;
(R)—N$^1$-[4-(3-ethylaminopiperidin-1-yl)-6-propylpyrimidin-2-yl]-3-nitrobenzene-1,4-diamine;
(R)—N$^1$-[4-(3-ethylaminopiperidin-1-yl)-6-propylpyrimidin-2-yl]-4-fluorobenzene-1,3-diamine;
(R)—N$^1$-[4-(3-ethylaminopiperidin-1-yl)-6-propylpyrimidin-2-yl]-5-(trifluoromethyl)benzene-1,3-diamine;
(R)—N$^1$-[4-(3-ethylaminopiperidin-1-yl)-6-propylpyrimidin-2-yl]-3-(trifluoromethyl)benzene-1,4-diamine;
(R)-3-amino-5-[4-(3-ethylaminopiperidin-1-yl)-6-propylpyrimidin-2-ylamino]benzonitrile;
(R)-5-[4-(3-aminopiperidin-1-yl)-6-butylpyrimidin-2-ylamino]-2-methylbenzonitrile;
(R)-5-[4-(3-aminopiperidin-1-yl)-6-butylpyrimidin-2-ylamino]-2-fluorobenzonitrile;
(R)—N-{1-[6-butyl-2-(3-cyano-4-methylphenylamino)pyrimidin-4-yl]piperidin-3-yl}acetamide;
(S)-5-[4-(3-ethylaminopiperidin-1-yl)-6-propylpyrimidin-2-ylamino]-2-methylbenzonitrile;
5-[4-(3-ethylaminopiperidin-1-yl)-6-propylpyrimidin-2-ylamino]-2-methylbenzonitrile;
N-{1-[6-butyl-2-(3-cyano-4-methylphenylamino)pyrimidin-4-yl]piperidin-3-yl}acetamide;
(R)-5-({4-butyl-6-[3-(ethylamino)piperidin-1-yl]pyrimidin-2-yl}amino)-2-methylbenzonitrile;
(R)-5-({4-butyl-6-[3-(butylamino)piperidin-1-yl]pyrimidin-2-yl}amino)-2-methylbenzonitrile;
(R)-5-({4-butyl-6-[3-(pentylamino)piperidin-1-yl]pyrimidin-2-yl}amino)-2-methylbenzonitrile;
(R)-5-({4-butyl-6-[3-(isobutylamino)piperidin-1-yl]pyrimidin-2-yl}amino)-2-methylbenzonitrile;
(R)-5-({4-butyl-6-[3-(isopentylamino)piperidin-1-yl]pyrimidin-2-yl}amino)-2-methylbenzonitrile;
(R)-5-({4-butyl-6-[3-(neopentylamino)piperidin-1-yl]pyrimidin-2-yl}amino)-2-methylbenzonitrile;
(R)-5-{[4-butyl-6-(3-{[3-(methylthio)propyl]amino}piperidin-1-yl)pyrimidin-2-yl]amino}-2-methylbenzonitrile;
(R)-4-fluoro-N$^1$-{4-[3-(methylamino)piperidin-1-yl]-6-propylpyrimidin-2-yl}benzene-1,3-diamine;

(R)-4-chloro-N¹-{4-[3-(methylamino)piperidin-1-yl]-6-propylpyrimidin-2-yl}benzene-1,3-diamine;
(R)-2-amino-5-({4-[3-(methylamino)piperidin-1-yl]-6-propylpyrimidin-2-yl}amino)benzonitrile;
(R)—N-(3-methoxy-4-methylphenyl)-4-[3-(methylamino)piperidin-1-yl]-6-propylpyrimidin-2-amine;
(R)-4-methyl-N¹-{4-[3-(methylamino)piperidin-1-yl]-6-propylpyrimidin-2-yl}benzene-1,3-diamine;
(R)-5-({4-butyl-6-[3-(methylamino)piperidin-2-yl}amino)-2-methylbenzonitrile;
(R)-5-({4-butyl-6-[3-(methylamino)piperidin-2-yl}amino)-2-fluorobenzonitrile;
(R)—N¹-{4-butyl-6-[3-(methylamino)piperidin-1-yl]pyrimidin-2-yl}-5-(trifluoromethyl)benzene-1,3-diamine;
(R)—N¹-{4-butyl-6-[3-(methylamino)piperidin-1-yl]pyrimidin-2-yl}-3-(trifluoromethyl)benzene-1,4-diamine;
(R)-3-amino-5-({4-butyl-6-[3-(methylamino)piperidin-1-yl]pyrimidin-2-yl}amino)benzonitrile;
(R)-2-amino-5-({4-butyl-6-[3-(methylamino)piperidin-1-yl]pyrimidin-2-yl}amino)benzonitrile;
(R)—N¹-{4-butyl-6-[3-(methylamino)piperidin-1-yl]pyrimidin-2-yl}-4-fluorobenzene-1,3-diamine;
(R)-4-butyl-N-(3-methoxy-4-methylphenyl)-6-[3-(methylamino)piperidin-1-yl]pyrimidin-2-amine;
(R)—N¹-{4-butyl-6-[3-(methylamino)piperidin-1-yl]pyrimidin-2-yl}-4-methylbenzene-1,3-diamine;
(R)-4-butyl-N-[4-fluoro-3-(trifluoromethyl)phenyl]-6-[3-(methylamino)piperidin-1-yl]pyrimidin-2-amine;
(R)—N¹-{4-[3-(methylamino)piperidin-1-yl]-6-propylpyrimidin-2-yl}-3-nitrobenzene-1,4-diamine;
(R)—N-(3,4-dimethylphenyl)-4-[3-(methylamino)piperidin-1-yl]-6-propylpyrimidin-2-amine;
(R)—N-(3-fluoro-4-methylphenyl)-4-[3-(methylamino)piperidin-1-yl]-6-propylpyrimidin-2-amine;
(R)—N-[4-methyl-3-(trifluoromethyl)phenyl]-4-[3-(methylamino)piperidin-1-yl]-6-propylpyrimidin-2-amine;
(R)-4-methoxy-N¹-{4-[3-(methylamino)piperidin-1-yl]-6-propylpyrimidin-2-yl}benzene-1,3-diamine;
(R)—N-{4-[3-(methylamino)piperidin-1-yl]-6-propylpyrimidin-2-yl}-1H-indazol-6-amine;
(R)—N⁴-{4-[3-(methylamino)piperidin-1-yl]-6-propylpyrimidin-2-yl}benzene-1,2,4-triamine;
(R)—N¹-{4-butyl-6-[3-(methylamino)piperidin-1-yl]pyrimidin-2-yl}-3-nitrobenzene-1,4-diamine;
(R)-3-({4-butyl-6-[3-(methylamino)piperidin-1-yl]pyrimidin-2-yl}amino)benzonitrile;
(R)-4-butyl-N-(3,4-dimethylphenyl)-6-[3-(methylamino)piperidin-1-yl]pyrimidin-2-amine;
(R)-4-butyl-N-(3-fluoro-4-methylphenyl)-6-[3-(methylamino)piperidin-1-yl]pyrimidin-2-amine;
(R)-4-butyl-N-[4-methyl-3-(trifluoromethyl)phenyl]-6-[3-(methylamino)piperidin-1-yl]pyrimidin-2-amine;
(R)—N¹-{4-butyl-6-[3-(methylamino)piperidin-1-yl]pyrimidin-2-yl}-4-methoxybenzene-1,3-diamine;
(R)—N-{4-butyl-6-[3-(methylamino)piperidin-1-yl]pyrimidin-2-yl}-1H-indazol-6-amine;
(R)—N⁴-{4-butyl-6-[3-(methylamino)piperidin-1-yl]pyrimidin-2-yl}benzene-1,2,4-triamine;
(R)-4-(3-aminopiperidin-1-yl)-6-butyl-N-(3-nitrophenyl)pyrimidin-2-amine;
(R)—N¹-[4-(3-aminopiperidin-1-yl)-6-butylpyrimidin-2-yl]-3-nitrobenzene-1,4-diamine;
(R)-4-(3-aminopiperidin-1-yl)-6-butyl-N-(4-fluoro-3-nitrophenyl)pyrimidin-2-amine;
(R)-4-(3-aminopiperidin-1-yl)-6-butyl-N-(4-methyl-3-nitrophenyl)pyrimidin-2-amine;
(R)—N¹-[4-(3-aminopiperidin-1-yl)-6-butylpyrimidin-2-yl]-3-(trifluoromethyl)benzene-1,4-diamine;
(R)—N¹-[4-(3-aminopiperidin-1-yl)-6-butylpyrimidin-2-yl]-5-(trifluoromethyl)benzene-1,3-diamine;
(R)-3-amino-5-{[4-(3-aminopiperidin-1-yl)-6-butylpyrimidin-2-yl]amino}benzonitrile;
(R)-4-(3-aminopiperidin-1-yl)-6-butyl-N-[4-methyl-3-(trifluoromethyl)phenyl]pyrimidin-2-amine;
(R)-4-(3-aminopiperidin-1-yl)-6-butyl-N-(3-fluoro-4-methylphenyl)pyrimidin-2-amine;
(R)-4-(3-aminopiperidin-1-yl)-6-butyl-N-(3-methoxy-4-methylphenyl)pyrimidin-2-amine;
(R)—N¹-[4-(3-aminopiperidin-1-yl)-6-butylpyrimidin-2-yl]-4-methylbenzene-1,3-diamine;
(R)-4-(3-aminopiperidin-1-yl)-6-butyl-N-(3,4-dimethylphenyl)pyrimidin-2-amine;
(R)-4-(3-aminopiperidin-1-yl)-6-butyl-N-[4-fluoro-3-(trifluoromethyl)phenyl]pyrimidin-2-amine;
(R)—N¹-[4-(3-aminopiperidin-1-yl)-6-butylpyrimidin-2-yl]-4-fluorobenzene-1,3-diamine;
(R)-2-amino-5-{[4-(3-aminopiperidin-1-yl)-6-butylpyrimidin-2-yl]amino}benzonitrile;
(R)-3-{[4-(3-aminopiperidin-1-yl)-6-butylpyrimidin-2-yl]amino}benzonitrile;
(R)—N¹-[4-(3-aminopiperidin-1-yl)-6-butylpyrimidin-2-yl]benzene-1,4-diamine;
(R)-4-(3-aminopiperidin-1-yl)-6-butyl-N-(4-chloro-3-nitrophenyl)pyrimidin-2-amine; and
(R)—N⁴-[4-(3-aminopiperidin-1-yl)-6-butylpyrimidin-2-yl]benzene-1,2,4-triamine.

In the use, the pharmaceutical composition, the treatment method, and the compound according to the present invention, still more preferable compounds in terms of pharmacological activity include the compound (or its pharmaceutically acceptable salt) described in Table 2-1 and Table 2-1.

The present invention includes, within its scope, a process for preparing a compound of Formula 1 or its pharmaceutically acceptable salt, which comprises reacting a compound of Formula 2 with a compound of Formula 3 to obtain a compound of Formula 4; performing a methylation of the compound of Formula 4 to obtain a compound of Formula 5; reacting the compound of Formula 5 with $R_1$—$NH_2$ to obtain a compound of Formula 6; performing a halogenation of the compound of Formula 6 to obtain a compound of Formula 7; and reacting the compound of Formula 7 with $R_2$—H to obtain a compound of Formula 1:

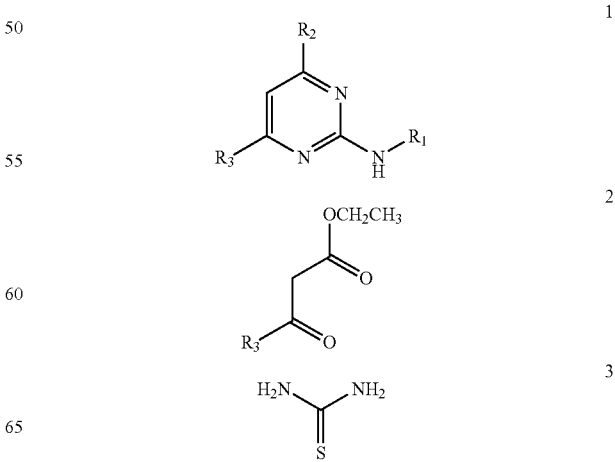

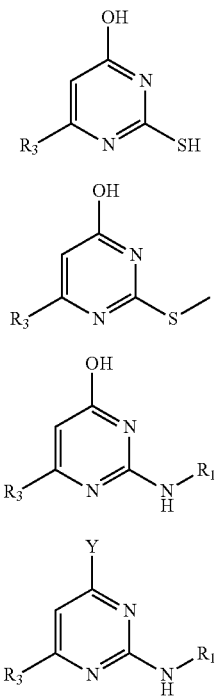

wherein, $R_1$, $R_2$, and $R_3$ are the same as defined in the above; and Y is halogen.

The compounds of Formula 2 and 3 are commercially available. The reaction between the compound of Formula 2 and the compound of Formula 3 may be performed in the presence of a base and a solvent. The base may be potassium carbonate, sodium carbonate, etc and the solvent may be an aqueous solvent such as water. Typically, the reaction may be carried out under heating.

The methylation of the compound of Formula 4 may be carried out using a methylating agent such as iodomethane. The methylation may be performed in the presence of a base and a solvent. The base may be sodium hydroxide, potassium hydroxide, etc and the solvent may be an aqueous solvent such as water. Typically, the methylation may be carried out at room temperature or under heating.

The reaction between the compound of Formula 5 and $R_1$—$NH_2$ may be performed in the absence of a solvent or in the presence of a solvent such as diglyme. The reaction may be carried out at a temperature ranging from 140° C. to 180° C.

The halogenation of the compound of Formula 6 may be carried out using a halogenating agent such as phosphorus oxychloride. The halogenation may be performed preferably at a temperature of about 100° C. or higher. And also, for improving reaction rate and/or yield, the halogenation may be performed in the presence of N,N-dimethylaniline or N,N-dimethylformamide in a catalytic amount.

The reaction between the compound of Formula 7 and $R_2$—H may be performed in the presence of an organic solvent, such as anhydrous tetrahydrofuran, alcohol, and 1,4-dioxane. Typically, the reaction may be carried out under heating. And also, for improving reaction rate and/or yield, the reaction may be performed in the presence of a metallic catalyst (e.g., palladium), a ligand, and a base such as cesium carbonate, isopropylethylamine; or performed under microwave ranging from 300 W to 600 W.

The compound of Formula 5 may be also prepared by reacting a compound of Formula 2 with a compound of Formula 8:

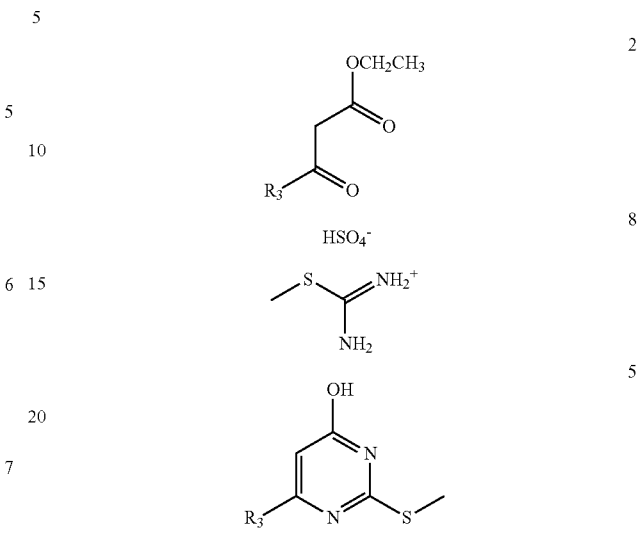

wherein, $R_3$ is the same as defined in the above.

The compound of Formula 8 is commercially available. The reaction between the compound of Formula 2 and the compound of Formula 8 may be performed in the presence of a base and a solvent. The base may be potassium carbonate, sodium carbonate, etc and the solvent may be an aqueous solvent such as water. Typically, the reaction may be carried out at room temperature or under heating.

The compound of Formula 6 may be also prepared by reacting a compound of Formula 2 with a compound of Formula 9:

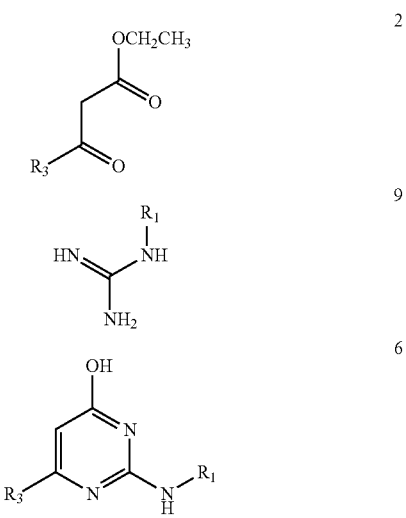

wherein, $R_1$ and $R_3$ are the same as defined in the above.

The compound of Formula 9 may be easily prepared by using known methods, e.g., EP0560726. The reaction between the compound of Formula 2 and the compound of Formula 9 may be performed in the presence of a base and a solvent. The base may be sodium methoxide, sodium ethoxide, etc and the solvent may be an alcohol. Typically, the reaction may be carried out under heating.

The present invention also provides a process for preparing a compound of Formula 1 or its pharmaceutically acceptable salt, which comprises performing a halogenation of a compound of Formula 4 to obtain a compound of Formula 10; reacting the compound of Formula 10 with $R_2H$ to obtain a compound of Formula 11; and reacting the compound of Formula 11 with $R_1$—$NH_2$ to obtain a compound of Formula 1:

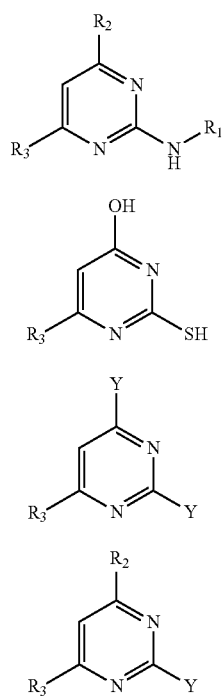

wherein, $R_1$, $R_2$, and $R_3$ are the same as defined in the above; and Y is halogen.

The halogenation of the compound of Formula 4 may be carried out using a halogenating agent such as phosphorus oxychloride. The halogenation may be performed preferably at a temperature of about 100° C. or higher. And also, for improving reaction rate and/or yield, the halogenation may be performed in the presence of N,N-dimethylaniline or N,N-dimethylformamide in a catalytic amount.

The reaction between the compound of Formula 10 and $R_2H$ may be performed in the presence of an organic solvent, such as anhydrous tetrahydrofuran, alcohol, chloroform, or N,N-dimethylformamide. Typically, the reaction may be carried out at room temperature or under heating. And also, for improving reaction rate and/or yield, the reaction may be performed in the presence of a base such as triethylamine and diisopropylethylamine.

The reaction between the compound of Formula 11 and $R_1$—$NH_2$ may be performed in the presence of an organic solvent such as alcohol, toluene, 1,4-dioxane, and N,N-dimethylformamide. The reaction may be carried out under heating. And also, for improving reaction rate and/or yield, the reaction may be performed in the presence of a metallic catalyst (e.g., palladium), a ligand, and a base (e.g., cesium carbonate); or performed under microwave ranging from 300 W to 600 W.

The compound of Formula 10 may be also prepared by reacting a compound of Formula 5 with an acid to obtain a compound of Formula 12; and then performing a halogenation of the compound of Formula 12:

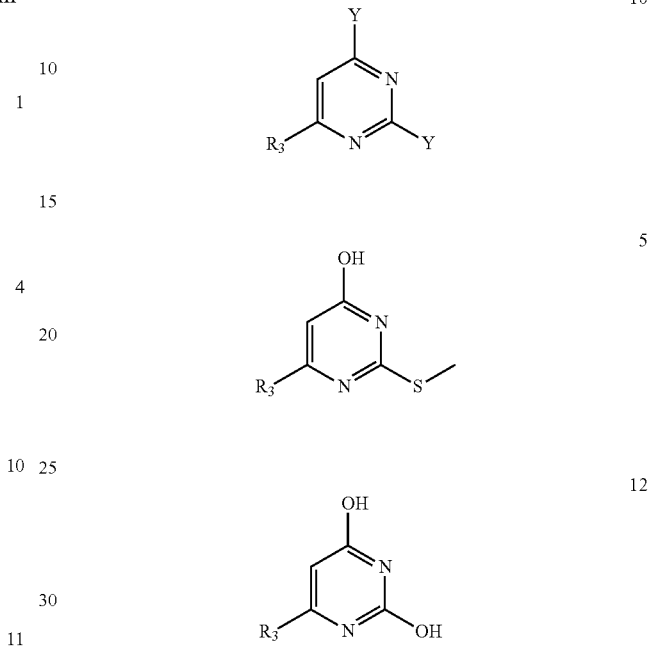

wherein, $R_3$ and Y are the same as defined in the above.

The reaction between the compound of Formula 5 and the acid may be performed using an organic acid (e.g., acetic acid, etc.) and an inorganic acid (e.g., hydrochloric acid, etc.). The reaction may be performed in an aqueous solvent such as water. Typically, the reaction may be carried out under heating.

The halogenation of the compound of Formula 12 may be carried out using a halogenating agent such as phosphorus oxychloride. The halogenation may be performed preferably at a temperature of about 100° C. or higher. And also, for improving reaction rate and/or yield, the halogenation may be performed in the presence of N,N-dimethylaniline or N,N-dimethylformamide in a catalytic amount.

In accordance with an embodiment of the present invention, there is provided a process for preparing a compound of Formula 1b or its pharmaceutically acceptable salt, which comprises reacting a compound of Formula 1a with an organic acid or an acyl halide:

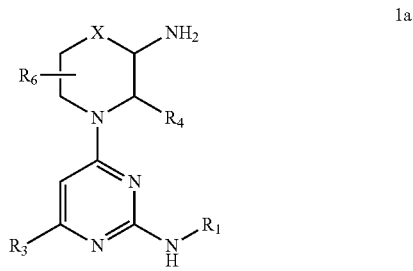

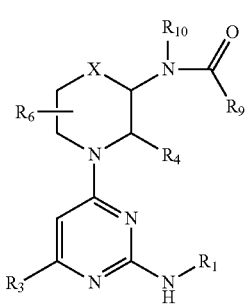

1b wherein, $R_1$, $R_3$, $R_4$, $R_6$, $R_9$, $R_{10}$, and X are the same as defined in the above.

The reaction between the compound of Formula 1a and the organic acid may be performed through amide coupling reaction, using a coupling agent such as (benzotriazol-1-yloxy)-tris-(dimethylamino)phosphonium hexafluorophosphate, N-(3-dimethylaminopropyl)-N'-ethylcarbodiimide hydrochloride, and 1-hydroxybenzotriazole hydrate; and a base such as diisopropylethylamine or triethylamine. The coupling reaction may be performed in an organic solvent such as dichloromethane, or N,N-dimethylformamide. Typically, the coupling reaction is performed at room temperature.

And also, the reaction between the compound of Formula 1a and the acyl halide may be performed through amide coupling reaction, using an organic base (e.g., diisopropylethylamine, triethylamine, etc) or an inorganic base (e.g., sodium hydroxide). The coupling reaction may be performed in an organic solvent such as dichloromethane or a mixed solvent of an organic solvent and water. Typically, the coupling reaction is performed at room temperature.

The compound of Formula 1b or its pharmaceutically acceptable salt may be also prepared by reacting a compound of Formula 11a with an organic acid or an acyl halide to obtain a compound of Formula 11b; and then reacting the compound of Formula 11b with $R_1$—$NH_2$ to obtain a compound of Formula 1b:

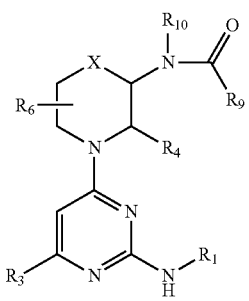

1b

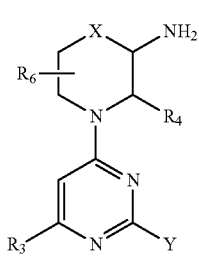

11a

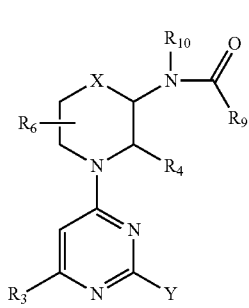

11b wherein, $R_1$, $R_3$, $R_4$, $R_6$, $R_9$, $R_{10}$, and X are the same as defined in the above; and Y is halogen.

The reaction between the compound of Formula 11a and the organic acid may be performed through amide coupling reaction, using a coupling agent such as (benzotriazol-1-yloxy)-tris-(dimethylamino)phosphonium hexafluorophosphate, N-(3-dimethylaminopropyl)-N'-ethylcarbodiimide hydrochloride, and 1-hydroxybenzotriazole hydrate; and a base such as diisopropylethylamine or triethylamine. The coupling reaction may be performed in an organic solvent such as dichloromethane, or N,N-dimethylformamide. Typically, the coupling reaction is performed at room temperature.

And also, the reaction between the compound of Formula 11a and the acyl halide may be performed through amide coupling reaction, using an organic base (e.g., diisopropylethylamine, triethylamine, etc) or an inorganic base (e.g., sodium hydroxide, etc). The coupling reaction may be performed in an organic solvent such as dichloromethane or a mixed solvent of an organic solvent and water. Typically, the coupling reaction is performed at room temperature.

The reaction between the compound of Formula 11b and $R_1$—$NH_2$ may be performed in an organic solvent such as alcohol, toluene, 1,4-dioxane, and N,N-dimethylformamide, etc. Typically, the reaction may be performed under heating. And also, for improving reaction rate and/or yield, the reaction may be performed in the presence of a metallic catalyst (e.g., palladium), a ligand, and a base (e.g., cesium carbonate); or performed under microwave ranging from 300 W to 600 W.

In accordance with another embodiment of the present invention, there is provided a process for preparing a compound of Formula 1c or its pharmaceutically acceptable salt, which comprises performing a reductive amination using an aldehyde or a ketone with respect to a compound of Formula 1a:

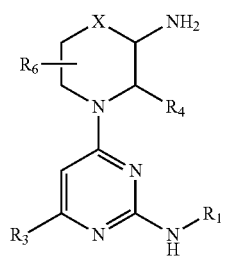

1a

-continued

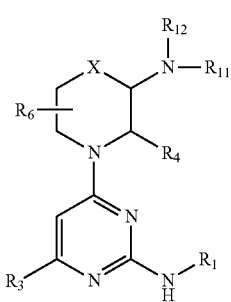

1c wherein, $R_1$, $R_3$, $R_4$, $R_6$, $R_{11}$, $R_{12}$, and X are the same as defined in the above.

The reductive amination may be performed using a reducing agent such as sodium borohydride, sodium triacetoxyborohydride, and sodium cyanoborohydride. The reductive amination may be performed in an organic solvent (e.g., alcohol) at room temperature or at low temperature (e.g., at 0° C. or less). And also, for improving reaction rate and/or yield, the reaction may be performed in the presence of acetic acid, etc.

The compound of Formula 1c or its pharmaceutically acceptable salt may be prepared by introducing an amine-protecting group to a compound of Formula 11a to obtain a compound of Formula 11c, performing an alkylation of the compound of Formula 11c to obtain a compound of Formula 11d, and reacting a compound of Formula 11d with $R_1$—$NH_2$, followed by removing the amine-protecting group:

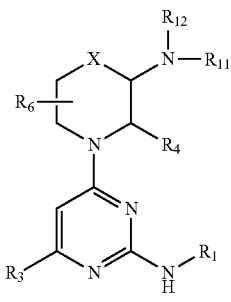

1c

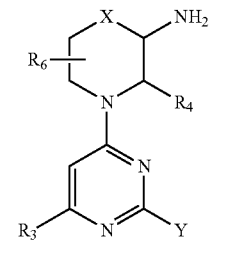

11a

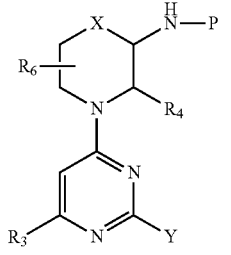

11c

-continued

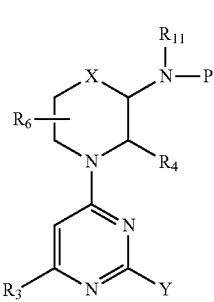

11d wherein, $R_1$, $R_3$, $R_4$, $R_6$, $R_{11}$, and X are the same as defined in the above; Y is halogen; and $R_{12}$ is hydrogen. P is an amine-protecting group such as tert-butoxycarbonyl.

The reaction for introducing an amine-protecting group to the compound of Formula 11a may be performed in an organic solvent such as dichloromethane, chloroform, and 1,4-dioxane at room temperature or at low temperature (e.g., at 0° C. or less). And also, the reaction may be performed in the presence of a base such as triethylamine, diisopropylethylamine, and 4-dimethylaminopyridine.

The alkylation of the compound of Formula 11c may be performed using an alkyl halide. The alkylation may be performed in the presence of a base (e.g., sodium hydride) in an organic solvent (e.g., N,N-dimethylformamide). The alkylation may be performed at room temperature or under heating.

The reaction between the compound of Formula 11d with $R_1$—$NH_2$ may be performed in an organic solvent such as alcohol, toluene, 1,4-dioxane, N,N-dimethylformamide. Typically, the reaction is performed under heating. And also, for improving reaction rate and/or yield, the reaction may be performed in the presence of a metallic catalyst (e.g., palladium), a ligand, and a base (e.g., cesium carbonate); or performed under microwave ranging from 300 W to 600 W. The reaction for removing the amine-protecting group may be performed using an acid (e.g., hydrochloric acid, trifluoroacetic acid, etc) in an organic solvent such as ethyl acetate and methanol. Typically, the reaction may be performed at room temperature or at low temperature (e.g., at 0° C. or less).

The compound of Formula 11d may be also prepared by performing a reductive amination with respect to a compound of Formula 11a to obtain a compound of Formula 11e, and then introducing an amine-protecting group to the compound of Formula 11e:

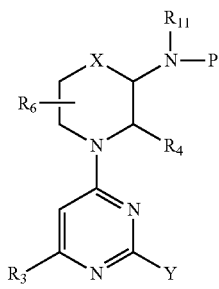

11d

-continued

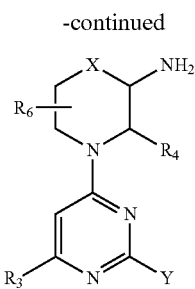
11a

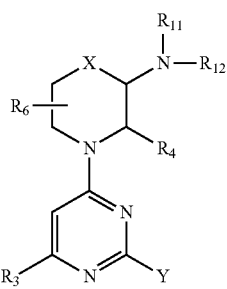
11e wherein, $R_3$, $R_4$, $R_6$, $R_{11}$, and X are the same as defined in the above; Y is halogen; and $R_{12}$ is hydrogen. P is an amine-protecting group such as tert-butoxycarbonyl.

The reductive amination of the compound of Formula 11a may be performed using a reducing agent such as sodium borohydride, sodium triacetoxyborohydride, and sodium cyanoborohydride. The reductive amination may be in an organic solvent (e.g., alcohol) at room temperature or at low temperature (e.g., at 0° C. or less). And also, for improving reaction rate and/or yield, the reaction may be performed in the presence of acetic acid, etc.

The reaction for introducing an amine-protecting group to the compound of Formula 11e may be performed in an organic solvent such as dichloromethane, chloroform, and 1,4-dioxane at room temperature or at low temperature (e.g., at 0° C. or less). And also, the reaction may be performed in the presence of a base such as triethylamine, diisopropylethylamine, and 4-dimethylaminopyridine.

The following examples and experimental examples are provided for illustration purposes only, and are not intended to limit the scope of the invention.

Preparation 1. 4-chloro-N-(4-fluorophenyl)-6-propylpyrimidin-2-amine

<Step 1>
2-(methylthio)-6-propylpyrimidin-4(3H)-one

A mixture of 6-n-propyl-2-thiouracil (25.0 g, 0.15 mol), sodium hydroxide (5.9 g, 0.15 mol), iodomethane (10.2 ml, 0.17 mol), and water (300 ml) was stirred at room temperature overnight and then filtered. The resulting solid was dried in vacuo to give the titled compound (25.0 g) as a white solid. The product was used in the subsequent reaction without further purification.

<Step 2> 2-(4-fluorophenylamino)-6-propylpyrimidin-4(3H)-one

A mixture of 2-(methylthio)-6-propylpyrimidin-4(3H)-one (3.7 g, 0.02 mol) prepared in Step 1 and 4-fluoroaniline (6.7 g, 0.06 mol) was stirred at 160° C. overnight. The reaction mixture was cooled to room temperature, and then ethanol (50 ml) and charcoal (1 g) were added thereto. The reaction mixture was stirred for 1 hour and then filtered. The filtrate was concentrated under reduced pressure. Ethanol (20 ml) was added to the resulting residue, which was then stirred for 1 hour. The reaction mixture was filtered to give the titled compound as a gray solid.

$^1$H-NMR (400 MHz, CD$_3$OD) δ 7.70-7.50 (m, 2H), 7.07 (t, 2H), 5.75 (s, 1H), 2.43 (t, 2H), 1.70 (q, 2H), 0.98 (t, 3H)

<Step 3> 4-chloro-N-(4-fluorophenyl)-6-propylpyrimidin-2-amine 2-(4-Fluorophenylamino)-6-propylpyrimidin-4(3H)-one (2.2 g, 8.9 mmol) prepared in Step 2 was added to phosphorus oxychloride (1.5 ml, 16.2 mmol), which was then stirred at 110° C. for 5 hours. After cooling the reaction mixture to room temperature, an ice water was added to the reaction mixture, which was then basified to pH 9 with sodium hydroxide. The aqueous layer was extracted with ethyl acetate. The resulting organic layer was dried on anhydrous sodium sulfate and then concentrated under reduced pressure. The resulting residue was purified with silica gel column chromatography (ethyl acetate) to give 2.2 g of the titled compound as a yellow solid.

$^1$H-NMR (400 MHz, CDCl$_3$) δ 7.65-7.50 (m, 2H), 7.03 (t, 2H), 6.63 (s, 1H), 2.60 (t, 2H), 1.75 (q, 2H), 0.99 (t, 3H)

Preparation 2. 4-butyl-6-chloro-N-(4-fluorophenyl)pyrimidin-2-amine

<Step 1>
6-butyl-2-thioxo-2,3-dihydropyrimidin-4(1H)-one

A mixture of thiourea (2.4 g, 31.5 mmol), potassium carbonate (5.5 g, 39.5 mmol), 3-oxoheptanoic acid ethyl ester (6.8 g, 39.5 mmol), and water (40 ml) was stirred at 100° C. for 1 hour. After cooling the reaction mixture to room temperature, water (6 ml) and conc. hydrochloric acid (6 ml) were added to the reaction mixture, which was then extracted with ethyl acetate. The organic layer was concentrated under reduced pressure. The resulting residue was washed with n-hexane and then filtered. The resulting white solid was dried in vacuo to give 1 g of the titled compound. The product was used in the subsequent reaction without further purification.

<Step 2>
6-butyl-2-(methylthio)pyrimidin-4(3H)-one

A mixture of 6-butyl-2-thioxo-2,3-dihydropyrimidin-4 (1H)-one (0.4 g, 2.2 mmol) prepared in Step 1, sodium hydroxide (0.1 g, 2.2 mmol), iodomethane (0.15 ml, 2.4 mmol), and water (3 ml) was stirred at room temperature overnight and then filtered. The resulting white solid (0.2 g) was dried in vacuo and then used in the subsequent reaction without further purification.

<Step 3>
6-butyl-2-(4-fluorophenylamino)pyrimidin-4(3H)-one

A mixture of 6-butyl-2-(methylthio)pyrimidin-4(3H)-one (0.16 g, 0.81 mmol) in prepared in Step 2 and 4-fluoroaniline (0.28 g, 2.5 mmol) was stirred at 160° C. overnight. After cooling the reaction mixture to room temperature, ethyl acetate (3 ml) was added thereto. The reaction mixture was stirred for 1 hour and then filtered to give 0.2 g of the titled compound as a white solid.

$^1$H-NMR (400 MHz, CD$_3$OD) δ 7.70-7.50 (m, 2H), 7.07 (t, 2H), 5.75 (s, 1H), 2.46 (t, 2H), 1.70-1.60 (m, 2H), 1.39 (q, 2H), 0.95 (t, 3H)

<Step 4> 4-butyl-6-chloro-N-(4-fluorophenyl)pyrimidin-2-amine

The titled compound (0.17 g) as a yellow oil was prepared in accordance with the same procedures as in Step 3 of Preparation 1, using 6-butyl-2-(4-fluorophenylamino)pyrimidin-4(3H)-one (0.2 g, 0.8 mmol) prepared in Step 3.

$^1$H-NMR (400 MHz, CDCl$_3$) δ 7.65-7.50 (m, 2H), 7.09 (brs, 1H), 7.03 (t, 2H), 6.63 (s, 1H), 2.62 (t, 2H), 1.80-1.60 (m, 2H), 1.40 (q, 2H), 0.95 (t, 3H)

Preparation 3. 2-[1-(2-chloro-6-propylpyrimidin-4-yl)-piperidin-2-yl]ethanol

<Step 1> 2,4-dichloro-6-propylpyrimidine

Phosphorus oxychloride (100 ml) was slowly added to 6-propyl-2-thiouracil (17.7 g, 0.1 mol) at room temperature, which was then stirred at 110° C. overnight. The reaction mixture was added to an ice water and then neutralized with a saturated aqueous solution of sodium bicarbonate. The reaction mixture was extracted with dichloromethane. The organic layer was dried on anhydrous magnesium sulfate, filtered, and then concentrated under reduced pressure. The resulting residue was purified with silica gel column chromatography (n-hexane/ethyl acetate=50/1) to give 10.3 g of the titled compound as a pale yellow oil.

$^1$H-NMR (400 MHz, CDCl$_3$) δ 7.16 (s, 1H), 2.73 (t, 2H), 1.78 (m, 2H), 0.99 (t, 3H)

<Step 2> 2-[1-(2-chloro-6-propylpyrimidin-4-yl)piperidin-2-yl]ethanol 2,4-Dichloro-6-propylpyrimidine (3 g, 15.7 mmol) prepared in Step 1 was dissolved in chloroform (20 ml), and then 2-piperidineethanol (5.07 g, 39.3 mmol) was added thereto at 0° C. The reaction mixture was stirred at 60° C. overnight and then cooled to room temperature. The reaction mixture was concentrated under reduced pressure. The resulting residue was purified with silica gel column chromatography (n-hexane/ethyl acetate=1/1) to give 2.3 g of the titled compound as a pale yellow oil.

$^1$H-NMR (400 MHz, CDCl$_3$) δ 6.27 (s, 1H), 4.92 (br, 1H), 3.83 (br, 1H), 3.65 (m, 1H), 3.35 (m, 1H), 3.02 (m, 1H), 2.52 (m, 2H), 2.05 (m, 1H), 1.79-1.62 (m, 6+2H), 1.53 (m, 1H), 0.96 (t, 3H)

Preparation 4. 3-(4-chloro-6-propylpyrimidin-2-ylamino)benzonitrile

<Step 1> 3-(6-oxo-4-propyl-1,6-dihydropyrimidin-2-ylamino)benzonitrile

A mixture of 2-(methylthio)-6-propylpyrimidin-4(3H)-one (6.4 g, 34.7 mmol) prepared in Step 1 of Preparation 1 and 3-aminobenzonitrile (12.3 g, 104.1 mmol) was stirred at 160° C. overnight. The reaction mixture was cooled to room temperature and then ethanol (50 ml) was added thereto. The reaction mixture was stirred for 1 hour and then filtered to give 3.5 g of the titled compound as a pale brown solid.

$^1$H-NMR (400 MHz, CD$_3$OD) δ 8.22 (s, 1H), 7.90-7.80 (m, 1H), 7.55-7.45 (m, 1H), 7.45-7.35 (m, 1H), 5.84 (s, 1H), 2.49 (t, 2H), 1.80-1.65 (m, 2H), 1.00 (t, 3H)

<Step 2> 3-(4-chloro-6-propylpyrimidin-2-ylamino)benzonitrile 3-(6-oxo-4-propyl-1,6-dihydropyrimidin-2-ylamino)benzonitrile (3.3 g, 13.0 mmol) prepared in Step 1 was added to phosphorus oxychloride (10 ml). The reaction mixture was stirred at 110° C. for 2 hours and then cooled to room temperature. The reaction mixture was added to an ice water and then basified to pH 9 with sodium hydroxide. The aqueous layer was extracted with ethyl acetate. The resulting organic layer was dried on anhydrous sodium sulfate and then concentrated under reduced pressure. The resulting residue was purified with silica gel column chromatography (n-hexane/ethyl acetate=10/1) to give 3.2 g of the titled compound as a yellow solid.

$^1$H-NMR (400 MHz, CDCl$_3$) δ 8.18 (s, 1H), 7.75-7.65 (m, 1H), 7.50-7.20 (m, 3H), 6.72 (s, 1H), 2.65 (t, 2H), 1.78 (q, 2H), 1.01 (t, 3H)

Preparation 5. 2-chloro-4-(piperidin-1-yl)-6-propylpyrimidine 2,4-dichloro-6-propylpyrimidine (2 g, 10.5 mmol) prepared in Step 1 of Preparation 3 was dissolved in tetrahydrofuran (20 ml), and then piperidine (1 g, 11.7 mmol) was added thereto at room temperature. The reaction mixture was stirred under heating at 60° C. overnight and then cooled to room temperature. The reaction mixture was concentrated under reduced pressure. The resulting residue was purified with silica gel column chromatography (n-hexane/ethyl acetate=2/1) to give 2 g of the titled compound as a pale yellow oil. The product was used in the subsequent reaction without further purification.

Preparation 6. N-(4-chloro-6-propylpyrimidin-2-yl)-1H-indol-6-amine

<Step 1> 2-(1H-indol-6-ylamino)-6-propylpyrimidin-4(3H)-one

A mixture of 2-(methylthio)-6-propylpyrimidin-4(3H)-one (1 g, 5.43 mmol) prepared in Step 1 of Preparation 1 and 6-aminoindole (789 mg, 5.97 mmol) was stirred at 150° C. overnight and then cooled to room temperature. The resulting residue was purified with silica gel column chromatography (dichloromethane/methanol=40/1) to give 1.4 g of the titled compound as a pale brown solid.

$^1$H-NMR (400 MHz, CD$_3$OD) δ 7.81 (s, 1H), 7.51 (d, 1H), 7.21 (d, 1H), 6.95 (dd, 1H), 6.42 (d, 1H), 5.70 (s, 1H), 2.44 (dd, 1H), 1.75-1.70 (m, 2H), 0.99 (t, 3H).

<Step 2> N-(4-chloro-6-propylpyrimidin-2-yl)-1H-indol-6-amine

A solution of 2-(1H-indol-6-ylamino)-6-propylpyrimidin-4(3H)-one (1.2 g, 4.47 mmol) prepared in Step 1, phosphorus oxychloride (822 mg, 5.37 mmol), and diisopropylethylamine (1.9 ml, 10.7 mmol) in 1,4-dioxane (45 ml) was refluxed under stirring for 30 minutes. The reaction mixture was cooled to room temperature and then concentrated under reduced pressure. The resulting residue was purified with silica gel column chromatography (n-hexane/ethyl acetate=4/1) to give 1.1 g of the titled compound as a white solid.

¹H-NMR (400 MHz, CDCl₃) δ 8.17 (brs, 1H), 8.05 (s, 1H), 7.53 (d, 1H), 7.25 (d, 1H), 7.11 (dd, 1H), 6.98 (dd, 1H), 6.58 (s, 1H), 6.48 (s, 1H), 2.59 (dd, 2H), 1.81-1.71 (m, 2H), 0.99 (t, 3H).

Preparation 7. 5-(4-chloro-6-propylpyrimidin-2-ylamino)-2-methylbenzonitrile

<Step 1> 2-methyl-5-(6-oxo-4-propyl-1,6-dihydro-pyrimidin-2-ylamino)benzonitrile A mixture of 2-(methylthio)-6-propylpyrimidin-4(3H)-one (5 g, 27.1 mmol) prepared in Step 1 of Preparation 1 and 5-amino-2-methylbenzonitrile (7 g, 53 mmol) was stirred at 160° C. overnight. The reaction mixture was cooled to room temperature and then ethanol (30 ml) was added thereto. The reaction mixture was stirred for 1 hour and then filtered to give 6.3 g of the titled compound as a pale yellow solid.

¹H-NMR (400 MHz, CD₃OD) δ 8.12 (d, 1H), 7.70-7.60 (m, 1H), 7.35 (d, 1H), 5.80 (s, 1H), 2.50-2.40 (m, 5H), 1.73 (q, 2H), 0.99 (t, 3H)

<Step 2> 5-(4-chloro-6-propylpyrimidin-2-ylamino)-2-methylbenzonitrile

2-Methyl-5-(6-oxo-4-propyl-1,6-dihydropyrimidin-2-ylamino)benzonitrile (6.3 g, 23.5 mmol) prepared in Step 1 was added to phosphorus oxychloride (10 ml). The reaction mixture was stirred at 110° C. for 2 hours and then cooled to room temperature. The reaction mixture was added to an ice water and then basified to pH 9 with sodium hydroxide. The aqueous layer was extracted with ethyl acetate. The resulting organic layer was dried on anhydrous sodium sulfate and then concentrated under reduced pressure to give 6 g of the titled compound as a yellow solid. The product was used in the subsequent reaction without further purification.

Preparation 8. 5-(4-chloro-6-propylpyrimidin-2-ylamino)-2-fluorobenzonitrile

<Step 1> 2-fluoro-5-(6-oxo-4-propyl-1,6-dihydropyrimidin-2-ylamino)benzonitrile

A mixture of 2-(methylthio)-6-propylpyrimidin-4(3H)-one (8.8 g, 47.8 mmol) prepared in Step 1 of Preparation 1 and 5-amino-2-fluorobenzonitrile (7.9 g, 57.2 mmol) was stirred at 160° C. overnight. The reaction mixture was cooled to 70° C. and then ethanol (50 ml) was added thereto. The reaction mixture was stirred for 1 hour and then filtered to give 10 g of the titled compound as a pale brown solid. The product was used in the subsequent reaction without further purification <Step 2> 5-(4-chloro-6-propylpyrimidin-2-ylamino)-2-fluorobenzonitrile The titled compound (10.8 g) as a pale brown solid was prepared in accordance with the same procedures as in Step 2 of Preparation 4, using 2-fluoro-5-(6-oxo-4-propyl-1,6-dihydropyrimidin-2-ylamino)benzonitrile (10 g, 36.7 mmol) prepared in Step 1.

¹H-NMR (400 MHz, CDCl₃) δ 8.20-8.10 (m, 1H), 7.75-7.65 (m, 1H), 7.30-7.10 (m, 2H), 6.72 (s, 1H), 2.64 (t, 2H), 1.77 (q, 2H), 1.00 (t, 3H)

Preparation 9. 4-chloro-6-ethyl-N-(4-fluorophenyl)pyrimidin-2-amine

<Step 1> 6-ethyl-2-(4-fluorophenylamino)pyrimidin-4-ol

A mixture of ethylpropionyl acetate (1.03 ml, 7.18 mmol), N-(4-fluorophenyl)guanidine (1 g, 6.53 mmol), sodium methoxide (0.39 g, 7.18 mmol), and ethanol (30 ml) was refluxed under stirring overnight. The reaction mixture was cooled to room temperature and then concentrated under reduced pressure. The resulting residue was dissolved in water, acidified to pH 4 with a 1N hydrochloric acid solution, and then filtered. The resulting white solid (0.82 g) was dried in vacuo and then used in the subsequent reaction without further purification.

<Step 2> 4-chloro-6-ethyl-N-(4-fluorophenyl)pyrimidin-2-amine

6-Ethyl-2-(4-fluorophenylamino)-pyrimidin-4-ol (0.82 g, 3.52 mmol) prepared in Step 1 was added to phosphorus oxychloride (1.5 ml, 16.2 mmol), which was then stirred at 110° C. for 1 hour. After cooling the reaction mixture to room temperature, the reaction mixture was added to an ice water and then basified to pH 9 with potassium hydroxide. The aqueous layer was extracted with dichloromethane. The resulting organic layer was dried on anhydrous sodium sulfate and then concentrated under reduced pressure. The resulting residue was purified with silica gel column chromatography (ethyl acetate/n-hexane=2/1) to give 432.2 mg of the titled compound as a white solid.

¹H-NMR (400 MHz, CDCl₃) δ 7.18 (m, 2H), 7.08 (m, 2H), 6.63 (s, 1H), 2.61 (m, 2H), 1.23 (t, 3H)

Preparation 10. 4-chloro-N-(4-fluorophenyl)-6-methylpyrimidin-2-amine

<Step 1> 2-(4-fluorophenylamino)-6-methylpyrimidin-4-ol

The titled compound (8.2 g) was prepared in accordance with the same procedures as in Step 1 of Preparation 9, using ethyl acetoacetate (10 g, 76.8 mmol), N-(4-fluorophenyl)guanidine (10.7 g, 69.8 mmol) and sodium methoxide (4.2 g, 7.18 mmol). The product was used in the subsequent step without further purification.

<Step 2> 4-chloro-N-(4-fluorophenyl)-6-methylpyrimidin-2-amine

The titled compound (4.5 g) in the form of white solid was prepared in accordance with the same procedures as in Step 2 of Preparation 9, using 2-(4-fluorophenylamino)-6-methylpyrimidin-4-ol (8.2 g, 37.4 mmol) prepared in Step 1 and phosphorus oxychloride (15.9 ml, 172.0 mmol).

¹H-NMR (400 MHz, CDCl₃) δ 7.57-7.54 (m, 2H), 7.21 (brs, 1H), 7.05-7.01 (m, 2H), 6.64 (s, 1H), 2.39 (s, 3H)

Preparation 11. 4-(2-chloro-6-propylpyrimidin-4-yl)morpholine 2,4-dichloro-6-propylpyrimidine (1 g, 5.23 mmol) prepared in Step 1 of Preparation 3 and morpholine (683 mg, 7.85 mmol) were dissolved in ethanol (30 ml). The reaction mixture was stirred at room temperature for 4 hours and then concentrated under reduced pressure. The resulting residue was purified with silica gel column chromatography (n-hexane/ethyl acetate=2/1) to give 550 mg of the titled compound.

$^1$H-NMR (400 MHz, CD$_3$OD) δ 6.22 (s, 1H), 3.75 (d, 4H), 3.55 (d, 4H), 2.54 (dd, 1H), 1.76-1.66 (m, 2H), 0.99 (t, 3H)

Preparation 12. 3-(4-butyl-6-chloropyrimidin-2-ylamino)benzonitrile

<Step 1>
6-butyl-2-(methylthio)pyrimidin-4(3H)-one

A solution of ethyl 3-oxoheptanoate (10 g, 58.1 mmol), 2-methyl-2-thiopseudourea sulfate (11.7 g, 63.9 mmol), and sodium carbonate (9.8 g, 92.9 mmol) in water (116 ml) was stirred at room temperature for 2 days and then filtered. The resulting white solid was washed with water, and then dried in vacuo to give the titled compound (11 g). The product was used in the subsequent step without further purification.

<Step 2> 3-(4-butyl-6-oxo-1,6-dihydropyrimidin-2-ylamino)benzonitrile

A solution of 6-butyl-2-(methylthio)pyrimidin-4(3H)-one (500 mg, 2.52 mmol) prepared in Step 1 and 3-aminobenzonitrile (298 mg, 2.52 mmol) in n-butanol (3 ml) was stirred at 170° C. overnight. The reaction mixture was cooled to room temperature and then purified with silica gel column chromatography (dichloromethane/methanol=50/1) to give 310 mg of the titled compound as a brown solid.

$^1$H-NMR (400 MHz, CDCl$_3$) δ 9.47 (brs 1H), 8.27 (s, 1H), 7.80 (d, 1H), 7.37 (d, 1H), 5.88 (s, 1H), 2.58 (dd, 2H), 1.74-1.70 (m, 2H), 1.46-1.40 (m, 2H), 0.98 (t, 3H)

<Step 3> 3-(4-butyl-6-chloropyrimidin-2-ylamino)benzonitrile

The titled compound in the form of pale yellow solid was prepared in accordance with the same procedures as in Step 2 of Preparation 9, using 3-(4-butyl-6-oxo-1,6-dihydropyrimidin-2-ylamino)benzonitrile prepared in Step 2 and phosphorus oxychloride.

$^1$H-NMR (400 MHz, CDCl$_3$) δ 8.19 (s, 1H), 7.69 (d, 1H), 7.42 (t, 1H), 7.33 (d, 1H), 7.26 (brs, 1H), 6.72 (s, 1H), 2.67 (t, 2H), 1.80-1.65 (m, 2H), 1.50-1.30 (m, 2H), 0.97 (t, 3H); (Yield: 80%)

Preparation 13. 5-(4-butyl-6-chloropyrimidin-2-ylamino)-2-methylbenzonitrile

<Step 1> 5-(4-butyl-6-oxo-1,6-dihydropyrimidin-2-ylamino)-2-methylbenzonitrile

A mixture of 6-butyl-2-(methylthio)pyrimidin-4(3H)-one (800 mg, 4.03 mmol) prepared in Step 1 of Preparation 12 and 5-amino-2-methylbenzonitrile (586 mg, 4.44 mmol) was stirred at 170° C. for 6 hours. The reaction mixture was cooled to room temperature and then purified with silica gel column chromatography (dichloromethane/methanol=100/1) to give 650 mg of the titled compound as a brown solid.

$^1$H-NMR (400 MHz, CDCl$_3$) δ 9.45 (brs 1H), 8.10 (s, 1H), 7.63 (d, 1H), 7.25 (d, 1H), 5.78 (s, 1H), 2.55-2.48 (m, 5H), 1.70-1.65 (m, 2H), 1.44-1.37 (m, 2H), 0.98 (t, 3H)

<Step 2> 5-(4-butyl-6-chloropyrimidin-2-ylamino)-2-methylbenzonitrile

The titled compound in the form of white solid was prepared in accordance with the same procedures as in Step 2 of Preparation 9, using 5-(4-butyl-6-oxo-1,6-dihydropyrimidin-2-ylamino)-2-methylbenzonitrile prepared in Step 1 and phosphorus oxychloride.

$^1$H-NMR (400 MHz, CDCl$_3$) δ 8.08 (d, 1H), 7.57 (dd, 1H), 7.25 (m, 2H), 6.69 (s, 1H), 2.65 (dd, 2H), 2.51 (s, 3H), 1.75-1.68 (m, 2H), 1.45-1.36 (m, 2H), 0.96 (t, 3H); (Yield: 85%)

Preparation 14. 2-chloro-4-(2-ethylpiperidin-1-yl)-6-propylpyrimidine

A solution of 2,4-dichloro-6-propylpyrimidine (1 g, 5.23 mmol) prepared in Step 1 of Preparation 3, 2-ethylpiperidine (888 mg, 7.85 mmol), diisopropylethylamine (1.8 ml, 10.46 mmol) in chloroform (52 ml) was stirred at 60° C. overnight. The reaction mixture was cooled to room temperature and then extracted with dichloromethane. The organic layer was dried on anhydrous sodium sulfate and then filtered. The filtrate was concentrated under reduced pressure. The resulting residue was purified with silica gel column chromatography (n-hexane/ethyl acetate=10/1) to give 700 mg of the titled compound as a white solid.

Preparation 15. (R)-tert-butyl 4-(2-chloro-6-propylpyrimidin-4-yl)-3-methylpiperazin-1-carboxylate A solution of 2,4-dichloro-6-propylpyrimidine (0.8 g, 4.19 mmol) prepared in Step 1 of Preparation 3, (R)-tert-butyl 3-methylpiperazine-1-carboxylate (0.92 g, 4.61 mmol), and diisopropylethylamine (1.5 ml, 8.38 mmol) in chloroform (52 ml) was stirred at 60° C. overnight. The reaction mixture was concentrated under reduced pressure. The resulting residue was purified with silica gel column chromatography (n-hexane/ethyl acetate=4/1) to give 1.3 g of the titled compound as a colorless liquid.

$^1$H-NMR (400 MHz, CD$_3$OD) δ 6.21 (s, 1H), 4.47-3.90 (m, 4H), 3.25-2.96 (m, 3H), 2.54 (dd, 1H), 1.75-1.66 (m, 2H), 1.49 (s, 9H), 1.21 (d, 3H), 0.96 (t, 3H)

Preparation 16. 2,5-diaminobenzonitrile

A mixture of 5-nitroanthranilonitrile (200 mg, 1.23 mmol) and palladium/charcoal (10 mg, 10 wt %) in methanol (3 ml) was stirred at room temperature under hydrogen atmosphere overnight and then filtered through a celite pad. The resulting filtrate was concentrated under reduced pressure. The resulting residue was purified with silica gel column chromatography (n-hexane/ethyl acetate=1/2) to give 160.3 mg of the titled compound as a pale yellow solid.

$^1$H-NMR (400 MHz, CDCl$_3$) δ 6.79 (d, 1H), 6.72 (s, 1H), 6.61 (d, 1H), 4.01 (brs, NH), 3.45 (brs, NH)

Preparation 17. (S)-2-[1-(2-chloro-6-propylpyrimidin-4-yl)piperidin-2-yl]ethanol A solution of 2,4-dichloro-6-propylpyrimidine (300 mg, 1.57 mmol) prepared in Step 1 of Preparation 3, (S)-2-piperidineethanol hydrochloride (286 mg, 1.73 mmol) and triethylamine (460 μl, 3.30 mmol) in N,N-dimethylformamide (7 ml) was stirred at 80° C. overnight. The reaction mixture was cooled to room temperature and then concentrated under reduced pressure. The resulting residue was dissolved in ethyl acetate. The solution was washed with water, dried on anhydrous sodium sulfate, and then concentrated under reduced pressure. The resulting residue was purified with silica gel column chromatography (n-hexane/ethyl acetate=2/5) to give 251.7 mg of the titled compound as a colorless oil.

$^1$H-NMR (400 MHz, CDCl$_3$) δ 6.29 (s, 1H), 4.91 (brs, 1H), 3.87 (brs, 1H), 3.62 (m, 1H), 3.36 (m, 1H), 3.01 (m, 1H), 2.52 (t, 2H), 2.07 (m, 1H), 1.69 (m, 6H), 1.51 (m, 1H), 0.96 (t, 3H)

Preparation 18. (R)-2-[1-(2-chloro-6-propylpyrimidin-4-yl)-piperidin-2-yl]ethanol The titled compound in the form of pale yellow oil was prepared in accordance with the same procedures as Preparation 17, using 2,4-dichloro-6-propylpyrimidine prepared in Step 1 of Preparation 3 and (R)-2-piperidineethanol hydrochloride.

$^1$H-NMR (400 MHz, CDCl$_3$) δ 6.28 (s, 1H), 4.92 (brs, 1H), 3.86 (brs, 1H), 3.62 (m, 1H), 3.35 (m, 1H), 3.01 (m, 1H), 2.52 (t, 2H), 2.07 (m, 1H), 1.69 (m, 6H), 1.51 (m, 1H), 0.96 (t, 3H); (Yield: 32%)

Preparation 19. 1-(2-chloro-6-propylpyrimidin-4-yl)decahydroquinoline

The titled compound in the form of pale yellow oil was prepared in accordance with the same procedures as Preparation 17, using 2,4-dichloro-6-propylpyrimidine prepared in Step 1 of Preparation 3 and decahydroquinoline.

$^1$H-NMR (400 MHz, CDCl$_3$) δ 6.03 (s, 1H), 4.46 (m, 1H), 3.09 (m, 2H), 2.53 (t, 2H), 2.07 (d, 1H), 1.86-1.65 (m, 9H), 1.45-1.13 (m, 5H), 0.97 (t, 3H); (Yield: 34%)

Preparation 20. (S)-tert-butyl 1-(2-chloro-6-propylpyrimidin-4-yl)piperidin-3-ylcarbamate 2,4-Dichloro-6-propylpyrimidine (1.5 g, 7.85 mmol) prepared in Step 1 of Preparation 3 was dissolved in ethanol (10 ml) and then (3S)-(−)-3-(tert-butoxycarbonylamino)piperidine (3 g, 15.7 mmol) was added thereto at 0° C. The reaction mixture was stirred at room temperature overnight and then concentrated under reduced pressure. The resulting residue was purified with silica gel column chromatography (n-hexane/ethyl acetate=1/1) to give 1.1 g of the titled compound as a white solid.

$^1$H-NMR (400 MHz, CDCl$_3$) δ 6.29 (s, 1H), 4.58 (br, 1H), 3.78-3.41 (m, 6H), 2.52 (t, 2H), 1.98 (m, 1H), 1.75 (br, 1H), 1.71 (m, 2H), 1.60 (s, 9H), 0.95 (t, 3H); (Yield: 75%)

Preparation 21. 1-ethyl-1H-indol-6-amine

<Step 1> 1-ethyl-6-nitro-1H-indole

6-Nitroindole (200 mg, 1.23 mmol) was dissolved in anhydrous N,N-dimethylformamide (2 ml) and then 60 wt % sodium hydride (71 mg, 1.85 mmol) and iodoethane (120 µl, 1.48 mmol) was added thereto at 0° C. The reaction mixture was stirred at room temperature overnight. Water was added to the reaction mixture, which was then extracted with ethyl acetate. The organic layer was washed with brine, dried on anhydrous magnesium sulfate, filtered, and then concentrated under reduced pressure to give 210 mg of the titled compound as a pale yellow solid. The product was used in the subsequent reaction without further purification.

<Step 2> 1-ethyl-1H-indol-6-amine

To 1-ethyl-6-nitro-1H-indole (210 mg, 1.1 mmol) prepared in Step 1, was added a methanol/water solution (1:1; 5 ml). Iron (25 mg) and ammonium chloride (127 mg, 2.38 mmol) were added to the resulting suspension, which was then refluxed under stirring for 4 hours. After cooling the reaction mixture to room temperature, an aqueous solution of sodium carbonate was added to the reaction mixture, which was then stirred for 30 minutes. The reaction mixture was filtered through a celite pad. The resulting filtrate was concentrated under reduced pressure to give 100 mg of the titled compound as a pale yellow oil. The product was used in the subsequent reaction without further purification.

Preparation 22. 2,3-dimethylbenzofuran-5-amine

<Step 1> 3-(4-nitrophenoxy)-butan-2-one

Acetone (16 ml) and 3-chloro-2-butanone (1.75 ml, 17.3 mmol) were added to a mixture of 4-nitrophenol (2 g, 14.4 mmol), potassium carbonate (6 g, 43.2 mmol), and potassium iodide (40 mg), which was then refluxed under stirring for 10 hours. The reaction mixture was cooled to room temperature and then filtered through a celite pad. The resulting filtrate was concentrated under reduced pressure. The resulting residue was purified with silica gel column chromatography (n-hexane/ethyl acetate=10/1) to give 2.1 g of the titled compound as a pale yellow oil.

<Step 2> 2,3-dimethyl-5-nitrobenzofuran 3-(4-Nitrophenoxy)-butan-2-one (2.1 g, 0.01 mol) prepared in Step 1 was dissolved in toluene (20 ml) and then polyphosphoric acid (50 g) was added thereto. The reaction mixture was stirred at 100° C. for 5 hours and then cooled to room temperature. Water was added to the reaction mixture, which was then extracted with diethyl ether. The organic layer was dried on anhydrous sodium sulfate, filtered, and then concentrated under reduced pressure. The resulting residue was purified with silica gel column chromatography (n-hexane/ethyl acetate=5/1) to give 1.8 g of the titled compound as a pale yellow oil.

<Step 3> 2,3-dimethylbenzofuran-5-amine 2,3-Dimethyl-5-nitrobenzofuran (1.8 g, 9.3 mmol) prepared in Step 2 was dissolved in a mixed solvent of methanol and tetrahydrofuran (1:1, 50 ml) and then palladium/charcoal (1.5 g) was added thereto. The reaction mixture was stirred at room temperature under hydrogen atmosphere (30 bar) for 3 hours and then filtered through a celite pad. The resulting filtrate was concentrated under reduced pressure to give 1.5 g of the titled compound as a pale yellow solid. The product was used in the subsequent reaction without further purification.

Preparation 23. (R)-tert-butyl 1-(2-chloro-6-propylpyrimidin-4-yl)piperidin-3-yl(cyclopropylmethyl)carbamate <Step 1> (R)-1-(2-chloro-6-propylpyrimidin-4-yl)piperidin-3-amine Diisopropylethylamine (9.1 ml, 52.2 mmol) was added to a solution of 2,4-dichloro-6-propylpyrimidine (3.31 g, 17.3 mmol) prepared in Step 1 of Preparation 3 and (R)-(−)-3-aminopiperidine dihydrochloride (3 g, 17.3 mmol) in ethanol (90 ml), which was then stirred at 50° C. overnight. The reaction mixture was cooled to room temperature and then concentrated under reduced pressure. The product was used in the subsequent reaction without further purification.

<Step 2> (R)-1-(2-chloro-6-propylpyrimidin-4-yl)-N-(cyclopropylmethyl)piperidin-3-amine A solution of (R)-1-(2-chloro-6-propylpyrimidin-4-yl)piperidin-3-amine (510 mg, 2.01 mmol) prepared in Step 1 and cyclopropane carboxaldehyde (0.15 ml, 2.01 mmol) in methanol (10 ml) was stirred at room temperature for 1 hour and then sodium triacetoxyborohydride (850 mg, 4.02 mmol) was added thereto. The reaction mixture was stirred at room temperature overnight and then an aqueous saturated solution of sodium bicarbonate was added thereto so as to terminate the reaction. The reaction mixture was extracted with dichloromethane. The organic layer was washed with an aqueous saturated solution of sodium bicarbonate, dried on anhydrous sodium sulfate, filtered, and then concentrated. The resulting residue was purified with silica gel column chromatography (ethyl acetate/methanol=50/1) to give 360 mg of the titled compound as a yellow oil.
$^1$H-NMR (400 MHz, CDCl$_3$) δ 6.10 (s, 1H), 4.24-3.92 (m, 2H), 2.97 (t, 1H), 2.79 (t, 1H), 2.53 (m, 1H), 2.41 (m, 4H), 1.91 (m, 1H), 1.65 (m, 1H), 1.57 (m, 2H), 1.41-1.21 (m, 3H), 0.83 (m, 4H), 0.37 (d, 2H), 0.00 (d, 2H)

<Step 3> (R)-tert-butyl 1-(2-chloro-6-propylpyrimidin-4-yl)piperidin-3-yl(cyclopropylmethyl)carbamate Di-tert-butyldicarbonate (307 mg, 1.41 mmol) was added at 0° C. to a solution of (R)-1-(2-chloro-6-propylpyrimidin-4-yl)-N-(cyclopropylmethyl)piperidin-3-amine (360 mg, 1.17 mmol) prepared in Step 2 and 4-dimethylaminopyridine (29 mg, 0.24 mmol) in dichloromethane (6 ml). The reaction mixture was stirred at room temperature overnight and then dichloromethane was added thereto. The reaction mixture was washed with a 1N hydrochloric acid solution, dried on anhydrous magnesium sulfate, and then concentrated under reduced pressure. The resulting residue was purified with silica gel column chromatography (ethyl acetate/n-hexane=1/3) to give 218 mg of the titled compound as a yellow oil.
$^1$H-NMR (400 MHz, CD$_3$OD) δ 6.27 (s, 1H), 4.45-4.32 (brs, 2H), 3.42 (m, 2H), 3.24-3.04 (m, 2H), 2.81 (m, 1H), 2.53 (m, 2H), 2.26 (m, 1H), 2.01 (m, 1H), 1.69 (m, 2H), 1.55 (s, 9H), 1.26 (m, 2H), 1.07 (m, 1H), 0.96 (t, 3H), 0.61 (m, 2H), 0.29 (m, 2H)

Preparation 24. (R)—N-[1-(6-butyl-2-chloropyrimidin-4-yl)piperidin-3-yl]acetamide <Step 1> 6-butylpyrimidin-2,4-diol A mixture of 6-butyl-2-(methylthio)pyrimidin-4(3H)-one (2.1 g, 10.6 mmol) prepared in Step 1 of Preparation 12, acetic acid (15 ml) and water (7 ml) was refluxed under stirring for 2 days. The reaction mixture was cooled to room temperature and then concentrated under reduced pressure. The resulting residue was dried in vacuo to give 1.7 g of the titled compound as a pale yellow solid.
$^1$H-NMR (400 MHz, DMSO-d$_6$) δ 10.87 (brs, OH), 10.78 (brs, OH), 5.31 (s, 1H), 2.27 (m, 2H), 1.50 (m, 2H), 1.27 (m, 2H), 0.88 (t, 3H)

<Step 2> 4-butyl-2,6-dichloropyrimidine

A mixture of 6-butylpyrimidin-2,4-diol (1.7 g, 10.2 mmol) prepared in Step 1 and phosphorus oxychloride (5 ml) was refluxed under stirring for 1 hour. The reaction mixture was cooled to room temperature, added to an ice water, and then basified to pH 8 with sodium bicarbonate. The aqueous layer was extracted with ethyl acetate. The resulting organic layer was dried on anhydrous magnesium sulfate and then concentrated under reduced pressure. The resulting residue was purified with silica gel column chromatography (ethyl acetate/n-hexane=1/50) to give 1.4 g of the titled compound as a brown oil.
$^1$H-NMR (400 MHz, CDCl$_3$) δ 7.16 (s, 1H), 2.75 (t, 2H), 1.71 (m, 2H), 1.40 (m, 2H), 0.95 (t, 3H)

<Step 3> (R)-1-(6-butyl-2-chloropyrimidin-4-yl)piperidin-3-amine

The titled compound in the form of pale yellow oil was prepared in accordance with the same procedures as in Step 1 of Preparation 23, using 4-butyl-2,6-dichloropyrimidine prepared in Step 2 and (R)-(−)-3-aminopiperidine dihydrochloride. The product was used in the subsequent reaction without further purification.

<Step 4> (R)—N-[1-(6-butyl-2-chloropyrimidin-4-yl)piperidin-3-yl]acetamide

Acetyl chloride (0.36 ml, 5.1 mmol) was added at 0° C. to a solution of (R)-1-(6-butyl-2-chloropyrimidin-4-yl)piperidin-3-amine (1.2 g, 4.6 mmol) prepared in Step 3 and triethylamine (0.96 ml, 6.9 mmol) in dichloromethane (30 ml). The reaction mixture was stirred at room temperature for 3 hours and then dichloromethane was added thereto. The reaction mixture was washed with water, dried on anhydrous magnesium sulfate, and then concentrated under reduced pressure. The resulting residue was purified with silica gel column chromatography (ethyl acetate/n-hexane=5/1) to give 0.8 g of the titled compound as a white solid.
$^1$H-NMR (400 MHz, CDCl$_3$) δ 6.31 (s, 1H), 5.60 (brs, NH), 3.98 (m, 1H), 3.85-3.82 (m, 2H), 3.54-3.42 (m, 2H), 2.55 (t, 2H), 1.98 (s, 3H+1H), 1.66-1.57 (m, 3H+2H), 1.36 (m, 2H), 0.93 (t, 3H)

Preparation 25. (R)—N-[1-(2-chloro-6-propylpyrimidin-4-yl)piperidin-3-yl]-2-hydroxyacetamide A mixture of (R)-1-(2-chloro-6-propylpyrimidin-4-yl)piperidin-3-amine (1.33 g, 5.23 mmol) prepared in Step 1 of Preparation 23, glycolic acid (0.44 g, 5.79 mmol), N-(3-dimethylaminopropyl)-N'-ethylcarbodiimide hydrochloride (1.1 g, 5.79 mmol), 1-hydroxybenzotriazole hydrate (0.78 g, 5.79 mmol), diisopropylethylamine (1.8 ml, 10.3 mmol), and dichloromethane (30 ml) was stirred at room temperature for 3 days. The reaction mixture was diluted with dichloromethane, washed with water and an aqueous saturated solution of sodium bicarbonate, dried on anhydrous sodium sulfate, and then concentrated under reduced pressure. The resulting residue was purified with silica gel column chromatography (dichloromethane/methanol=20/1) to give 0.6 g of the titled compound as a white solid.
$^1$H-NMR (400 MHz, CDCl$_3$) δ 6.57 (s, NH), 6.31 (s, 1H), 4.11 (s, 2H), 4.04 (m, 1H), 3.90 (m, 2H), 3.49 (m, 3H), 2.53 (m, 2H), 2.40 (m, 1H), 2.00 (m, 1H), 1.70-1.69 (m, 4H), 0.95 (m, 3H)

Preparation 26. (R)-tert-butyl [1-(2-chloro-6-propylpyrimidin-4-yl)piperidin-3-yl]carbamate Di-tert-butyldicarbonate (410 mg, 1.88 mmol) was added at 0° C. to a solution of (R)-1-(2-chloro-6-propylpyrimidin- 4-yl)piperidin-3-amine (400 mg, 1.57 mmol) prepared in Step 1 of Preparation 23 and triethylamine (2.63 ml, 1.88 mmol) in 1,4-dioxane (10 ml). The reaction mixture was stirred at room temperature overnight and then concentrated under reduced pressure. The resulting residue was purified with silica gel column chromatography (ethyl acetate/n-hexane=1/3) to give 440 mg of the titled compound as a pale yellow solid.

$^1$H-NMR (400 MHz, CD$_3$OD) δ 6.29 (s, 1H), 4.60 (brs, 1H), 3.90-3.30 (m, 4H), 2.52 (t, 2H), 2.00-1.90 (m, 1H), 1.85-1.50 (m, 5H), 1.45 (s, 9H), 0.95 (t, 3H)

Preparation 27. (R)-tert-butyl [1-(6-butyl-2-chloro-pyrimidin-4-yl)piperidin-3-yl]carbamate Di-tert-butyl dicarbonate (6.4 g, 29.3 mmol) was added at room temperature to a solution of (R)-1-(6-butyl-2-chloro-pyrimidin-4-yl)piperidin-3-amine (6.6 g, 24.4 mmol) prepared in Step 3 of Preparation 24, triethylamine (4.1 ml, 29.3 mmol) in 1,4-dioxane (100 ml). The reaction mixture was stirred overnight and then concentrated under reduced pressure. The resulting residue was purified with silica gel column chromatography (n-hexane/ethyl acetate=1/6) to give 7 g of the titled compound as a pale yellow solid.

$^1$H-NMR (400 MHz, CDCl$_3$) δ 6.29 (s, 1H), 6.59 (m, 1H), 4.12 (m, 2H), 3.79 (m, 1H), 3.68 (m, 1H), 3.56 (m, 1H), 3.40 (m, 1H), 2.54 (m, 2H), 1.98 (m, 1H), 1.74 (m, 1H), 1.63 (m, 4H), 1.45 (s, 9H), 1.32 (m, 2H), 0.93 (t, 3H)

Preparation 28. (R)-tert-butyl [1-(2-chloro-6-propylpyrimidin-4-yl)piperidin-3-yl](methyl)carbamate Sodium hydride (114 mg, 2.96 mmol, 60 wt %) was added at 0° C. to a solution of (R)-tert-butyl [1-(2-chloro-6-propylpyrimidin-4-yl)piperidin-3-yl)]carbamate (700 mg, 1.97 mmol) prepared in Preparation 26 in N,N-dimethylformamide (2 ml). The reaction mixture was stirred for 30 minutes and iodomethane (184 μl, 2.28 mmol) was added thereto. The reaction mixture was stirred at room temperature overnight and then water was added thereto. The reaction mixture was concentrated under reduced pressure. The resulting residue was dissolved in ethyl acetate. The solution was washed with water, dried on anhydrous sodium sulfate, and then concentrated under reduced pressure. The resulting residue was purified with silica gel column chromatography (n-hexane/ethyl acetate=5/1) to give 550 mg of the titled compound as a white solid.

$^1$H-NMR (400 MHz, CDCl$_3$) δ 6.25 (s, 1H), 4.31 (m, 2H), 4.11 (m, 1H), 2.90 (m, 1H), 2.83 (s, 3H), 2.74 (m, 1H), 2.53 (m, 2H), 1.94-1.89 (m, 2H), 1.76 (m, 3H), 1.48 (s, 9H), 0.96 (t, 3H)

Preparation 29. (R)-tert-butyl [1-(6-butyl-2-chloro-pyrimidin-4-yl)piperidin-3-yl](methyl)carbamate Sodium hydride (344 mg, 8.95 mmol, 60 wt %) was added at 0° C. to a solution of (R)-tert-butyl [1-(6-butyl-2-chloro-pyrimidin-4-yl)piperidin-3-yl](methyl)carbamate (2.2 g, 5.96 mmol) prepared in Preparation 27 in N,N-dimethylformamide (40 ml). The reaction mixture was stirred for 30 minutes and iodomethane (558 μl, 8.95 mmol) was added thereto. The reaction mixture was stirred at room temperature overnight and then water was added thereto. The reaction mixture was concentrated under reduced pressure. The resulting residue was dissolved in ethyl acetate. The solution was washed with water, dried on anhydrous sodium sulfate, and then concentrated under reduced pressure. The resulting residue was purified with silica gel column chromatography (n-hexane/ethyl acetate=5/1) to give 2.1 g of the titled compound as a white solid.

$^1$H-NMR (400 MHz, CDCl$_3$) δ 6.25 (s, 1H), 4.40-4.26 (m, 2H), 3.84 (br, 1H), 2.93 (m, 1H), 2.83 (s, 3H), 2.71 (m, 1H), 2.55 (m, 2H), 1.91 (m, 2H), 1.77 (m, 1H), 1.66 (m, 2H), 1.49 (s, 9H), 1.41 (m, 2H), 0.95 (t, 3H)

Preparation 30. (R)-tert-butyl [1-(2-chloro-6-propylpyrimidin-4-yl)piperidin-3-yl](ethyl)carbamate Sodium hydride (114 mg, 2.96 mmol, 60 wt %) was added at 0° C. to a solution of (R)-tert-butyl [1-(2-chloro-6-propylpyrimidin-4-yl)piperidin-3-yl)]carbamate (700 mg, 1.97 mmol) prepared in Preparation 26 in N,N-dimethylformamide (2 ml). The reaction mixture was stirred for 30 minutes and iodoethane (237 μl, 2.28 mmol) was added thereto. The reaction mixture was stirred at room temperature overnight and then water was added thereto. The reaction mixture was concentrated under reduced pressure. The resulting residue was dissolved in ethyl acetate. The solution was washed with water, dried on anhydrous sodium sulfate, and then concentrated under reduced pressure. The resulting residue was purified with silica gel column chromatography (n-hexane/ethyl acetate=5/1) to give 510 mg of the titled compound as a white solid.

$^1$H-NMR (400 MHz, CDCl$_3$) δ 6.26 (s, 1H), 4.32 (m, 2H), 3.64 (br, 1H), 3.22 (br, 2H), 3.00 (m, 1H), 2.75 (m, 1H), 2.59 (m, 2H), 2.04 (m, 2H), 1.75 (m, 2H), 1.49 (s, 9H), 1.20 (t, 3H), 0.99 (t, 3H)

Preparation 31. (R)—N-[1-(2-chloro-6-propylpyrimidin-4-yl)piperidin-3-yl]acetamide Acetyl chloride (215 μl, 3.02 mmol) and triethylamine (958 μl, 6.88 mmol) were added to a solution of (R)-1-(2-chloro-6-propylpyrimidin-4-yl)piperidin-3-amine (700 mg, 2.75 mmol) prepared in Step 1 of Preparation 23 in dichloromethane (5 ml). The reaction mixture was stirred at room temperature for 18 hours and then diluted with dichloromethane (5 ml). Water was added to the reaction mixture. The separated organic layer was dried on anhydrous magnesium sulfate, filtered, and then concentrated under reduced pressure. The resulting residue was purified with silica gel column chromatography (n-hexane/ethyl acetate=5/1) to give 550 mg of the titled compound as a white solid.

$^1$H-NMR (400 MHz, CD$_3$OD) δ 6.54 (s, 1H), 4.06 (m, 2H), 3.79 (br, 1H), 3.31 (m, 1H), 3.19 (m, 1H), 2.51 (m, 2H), 2.08 (m, 1H), 1.98 (s, 3H), 1.84 (m, 1H), 1.68 (m, 2H), 1.60 (m, 2H), 0.99 (t, 3H)

The synthetic method for the compounds (including the salt thereof) of the present invention is described in the following working examples. And also, the compounds of the following working examples and the NMR spectrum data are shown in the subsequent Tables 1-1 to 1-37.

Example 1

A solution of 4-chloro-N-(4-fluorophenyl)-6-propylpyrimidin-2-amine (20 mg, 0.08 mmol) prepared in Preparation 1 and piperidine (30 mg, 0.35 mmol) in isopropanol (0.5 ml) was stirred at 100° C. overnight. The reaction mixture was cooled to room temperature and then concentrated under reduced pressure. The resulting residue was purified with silica gel column chromatography (n-hexane/ethyl acetate=1/1) to give 11.2 mg of the product as a pale yellow solid.

Examples 2 to 6

The products of Examples 2 to 6 were prepared in accordance with the same procedures as in Example 1, using 4-chloro-N-(4-fluorophenyl)-6-propylpyrimidin-2-amine prepared in Preparation 1; and morpholine, azepane, 2-methylpiperidine, 3-methylpiperidine, or thiomorpholine.

Example 7

A solution of 4-chloro-N-(4-fluorophenyl)-6-propylpyrimidin-2-amine (20 mg, 0.08 mmol) prepared in Preparation 1 and 2,5-dimethylpiperazine (30 mg, 0.26 mmol) in isopropanol (0.5 ml) was stirred at 100° C. overnight. The reaction mixture was cooled to room temperature and then concentrated under reduced pressure. The resulting residue was purified with silica gel column chromatography (n-hexane/ethyl acetate=1/1) and then dissolved in ethyl acetate (2 ml). The resulting solution was saturated with hydrogen chloride gas and then filtered to give 5.2 mg of the product as a pale yellow solid.

Examples 8 to 12

The products of Examples 8 to 12 were prepared in accordance with the same procedures as in Example 7, using 4-chloro-N-(4-fluorophenyl)-6-propylpyrimidin-2-amine prepared in Preparation 1; and 1,2,3,6-tetrahydropyridine, decahydroquinoline, decahydroisoquinoline, 4-phenylpiperidine, or morpholine.

Examples 13 to 19

The products of Examples 13 to 19 were prepared in accordance with the same procedures as in Example 1, using 4-chloro-N-(4-fluorophenyl)-6-propylpyrimidin-2-amine prepared in Preparation 1; and piperazine, 2-ethylpiperidine, 2-piperidineethanol, ethyl piperidin-2-carboxylate, piperidin-4-carboxamide, 4-piperidinemethanol, or piperidone.

Examples 20 to 23

The products of Examples 20 to 23 were prepared in accordance with the same procedures as in Example 1, using 4-butyl-6-chloro-N-(4-fluorophenyl)pyrimidin-2-amine prepared in Preparation 2; and piperidine, 2-ethylpiperidine, 2-piperidineethanol, or morpholine.

Example 24

A solution of 2-[1-(2-chloro-6-propylpyrimidin-4-yl)-piperidin-2-yl]ethanol (20 mg, 0.07 mmol) prepared in Preparation 3 and 4-chloro-3-nitroaniline (20 mg, 0.17 mmol) in n-butanol (1 ml) was refluxed under stirring overnight. The reaction mixture was cooled to room temperature and then concentrated under reduced pressure. The resulting residue was purified with silica gel column chromatography (n-hexane/ethyl acetate=4/1) to give 6.2 mg of the product as a pale yellow solid.

Example 25

The product in the form of pale yellow solid was prepared in accordance with the same procedures as in Example 24, using 2-[1-(2-chloro-6-propylpyrimidin-4-yl)-piperidin-2-yl]ethanol prepared in Preparation 3 and 3-(methylthio)aniline.

Examples 26 to 31

The products of Examples 26 to 31 were prepared in accordance with the same procedures as in Example 1, using 4-chloro-N-(4-fluorophenyl)-6-propylpyrimidin-2-amine prepared in Preparation 1; and 2,6-dimethylmorpholine, 8-azabicyclo[3.2.1]octan-3-ol, 3-acetamidopiperidine, 1,3-di-4-piperidylpropane, 3-(benzyloxy)piperidine, or 3-oxa-8-azabicyclo[3.2.1]octane.

Example 32

A mixture of 2-chloro-4-(piperidin-1-yl)-6-propylpyrimidine (15 mg, 0.06 mmol) prepared in Preparation 5 and 5-aminoindole (20 mg, 0.15 mmol) in n-butanol (1 ml) was refluxed under stirring overnight. The reaction mixture was cooled to room temperature and then concentrated under reduced pressure. The resulting residue was purified with silica gel column chromatography (dichloromethane/methanol=50/1) to give 5.3 mg of the product as a pale yellow solid.

Examples 33 to 47

The products of Examples 33 to 47 were prepared in accordance with the same procedures as in Example 32, using 2-chloro-4-(piperidin-1-yl)-6-propylpyrimidine prepared in Preparation 5; and 3-chloro-4-methylaniline, 6-aminoquinoline, 3-(trifluoromethyl)aniline, 2-(trifluoromethyl)-1H-benzo[d]imidazol-5-amine, 3-(methylthio)aniline, 5-methoxy-2-methylaniline, 5-chloro-2-methylaniline, 4-fluoro-3-nitroaniline, 4-methoxyaniline, 3-methoxyaniline, 3-chloroaniline, 3-nitroaniline, 4-chloro-3-nitroaniline, 3-aminobenzonitrile, or 4-methyl-3-nitroaniline.

Example 48

A solution of 4-chloro-N-(4-fluorophenyl)-6-methylpyrimidin-2-amine (30 mg, 0.13 mmol) prepared in Preparation 10, 1-ethylpiperazine (28.8 mg, 0.25 mmol), and diisopropylethylamine (65.7 μl, 0.38 mmol) in tetrahydrofuran (1 ml) was stirred at 75° C. for 6 hours. The reaction mixture was cooled to room temperature and then concentrated under reduced pressure. The resulting residue was purified with silica gel column chromatography (dichloromethane/methanol=50/1) to give 50.1 mg of the product as a white solid.

Examples 49 to 60

The products of Examples 49 to 60 were prepared in accordance with the same procedures as in Example 48, using 4-chloro-N-(4-fluorophenyl)-6-methylpyrimidin-2-amine prepared in Preparation 10; and 1-(4-methoxyphenyl)piperazine, 1-(4-fluorophenyl)piperazine, morpholine, 4-piperidone hydrochloride, piperidine, azetidine hydrochloride, 3-hydroxypiperidine hydrochloride, 4-hydroxypiperidine, 2-methylpiperidine, 3-methylpiperidine, cis-3,5-dimethylpiperidine, or hexamethyleneimine.

Example 61

A mixture of 4-chloro-N-(4-fluorophenyl)-6-methylpyrimidin-2-amine (30 mg, 0.13 mmol) prepared in Preparation 10, 2-ethylpiperidine (28.5 mg, 0.25 mmol), and diisopropylethylamine (65.7 μl, 0.38 mmol) in isopropanol (1 ml) was reacted in a microwave reactor (300 W) for 2 hours. The reaction mixture was cooled to room temperature and then concentrated under reduced pressure. The resulting residue was purified with silica gel column chromatography (n-hexane/ethyl acetate=4/1) to give 30.1 mg of the product as a colorless liquid.

Examples 62 to 72

The products of Examples 62 to 72 were prepared in accordance with the same procedures as in Example 61, using 4-chloro-N-(4-fluorophenyl)-6-methylpyrimidin-2-amine prepared in Preparation 10; and cis-2,6-dimethylpiperidine, 4-phenylpiperidine, piperazine hydrate, 1-methylpiperazine, 2,5-dimethylpiperazine, 2,6-dimethylpiperazine, decahydroquinoline, decahydroisoquinoline, 1,2,3,6-tetrahydropyridine, 2-piperidineethanol, or 2-piperidinemethanol.

Examples 73 and 74

The products of Examples 73 and 74 were prepared in accordance with the same procedures as in Example 61, using N-(4-chloro-6-propylpyrimidin-2-yl)-1H-indol-6-amine prepared in Preparation 6; and decahydroquinoline or 2-piperidineethanol.

Example 75

2-{1-[2-(1H-indol-6-ylamino)-6-propylpyrimidin-4-yl]piperidin-2-yl}ethanol (20 mg, 0.05 mmol) prepared in Example 74 was dissolved in ethyl acetate (1 ml) and then hydrogen chloride gas was added thereto. The reaction mixture was stirred at room temperature for 1 hour and then filtered to give 8 mg of the product as a white solid.

Examples 76 to 78

The products of Examples 76 to 78 were prepared in accordance with the same procedures as in Example 61, using N-(4-chloro-6-propylpyrimidin-2-yl)-1H-indol-6-amine prepared in Preparation 6; and piperidine, morpholine, or 2-ethylpiperidine.

Example 79

A solution of 4-(2-chloro-6-propylpyrimidin-4-yl)morpholine (550 mg, 2.28 mmol) prepared in Preparation 11 and 6-aminoindole (300 mg, 2.28 mmol) in n-butanol (2.3 ml) was refluxed under stirring for 1 hour and then cooled to room temperature. Ethyl acetate was added to the reaction mixture. The resulting precipitate was collected by filtration and then washed with ethyl acetate to give 760 mg of the product as a white solid.

Examples 80 and 81

The products of Examples 80 and 81 were prepared in accordance with the same procedures as in Example 61, using 3-(4-chloro-6-propylpyrimidin-2-ylamino)benzonitrile prepared in Preparation 4; and (R)-3-ethylmorpholine or (R)-tert-butyl 3-methylpiperazine-1-carboxylate.

Example 82

Hydrogen chloride gas was added at 0° C. for 1 minute to a solution of (R)-tert-butyl 4-[2-(3-cyanophenylamino)-6-propylpyrimidin-4-yl]-3-methylpiperazin-1-carboxylate (20 mg, 0.05 mmol) prepared in Example 81 in ethyl acetate (3 ml). The reaction mixture was stirred at room temperature for 2 hours and then filtered to give 19.3 mg of the product as a white solid.

Example 83

A solution of 4-(2-chloro-6-propylpyrimidin-4-yl)morpholine (20 mg, 0.08 mmol) prepared in Preparation 11 and 3-nitroaniline (12.6 mg, 0.09 mmol) in n-butanol (0.5 ml) was reacted in a microwave reactor (450 W) for 40 minutes. The reaction mixture was cooled to room temperature. The resulting precipitate was collected by filtration and then washed with ethyl acetate to give 22.1 mg of the product as a yellow solid.

Examples 84 to 94

The products of Examples 84 to 94 were prepared in accordance with the same procedures as in Example 79, using 4-(2-chloro-6-propylpyrimidin-4-yl)morpholine prepared in Preparation 11; and 4-fluoro-3-nitroaniline, 4-chloro-3-nitroaniline, 3-methoxyaniline, 4-methoxyaniline, 3-(methylthio)aniline, 3-chloroaniline, 2-chloro-4-aminotoluene, 3-(trifluoromethyl)aniline, 5-aminoindole, 5-amino-2-(trifluoromethyl)benzimidazole, or 6-aminoquinoline.

Example 95

A solution of 4-(2-chloro-6-propylpyrimidin-4-yl)morpholine (20 mg, 0.08 mmol) prepared in Preparation 11 and 3-aminobenzonitrile (12.6 mg, 0.09 mmol) in n-butanol (0.5 ml) was reacted in a microwave reactor (450 W) for 40 minutes. The reaction mixture was cooled to room temperature and then concentrated under reduced pressure. The resulting residue was purified with silica gel column chromatography (dichloromethane/methanol=50/1) to give 20.1 mg of the product as a white solid.

Example 96

A mixture of 4-(2-chloro-6-propylpyrimidin-4-yl)morpholine (25 mg, 0.1 mmol) prepared in Preparation 11, 5-methoxy-2-methylaniline (14.1 mg, 0.103 mmol), palladium acetate (1.2 mg, 0.005 mmol), 4,5-bis(diphenylphosphino)-9,9-dimethylxanthene (3 mg, 0.005 mmol), cesium carbonate (67.0 mg, 0.21 mmol), and 1,4-dioxane (0.5 ml) was reacted in a microwave reactor (600 W) for 30 minutes. The reaction mixture was cooled to room temperature and then water was added thereto. The reaction mixture was extracted with dichloromethane. The resulting organic layer was dried on anhydrous sodium sulfate and then filtered. The filtrate was concentrated under reduced pressure. The resulting residue was purified with silica gel column chromatography (dichloromethane/methanol=50/1) to give 19 mg of the product as a white solid.

Examples 97 and 98

The products of Examples 97 and 98 were prepared in accordance with the same procedures as in Example 96, using 4-(2-chloro-6-propylpyrimidin-4-yl)morpholine prepared in Preparation 11; and 5-chloro-2-methylaniline or 3-aminoquinoline.

Examples 99 to 111

The products of Examples 99 to 111 were prepared in accordance with the same procedures as in Example 95, using 2-chloro-4-(2-ethylpiperidin-1-yl)-6-propylpyrimidine prepared in Preparation 14; and 3-nitroaniline, 4-fluoro-3-nitroaniline, 4-chloro-3-nitroaniline, 3-anisidine, 4-anisidine, 3-(methylthio)aniline, 3-chloroaniline, 2-chloro-4-aminotoluene, 3-(trifluoromethyl)aniline, 5-aminoindole, 5-amino-2-(trifluoromethyl)benzimidazole, 6-aminoquinoline, or 3-aminobenzonitrile.

Examples 112 to 114

The products of Examples 112 to 114 were prepared in accordance with the same procedures as in Example 96, using 2-chloro-4-(2-ethylpiperidin-1-yl)-6-propylpyrimidine prepared in Preparation 14; and 5-methoxy-2-methylaniline, 5-chloro-2-methylaniline, or 3-aminoquinoline.

Example 115

N-(4-chloro-3-nitrophenyl)-4-(2-ethylpiperidin-1-yl)-6-propylpyrimidin-2-amine (20 mg, 0.05 mmol) prepared in Example 101 was dissolved in ethyl acetate (1 ml) and hydrogen chloride gas was added thereto. The reaction mixture was stirred at room temperature for 1 hour and then filtered to give 15.5 mg of the product as a white solid.

Example 116

The product in the form of white solid was prepared in accordance with the same procedures as in Example 115, using 3-[4-(2-ethylpiperidin-1-yl)-6-propylpyrimidin-2-ylamino]benzonitrile prepared in Example 111.

Examples 117 to 130

The products of Examples 117 to 130 were prepared in accordance with the same procedures as in Example 95, using (R)-tert-butyl 4-(2-chloro-6-propylpyrimidin-4-yl)-3-methylpiperazin-1-carboxylate prepared in Preparation 15; and 4-chloro-3-nitroaniline, 6-aminoindole, 3-(trifluoromethyl)aniline, 3-nitroaniline, 4-fluoro-3-nitroaniline, 4-methyl-3-nitroaniline, 4-fluorobenzene-1,3-diamine, 2-(trifluoromethyl)benzene-1,4-diamine, 5-amino-2-fluorobenzonitrile, 5-amino-2-methylbenzonitrile, 2,5-diaminobenzonitrile, 2-nitrobenzene-1,4-diamine, 3,5-diaminobenzonitrile, or 3-aminobenzamide.

Example 131

A mixture of 2-[1-(2-chloro-6-propylpyrimidin-4-yl)piperidin-2-yl]ethanol (35 mg, 0.12 mmol) prepared in Preparation 3, 3-aminobenzonitrile (18 mg, 0.15 mmol), and n-butanol (1 ml) was refluxed under stirring overnight. The reaction mixture was cooled to room temperature and then concentrated under reduced pressure. The resulting residue was purified with silica gel column chromatography (dichloromethane/methanol=20/1) to give 43.7 mg of the product as a pale yellow solid.

Example 132

<Step 1> 2-{1-[2-(4-chloro-3-nitrophenylamino)-6-propylpyrimidin-4-yl]piperidin-2-yl}ethanol The titled compound (150 mg) in the form of white solid was prepared in accordance with the same procedures as in Example 131, using 2-[1-(2-chloro-6-propylpyrimidin-4-yl)-piperidin-2-yl]ethanol prepared in Preparation 3 and 4-chloro-3-nitroaniline.

<Step 2> 2-{1-[2-(4-chloro-3-nitrophenylamino)-6-propylpyrimidin-4-yl]piperidin-2-yl}ethanol hydrochloride The titled compound in the form of white solid was prepared in accordance with the same procedures as in Example 115, using 2-{1-[2-(4-chloro-3-nitrophenylamino)-6-propylpyrimidin-4-yl]piperidin-2-yl}ethanol prepared in Step 1.

Example 133

The product in the form of pale yellow solid was prepared in accordance with the same procedures as in Example 132, using 2-[1-(2-chloro-6-propylpyrimidin-4-yl)piperidin-2-yl]ethanol and 3-(methylthio)aniline prepared in Preparation 3.

Examples 134 to 147

The products of Examples 134 to 147 were prepared in accordance with the same procedures as in Example 131, using 2-[1-(2-chloro-6-propylpyrimidin-4-yl)piperidin-2-yl]ethanol prepared in Preparation 3; and 1-ethyl-1H-indol-6-amine prepared in Preparation 21, 5-aminoindole, 5-amino-2-(trifluoromethyl)benzimidazole, 4-methoxyaniline, 3-methoxyaniline, 5-methoxy-2-methylaniline, 4-amino-2-chlorotoluene, 3-nitroaniline, 4-fluoro-3-nitroaniline, 2,3-dimethylbenzofuran-5-amine prepared in Preparation 22, 6-aminoquinoline, 3-chloroaniline, 7-amino-4-methyl-2H-chromen-2-one, or 3-(trifluoromethyl)aniline.

Example 148

3-Aminoquinoline (22 mg, 0.15 mmol) was added to a mixture of 2-[1-(2-chloro-6-propylpyrimidin-4-yl)piperidin-2-yl]ethanol (35 mg, 0.12 mmol) prepared in Preparation 3, palladium acetate (0.5 mg, 2 mol %), 4,5-bis(diphenylphosphino)-9,9-dimethylxanthene (2.1 mg, 3 mol %), cesium carbonate (78 mg, 0.24 mmol), and anhydrous 1,4-dioxane (1 ml). The reaction mixture was stirred in a microwave reactor (600 W) for 1 hour and then cooled to room temperature. The reaction mixture was suspended in dichloromethane and then filtered through a celite pad. The resulting filtrate was concentrated under reduced pressure. The resulting residue was purified with silica gel column chromatography (dichloromethane/methanol=20/1) to give 45.5 mg of the product as a pale yellow solid.

Example 149

The product in the form of white solid was prepared in accordance with the same procedures as in Example 115, using 3-{4-[2-(2-hydroxyethyl)piperidin-1-yl]-6-propylpyrimidin-2-ylamino}benzonitrile prepared in Example 131.

Examples 150 to 152

The products of Examples 150 to 152 were prepared in accordance with the same procedures as in Example 132, using (S)-tert-butyl 1-(2-chloro-6-propylpyrimidin-4-yl)piperidin-3-ylcarbamate prepared in Preparation 20; and 5-amino-2-methylbenzonitrile, 3-nitroaniline, or 3-aminobenzonitrile.

Example 153

(R)-(−)-3-Aminopiperidine dihydrochloride (18 mg, 0.1 mmol), sodium bicarbonate (42 mg, 0.5 mmol), and molecular sieve (1 g) were added to a solution of 5-(4-chloro-6-propylpyrimidin-2-ylamino)-2-methylbenzonitrile (30 mg, 0.1 mmol) prepared in Preparation 7 in ethanol. The reaction mixture was stirred at 130° C. overnight. The reaction mixture was cooled to room temperature and then filtered to discard insoluble materials. The filtrate was concentrated under reduced pressure. The resulting residue was purified with silica gel column chromatography (methanol/dichloromethane=1/10) to give 19.2 mg of the product as a pale yellow solid.

Example 154

<Step 1> (S)-5-[4-(3-aminopiperidin-1-yl)-6-propylpyridin-2-ylamino]-2-methylbenzonitrile The titled compound in the form of white solid was prepared in accordance with the same procedures as in Example 153, using 5-(4-chloro-6-propylpyrimidin-2-ylamino)-2-methylbenzonitrile prepared in Preparation 7 and (S)-(−)-3-aminopiperidine.

<Step 2> (S)-5-{4-[3-(butylamino)piperidin-1-yl]-6-propylpyrimidin-2-ylamino}-2-methylbenzonitrile Butyraldehyde (6.5 mg, 0.09 mmol) was added to a solution of (S)-5-[4-(3-aminopiperidin-1-yl)-6-propylpyridin-2-ylamino]-2-methylbenzonitrile (24.5 mg, 0.07 mmol) prepared in Step 1 in methanol (1 ml). The reaction mixture was stirred at room temperature for 30 minutes and then sodium cyanoborohydride (6.84 mg, 0.11 mmol) was added thereto. The reaction mixture was stirred at room temperature overnight and then a 1N hydrochloric acid solution was added thereto. The reaction mixture was stirred for 30 minutes, neutralized with a 1N sodium hydroxide solution, and then extracted with ethyl acetate. The organic layer was dried on anhydrous magnesium sulfate, filtered, and then concentrated under reduced pressure. The resulting residue was purified with silica gel column chromatography (ethyl acetate/methanol=20/1) to give 10.2 mg of the product as a pale yellow solid.

Examples 155 to 164

The products of Examples 155 to 164 were prepared in accordance with the same procedures as in Step 2 of Example 154, using (S)-5-[4-(3-aminopiperidin-1-yl)-6-propylpyridin-2-ylamino]-2-methylbenzonitrile prepared in Step 1 of Example 154; and pentanal, isobutylaldehyde, 3-methylbutanal, pivaldehyde, pyrrole-2-carboxaldehyde, 2-thiophenecarboxaldehyde, 4,5-dimethyl-2-furaldehyde, 3-(methylthio)propionaldehyde, cyclopropane carboxaldehyde, or 4-hydroxybenzaldehyde.

Examples 165 and 166

The products of Examples 165 and 166 in the form of pale yellow solid were prepared in accordance with the same procedures as in Step 2 of Example 154, using (S)-5-[4-(3-aminopiperidin-1-yl)-6-propylpyridin-2-ylamino]-2-methylbenzonitrile prepared in Step 1 of Example 154; and acetaldehyde or cyclopropane carboxaldehyde.

Example 167

The product in the form of pale yellow solid was prepared in accordance with the same procedures as in Step 2 of Example 154, using (R)-5-[4-(3-aminopiperidin-1-yl)-6-propylpyridin-2-ylamino]-2-methylbenzonitrile prepared in Example 153 and cyclopropane carboxaldehyde.

Example 168

A solution of 4-chloro-6-ethyl-N-(4-fluorophenyl)pyrimidin-2-amine (20 mg, 0.08 mmol) prepared in Preparation 9 and piperidine (9.4 μl, 0.10 mmol) in isopropanol (0.5 ml) was stirred at 100° C. overnight. The reaction mixture was cooled to room temperature and then concentrated under reduced pressure. The resulting residue was purified with silica gel column chromatography (dichloromethane/methanol=40/1) to give 6.2 mg of the product as a pale yellow oil.

Examples 169 to 172

The products of Examples 169 to 172 were prepared in accordance with the same procedures as in Example 168, using 4-chloro-6-ethyl-N-(4-fluorophenyl)pyrimidin-2-amine prepared in Preparation 9; and decahydroquinoline, 2-ethylpiperidine, 2-piperidineethanol, or morpholine.

Example 173

The product was prepared in accordance with the same procedures as in Example 115, using N-[4-(piperidin-1-yl)-6-propylpyrimidin-2-yl]-1H-indol-6-amine prepared in Example 76.

Examples 174 to 179

The products of Examples 174 to 179 were prepared in accordance with the same procedures as in Example 131, using 2-[1-(2-chloro-6-propylpyrimidin-4-yl)piperidin-2-yl]ethanol prepared in Preparation 3; and 4-methyl-3-nitroaniline, 2-(trifluoromethyl)-1,4-phenylenediamine, 2-nitro-1,4-phenylenediamine, 5-amino-2-methylbenzonitrile, 5-amino-2-fluorobenzonitrile, or 2,5-diaminobenzonitrile prepared in Preparation 16.

Example 180

A mixture of 2-{1-[2-(4-methyl-3-nitrophenylamino)-6-propylpyrimidin-4-yl]piperidin-2-yl}ethanol (17 mg, 0.04 mmol) prepared in Example 174, palladium/charcoal (10 mg, 10 wt %), and methanol (2 ml) was stirred under hydrogen atmosphere at room temperature for 1 hour. The reaction mixture was filtered through celite pad. The filtrate was concentrated under reduced pressure. The resulting residue was purified with silica gel column chromatography (dichloromethane/methanol=70/1) to give 4.2 mg of the product as a pale yellow solid.

Example 181

The product in the form of pale yellow solid was prepared in accordance with the same procedures as in Example 180, using 2-{1-[2-(4-fluoro-3-nitrophenylamino)-6-propylpyrimidin-4-yl]piperidin-2-yl}ethanol prepared in Example 142.

Example 182

The product in the form of pale yellow solid was prepared in accordance with the same procedures as in Example 180, using 2-{1-[2-(4-chloro-3-nitrophenylamino)-6-propylpyrimidin-4-yl]piperidin-2-yl}ethanol prepared in Example 24.

Example 183

<Step 1> 1-(6-{4-[2-(2-hydroxyethyl)piperidin-1-yl]-6-propylpyrimidin-2-ylamino}indolin-1-yl)ethanone The titled compound in the form of pale yellow oil was prepared in accordance with the same procedures as in Example 131, using 2-[1-(2-chloro-6-propylpyrimidin-4-yl)piperidin-2-yl]ethanol prepared in Preparation 3 and 1-acetyl-6-aminoindoline. The product was used in the subsequent step without further purification. (Yield: 77%).

<Step 2> 2-{1-[2-(indolin-6-ylamino)-6-propylpyrimidin-4-yl]piperidin-2-yl}ethanol A mixture of 1-(6-{4-[2-(2-hydroxyethyl)piperidin-1-yl]-6-propylpyrimidin-2-ylamino}indolin-1-yl)ethanone (35.8 mg, 0.12 mmol) prepared in Step 1 and a 10% hydrochloric acid solution (1.5 ml) was refluxed under stirring for 2 hours. The reaction mixture was cooled to room temperature, controlled to pH 5 with a 2N sodium hydroxide solution, and then extracted with dichloromethane. The resulting organic layer was dried on anhydrous sodium sulfate and then concentrated under reduced pressure. The resulting residue was purified with silica gel column chromatography (dichloromethane/methanol=30/1) to give 11.4 mg of the titled compound as a colorless solid.

Examples 184 and 185

The products of Examples 184 and 185 were prepared in accordance with the same procedures as in Example 131, using (S)-2-[1-(2-chloro-6-propylpyrimidin-4-yl)piperidin-2-yl]ethanol prepared in Preparation 17; and 4-chloro-3-nitroaniline or 2-nitro-1,4-phenylenediamine.

Example 186

The product in the form of pale yellow solid was prepared in accordance with the same procedures as in Example 131, using (R)-2-[1-(2-chloro-6-propylpyrimidin-4-yl)piperidin-2-yl]ethanol prepared in Preparation 18 and 2-nitro-1,4-phenylenediamine.

Example 187

A solution of 1-(2-chloro-6-propylpyrimidin-4-yl)decahydroquinoline (25.6 mg, 0.09 mmol) prepared in Preparation 19 and 3-aminobenzonitrile (12.3 mg, 0.10 mmol) in n-butanol (1 ml) was stirred at 120° C. overnight. The reaction mixture was concentrated under reduced pressure. The resulting residue was purified with silica gel column chromatography (dichloromethane/methanol=70/1) to give 10.8 mg of the product as a pale yellow oil.

Examples 188 to 202

The products of Examples 188 to 202 were prepared in accordance with the same procedures as in Example 187, using 1-(2-chloro-6-propylpyrimidin-4-yl)decahydroquinoline prepared in Preparation 19; and 3-nitroaniline, 4-fluoro-3-nitroaniline, 4-chloro-3-nitroaniline, 3-methoxyaniline, 5-methoxy-2-methylaniline, 4-methoxyaniline, 3-(trifluoromethyl)aniline, 3-chloroaniline, 5-chloro-2-methylaniline, 2-chloro-4-aminotoluene, 3-(methylthio)aniline, 5-aminoindole, 5-amino-2-(trifluoromethyl)benzimidazole, 6-aminoquinoline, or 7-amino-4-methyl-2H-chromen-2-one.

Example 203

A mixture of 1-(2-chloro-6-propylpyrimidin-4-yl)decahydroquinoline (25 mg, 0.09 mmol) prepared in Preparation 19, palladium acetate (0.38 mg, 0.002 mmol), 4,5-bis(diphenylphosphino)-9.9-dimethylxanthene (1.48 mg, 0.003 mmol), cesium carbonate (55 mg, 0.17 mmol), 3-aminoquinoline (12.3 mg, 0.09 mmol), and 1,4-dioxane (0.4 ml) was stirred in a microwave reactor (600 W) for 2 hours. The reaction mixture was concentrated under reduced pressure. The resulting residue was purified with silica gel column chromatography (dichloromethane/methanol=30/1) to give 2 mg of the product as a white solid.

Example 204

The product in the form of pale red solid was prepared in accordance with the same procedures as in Example 115, using N-[4-(octahydroquinoline-1(2H)-yl)-6-propylpyrimidin-2-yl]-1H-indol-6-amine prepared in Example 73.

Examples 205 to 219

The products of Examples 205 to 219 were prepared in accordance with the same procedures as in Step 2 of Example 154, using (R)-5-[4-(3-aminopiperidin-1-yl)-6-propylpyrimidin-2-ylamino]-2-methylbenzonitrile prepared in Example 153; and acetaldehyde, propionaldehyde, butyraldehyde, valeraldehyde, isobutyraldehyde, isovaleraldehyde, pivaldehyde, acetone, pyrrole-2-carboxaldehyde, 2-thiophenecarboxaldehyde, 4,5-dimethyl-2-furaldehyde, 3-(methylthio)propionaldehyde, cyclopropane carboxaldehyde, cyclopentane carboxaldehyde, or 4-hydroxybenzaldehyde.

Example 220

Acetyl chloride (31 μl, 0.44 mmol) and triethylamine (100 μl, 0.73 mmol) were added to a solution of (R)-5-[4-(3-aminopiperidin-1-yl)-6-propylpyrimidin-2-ylamino]-2-methylbenzonitrile (100 mg, 0.29 mmol) prepared in Example 153 in dichloromethane (2 ml). The reaction mixture was stirred at room temperature for 18 hours and then diluted with dichloromethane (5 ml). Water was added to the reaction mixture. The separated organic layer was dried on anhydrous magnesium sulfate, filtered, and then concentrated under reduced pressure. The resulting residue was purified with silica gel column chromatography (n-hexane/ethyl acetate=1/1) and then dissolved in ethyl acetate (2 ml). The resulting solution was saturated with hydrogen chloride gas and then filtered to give 56 mg of the product as a white solid.

Example 221

(R)-(−)-3-aminopiperidine dihydrochloride (190 mg, 1.10 mmol), sodium bicarbonate (461.1 mg, 5.50 mmol), and molecular sieve (1 g) were added to a solution of 3-(4-chloro-6-propylpyrimidin-2-ylamino)benzonitrile (299.4 mg, 1.10 mmol) prepared in Preparation 4 in ethanol (5.5 ml). The reaction mixture was stirred at 130° C. overnight.

The reaction mixture was cooled to room temperature and then filtered to discard insoluble materials. The filtrate was concentrated under reduced pressure. The resulting residue was purified with silica gel column chromatography (methanol/dichloromethane=1/10) to give 334 mg of the product as a pale yellow oil. The product (84 mg) was dissolved in ethyl acetate (2 ml). The resulting solution was saturated with hydrogen chloride gas and then filtered to give 90.7 mg of the product as a white solid.

Example 222

The product in the form of white solid was prepared in accordance with the same procedures as in Example 221, using 5-(4-chloro-6-propylpyrimidin-2-ylamino)-2-fluorobenzonitrile prepared in Preparation 8 and (R)-(−)-3-aminopiperidine dihydrochloride.

Example 223

(R)-3-[4-(3-aminopiperidin-1-yl)-6-propylpyrimidin-2-ylamino]benzonitrile (120 mg, 0.36 mmol) [obtained by treating (R)-3-[4-(3-aminopiperidin-1-yl)-6-propylpyrimidin-2-ylamino]benzonitrile dihydrochloride prepared in Example 221 with an aqueous saturated solution of sodium bicarbonate] was dissolved in methanol (5 ml). Propionaldehyde (25.6 µl, 0.36 mmol) was added to the solution, which was then stirred at room temperature for 1 hour. Sodium cyanoborohydride (151 mg, 0.72 mmol) was added to the reaction mixture, which was then stirred at room temperature overnight. A 1N hydrochloric acid solution was added to the reaction mixture, which was then stirred at 30 minutes. The reaction mixture was neutralized with a 1N sodium hydroxide solution and then extracted with ethyl acetate. The organic layer was dried on anhydrous magnesium sulfate, filtered, and then concentrated under reduced pressure. The resulting residue was purified with silica gel column chromatography (ethyl acetate/methanol=10/1) to give 13.6 mg of the product as a colorless oil.

Example 224

The product in the form of colorless oil was prepared in accordance with the same procedures as in Example 223, using cyclopropane carboxaldehyde and (R)-3-[4-(3-aminopiperidin-1-yl)-6-propylpyrimidin-2-ylamino]benzonitrile [obtained by treating (R)-3-[4-(3-aminopiperidin-1-yl)-6-propylpyrimidin-2-ylamino]benzonitrile dihydrochloride prepared in Example 221 with an aqueous saturated solution of sodium bicarbonate]. The resulting product was dissolved in ethyl acetate (2 ml). The solution was saturated with hydrogen chloride gas and then filtered to give the product as a white solid.

Example 225

The product in the form of colorless oil was prepared in accordance with the same procedures as in Example 223, using propionaldehyde and (R)-5-[4-(3-aminopiperidin-1-yl)-6-propylpyrimidin-2-ylamino]-2-fluorobenzonitrile [obtained by treating (R)-5-[4-(3-aminopiperidin-1-yl)-6-propylpyrimidin-2-ylamino]-2-fluorobenzonitrile dihydrochloride prepared in Example 222 with an aqueous saturated solution of sodium bicarbonate].

Example 226

The product in the form of white solid was prepared in accordance with the same procedures as in Example 224, using cyclopropane carboxaldehyde and (R)-5-[4-(3-aminopiperidin-1-yl)-6-propylpyrimidin-2-ylamino]-2-fluorobenzonitrile [obtained by treating (R)-5-[4-(3-aminopiperidin-1-yl)-6-propylpyrimidin-2-ylamino]-2-fluorobenzonitrile dihydrochloride prepared in Example 222 with an aqueous saturated solution of sodium bicarbonate].

Example 227

A solution of (R)-tert-butyl 1-(2-chloro-6-propylpyrimidin-4-yl)piperidin-3-yl(cyclopropylmethyl)carbamate (36.4 mg, 0.09 mmol) prepared in Preparation 23 and 4-fluorobenzene-1,3-diamine (13.5 mg, 0.11 mmol) in n-butanol (0.5 ml) was stirred at 120° C. for 2 days. The reaction mixture was concentrated under reduced pressure. The resulting residue was purified with silica gel column chromatography (dichloromethane/methanol=10/1) to give 9.9 mg of the product as a pale yellow oil.

Examples 228 to 231

The products of Examples 228 to 231 were prepared in accordance with the same procedures as in Example 227, using (R)-tert-butyl 1-(2-chloro-6-propylpyrimidin-4-yl)piperidin-3-yl(cyclopropylethyl)carbamate prepared in Preparation 23; and 2-nitrobenzene-1,4-diamine, 3,5-diaminobenzonitrile, 2-(trifluoromethyl)benzene-1,4-diamine, or 5-(trifluoromethyl)benzene-1,3-diamine.

Example 232

A solution of (R)—N-[1-(6-butyl-2-chloropyrimidin-4-yl)piperidin-3-yl]acetamide (165 mg, 0.53 mmol) prepared in Preparation 24 and 2-nitro-1,4-phenylenediamine (90 mg, 0.58 mmol) in n-butanol (2 ml) was stirred at 130° C. for 2 hours. The reaction mixture was cooled to room temperature and then dichloromethane (3 ml) was added thereto. The reaction mixture was stirred at room temperature for 1 hour and then filtered. The resulting solid was dried in vacuo to give 120 mg of the product as a pale yellow solid.

Examples 233 to 243

The products of Examples 233 to 243 were prepared in accordance with the same procedures as in Example 232, using (R)—N-[1-(6-butyl-2-chloropyrimidin-4-yl)piperidin-3-yl]acetamide prepared in Preparation 24; and 4-methyl-3-nitroaniline, 4-fluoro-3-nitroaniline, 4-chloro-3-nitroaniline, 3,5-diaminobenzonitrile, 5-(trifluoromethyl)benzene-1,3-diamine, 2-(trifluoromethyl)benzene-1,4-diamine, 4-fluoro-3-trifluoromethylphenylamine, 5-amino-2-fluorobenzonitrile, 4-fluoro-1,3-phenylenediamine, 4-chloro-1,3-phenylenediamine, or 2,5-diaminobenzonitrile prepared in Preparation 16.

Example 244

A mixture of (R)—N-[1-(2-chloro-6-propylpyrimidin-4-yl)piperidin-3-yl]-2-hydroxyacetamide (22 mg, 0.07 mmol) prepared in Preparation 25 and 5-amino-2-methylbenzonitrile (10.6 mg, 0.08 mmol) in n-butanol (0.5 ml) was stirred in a microwave reactor (600 W) for 1 hour. The reaction mixture was concentrated under reduced pressure. The resulting residue was purified with silica gel column chromatography (dichloromethane/methanol=20/1) to give 7.5 mg of the product as a yellow oil.

Examples 245 to 254

The products of Examples 245 to 254 were prepared in accordance with the same procedures as in Example 244, using (R)—N-[1-(2-chloro-6-propylpyrimidin-4-yl)piperidin-3-yl]-2-hydroxyacetamide prepared in Preparation 25; and 3-aminobenzonitrile, 5-amino-2-fluorobenzonitrile, 5-(trifluoromethyl)benzene-1,3-diamine, 2-(trifluoromethyl)benzene-1,4-diamine, 4-fluoro-3-trifluoromethylphenylamine, 4-fluoro-1,3-phenylenediamine, 4-chloro-1,3-phenylenediamine, 2,4-diaminotoluene, 2-chloro-4-aminotoluene, or 4-methyl-3-(trifluoromethyl)aniline.

Example 255

A mixture of (R)—N-[1-(2-chloro-6-propylpyrimidin-4-yl)piperidin-3-yl]-2-hydroxyacetamide (20 mg, 0.06 mmol) prepared in Preparation 25 and 3,5-diaminobenzonitrile (10.2 mg, 0.08 mmol) in n-butanol (0.5 ml) was stirred in a microwave reactor (600 W) for 1 hour. The reaction mixture was cooled to room temperature and then ethyl acetate (2 ml) was added thereto. The reaction mixture was stirred at room temperature for 1 hour and then filtered. The resulting solid was dried in vacuo to give 3.9 mg of the product as a pale yellow solid.

Example 256

A solution of (R)-tert-butyl [1-(2-chloro-6-propylpyrimidin-4-yl)piperidin-3-yl]carbamate (82 mg, 0.23 mmol) prepared in Preparation 26 and 5-(trifluoromethyl)benzene-1,3-diamine (44 mg, 0.25 mmol) in n-butanol (1 ml) was stirred at 130° C. for 3 hours. The reaction mixture was cooled to room temperature and then concentrated under reduced pressure. The resulting residue was purified with silica gel column chromatography (dichloromethane/methanol=20/1) and then dissolved in ethyl acetate/methanol (1 ml/1 ml). The resulting solution was saturated with hydrogen chloride gas and then filtered to give 55.5 mg of the product as a white solid.

Examples 257 to 266

The products of Examples 257 to 266 were prepared in accordance with the same procedures as in Example 256, using (R)-tert-butyl [1-(2-chloro-6-propylpyrimidin-4-yl)piperidin-3-yl]carbamate prepared in Preparation 26; and 2-(trifluoromethyl)benzene-1,4-diamine, 3-fluoro-4-methylaniline, 4-fluoro-1,3-phenylenediamine, 3,5-diaminobenzonitrile, 2,5-diaminobenzonitrile prepared in Preparation 16, 4-chloro-1,3-phenylenediamine, 4-methyl-3-(trifluoromethyl)aniline, 6-aminoindole, 4-methyl-3-nitroaniline, or 2-nitrobenzene-1,4-diamine.

Example 267

(R)-5-{4-[3-(cyclopropylmethylamino)piperidin-1-yl]-6-propylpyrimidin-2-ylamino}-2-methylbenzonitrile (20 mg, 0.05 mmol) prepared in Example 217 was dissolved in ethyl acetate (1 ml), and then hydrogen chloride gas was added thereto. The reaction mixture was stirred at room temperature for 1 hour and then filtered to give 14 mg of the product as a white solid.

Example 268

The product in the form of white solid was prepared in accordance with the same procedures as in Example 220, using (R)-5-[4-(3-aminopiperidin-1-yl)-6-propylpyrimidin-2-ylamino]-2-fluorobenzonitrile dihydrochloride prepared in Example 222.

Example 269

The product in the form of white solid was prepared in accordance with the same procedures as in Step 2 of Example 154, using (R)-5-[4-(3-aminopiperidin-1-yl)-6-propylpyrimidin-2-ylamino]-2-methylbenzonitrile prepared in Example 153 and acetaldehyde.

Example 270

The reactions were performed in accordance with the same procedures as in Step 2 of Example 154, using (R)-5-[4-(3-aminopiperidin-1-yl)-6-propylpyrimidin-2-ylamino]-2-fluorobenzonitrile dihydrochloride prepared in Example 222 and acetaldehyde. The resulting intermediate product was treated with hydrogen chloride gas to give the product as a white solid

Example 271

The product in the form of white solid was prepared in accordance with the same procedures as in Step 2 of Example 154, using (R)-5-[4-(3-aminopiperidin-1-yl)-6-propylpyrimidin-2-ylamino]-2-fluorobenzonitrile dihydrochloride prepared in Example 222 and acetaldehyde.

Example 272

<Step 1> (R)-3-{[4-(3-aminopiperidin-1-yl)-6-butylpyrimidin-2-yl]amino}benzonitrile The titled compound in the form of white solid was prepared in accordance with the same procedures as in Example 153, using 3-(4-butyl-6-chloropyrimidin-2-ylamino)benzonitrile prepared in Preparation 12.

<Step 2> (R)—N-{1-[6-butyl-2-(3-cyanophenylamino)-pyrimidin-4-yl]-piperidin-3-yl}-acetamide hydrochloride The titled compound in the form of white solid was prepared in accordance with the same procedures as in Example 220, using (R)-3-{[4-(3-aminopiperidin-1-yl)-6-butylpyrimidin-2-yl]amino}benzonitrile prepared in Step 1.

Example 273

A mixture of (R)—N-[1-(2-chloro-6-propylpyrimidin-4-yl)piperidin-3-yl]acetamide (60 mg, 0.2 mmol) prepared in Preparation 31 and 3-aminobenzonitrile (28 mg, 0.24 mmol) in n-butanol (1 ml) was refluxed under stirring overnight. The reaction mixture was cooled to room temperature and then concentrated under reduced pressure. The resulting residue was purified with silica gel column chromatography (n-hexane/ethyl acetate=1/1) and then dissolved in ethyl acetate. Hydrogen chloride gas was added to the solution and the resulting precipitate was collected by filtration to give 68.8 mg of the product as a pale yellow solid.

Examples 274 to 279

The products of Examples 274 to 279 were prepared in accordance with the same procedures as in Example 273, using (R)—N-[1-(2-chloro-6-propylpyrimidin-4-yl)piperidin-3-yl]acetamide prepared in Preparation 31; and 3,5-diaminobenzonitrile, 2-nitro-1,4-phenylenediamine, 4-fluoro-1,3-diaminobenzene, 5-amino-2-fluorobenzotrifluoride, 5-(trifluoromethyl)-1,3-phenylenediamine or 2-(trifluoromethyl)-1,4-phenylenediamine.

Example 280

The product in the form of white solid was prepared in accordance with the same procedures as in Example 267, using (R)-5-{4-[3-(ethylamino)piperidin-1-yl]-6-propylpyrimidin-2-ylamino}-2-methylbenzonitrile prepared in Example 205.

Example 281

The product in the form of pale yellow solid was prepared in accordance with the same procedures as in Example 267, using (R)-5-[4-(3-ethylaminopiperidin-1-yl)-6-propylpyrimidin-2-ylamino]-2-fluorobenzonitrile prepared in Example 271.

Example 282

A solution of (R)-tert-butyl [1-(2-chloro-6-propylpyrimidin-4-yl)piperidin-3-yl](methyl)carbamate (50 mg, 0.14 mmol) prepared in Preparation 28 and 5-amino-2-fluorobenzonitrile (23 mg, 0.17 mmol) in n-butanol (1 ml) was refluxed under stirring overnight. The reaction mixture was cooled to room temperature and then concentrated under reduced pressure. The resulting residue was purified with silica gel column chromatography (n-hexane/ethyl acetate=1/1→dichloromethane/methanol=10/1) and then dissolved in methanol. Hydrogen chloride gas was added to the solution. The reaction mixture was stirred at room temperature for 5 hours and then filtered to give 23 mg of the product as a pale yellow solid.

Examples 283 to 287

The products of Examples 283 to 287 were prepared in accordance with the same procedures as in Example 282, using (R)-tert-butyl [1-(2-chloro-6-propylpyrimidin-4-yl)piperidin-3-yl](methyl)carbamate prepared in Preparation 28; and 5-amino-2-methylbenzonitrile, 5-(trifluoromethyl)-1,3-phenylenediamine, 2-(trifluoromethyl)-1,4-phenylenediamine, 3,5-diaminobenzonitrile, or 4-fluoro-3-(trifluoromethyl)aniline.

Example 288

A solution of (R)-tert-butyl [1-(2-chloro-6-propylpyrimidin-4-yl)piperidin-3-yl](ethyl)carbamate (85 mg, 0.22 mmol) prepared in Preparation 30 and 2-nitro-1,4-phenylenediamine (41 mg, 0.27 mmol) in n-butanol (1 ml) was refluxed under stirring overnight. The reaction mixture was cooled to room temperature and then concentrated under reduced pressure. The resulting residue was purified with silica gel column chromatography (n-hexane/ethyl acetate=1/1→dichloromethane/methanol=10/1) and then dissolved in methanol. Hydrogen chloride gas was added to the solution. The reaction mixture was stirred at room temperature for 5 hours and then filtered to give 104 mg of the product as a pale red solid.

Examples 289 to 292

The products of Examples 289 to 292 were prepared in accordance with the same procedures as in Example 288, using (R)-tert-butyl [1-(2-chloro-6-propylpyrimidin-4-yl)piperidin-3-yl](ethyl)carbamate prepared in Preparation 30; and 4-fluoro-1,3-diaminobenzene, 5-(trifluoromethyl)-1,3-phenylenediamine, 2-(trifluoromethyl)-1,4-phenylenediamine or 3,5-diaminobenzonitrile.

Example 293

The product was prepared in accordance with the same procedures as in Example 153, using 5-(4-butyl-6-chloropyrimidin-2-ylamino)-2-methylbenzonitrile prepared in Preparation 13 and (R)-(−)-3-aminopiperidine dihydrochloride.

Example 294

<Step 1> 5-[(4-butyl-6-chloropyrimidin-2-yl)amino]-2-fluorobenzonitrile

The titled compound in the form of pale yellow solid was prepared in accordance with the same procedures as in Steps 2 and 3 of Preparation 12, using 6-butyl-2-(methylthio)pyrimidin-4(3H)-one prepared in Step 1 of Preparation 12 and 5-amino-2-fluorobenzonitrile.

<Step 2> (R)-5-[4-(3-aminopiperidin-1-yl)-6-butylpyrimidin-2-ylamino]-2-fluorobenzonitrile The titled compound was prepared in accordance with the same procedures as in Example 153, using 5-[(4-butyl-6-chloropyrimidin-2-yl)amino]-2-fluorobenzonitrile prepared in Step 1 and (R)-(−)-3-aminopiperidine dihydrochloride.

Example 295

The product was prepared in accordance with the same procedures as in Example 220, using (R)-5-[4-(3-aminopiperidin-1-yl)-6-butylpyrimidin-2-ylamino]-2-methylbenzonitrile prepared in Example 293.

Example 296

<Step 1> (S)-5-{[4-(3-aminopiperidin-1-yl)-6-propylpyrimidin-2-yl]amino}-2-methylbenzonitrile The titled compound in the form of pale yellow oil was prepared in accordance with the same procedures as in Example 153, using 5-(4-chloro-6-propylpyrimidin-2-ylamino)-2-methylbenzonitrile prepared in Preparation 7 and (S)-(+)-3-aminopiperidine dihydrochloride.

<Step 2> (S)-5-[4-(3-ethylaminopiperidin-1-yl)-6-propylpyrimidin-2-ylamino]-2-methylbenzonitrile The titled compound in the form of pale yellow solid was prepared in accordance with the same procedures as in Step 2 of Example 154, using (S)-5-{[4-(3-aminopiperidin-1-yl)-6-propylpyrimidin-2-yl]amino}-2-methylbenzonitrile prepared in Step 1 and acetaldehyde.

<Step 3> (S)-5-[4-(3-ethylaminopiperidin-1-yl)-6-propylpyrimidin-2-ylamino]-2-methylbenzonitrile dihydrochloride The titled compound in the form of white solid was prepared in accordance with the same procedures as in Example 267, using (S)-5-[4-(3-ethylaminopiperidin-1-yl)-6-propylpyrimidin-2-ylamino]-2-methylbenzonitrile prepared in Step 2.

Example 297

<Step 1> 5-{[4-(3-aminopiperidin-1-yl)-6-propylpyrimidin-2-yl]amino}-2-methylbenzonitrile The titled compound in the form of pale yellow oil was prepared in accordance with the same procedures as in Example 153, using 5-(4-chloro-6-propylpyrimidin-2-ylamino)-2-methylbenzonitrile prepared in Preparation 7 and 3-aminopiperidine dihydrochloride.

<Step 2> 5-[4-(3-ethylaminopiperidin-1-yl)-6-propylpyrimidin-2-ylamino]-2-methylbenzonitrile The titled compound in the form of pale yellow solid was prepared in accordance with the same procedures as in Step 2 of Example 154, using 5-{[4-(3-aminopiperidin-1-yl)-6-propylpyrimidin-2-yl]amino}-2-methylbenzonitrile prepared in Step 1 and acetaldehyde.

<Step 3> 5-[4-(3-ethylaminopiperidin-1-yl)-6-propylpyrimidin-2-ylamino]-2-methylbenzonitrile dihydrochloride The titled compound in the form of white solid was prepared in accordance with the same procedures as in Example 267, using 5-[4-(3-ethylaminopiperidin-1-yl)-6-propylpyrimidin-2-ylamino]-2-methylbenzonitrile prepared in Step 2.

Example 298

<Step 1> N-{1-[6-butyl-2-(3-cyano-4-methylphenylamino)pyrimidin-4-yl]piperidin-3-yl}acetamide The titled compound in the form of pale yellow oil was prepared in accordance with the same procedures as in Example 153, using 5-(4-butyl-6-chloropyrimidin-2-ylamino)-2-methylbenzonitrile prepared in Preparation 13 and 3-acetamidopiperidine.

<Step 2> N-{1-[6-butyl-2-(3-cyano-4-methylphenylamino)pyrimidin-4-yl]piperidin-3-yl}acetamide hydrochloride The titled compound in the form of pale yellow solid was prepared in accordance with the same procedures as in Example 267, using N-{1-[6-butyl-2-(3-cyano-4-methylphenylamino)pyrimidin-4-yl]piperidin-3-yl}acetamide prepared in Step 1.

Examples 299 to 305

The products of Examples 299 to 305 were prepared in accordance with the same procedures as in Step 2 of Example 154, using (R)-5-[4-(3-aminopiperidin-1-yl)-6-butylpyrimidin-2-ylamino]-2-methylbenzonitrile prepared in Example 293; and acetaldehyde, butyraldehyde, valeraldehyde, isobutyraldehyde, isovaleraldehyde, pivaldehyde or 3-(methylthio)propionaldehyde.

Examples 306 to 310

The products of Examples 306 to 310 were prepared in accordance with the same procedures as in Example 282, using (R)-tert-butyl [1-(2-chloro-6-propylpyrimidin-4-yl)piperidin-3-yl](methyl)carbamate prepared in Preparation 28; and 4-fluoro-1,3-diaminobenzene, 4-chloro-1,3-diaminobenzene, 2,5-diaminobenzonitrile prepared in Preparation 16, 3-methoxy-4-methylaniline or 2,4-diaminotoluene.

Example 311

A solution of (R)-tert-butyl [1-(6-butyl-2-chloropyrimidin-4-yl)piperidin-3-yl](methyl)carbamate (40 mg, 0.1 mmol) prepared in Preparation 29, 5-amino-2-methylbenzonitrile (15.9 mg, 0.12 mmol) in n-butanol (1 ml) was refluxed under stirring for 2 hours. The reaction mixture was cooled to room temperature and then concentrated under reduced pressure. The resulting residue was purified with silica gel column chromatography (n-hexane/ethyl acetate=1/1→dichloromethane/methanol=10/1) and then dissolved in methanol. Hydrogen chloride gas was added to the solution. The reaction mixture was stirred at room temperature for 5 hours and then filtered to give 33.5 mg of the product as a pale yellow solid.

Examples 312 to 320

The products of Examples 312 to 320 were prepared in accordance with the same procedures as in Example 311, using (R)-tert-butyl [1-(6-butyl-2-chloropyrimidin-4-yl)piperidin-3-yl](methyl)carbamate prepared in Preparation 29; and 5-amino-2-fluorobenzonitrile, 5-(trifluoromethyl)-1,3-phenylenediamine, 2-(trifluoromethyl)-1,4-phenylenediamine, 3,5-diaminobenzonitrile, 2,5-diaminobenzonitrile prepared in Preparation 16, 4-fluoro-1,3-diaminobenzene, 3-methoxy-4-methylaniline, 2,4-diaminotoluene, or 5-amino-2-fluorobenzotrifluoride.

Examples 321 to 326

The products of Examples 321 to 326 were prepared in accordance with the same procedures as in Example 282, using (R)-tert-butyl (1-[2-chloro-6-propylpyrimidin-4-yl]piperidin-3-yl)(methyl)carbamate prepared in Preparation 28; and 2-nitro-1,4-phenylenediamine, 3,4-dimethylaniline, 3-fluoro-4-methylaniline, 4-methyl-3-(trifluoromethyl)aniline, 2,4-diaminoanisole or 6-aminoindazole.

Example 327

Palladium/charcoal (25 mg, 10 wt %) was added to a solution of (R)—N$^1$-{4-[3-(methylamino)piperidin-1-yl]-6-propylpyrimidin-2-yl}-3-nitrobenzene-1,4-diamine dihydrochloride (20 mg, 0.04 mmol) prepared in Example 321 in methanol (2 ml). The reaction mixture was stirred at room temperature under hydrogen atmosphere (30 bar) for 3 hours and then filtered through a celite pad. The resulting filtrate was concentrated under reduced pressure. The resulting residue was purified with silica gel column chromatography (dichloromethane/methanol=10/1) to give 3.5 mg of the product as a pale yellow solid.

Examples 328 to 334

The products of Examples 328 to 334 were prepared in accordance with the same procedures as in Example 282, using (R)-tert-butyl [1-(6-butyl-2-chloropyrimidin-4-yl)piperidin-3-yl](methyl)carbamate prepared in Preparation 29; and 2-nitro-1,4-phenylenediamine, 3-aminobenzonitrile, 3,4-dimethylaniline, 3-fluoro-4-methylaniline, 4-methyl-3-(trifluoromethyl)aniline, 2,4-diaminoanisole or 6-aminoindazole.

Example 335

The product was prepared in accordance with the same procedures as in Example 327, using (R)—$N^1$-{4-butyl-6-[3-(methylamino)piperidin-1-yl]pyrimidin-2-yl}-3-nitrobenzene-1,4-diamine dihydrochloride prepared in Example 328.

Example 336

A solution of (R)-tert-butyl [1-(6-butyl-2-chloropyrimidin-4-yl)piperidin-3-yl]carbamate (40 mg, 0.11 mmol) prepared in Preparation 27 and 3-nitroaniline (16.6 mg, 0.12 mmol) in n-butanol (1 ml) was refluxed under stirring for 2 hours and then concentrated under reduced pressure. The resulting residue was purified with silica gel column chromatography (n-hexane/ethyl acetate=1/1→dichloromethane/methanol=10/1) and then dissolved in methanol (2 ml). The resulting solution was saturated with hydrogen chloride gas. The reaction mixture was stirred at room temperature for 5 hours and then filtered. The filtrate was concentrated under reduced pressure. Ethyl acetate (2 ml) was added to the resulting residue, which was then stirred. The reaction mixture was filtered to give 35 mg of the product as a white solid.

Examples 337 to 353

The products of Examples 337 to 353 were prepared in accordance with the same procedures as in Example 336, using (R)-tert-butyl [1-(6-butyl-2-chloropyrimidin-4-yl)piperidin-3-yl]carbamate prepared in Preparation 27; and 2-nitro-1,4-phenylenediamine, 4-fluoro-3-nitroaniline, 4-methyl-3-nitroaniline, 2-(trifluoromethyl)-1,4-phenylenediamine, 5-(trifluoromethyl)-1,3-phenylenediamine, 3,5-diaminobenzonitrile, 4-methyl-3-(trifluoromethyl)aniline, 3-fluoro-4-methylaniline, 3-methoxy-4-methylaniline, 2,4-diaminotoluene, 3,4-dimethylaniline, 5-amino-2-fluorobenzotrifluoride, 4-fluoro-1,3-diaminobenzene, 2,5-diaminobenzonitrile prepared in Preparation 16, 3-aminobenzonitrile, 1,4-phenylenediamine, or 4-chloro-3-nitroaniline.

Example 354

The product was prepared in accordance with the same procedures as in Example 327, using (R)—$N^1$-[4-(3-aminopiperidin-1-yl)-6-butylpyrimidin-2-yl]-3-nitrobenzene-1,4-diamine dihydrochloride prepared in Example 337.

The compounds of Examples 1 to 354 and the NMR spectrum data thereof are shown in Tables 1-1 to 1-37 below.

TABLE 1-1

| Example | Compound | NMR Spectrum |
|---|---|---|
| 1 | N-(4-fluorophenyl)-4-(piperidin-1-yl)-6-propylpyrimidin-2-amine | $^1$H-NMR(400 MHz, CDCl$_3$) δ 7.60-7.50(m, 2H), 6.98(t, 2H), 5.90(s, 1H), 3.58(t, 4H), 2.45(t, 2H), 1.80-1.50(m, 6H), 0.98(t, 3H) |
| 2 | N-(4-fluorophenyl)-4-morpholino-6-propylpyrimidin-2-amine | $^1$H-NMR(400 MHz, CDCl$_3$) δ 7.60-7.50(m, 2H), 6.99(t, 2H), 5.89(s, 1H), 3.78(t, 4H), 3.58(t, 4H), 2.48(t, 2H), 1.72(q, 2H), 0.98(t, 3H) |
| 3 | 4-(azepan-1-yl)-N-(4-fluorophenyl)-6-propylpyrimidin-2-amine | $^1$H-NMR(400 MHz, CDCl$_3$) δ 7.60-7.50(m, 2H), 6.96(t, 2H), 5.80(s, 1H), 3.90-3.30(m, 4H), 2.45(t, 2H), 1.90-1.65(m, 6H), 1.60-1.50(m, 4H), 0.98(t, 3H) |
| 4 | N-(4-fluorophenyl)-4-(2-methylpiperidin-1-yl)-6-propylpyrimidin-2-amine | $^1$H-NMR(400 MHz, CDCl$_3$) δ 7.60-7.50(m, 2H), 6.97(t, 2H), 5.88(s, 1H), 4.70-4.60(m, 1H), 4.21(d, 1H), 2.93(t, 1H), 2.45(t, 2H), 1.80-1.60(m, 7H), 1.19(d, 3H), 0.98(t, 3H) |
| 5 | N-(4-fluorophenyl)-4-(3-methylpiperidin-1-yl)-6-propylpyrimidin-2-amine | $^1$H-NMR(400 MHz, CDCl$_3$) δ 7.60-7.50(m, 2H), 6.97(t, 2H), 5.90(s, 1H), 4.30-4.10(m, 2H), 2.85(t, 1H), 2.52(t, 1H), 2.45(t, 2H), 1.85(d, 1H), 1.80-1.60(m, 4H), 1.60-1.45(m, 1H), 1.20(q, 1H), 1.00-0.90(m, 6H) |
| 6 | N-(4-fluorophenyl)-4-propyl-6-thiomorpholinopyrimidin-2-amine | $^1$H-NMR(400 MHz, CDCl$_3$) δ 7.55-7.45(m, 2H), 6.98(t, 2H), 5.87(s, 1H), 4.00-3.90(m, 4H), 2.70-2.60(m, 4H), 2.47(t, 2H), 1.72(q, 2H), 0.97(t, 3H) |
| 7 | 4-(2,5-dimethylpiperazin-1-yl)-N-(4-fluorophenyl)-6-propylpyrimidin-2-amine dihydrochloride | $^1$H-NMR(400 MHz, CD$_3$OD) δ 7.60-7.50(m, 2H), 7.18(t, 2H), 6.59(d, 1H), 3.50-3.30(m, 2H), 3.20-3.00(m, 2H), 2.90-2.70(m, 2H), 2.65(t, 2H), 1.77(q, 2H), 1.39(d, 6H), 1.05(t, 3H) |
| 8 | 4-(5,6-dihydropyridin-1(2H)-yl)-N-(4-fluorophenyl)-6-propylpyrimidin-2-amine hydrochloride | $^1$H-NMR(400 MHz, CDCl$_3$) δ 7.60-7.50(m, 2H), 7.04(t, 2H), 6.00-5.80(m, 2H), 5.78(brs, 1H), 4.29(brs, 1H), 4.00(d, 2H), 3.69(s, 1H), 2.65(t, 2H), 2.40-2.20(m, 2H), 1.86(q, 2H), 1.03(t, 3H) |
| 9 | N-(4-fluorophenyl)-4-(decahydroquinolin-1(2H)-yl)-6-propylpyrimidin-2-amine hydrochloride | $^1$H-NMR(400 MHz, CDCl$_3$) δ 10.53(brs, 1H), 7.60-7.50(m, 2H), 7.02(t, 2H), 5.79(s, 1H), 3.40-3.20(m, 1H), 2.62(t, 2H), 2.10-2.00(m, 1H), 2.00-1.60(m, 11H), 1.50-1.30(m, 4H), 1.30-1.10(m, 3H), 1.19(t, 3H) |
| 10 | N-(4-fluorophenyl)-4-[decahydroisoquinolin-1(2H)-yl]-6-propylpyrimidin-2-amine hydrochloride | $^1$H-NMR(400 MHz, CDCl$_3$) δ 7.60-7.50(m, 2H), 7.03(t, 2H), 5.90(d, 1H), 4.40(dd, 1H), 3.75(dd, 1H), 3.40-3.20(m, 2H), 2.70-2.50(m, 2H), 2.10-1.70(m, 5H), 1.70-1.50(m, 5H), 1.40-1.20(m, 4H), 1.10-1.00(m, 3H) |

TABLE 1-2

| Example | Compound | NMR Spectrum |
|---|---|---|
| 11 | N-(4-fluorophenyl)-4-(4-phenylpiperidin-1-yl)-6-propylpyrimidin-2-amine hydrochloride | $^1$H-NMR(400 MHz, CDCl$_3$) δ 7.60-7.50(m, 2H), 7.03(t, 2H), 5.90(d, 1H), 4.40(dd, 1H), 3.75(dd, 1H), 3.40-3.20(m, 2H), 2.70-2.50(m, 2H), 2.10-1.70(m, 5H), 1.70-1.50(m, 5H), 1.40-1.20(m, 4H), 1.10-1.00(m, 3H) |
| 12 | N-(4-fluorophenyl)-4-morpholino-6-propylpyrimidin-2-amine hydrochloride | $^1$H-NMR(400 MHz, CD$_3$OD) δ 7.50-7.40(m, 2H), 7.15(t, 2H), 6.44(s, 1H), 3.80-3.60(m, 8H), 2.62(t, 2H), 1.74(q, 2H), 1.04(t, 3H) |
| 13 | N-(4-fluorophenyl)-4-(piperazin-1-yl)-6-propylpyrimidin-2-amine | $^1$H-NMR(400 MHz, CD$_3$OD) δ 7.60-7.50(m, 2H), 6.98(t, 2H), 6.07(s, 1H), 3.61(t, 4H), 2.86(t, 4H), 2.46(t, 2H), 1.71(q, 2H), 0.97(t, 3H) |
| 14 | 4-(2-ethylpiperidin-1-yl)-N-(4-fluorophenyl)-6-propylpyrimidin-2-amine | $^1$H-NMR(400 MHz, CDCl$_3$) δ 7.60-7.50(m, 2H), 6.97(t, 2H), 5.87(s, 1H), 4.45-4.30(m, 1H), 4.30-4.10(m, 1H), 2.90(t, 1H), 2.44(t, 2H), 1.80-1.40(m, 8H), 0.98(t, 3H), 0.90(t, 3H) |
| 15 | 2-{1-[2-(4-fluorophenylamino)-6-propylpyrimidin-4-yl]piperidin-2-yl}ethanol | $^1$H-NMR(400 MHz, CDCl$_3$) δ 7.60-7.50(m, 2H), 7.00(t, 2H), 6.72(brs, 1H), 5.92(s, 1H), 4.95-4.85(m, 1H), 3.90-3.80(m, 1H), 3.60-3.50(m, 1H), 3.30(t, 1H), 2.95(t, 1H), 2.46(t, 2H), 2.10-2.00(m, 1H), 1.80-1.60(m, 7H), 1.30-1.20(m, 2H), 0.99(t, 3H) |
| 16 | ethyl 1-[2-(4-fluorophenylamino)-6-propylpyrimidin-4-yl]piperidin-2-carboxylate | $^1$H-NMR(400 MHz, CDCl$_3$) δ 7.50-7.40(m, 2H), 6.97(t, 2H), 6.78(brs, 1H), 5.96(s, 1H), 4.20-4.10(m, 2H), 3.93(brs, 1H), 3.22(t, 1H), 2.48(t, 2H), 2.29(d, 1H), 1.90-1.70(m, 6H), 1.70-1.50(m, 1H), 1.45-1.30(m, 1H), 1.23(t, 3H), 0.98(t, 3H) |
| 17 | 1-[2-(4-fluorophenylamino)-6-propylpyrimidin-4-yl]piperidin-4-carboxamide | $^1$H-NMR(400 MHz, CDCl$_3$) δ 7.60-7.50(m, 2H), 6.98(t, 2H), 6.88(brs, 1H), 5.92(s, 1H), 5.42(d, 2H), 4.39(d, 2H), 2.97(t, 2H), 2.50-2.40(m, 3H), 1.97(d, 2H), 1.80-1.60(m, 4H), 0.98(t, 3H) |
| 18 | {1-[2-(4-fluorophenylamino)-6-propylpyrimidin-4-yl]piperidin-4-yl}methanol | $^1$H-NMR(400 MHz, CDCl$_3$) δ 7.60-7.50(m, 2H), 6.97(t, 2H), 6.81(brs, 1H), 5.92(s, 1H), 4.40(d, 2H), 3.53(d, 2H), 2.88(t, 2H), 2.46(t, 2H), 1.90-1.60(m, 5H), 1.30-1.15(m, 2H), 0.98(t, 3H) |
| 19 | 1-[2-(4-fluorophenylamino)-6-propylpyrimidin-4-yl]piperidin-4-one | $^1$H-NMR(400 MHz, CDCl$_3$) δ 7.60-7.50(m, 2H), 7.00(t, 2H), 6.84(brs, 1H), 6.00(s, 1H), 3.93(t, 4H), 2.60-2.40(m, 6H), 1.74(q, 2H), 0.99(t, 3H) |
| 20 | 4-butyl-N-(4-fluorophenyl)-6-(piperidin-1-yl)pyrimidin-2-amine | $^1$H-NMR(400 MHz, CDCl$_3$) δ 7.60-7.50(m, 2H), 6.97(t, 2H), 6.79(brs, 1H), 5.90(s, 1H), 3.60-3.50(m, 4H), 2.48(t, 2H), 1.70-1.50(m, 8H), 1.39(q, 2H), 0.94(t, 3H) |

TABLE 1-3

| Example | Compound | NMR Spectrum |
|---|---|---|
| 21 | 4-butyl-6-(2-ethylpiperidin-1-yl)-N-(4-fluorophenyl)pyrimidin-2-amine | $^1$H-NMR(400 MHz, CDCl$_3$) δ 7.60-7.50(m, 2H), 6.97(t, 2H), 6.73(brs, 1H), 5.88(s, 1H), 4.50-4.30(m, 1H), 4.25-4.15(m, 1H), 2.92(t, 1H), 2.46(t, 2H), 1.80-1.55(m, 10H), 1.40(q, 2H), 1.00-0.85(m, 6H) |
| 22 | 2-{1-[6-butyl-2-(4-fluorophenylamino)pyrimidin-4-yl]piperidin-2-yl}ethanol | $^1$H-NMR(400 MHz, CDCl$_3$) δ 7.50-7.40(m, 2H), 6.99(t, 2H), 6.66(brs, 1H), 5.91(s, 1H), 4.91(brs, 1H), 3.90-3.80(m, 1H), 3.53(d, 1H), 3.31(t, 1H), 2.94(t, 1H), 2.48(t, 2H), 2.06(t, 1H), 1.80-1.55(m, 9H), 1.42(q, 2H), 0.97(t, 3H) |
| 23 | 4-butyl-N-(4-fluorophenyl)-6-morpholinopyrimidin-2-amine | $^1$H-NMR(400 MHz, CDCl$_3$) δ 7.55-7.45(m, 2H), 7.00(t, 2H), 6.86(brs, 1H), 5.88(s, 1H), 3.78(t, 4H), 3.58(t, 4H), 2.50(t, 2H), 1.70-1.60(m, 2H), 1.39(q, 2H), 0.94(t, 3H) |
| 24 | 2-{1-[2-(4-chloro-3-nitrophenylamino)-6-propylpyrimidin-4-yl]piperidin-2-yl}ethanol | $^1$H-NMR(400 MHz, CDCl$_3$) δ 8.78(s, 1H), 7.40-7.30(m, 1H), 7.30-7.20(m, 1H), 6.02(s, 1H), 5.00-4.90(m, 1H), 4.00-3.90(m, 1H), 3.60-3.50(m, 1H), 3.41(t, 1H), 2.98(t, 1H), 2.49(t, 2H), 2.20-2.05(m, 1H), 1.80-1.30(m, 9H), 0.97(t, 3H) |
| 25 | 2-(1-{2-[3-(methylthio)phenylamino]-6-propylpyrimidin-4-yl}piperidin-2-yl)ethanol | $^1$H-NMR(400 MHz, CDCl$_3$) δ 7.67(s, 1H), 7.20-7.10(m, 2H), 7.00-6.80(m, 2H), 5.93(s, 1H), 4.98(brs, 1H), 3.87(brs, 1H), 3.60-3.50(m, 1H), 3.33(t, 1H), 2.95(t, 1H), 2.49(s, 3H), 2.50-2.40(m, 1H), 2.10-2.00(m, 1H), 1.80-1.50(m, 9H), 0.99(t, 3H) |
| 26 | 4-(2,6-dimethylmorpholino)-N-(4-fluorophenyl)-6-propylpyrimidin-2-amine | $^1$H-NMR(400 MHz, CDCl$_3$) δ 7.60-7.50(m, 2H), 6.99(t, 2H), 6.84(brs, 1H), 5.89(s, 1H), 4.12(d, 2H), 3.70-3.55(m, 2H), 2.59(q, 2H), 2.48(t, 2H), 1.72(q, 2H), 1.26(d, 6H), 0.98(t, 3H) |

TABLE 1-3-continued

| Example | Compound | NMR Spectrum |
| --- | --- | --- |
| 27 | 8-[2-(4-fluorophenylamino)-6-propylpyrimidin-4-yl]-8-azabicyclo[3.2.1]octan-3-ol | $^1$H-NMR(400 MHz, CDCl$_3$) δ 7.60-7.50(m, 2H), 6.98(t, 2H), 6.80(brs, 1H), 5.81(s, 1H), 4.15-4.05(m, 1H), 2.45(t, 2H), 2.40-2.25(m, 2H), 2.25-2.10(m, 2H), 2.10-2.00(m, 2H), 1.80-1.50(m, 6H), 0.98(t, 3H) |
| 28 | N-{1-[2-(4-fluorophenylamino)-6-propylpyrimidin-4-yl]piperidin-3-yl}acetamide | $^1$H-NMR(400 MHz, CDCl$_3$) δ 7.60-7.45(m, 2H), 7.10-6.95(m, 2H), 6.86(brs, 1H), 5.96(s, 1H), 5.75(brs, 1H), 4.02(brs, 1H), 3.77(d, 1H), 3.65-3.40(m, 3H), 2.46(t, 2H), 1.91(s, 3H), 1.90-1.85(m, 1H), 1.80-1.55(m, 5H), 0.97(t, 3H) |
| 29 | N-(4-fluorophenyl)-4-{4-[3-(piperidin-4-yl)propyl]piperidin-1-yl}-6-propylpyrimidin-2-amine | $^1$H-NMR(400 MHz, CDCl$_3$) δ 7.60-7.50(m, 2H), 6.98(t, 2H), 6.76(brs, 1H), 5.90(s, 1H), 4.33(d, 2H), 2.84(t, 2H), 2.45(t, 2H), 1.80-1.60(m, 5H), 1.60-1.45(m, 1H), 1.45-1.30(m, 1H), 1.30-1.10(m, 4H), 0.98(t, 3H) |
| 30 | 4-[3-(benzyloxy)piperidin-1-yl]-N-(4-fluorophenyl)-6-propylpyrimidin-2-amine | $^1$H-NMR(400 MHz, CDCl$_3$) δ 7.60-7.50(m, 2H), 7.40-7.20(m, 5H), 6.97(t, 2H), 6.85(brs, 1H), 5.87(s, 1H), 4.58(d, 2H), 4.20(d, 1H), 3.90-3.80(m, 1H), 3.50-3.40(m, 1H), 3.30-3.10(m, 2H), 2.45(t, 2H), 2.10-2.00(m, 1H), 2.00-1.80(m, 3H), 1.69(q, 2H), 0.98(t, 3H) |

TABLE 1-4

| Example | Compound | NMR Spectrum |
| --- | --- | --- |
| 31 | 4-(3-oxa-8-azabicyclo[3.2.1]octan-8-yl)-N-(4-fluorophenyl)-6-propylpyrimidin-2-amine | $^1$H-NMR(400 MHz, CDCl$_3$) δ 7.55-7.45(m, 2H), 6.97(t, 2H), 6.88(brs, 1H), 5.82(s, 1H), 4.41(brs, 1H), 3.80(d, 2H), 3.61(d, 2H), 3.60-3.40(m, 1H), 2.47(t, 2H), 2.10-1.80(m, 4H), 1.72(q, 2H), 0.98(t, 3H) |
| 32 | N-[4-(piperidin-1-yl)-6-propylpyrimidin-2-yl]-1H-indol-5-amine | $^1$H-NMR(400 MHz, CDCl$_3$) δ 8.31(brs, 1H), 7.90(s, 1H), 7.52(brs, 1H), 7.30-7.20(m, 1H), 7.20-7.10(m, 1H), 6.50-6.40(m, 1H), 5.85(s, 1H), 3.70-3.50(m, 4H), 2.48(t, 2H), 1.74(q, 2H), 1.70-1.50(m, 6H), 0.98(t, 3H) |
| 33 | N-(3-chloro-4-methylphenyl)-4-(piperidin-1-yl)-6-propylpyrimidin-2-amine | $^1$H-NMR(400 MHz, CDCl$_3$) δ 8.32(brs, 1H), 7.88(d, 1H), 7.21(dd, 1H), 7.12(d, 1H), 5.90(s, 1H), 3.70-3.60(m, 4H), 2.52(t, 2H), 2.32(s, 3H), 1.80-1.60(m, 8H), 0.99(t, 3H) |
| 34 | N-[4-(piperidin-1-yl)-6-propylpyrimidin-2-yl]quinolin-6-amine | $^1$H-NMR(400 MHz, CDCl$_3$) δ 8.80-8.70(m, 1H), 8.36(d, 1H), 8.00(t, 2H), 7.70(d, 1H), 7.40-7.30(m, 1H), 7.17(brs, 1H), 5.97(s, 1H), 3.97(brs, 1H), 3.70-3.60(m, 4H), 2.51(t, 2H), 1.80-1.55(m, 6H), 1.01(t, 3H) |
| 35 | 4-(piperidin-1-yl)-6-propyl-N-[3-(trifluoromethyl)phenyl]pyrimidin-2-amine | $^1$H-NMR(400 MHz, CDCl$_3$) δ 8.38(s, 1H), 7.58(brs, 1H), 7.42(d, 1H), 7.35(t, 1H), 5.94(s, 1H), 3.70-3.60(m, 4H), 2.49(t, 2H), 1.80-1.55(m, 8H), 0.98(t, 3H) |
| 36 | N-[4-(piperidin-1-yl)-6-propylpyrimidin-2-yl]-2-(trifluoromethyl)-1H-benzo[d]imidazol-5-amine | $^1$H-NMR(400 MHz, CDCl$_3$) δ 8.13(s, 1H), 7.60-7.50(m, 1H), 7.22(d, 1H), 5.92(s, 1H), 3.60-3.50(m, 4H), 2.49(t, 2H), 1.73(q, 2H), 1.70-1.50(m, 6H), 0.93(t, 3H) |
| 37 | N-[3-(methylthio)phenyl]-4-(piperidin-1-yl)-6-propylpyrimidin-2-amine | $^1$H-NMR(400 MHz, CDCl$_3$) δ 9.05(brs, 1H), 7.69(d, 1H), 7.30-7.15(m, 2H), 6.93(d, 1H), 5.90(s, 1H), 3.70-3.60(m, 4H), 2.55(t, 2H), 2.48(s, 3H), 1.80(q, 2H), 1.70-1.60(m, 6H), 1.00(t, 3H) |
| 38 | N-(5-methoxy-2-methylphenyl)-4-(piperidin-1-yl)-6-propylpyrimidin-2-amine | $^1$H-NMR(400 MHz, CDCl$_3$) δ 7.76(brs, 1H), 7.05(d, 1H), 6.54(d, 1H), 5.90(s, 1H), 3.78(s, 3H), 3.70-3.55(m, 4H), 2.53(t, 2H), 2.30(s, 3H), 1.78(q, 2H), 1.75-1.55(m, 6H), 1.90(t, 3H) |
| 39 | N-(5-chloro-2-methylphenyl)-4-(piperidin-1-yl)-6-propylpyrimidin-2-amine | $^1$H-NMR(400 MHz, CDCl$_3$) δ 8.39(brs, 1H), 7.05(d, 1H), 6.87(d, 1H), 5.92(s, 1H), 3.65-3.55(m, 4H), 2.49(t, 2H), 2.29(s, 3H), 1.80-1.60(m, 8H), 0.99(t, 3H) |
| 40 | N-(4-fluoro-3-nitrophenyl)-4-(piperidin-1-yl)-6-propylpyrimidin-2-amine | $^1$H-NMR(400 MHz, CDCl$_3$) δ 9.00-8.90(m, 1H), 7.82(brs, 1H), 7.50-7.40(m, 1H), 7.17(t, 1H), 5.97(s, 1H), 3.70-3.60(m, 4H), 2.50(t, 2H), 1.80-1.60(m, 8H), 0.99(t, 3H) |

TABLE 1-5

| Example | Compound | NMR Spectrum |
|---|---|---|
| 41 | N-(4-methoxyphenyl)-4-(piperidin-1-yl)-6-propylpyrimidin-2-amine | $^1$H-NMR(400 MHz, CDCl$_3$) δ 8.11(brs, 1H), 7.48(dd, 2H), 6.85(dd, 2H), 5.86(s, 1H), 3.79(s, 3H), 3.65-3.55(m, 4H), 2.51(t, 2H), 1.77(q, 2H), 1.70-1.55(m, 6H), 0.99(t, 3H) |
| 42 | N-(3-methoxyphenyl)-4-(piperidin-1-yl)-6-propylpyrimidin-2-amine | $^1$H-NMR(400 MHz, CDCl$_3$) δ 7.98(brs, 1H), 7.46(s, 1H), 7.17(t, 1H), 7.02(d, 1H), 6.56(d, 1H), 5.90(s, 1H), 3.80(s, 3H), 3.70-3.60(m, 4H), 2.51(t, 2H), 1.80-1.55(m, 8H), 0.99(t, 3H) |
| 43 | N-(3-chlorophenyl)-4-(piperidin-1-yl)-6-propylpyrimidin-2-amine | $^1$H-NMR(400 MHz, CDCl$_3$) δ 8.50(brs, 1H), 7.92(s, 1H), 7.23(d, 1H), 7.20(t, 1H), 6.98(d, 1H), 5.93(s, 1H), 3.70-3.60(m, 4H), 2.53(t, 2H), 1.80-1.60(m, 8H), 1.00(t, 3H) |
| 44 | N-(3-nitrophenyl)-4-(piperidin-1-yl)-6-propylpyrimidin-2-amine | $^1$H-NMR(400 MHz, CDCl$_3$) δ 9.10(d, 1H), 7.86(brs, 1H), 7.79(d, 1H), 7.51(d, 1H), 7.38(t, 1H), 5.98(s, 1H), 3.70-3.60(m, 4H), 2.51(t, 2H), 1.80-1.60(m, 8H), 0.99(t, 3H) |
| 45 | N-(4-chloro-3-nitrophenyl)-4-(piperidin-1-yl)-6-propylpyrimidin-2-amine | $^1$H-NMR(400 MHz, CDCl$_3$) δ 8.83(s, 1H), 7.84(brs, 1H), 7.40-7.30(m, 2H), 5.98(s, 1H), 3.70-3.60(m, 4H), 2.50(t, 2H), 1.80-1.60(m, 8H), 0.99(t, 3H) |
| 46 | 3-[4-(piperidin-1-yl)-6-propylpyrimidin-2-ylamino]benzonitrile | $^1$H-NMR(400 MHz, CDCl$_3$) δ 8.39(brs, 1H), 8.24(s, 1H), 7.61(d, 1H), 7.36(t, 1H), 7.26(d, 1H), 5.97(s, 1H), 3.70-3.60(m, 4H), 2.53(t, 2H), 1.80-1.60(m, 8H), 1.00(t, 3H) |
| 47 | N-(4-methyl-3-nitrophenyl)-4-(piperidin-1-yl)-6-propylpyrimidin-2-amine | $^1$H-NMR(400 MHz, CDCl$_3$) δ 8.85(d, 1H), 7.32(d, 1H), 7.18(d, 1H), 5.95(s, 1H), 3.70-3.60(m, 4H), 2.53(s, 3H), 2.47(t, 2H), 1.80-1.60(m, 8H), 0.98(t, 3H) |
| 48 | 4-(4-ethylpiperazin-1-yl)-N-(4-fluorophenyl)-6-methylpyrimidin-2-amine | $^1$H-NMR(400 MHz, CDCl$_3$) δ 7.53-7.48(m, 2H), 7.20(s, 1H), 7.00-6.94(m, 2H), 5.90(s, 1H), 3.63(dd, 4H), 2.51-2.42(m, 6H), 2.25(s, 3H), 1.12(dd, 3H) |
| 49 | N-(4-fluorophenyl)-4-[4-(4-methoxyphenyl)piperazin-1-yl]-6-methylpyrimidin-2-amine | $^1$H-NMR(400 MHz, CDCl$_3$) δ 7.54-7.50(m, 2H), 7.03-6.87(m, 7H), 5.96(s, 1H), 3.77(s, 3H), 3.76(dd, 4H), 3.12(dd, 4H), 2.78(s, 3H) |
| 50 | N-(4-fluorophenyl)-4-[4-(4-fluorophenyl)piperazin-1-yl]-6-methylpyrimidin-2-amine | $^1$H-NMR(400 MHz, CDCl$_3$) δ 7.54-7.49(m, 2H), 7.03-6.87(m, 7H), 5.96(s, 1H), 3.76(dd, 4H), 3.16(dd, 4H), 2.28(s, 3H) |

TABLE 1-6

| Example | Compound | NMR Spectrum |
|---|---|---|
| 51 | N-(4-fluorophenyl)-4-methyl-6-(morpholin-4-yl)pyrimidin-2-amine | $^1$H-NMR(400 MHz, CDCl$_3$) δ 7.52-7.47(m, 2H), 7.01-6.95(m, 2H), 6.89(s, 1H), 5.89(s, 1H), 3.77(dd, 4H), 3.57(dd, 4H), 2.27(s, 3H) |
| 52 | 1-[2-(4-fluorophenylamino)-6-methylpyrimidin-4-yl]piperidin-4-one | $^1$H-NMR(400 MHz, CDCl$_3$) δ 7.53-7.50(m, 2H), 7.02-6.98(m, 2H), 6.90(s, 1H), 6.02(s, 1H), 3.93(dd, 4H), 2.53(dd, 4H), 2.30(s, 3H) |
| 53 | N-(4-fluorophenyl)-4-methyl-6-(piperidin-1-yl)pyrimidin-2-amine | $^1$H-NMR(400 MHz, CDCl$_3$) δ 7.53-7.50(m, 2H), 6.99-6.95(m, 3H), 5.91(s, 1H), 3.57(dd, 4H), 2.24(s, 3H), 1.69-1.57(m, 6H) |
| 54 | 4-(azetidin-1-yl)-N-(4-fluorophenyl)-6-methylpyrimidin-2-amine | $^1$H-NMR(400 MHz, CDCl$_3$) δ 7.60-7.57(m, 2H), 6.98-6.91(m, 3H), 5.56(s, 1H), 4.07(dd, 4H), 2.43-2.36(m, 2H), 2.24(s, 3H) |
| 55 | 1-[2-(4-fluorophenylamino)-6-methylpyrimidin-4-yl]piperidin-3-ol | $^1$H-NMR(400 MHz, CDCl$_3$) δ 7.53-7.50(m, 2H), 7.02-6.97(m, 2H), 5.96(s, 1H), 4.12-4.08(m, 3H), 3.76(d, 1H), 3.72-3.66(m, 1H), 3.36-3.05(m, 2H), 2.23(s, 3H), 2.22-2.20(m, 1H), 1.85-1.81(m, 1H), 1.58-1.51(m, 2H) |
| 56 | 1-[2-(4-fluorophenylamino)-6-methylpyrimidin-4-yl]piperidin-4-ol | $^1$H-NMR(400 MHz, CDCl$_3$) δ 7.52-7.49(m, 2H), 7.00-6.95(m, 2H), 5.93(s, 1H), 4.07-4.03(m, 2H), 3.96-3.92(m, 1H), 3.22(m, 2H), 2.25(s, 3H), 1.97-1.90(m, 2H), 1.58-1.50(m, 2H) |
| 57 | N-(4-fluorophenyl)-4-methyl-6-(2-methylpiperidin-1-yl)pyrimidin-2-amine | $^1$H-NMR(400 MHz, CDCl$_3$) δ 7.55-7.50(m, 2H), 7.01-6.95(m, 2H), 6.79(brs, 1H), 5.89(s, 1H), 4.61(brs, 1H), 4.21(d, 1H), 3.93(m, 1H), 2.25(s, 3H), 1.77-1.61(m, 6H), 1.18(d, 3H) |
| 58 | N-(4-fluorophenyl)-4-methyl-6-(3-methylpiperidin-1-yl)pyrimidin-2-amine | $^1$H-NMR(400 MHz, CDCl$_3$) δ 7.54-7.51(m, 2H), 7.00-6.96(m, 2H), 6.76(brs, 1H), 5.91(s, 1H), 4.21(brs, 2H), 2.86(m, 1H), 2.53(dd, 1H), 2.25(s, 3H), 1.86(dd, 1H), 1.75-1.61(m, 2H), 1.54-1.49(m, 1H), 1.22-1.16(m, 1H), 0.95(d, 3H) |
| 59 | 4-(3,5-cis-dimethylpiperidin-1-yl)-N-(4-fluorophenyl)-6-methylpyrimidin-2-amine | $^1$H-NMR (400 MHz, CDCl$_3$) δ 7.55-7.50 (m, 2H), 6.99-6.94(m, 3H), 5.91(s, 1H), 4.28(d, 2H), 2.53(dd, 1H), 2.32(dd, 2H), 2.25(s, 3H), 1.84(d, 1H), 1.67-1.57(m, 2H), 0.94(d, 6H). 0.77(m, 1H) |

TABLE 1-6-continued

| Example | Compound | NMR Spectrum |
| --- | --- | --- |
| 60 | 4-(azepan-1-yl)-N-(4-fluorophenyl)-6-methylpyrimidin-2-amine | $^1$H-NMR(400 MHz, CDCl$_3$) δ 7.57-7.54(m, 2H), 6.99-6.94(m, 2H), 6.85(brs, 1H), 5.81(s, 1H), 3.59-3.35(m, 4H), 2.25(s, 3H), 1.79(brs, 4H), 1.56(dd, 4H) |

TABLE 1-7

| Example | Compound | NMR Spectrum |
| --- | --- | --- |
| 61 | 4-(2-ethylpiperidin-1-yl)-N-(4-fluorophenyl)-6-methylpyrimidin-2-amine | $^1$H-NMR(400 MHz, CDCl$_3$) δ 7.54-7.49(m, 2H), 7.07(brs, 1H), 6.99-6.93(m, 2H), 5.88(s, 1H), 4.38(brs, 1H), 4.21(brs, 1H), 2.91(m, 1H), 2.23(s, 3H), 1.74-1.58(m, 7H), 1.50-1.45(m, 1H), 0.89(dd, 3H) |
| 62 | 4-((2R,6S)-2,6-dimethylpiperidin-1-yl)-N-(4-fluorophenyl)-6-methylpyrimidin-2-amine | $^1$H-NMR(400 MHz, CDCl$_3$) δ 7.56-7.50(m, 2H), 7.00-6.94(m, 2H), 6.78(brs, 1H), 5.87(s, 1H), 4.55(brs, 2H), 2.25(s, 3H), 1.89-1.82(m, 1H), 1.75-1.69(m, 4H), 1.68-1.52(m, 1H), 1.25(s, 3H), 1.23(s, 3H) |
| 63 | N-(4-fluorophenyl)-4-methyl-6-(4-phenylpiperidin-1-yl)pyrimidin-2-amine | $^1$H-NMR(400 MHz, CDCl$_3$) δ 7.55-7.51(m, 2H), 7.33-7.30(m, 2H), 7.24-7.22(m, 2H), 7.00-6.96(m, 2H), 6.82(brs, 1H), 5.98(s, 1H), 4.51(d, 2H), 2.97(m, 2H), 2.85-2.74(m, 1H), 2.28(s, 3H), 1.94(d, 2H), 1.76-1.69(m, 2H) |
| 64 | N-(4-fluorophenyl)-4-methyl-6-(piperazin-1-yl)pyrimidin-2-amine | $^1$H-NMR(400 MHz, CDCl$_3$) δ 7.53-7.48(m, 2H), 7.02-6.95(m, 3H), 5.90(s, 1H), 3.59(dd, 4H), 2.93(dd, 4H), 2.27(s, 3H) |
| 65 | N-(4-fluorophenyl)-4-methyl-6-(4-methylpiperazin-1-yl)pyrimidin-2-amine | $^1$H-NMR(400 MHz, CDCl$_3$) δ 7.51-7.49(m, 2H), 7.05(brs, 1H), 7.01-6.96(m, 2H), 5.91(s, 1H), 3.62(dd, 4H), 2.46(dd, 4H), 2.33(s, 3H), 2.26(s, 3H) |
| 66 | 4-(2,5-dimethylpiperazin-1-yl)-N-(4-fluorophenyl)-6-methylpyrimidin-2-amine | $^1$H-NMR(400 MHz, CDCl$_3$) δ 7.53-7.50(m, 2H), 7.00-6.96(m, 2H), 6.91(brs, 1H), 5.86(s, 1H), 4.33(dd, 1H), 3.88(dd, 1H), 3.33-3.29(m, 3H), 2.65(dd, 1H), 2.27(s, 3H), 1.27(d, 3H), 1.20(d, 3H) |
| 67 | 4-(3,5-dimethylpiperazin-1-yl)-N-(4-fluorophenyl)-6-methylpyrimidin-2-amine | $^1$H-NMR(400 MHz, CDCl$_3$) δ 7.54-7.50(m, 2H), 7.00-6.96(m, 2H), 6.89(brs, 1H), 5.91(s, 1H), 4.21(d, 2H), 2.89-2.84(m, 2H), 2.45(dd, 2H), 2.26(s, 3H), 1.14(s, 3H), 1.13(s, 3H) |
| 68 | N-(4-fluorophenyl)-4-methyl-6-(octahydroquinolin-1(2H)-yl)pyrimidin-2-amine | $^1$H-NMR(400 MHz, CDCl$_3$) δ 7.56-7.52(m, 2H), 7.07(brs, 1H), 6.99-6.94(m, 2H), 5.78(s, 1H), 4.17(dd, 1H), 3.29(m, 1H), 3.16(m, 1H), 2.24(s, 3H), 2.16(dd, 1H), 1.86-1.61(m, 6H), 1.49-1.09(m, 6H) |
| 69 | N-(4-fluorophenyl)-4-methyl-6-(octahydroisoquinolin-2(1H)-yl)pyrimidin-2-amine | $^1$H-NMR(400 MHz, CDCl$_3$) δ 7.54-7.50(m, 2H), 7.11(brs, 1H), 7.00-6.95(m, 2H), 5.89(s, 1H), 4.05(brs, 1H), 3.89(brs, 1H), 3.22(d, 1H), 3.13(dd, 1H), 2.24(s, 3H), 1.92-1.88(m, 1H), 1.82-1.78(m, 2H), 1.76-1.24(m, 9H) |
| 70 | 4-(5,6-dihydropyridin-1(2H)-yl)-N-(4-fluorophenyl)-6-methylpyrimidin-2-amine | $^1$H-NMR(400 MHz, CDCl$_3$) δ 7.56-7.50(m, 2H), 7.08(brs, 1H), 7.08-6.96(m, 2H), 5.94-5.89(m, 2H), 5.78-5.75(m, 1H), 4.00(brs, 2H), 3.74(dd, 2H), 2.26-2.22(m, 5H) |

TABLE 1-8

| Example | Compound | NMR Spectrum |
| --- | --- | --- |
| 71 | 2-{1-[2-(4-fluorophenylamino)-6-methylpyrimidin-4-yl]piperidin-2-yl}ethanol | $^1$H-NMR(400 MHz, CDCl$_3$) δ 7.47-7.43(m, 2H), 7.02-6.97(m, 2H), 6.87(brs, 1H), 5.93(s, 1H), 4.90(brs, 1H), 3.82(brs, 1H), 3.55-3.50(m, 1H), 3.28(dd, 1H), 2.93(m, 1H), 2.25(s, 3H), 2.08(dd, 1H), 1.78-1.28(m, 7H) |
| 72 | 2-{1-[2-(4-fluorophenylamino)-6-methylpyrimidin-4-yl]piperidin-2-yl}methanol | $^1$H-NMR(400 MHz, CDCl$_3$) δ 7.49-7.45(m, 2H), 7.01-6.94(m, 3H), 5.93(s, 1H), 4.68(brs, 1H), 4.11(brs, 1H), 3.90(dd, 1H), 3.70(dd, 1H), 3.00(dd, 1H), 2.21(s, 3H), 1.81-1.49(m, 6H) |
| 73 | N-[4-(octahydroquinolin-1(2H)-yl)-6-propylpyrimidin-2-yl]-1H-indol-6-amine | $^1$H-NMR(400MHz, CDCl$_3$) δ 8.09(brs, 1H), 7.97(s, 1H), 7.49(d, 1H), 7.12-7.08(m, 2H), 6.89(brs, 1H), 6.46(s, 1H), 5.75(s, 1H), 4.26(dd, 2H), 3.32(m, 1H), 3.18-3.15(m, 1H), 2.46(dd, 2H), 2.23(dd, 1H), 1.89-1.50(m, 10H), 1.38-1.26(m, 2H), 1.16-1.10(m, 2H), 0.99(t, 3H) |

TABLE 1-8-continued

| Example | Compound | NMR Spectrum |
| --- | --- | --- |
| 74 | 2-{1-[2-(1H-indol-6-ylamino)-6-propylpyrimidin-4-yl]piperidin-2-yl}ethanol | ¹H-NMR(400 MHz, CDCl₃) δ 8.44(brs, 1H), 7.95(s, 1H), 7.49(d, 1H), 7.07(dd, 1H), 6.99(dd, 2H), 6.43(s, 1H), 5.88(s, 1H), 5.05(brs, 1H), 3.84-3.72(m, 1H), 3.55-3.53(m, 1H), 3.45-3.38(m, 1H), 2.99-2.93(m, 1H), 2.47(dd, 2H), 2.11-2.05(m, 1H), 1.78-1.44(m, 9H), 0.99(t, 3H) |
| 75 | 2-{1-[2-(1H-indol-6-ylamino)-6-propylpyrimidin-4-yl]piperidin-2-yl}ethanol hydrochloride | ¹H-NMR(400 MHz, CDCl₃) δ 12.00(brs, 1H), 10.26(brs, 1H), 9.95(s, 1H), 8.64(s, 1H), 7.26(d, 1H), 7.14(t, 1H), 6.71(d, 1H), 6.35(s, 1H), 5.60-5.40(m, 2H), 5.29(s, 1H), 4.10-4.00(m, 1H), 3.79(brs, 1H), 3.65-3.50(m, 1H), 3.20(t, 1H), 2.15-2.05(m, 2H), 2.05-2.00(m, 1H), 1.90-1.60(m, 6H), 1.50-1.35(m, 3H), 0.85(t, 3H) |
| 76 | N-[4-(piperidin-1-yl)-6-propylpyrimidin-2-yl]-1H-indol-6-amine | ¹H-NMR(400 MHz, CDCl₃) δ 8.12(brs, 1H), 7.98(s, 1H), 7.49(d, 1H), 7.10-7.06(m, 2H), 6.96(brs, 1H), 6.47(dd, 1H), 5.89(s, 1H), 3.61(dd, 4H), 2.47(dd, 2H), 1.77-1.61(m, 8H), 0.97(t, 3H) |
| 77 | N-(4-morpholino-6-propylpyrimidin-2-yl)-1H-indol-6-amine | ¹H-NMR(400 MHz, CDCl₃) δ 8.18(brs, 1H), 7.90(s, 1H), 7.51(d, 1H), 7.11-7.07(m, 2H), 6.95(brs, 1H), 6.48(dd, 1H), 5.89(s, 1H), 3.77(dd, 4H), 3.60(dd, 4H), 2.50(dd, 2H), 1.77-1.72(m, 2H), 0.99(t, 3H) |
| 78 | N-[4-(2-ethylpiperidin-1-yl)-6-propylpyrimidin-2-yl]-1H-indol-6-amine | ¹H-NMR(400 MHz, CDCl₃) δ 8.08(brs, 1H), 7.98(s, 1H), 7.49(d, 1H), 7.10-7.07(m, 2H), 6.89(brs, 1H), 6.47(dd, 1H), 5.86(s, 1H), 4.44(brs, 1H), 4.28(brs, 1H), 2.92(m, 1H), 2.46(dd, 2H), 1.78-1.61(m, 9H), 1.54-1.48(m, 1H), 1.05(dd, 3H), 0.97(t, 3H) |
| 79 | N-(4-morpholino-6-propylpyrimidin-2-yl)-1H-indol-6-amine hydrochloride | ¹H-NMR(400 MHz, CD₃OD) δ 7.58-7.56(m, 2H), 7.27(d, 1H), 7.00(dd, 1H), 6.46(d, 1H), 6.39(s, 1H), 3.81-3.75(m, 8H), 2.60(dd, 2H), 1.77-1.71(m, 2H), 1.03(dd, 3H) |

TABLE 1-9

| Example | Compound | NMR Spectrum |
| --- | --- | --- |
| 80 | (R)-3-[4-(3-ethylmorpholino)-6-propylpyrimidin-2-ylamino]benzonitrile | ¹H-NMR(400 MHz, CD₃OD) δ 8.16(s, 1H), 7.59(dd, 1H), 7.34(dd, 1H), 7.23(d, 1H), 5.89(s, 1H), 4.08(brs, 1H), 4.00-3.94(m, 3H), 3.64-3.53(m, 2H), 3.28(m, 1H), 2.49(dd, 2H), 1.96-1.68(m, 4H), 0.99-0.91(m, 6H) |
| 81 | (R)-tert-butyl 4-[2-(3-cyanophenylamino)-6-propylpyrimidin-4-yl]-3-methylpiperazin-1-carboxylate | ¹H-NMR(400 MHz, CDCl₃) δ 8.22(s, 1H), 7.58(d, 1H), 7.35(dd, 1H), 7.23(d, 1H), 7.02(brs, 1H), 5.93(s, 1H), 4.54-3.95(m, 4H), 3.27-2.99(m, 3H), 2.50(dd, 2H), 1.76-1.70(m, 2H), 1.49(s, 3H), 1.24(d, 3H), 0.99(t, 3H) |
| 82 | (R)-3-[4-(2-methylpiperazin-1-yl)-6-propylpyrimidin-2-ylamino]benzonitrile dihydrochloride | ¹H-NMR(400 MHz, CD₃OD) δ 8.00(s, 1H), 7.78(d, 1H), 7.62-7.58(m, 2H), 6.64(s, 1H), 3.54-3.24(m, 7H), 2.71(dd, 2H), 1.83-1.78(m, 2H), 1.47(d, 3H), 1.06(t, 3H) |
| 83 | 4-morpholino-N-(3-nitrophenyl)-6-propylpyrimidin-2-amine hydrochloride | ¹H-NMR(400 MHz, CDCl₃) δ 11.30(s, 1H), 9.05(dd, 1H), 7.98(dd, 1H), 7.64(dd, 1H), 7.51(dd, 1H), 6.01(s, 1H), 3.88(brs, 8H), 2.68(dd, 2H), 1.92-1.84(m, 2H), 1.04(t, 3H) |
| 84 | N-(4-fluoro-3-nitrophenyl)-4-morpholino-6-propylpyrimidin-2-amine hydrochloride | ¹H-NMR(400 MHz, CDCl₃) δ 11.24(s, 1H), 8.88(d, 1H), 7.61(d, 1H), 7.28(d, 1H), 6.03(s, 1H), 3.87(brs, 8H), 2.68(dd, 2H), 1.91-1.85(m, 2H), 1.04(t, 3H) |
| 85 | N-(4-chloro-3-nitrophenyl)-4-morpholino-6-propylpyrimidin-2-amine hydrochloride | ¹H-NMR(400 MHz, CDCl₃) δ 11.39(s, 1H), 8.74(s, 1H), 7.57(s, 1H), 6.02(s, 1H), 3.87(brs, 8H), 2.68(dd, 2H), 1.91-1.83(m, 2H), 1.04(t, 3H) |
| 86 | N-(3-methoxyphenyl)-4-morpholino-6-propylpyrimidin-2-amine hydrochloride | ¹H-NMR(400 MHz, CDCl₃) δ 13.86(brs, 1H), 10.56(s, 1H), 7.28-7.12(m, 3H), 6.69(dd, 1H), 5.96(s, 1H), 3.79(s, 3H), 3.96-3.61(m, 8H), 2.64(dd, 2H), 1.89-1.83(m, 2H), 1.02(t, 3H) |
| 87 | N-(4-methoxyphenyl)-4-morpholino-6-propylpyrimidin-2-amine hydrochloride | ¹H-NMR(400 MHz, CDCl₃) δ 10.29(s, 1H), 7.42(d, 2H), 6.87(d, 2H), 5.87(s, 1H), 3.80(s, 3H), 3.80-3.71(m, 8H), 2.64(dd, 2H), 1.89-1.83(m, 2H), 1.02(t, 3H) |
| 88 | N-[3-(methylthio)phenyl]-4-morpholino-6-propylpyrimidin-2-amine hydrochloride | ¹H-NMR(400 MHz, CDCl₃) δ 7.51(s, 1H), 7.31-7.23(m, 2H), 7.01(d, 1H), 5.98(dd, 1H), 3.93-3.64(m, 8H), 2.64(dd, 2H), 2.46(s, 3H), 1.89-1.83(m, 2H), 1.03(t, 3H) |

TABLE 1-9-continued

| Example | Compound | NMR Spectrum |
| --- | --- | --- |
| 89 | N-(3-chlorophenyl)-4-morpholino-6-propylpyrimidin-2-amine hydrochloride | $^1$H-NMR(400 MHz, CDCl$_3$) δ 13.97(brs, 1H), 10.79(s, 1H), 7.78(s, 1H), 7.36(d, 1H), 7.26(dd, 1H), 7.11(d, 1H), 5.94(s, 1H), 3.83(brs, 8H), 2.66(dd, 2H), 1.90-1.84(m, 2H), 1.03(t, 3H) |

TABLE 1-10

| Example | Compound | NMR Spectrum |
| --- | --- | --- |
| 90 | N-(3-chloro-4-methylphenyl)-4-morpholino-6-propylpyrimidin-2-amine hydrochloride | $^1$H-NMR(400 MHz, CDCl$_3$) δ 13.83(brs, 1H), 10.64(s, 1H), 7.74(d, 1H), 7.25(dd, 1H), 7.17(d, 1H), 5.95(s, 1H), 3.90-3.65(m, 8H), 2.64(dd, 2H), 2.33(s, 3H), 1.89-1.84(m, 2H), 1.02(t, 3H) |
| 91 | 4-morpholino-6-propyl-N-[3-(trifluoromethyl)phenyl]pyrimidin-2-amine hydrochloride | $^1$H-NMR(400 MHz, CDCl$_3$) δ 8.28(s, 1H), 8.26(brs, 1H), 7.47(d, 1H), 7.39(dd, 1H), 7.26(d, 1H), 5.94(s, 1H), 3.80(brs, 4H), 3.67(brs, 4H), 2.55(dd, 2H), 1.81-1.75(m, 2H), 1.00(t, 3H) |
| 92 | N-(4-morpholino-6-propylpyrimidin-2-yl)-1H-indol-5-amine hydrochloride | $^1$H-NMR(400 MHz, CD$_3$OD) δ 7.61(s, 1H), 7.45(d, 1H), 7.32(s, 1H), 7.14(d, 1H), 6.48(s, 1H), 6.38(s, 1H), 3.80-3.74(m, 8H), 2.60(dd, 2H), 1.85-1.71(m, 2H), 1.04(t, 3H) |
| 93 | N-(4-morpholino-6-propylpyrimidin-2-yl)-2-(trifluoromethyl)-1H-benzo[d]imidazol-6-amine hydrochloride | $^1$H-NMR(400 MHz, CD$_3$OD) δ 8.03(s, 1H), 7.74(d, 1H), 7.45(d, 1H), 6.48(s, 1H), 3.85-3.78(m, 8H), 2.66(dd, 2H), 1.82-1.76(m, 2H), 1.07(t, 3H) |
| 94 | N-(4-morpholino-6-propylpyrimidin-2-yl)quinolin-6-amine hydrochloride | $^1$H-NMR(400 MHz, CDCl$_3$) δ 8.55(d, 1H), 8.08(d, 1H), 7.97(d, 1H), 7.87(s, 1H), 7.41(dd, 1H), 5.99(s, 1H), 3.83(brs, 8H), 2.66(dd, 2H), 1.91-1.85(m, 2H), 1.03(t, 3H) |
| 95 | 3-(4-morpholino-6-propylpyrimidin-2-ylamino)benzonitrile | $^1$H-NMR(400 MHz, CDCl$_3$) δ 8.07(s, 1H), 7.70(d, 1H), 7.48-7.41(m, 2H), 6.04(s, 1H), 3.85(brs, 8H), 2.67(dd, 2H), 1.91-1.85(m, 2H), 1.03(t, 3H) |
| 96 | N-(5-methoxy-2-methylphenyl)-4-morpholino-6-propylpyrimidin-2-amine | $^1$H-NMR(400 MHz, CDCl$_3$) δ 7.94(s, 1H), 7.04(d, 1H), 6.62(brs, 1H), 6.50(d, 1H), 5.89(d, 1H), 3.79(s, 3H), 3.79-3.77(m, 4H), 3.61(s, 4H), 2.50(dd, 2H), 2.25(s, 3H), 1.77-1.71(m, 2H), 0.98(t, 3H) |
| 97 | N-(5-chloro-2-methylphenyl)-4-morpholino-6-propylpyrimidin-2-amine | $^1$H-NMR(400 MHz, CDCl$_3$) δ 8.37(s, 1H), 7.04(d, 1H), 6.88(d, 1H), 6.62(brs, 1H), 5.91(d, 1H), 3.80-3.74(m, 4H), 3.62-3.57(m, 4H), 2.49(dd, 2H), 2.27(s, 3H), 1.77-1.71(m, 2H), 0.98(t, 3H) |
| 98 | N-(4-morpholino-6-propylpyrimidin-2-yl)quinolin-3-amine | $^1$H-NMR(400 MHz, CDCl$_3$) δ 9.01(s, 1H), 8.54(s, 1H), 8.02(d, 1H), 7.71(d, 1H), 7.55-7.49(m, 2H), 7.32(brs, 1H), 5.96(d, 1H), 3.79(s, 4H), 3.63(s, 4H), 2.54(dd, 2H), 1.80-1.72(m, 2H), 1.00(t, 3H) |
| 99 | 4-(2-ethylpiperidin-1-yl)-N-(3-nitrophenyl)-6-propylpyrimidin-2-amine | $^1$H-NMR(400 MHz, CDCl$_3$) δ 9.10(s, 1H), 7.77(d, 1H), 7.50(d, 1H), 7.37(dd, 1H), 7.19(brs, 1H), 5.95(s, 1H), 4.47(brs, 1H), 4.33(brs, 1H), 3.00(dd, 1H), 2.48(dd, 2H), 1.82-1.53(m, 10H), 1.00(t, 3H), 0.89(t, 3H) |

TABLE 1-11

| Example | Compound | NMR Spectrum |
| --- | --- | --- |
| 100 | 4-(2-ethylpiperidin-1-yl)-N-(4-fluoro-3-nitrophenyl)-6-propylpyrimidin-2-amine | $^1$H-NMR(400 MHz, CDCl$_3$) δ 8.93(d, 1H), 7.43(brs, 2H), 7.16(dd, 1H), 5.95(s, 1H), 4.44(brs, 1H), 4.29(brs, 1H), 3.00(dd, 1H), 2.48(dd, 2H), 1.78-1.49(m, 10H), 0.98(t, 3H), 0.89(t, 3H) |
| 101 | N-(4-chloro-3-nitrophenyl)-4-(2-ethylpiperidin-1-yl)-6-propylpyrimidin-2-amine | $^1$H-NMR(400 MHz, CDCl$_3$) δ 8.81(s, 1H), 7.36-7.26(m, 3H), 5.95(s, 1H), 4.41(brs, 1H), 4.27(brs, 1H), 2.97(dd, 1H), 2.47(dd, 2H), 1.78-1.48(m, 10H), 0.98(t, 3H), 0.88(t, 3H) |
| 102 | 4-(2-ethylpiperidin-1-yl)-N-(3-methoxyphenyl)-6-propylpyrimidin-2-amine | $^1$H-NMR(400 MHz, CDCl$_3$) δ 7.49(s, 1H), 7.16(dd, 2H), 7.01(d, 1H), 6.52(d, 1H), 5.87(s, 1H), 4.42(brs, 1H), 4.31(brs, 1H), 3.80(s, 3H), 2.94(dd, 1H), 2.46(dd, 2H), 1.78-1.47(m, 10H), 0.98(t, 3H), 0.90(t, 3H) |
| 103 | 4-(2-ethylpiperidin-1-yl)-N-(4-methoxyphenyl)-6-propylpyrimidin-2-amine | $^1$H-NMR(400 MHz, CDCl$_3$) δ 8.08(brs, 1H), 7.49(d, 2H), 6.85(d, 2H), 5.84(s, 1H), 4.42(brs, 1H), 4.24(brs, 1H), 3.79(s, 3H), 2.95(dd, 1H), 2.50(dd, 2H), 1.79-1.47(m, 10H), 0.99(t, 3H), 0.89(t, 3H) |

TABLE 1-11-continued

| Example | Compound | NMR Spectrum |
|---|---|---|
| 104 | 4-(2-ethylpiperidin-1-yl)-N-[3-(methylthio)phenyl]-6-propylpyrimidin-2-amine | $^1$H-NMR(400 MHz, CDCl$_3$) δ 7.88(brs, 1H), 7.73(s, 1H), 7.25(d, 1H), 7.18(dd, 1H), 6.88(d, 1H), 5.88(s, 1H), 4.44(brs, 1H), 4.30(brs, 1H), 2.97(dd, 1H), 2.51-2.48(m, 2H), 2.48(s, 3H), 1.76-1.51(m, 10H), 0.99(t, 3H), 0.90(t, 3H) |
| 105 | N-(3-chlorophenyl)-4-(2-ethylpiperidin-1-yl)-6-propylpyrimidin-2-amine | $^1$H-NMR(400 MHz, CDCl$_3$) δ 7.95(s, 1H), 7.49(brs, 1H), 7.26(d, 1H), 7.17(dd, 1H), 6.93(d, 1H), 5.90(s, 1H), 4.45(brs, 1H), 4.24(brs, 1H), 2.98(dd, 1H), 2.48(dd, 2H), 1.76-1.49(m, 10H), 0.99(t, 3H), 0.92(t, 3H) |
| 106 | N-(3-chloro-4-methylphenyl)-4-(2-ethylpiperidin-1-yl)-6-propylpyrimidin-2-amine | $^1$H-NMR(400 MHz, CDCl$_3$) δ 7.92(s, 1H), 7.17(d, 1H), 7.08(d, 1H), 6.85(brs, 1H), 5.87(s, 1H), 4.43(brs, 1H), 4.23(brs, 1H), 2.95(dd, 1H), 2.44(dd, 2H), 2.31(s, 3H), 1.74-1.48(m, 10H), 0.98(t, 3H), 0.91(t, 3H) |
| 107 | 4-(2-ethylpiperidin-1-yl)-6-propyl-N-[3-(trifluoromethyl)phenyl]pyrimidin-2-amine | $^1$H-NMR(400 MHz, CDCl$_3$) δ 8.35(s, 1H), 7.96(brs, 1H), 7.45(d, 1H), 7.36(dd, 1H), 7.22(d, 1H), 5.92(s, 1H), 4.45(brs, 1H), 4.29(brs, 1H), 2.99(dd, 1H), 2.50(dd, 2H), 1.81-1.49(m, 10H), 0.99(t, 3H), 0.88(t, 3H) |
| 108 | N-[4-(2-ethylpiperidin-1-yl)-6-propylpyrimidin-2-yl]-1H-indol-5-amine | $^1$H-NMR(400 MHz, CDCl$_3$) δ 9.42(brs, 1H), 8.50(brs, 1H), 7.86(s, 1H), 7.33-7.25(m, 2H), 7.21(s, 1H), 6.46(s, 1H), 5.84(s, 1H), 4.49-4.11(m, 2H), 3.00(dd, 1H), 2.55(dd, 2H), 1.86-1.50(m, 10H), 1.00(t, 3H), 0.90(t, 3H) |
| 109 | N-[4-(2-ethylpiperidin-1-yl)-6-propylpyrimidin-2-yl]-2-(trifluoromethyl)-1H-benzo[d]imidazol-6-amine | $^1$H-NMR(400 MHz, CDCl$_3$) δ 9.66(brs, 1H), 8.35(brs, 1H), 8.11(s, 1H), 7.59(d, 1H), 7.28(d, 1H), 5.90(s, 1H), 4.35(brs, 2H), 2.89(dd, 1H), 2.49(dd, 2H), 1.77-1.44(m, 10H), 0.94(t, 3H), 0.84(t, 3H) |

TABLE 1-12

| Example | Compound | NMR Spectrum |
|---|---|---|
| 110 | N-[4-(2-ethylpiperidin-1-yl)-6-propylpyrimidin-2-yl]quinolin-6-amine | $^1$H-NMR(400 MHz, CDCl$_3$) δ 8.74(d, 1H), 8.34(d, 1H), 8.00(dd, 2H), 7.72(dd, 1H), 7.32(dd, 1H), 7.16(brs, 1H), 5.94(s, 1H), 4.48(brs, 1H), 4.31(brs, 1H), 2.99(dd, 1H), 2.50(dd, 2H), 1.82-1.51(m, 10H), 1.00(t, 3H), 0.90(t, 3H) |
| 111 | 3-[4-(2-ethylpiperidin-1-yl)-6-propylpyrimidin-2-ylamino]benzonitrile | $^1$H-NMR(400 MHz, CDCl$_3$) δ 8.26(s, 1H), 7.56(d, 1H), 7.33(dd, 1H), 7.20(d, 1H), 7.04(brs, 1H), 5.94(s, 1H), 4.41(brs, 1H), 4.22(brs, 1H), 2.97(m, 1H), 2.47(dd, 2H), 1.79-1.48(m, 10H), 0.98(t, 3H), 0.89(t, 3H) |
| 112 | 4-(2-ethylpiperidin-1-yl)-N-(5-methoxy-2-methylphenyl)-6-propylpyrimidin-2-amine | $^1$H-NMR(400 MHz, CDCl$_3$) δ 8.02(s, 1H), 7.02(d, 1H), 6.62(brs, 1H), 6.47(dd, 1H), 5.88(s, 1H), 4.38(brs, 2H), 3.79(s, 3H), 2.90(dd, 1H), 2.48(dd, 2H), 2.25(s, 3H), 1.77-1.45(m, 10H), 0.98(t, 3H), 0.89(t, 3H) |
| 113 | N-(5-chloro-2-methylphenyl)-4-(2-ethylpiperidin-1-yl)-6-propylpyrimidin-2-amine | $^1$H-NMR(400 MHz, CDCl$_3$) δ 8.46(s, 1H), 7.04(d, 1H), 6.85(d, 1H), 6.57(brs, 1H), 5.90(s, 1H), 4.42(brs, 1H), 4.25(brs, 1H), 2.95(dd, 1H), 2.46(dd, 2H), 2.27(s, 3H), 1.75-1.48(m, 10H), 0.97(t, 3H), 0.89(t, 3H) |
| 114 | N-[4-(2-ethylpiperidin-1-yl)-6-propylpyrimidin-2-yl]quinolin-3-amine | $^1$H-NMR(400 MHz, CDCl$_3$) δ 8.93(d, 1H), 8.67(d, 1H), 8.01(d, 1H), 7.71(d, 1H), 7.55-7.46(m, 2H), 7.26(brs, 1H), 5.96(s, 1H), 4.46(brs, 1H), 4.31(brs, 1H), 2.98(m, 1H), 2.51(dd, 2H), 1.81-1.50(m, 10H), 1.00(t, 3H), 0.91(t, 3H) |
| 115 | N-(4-chloro-3-nitrophenyl)-4-(2-ethylpiperidin-1-yl)-6-propylpyrimidin-2-amine hydrochloride | $^1$H-NMR(400 MHz, CDCl$_3$) δ 8.80(d, 1H), 8.23(s, 1H), 7.53-7.47(m, 2H), 5.99(s, 1H), 5.11-3.21(m, 5H), 2.63(dd, 2H), 1.91-1.54(m, 10H), 1.03(t, 3H), 0.94(t, 3H) |
| 116 | 3-[4-(2-ethylpiperidin-1-yl)-6-propylpyrimidin-2-ylamino]benzonitrile hydrochloride | $^1$H-NMR(400 MHz, CDCl$_3$) δ 13.60(brs, 1H), 11.04(brs, 1H), 8.23(s, 1H), 7.66(d, 1H), 7.45-7.26(m, 2H), 5.96(brs, 1H), 4.89(brd, 1H), 3.90(brd, 1H), 3.15(brd, 1H), 2.65-2.62(m, 2H), 1.90-1.54(m, 10H), 1.04(t, 3H), 0.94(brs, 3H) |
| 117 | (R)-N-(4-chloro-3-nitrophenyl)-4-(2-methylpiperazin-1-yl)-6-propylpyrimidin-2-amine | $^1$H-NMR(400 MHz, CDCl$_3$) δ 8.85(d, 1H), 7.55(brs, 1H), 7.40(d, 1H), 7.32(dd, 1H), 5.95(s, 1H), 4.54(brs, 1H), 4.10(d, 1H), 3.25-3.19(m, 2H), 3.07-3.04(m, 2H), 2.85(dd, 1H), 2.51(dd, 2H), 1.77-1.69(m, 2H), 1.35(d, 3H), 0.98(t, 3H) |

TABLE 1-12-continued

| Example | Compound | NMR Spectrum |
| --- | --- | --- |
| 118 | (R)-N-[4-(2-methylpiperazin-1-yl)-6-propylpyrimidin-2-yl]-1H-indol-6-amine | $^1$H-NMR(400 MHz, CD$_3$OD) δ 7.68(s, 1H), 7.50(d, 1H), 7.20(d, 1H), 7.03(d, 1H), 6.41(d, 1H), 6.28(s, 1H), 4.87(brs, 1H), 4.49(d, 1H), 3.48-3.23(m, 4H), 3.08(m, 1H), 2.56(dd, 2H), 1.78-1.72(m, 2H), 1.38(d, 3H), 1.01(t, 3H) |
| 119 | (R)-N-(2-methylpiperazin-1-yl)-6-propyl-N-[3-(trifluoromethyl)phenyl]pyrimidin-2-amine | $^1$H-NMR(400 MHz, CDCl$_3$) δ 8.35(s, 1H), 8.01(brs, 1H), 7.43-7.36(m, 2H), 7.25(d, 1H), 5.92(s, 1H), 4.56(brs, 1H), 4.10(d, 1H), 3.28-3.19(m, 2H), 3.08-3.00(m, 2H), 2.85(m, 1H), 2.53(dd, 2H), 1.81-1.72(m, 2H), 1.37(d, 3H), 1.00(t, 3H) |

TABLE 1-13

| Example | Compound | NMR Spectrum |
| --- | --- | --- |
| 120 | (R)-N-(2-methylpiperazin-1-yl)-N-(3-nitrophenyl)-6-propylpyrimidin-2-amine | $^1$H-NMR(400 MHz, CD$_3$OD) δ 9.13(s, 1H), 7.76(d, 1H), 7.67(d, 1H), 7.45(dd, 1H), 6.19(d, 1H), 4.81(brd, 1H), 4.33(d, 1H), 3.30-3.23(m, 2H), 3.17(d, 2H), 2.97(m, 1H), 2.53(dd, 2H), 1.79-1.73(m, 2H), 1.35(d, 3H), 0.99(t, 3H) |
| 121 | (R)-N-(4-fluoro-3-nitrophenyl)-4-(2-methylpiperazin-1-yl)-6-propylpyrimidin-2-amine | $^1$H-NMR(400 MHz, CD$_3$OD) δ 8.96(dd, 1H), 7.64(dd, 1H), 7.28(dd, 1H), 6.17(s, 1H), 4.75(brs, 1H), 4.29(d, 1H), 3.27-3.21(m, 2H), 3.13(d, 2H), 2.93(m, 1H), 2.51(dd, 2H), 1.78-1.70(m, 2H), 1.33(d, 3H), 0.98(t, 3H) |
| 122 | (R)-N-(4-methyl-3-nitrophenyl)-4-(2-methylpiperazin-1-yl)-6-propylpyrimidin-2-amine | $^1$H-NMR(400 MHz, CD$_3$OD) δ 8.83(d, 1H), 7.49(dd, 1H), 7.27(d, 1H), 6.15(s, 1H), 4.77-4.75(m, 1H), 4.29(d, 1H), 3.26-3.19(m, 2H), 3.12(d, 2H), 2.92(m, 1H), 2.50(dd, 2H), 2.49(s, 3H), 1.77-1.70(m, 2H), 1.32(d, 3H), 0.98(t, 3H) |
| 123 | (R)-4-fluoro-N$^1$-[4-(2-methylpiperazin-1-yl)-6-propylpyrimidin-2-yl]benzene-1,3-diamine | $^1$H-NMR(400 MHz, CD$_3$OD) δ 7.07(dd, 1H), 6.89(dd, 1H), 6.79-6.77(m, 1H), 6.23(s, 1H), 4.87(brs, 1H), 4.47(d, 1H), 3.44-3.25(m, 4H), 3.10(m, 1H), 2.53(dd, 2H), 1.76-1.70(m, 2H), 1.36(d, 3H), 0.99(t, 3H) |
| 124 | (R)-N$^1$-[4-(2-methylpiperazin-1-yl)-6-propylpyrimidin-2-yl]-3-(trifluoromethyl)benzene-1,4-diamine | $^1$H-NMR(400 MHz, CD$_3$OD) δ 7.83(d, 1H), 7.32(dd, 1H), 6.82(d, 1H), 6.16(s, 1H), 4.87(brs, 1H), 4.40(dd, 1H), 3.39-3.21(m, 4H), 3.06(m, 1H), 2.50(dd, 2H), 1.76-1.70(m, 2H), 1.34(d, 3H), 0.98(t, 3H) |
| 125 | (R)-2-fluoro-5-[4-(2-methylpiperazin-1-yl)-6-propylpyrimidin-2-ylamino]benzonitrile | $^1$H-NMR(400 MHz, CD$_3$OD) δ 8.26-8.24(m, 1H), 7.82-7.78(m, 1H), 7.23(dd, 1H), 6.13(s, 1H), 4.59(brs, 1H), 4.16(d, 1H), 3.18-3.12(m, 2H), 3.04-2.98(m, 2H), 2.85-2.79(m, 1H), 2.50(dd, 2H), 1.76-1.69(m, 2H), 1.30(d, 3H), 0.98(t, 3H) |
| 126 | (R)-2-methyl-5-[4-(2-methylpiperazin-1-yl)-6-propylpyrimidin-2-ylamino]benzonitrile | $^1$H-NMR(400 MHz, CD$_3$OD) δ 8.19(d, 1H), 7.63(dd, 1H), 7.27(d, 1H), 6.15(s, 1H), 4.74-4.73(m, 1H), 4.27(d, 1H), 3.28-3.20(m, 2H), 3.15(d, 2H), 2.98-2.92(m, 1H), 2.51(dd, 2H), 2.45(s, 3H), 1.77-1.71(m, 2H), 1.34(d, 3H), 0.98(t, 3H) |
| 127 | (R)-2-amino-5-[4-(2-methylpiperazin-1-yl)-6-propylpyrimidin-2-ylamino]benzonitrile | $^1$H-NMR(400 MHz, CD$_3$OD) δ 7.70(s, 1H), 7.40(d, 1H), 6.80(d, 1H), 6.19(s, 1H), 4.88(brs, 1H), 4.40(d, 1H), 3.43-3.24(m, 4H), 3.10(m, 1H), 2.51(dd, 2H), 1.76-1.68(m, 2H), 1.36(d, 3H), 0.99(t, 3H) |
| 128 | (R)-N$^1$-[4-(2-methylpiperazin-1-yl)-6-propylpyrimidin-2-yl]-3-nitrobenzene-1,4-diamine | $^1$H-NMR(400 MHz, CD$_3$OD) δ 8.79(s, 1H), 7.34(d, 1H), 6.92(d, 1H), 6.14(s, 1H), 4.88(brs, 1H), 4.44(d, 1H), 3.40-3.24(m, 4H), 3.09(m, 1H), 2.50(dd, 2H), 1.76-1.71(m, 2H), 1.36(d, 3H), 0.98(t, 3H) |
| 129 | (R)-3-amino-5-[4-(2-methylpiperazin-1-yl)-6-propylpyrimidin-2-ylamino]benzonitrile | $^1$H-NMR(400 MHz, CD$_3$OD) δ 7.45(s, 1H), 7.12(s, 1H), 6.56(s, 1H), 6.18(s, 1H), 4.84(brd, 1H), 4.36(d, 1H), 3.39-3.20(m, 4H), 3.04(m, 1H), 2.52(dd, 2H), 1.77-1.69(m, 2H), 1.36(d, 3H), 0.98(t, 3H) |

TABLE 1-14

| Example | Compound | NMR Spectrum |
| --- | --- | --- |
| 130 | (R)-3-[4-(2-methylpiperazin-1-yl)-6-propylpyrimidin-2-ylamino]benzamide | $^1$H-NMR(400 MHz, CD$_3$OD) δ 8.43(s, 1H), 7.61(d, 1H), 7.45(d, 1H), 7.36(dd, 1H), 6.22(s, 1H), 4.96(brs, 1H), 4.52(d, 1H), 3.47-3.31(m, 4H), 3.14(dd, 1H), 2.53(dd, 2H), 1.78-1.72(m, 2H), 1.37(d, 3H), 0.99(t, 3H) |

TABLE 1-14-continued

| Example | Compound | NMR Spectrum |
|---|---|---|
| 131 | 3-{4-[2-(2-hydroxyethyl)piperidin-1-yl]-6-propylpyrimidin-2-ylamino}benzonitrile | $^1$H-NMR(400 MHz, CDCl$_3$) δ 8.19(s, 1H), 7.64(d, 1H), 7.36(t, 1H), 7.26(m, 1H), 6.05(s, 1H), 4.92(br, 1H), 4.01(br, 1H), 3.65(m, 1H), 3.46(m, 1H), 3.02(m, 1H), 2.52(t, 2H), 2.10-2.05(m, 2H), 1.81-1.72(m, 8H), 1.53(m, 1H), 0.99(t, 3H) |
| 132 | 2-{1-[2-(4-chloro-3-nitrophenylamino)-6-propylpyrimidin-4-yl]piperidin-2-yl}ethanol hydrochloride | $^1$H-NMR(400 MHz, CDCl$_3$) δ 13.39(br, 1H), 11.20(d, 1H), 8.78(s, 1H), 8.59(s, 1H), 7.67(m, 1H), 7.47(m, 3H), 7.24(m, 1H), 6.36(s, 1H), 5.98(s, 1H), 5.41(br, 1H), 4.90-4.87(br, 1H), 4.47(br, 1H), 3.83(br, 1H), 3.78(m, 1H), 3.57(m, 2H), 3.31(m, 1H), 3.03(m, 1H), 2.60(m, 4H), 2.09(m, 2H), 2.00-1.84(m, 16H), 1.60(br, 2H), 0.99(m, 6H) |
| 133 | 2-(1-{2-[3-(methylthio)phenylamino]-6-propylpyrimidin-4-yl}piperidin-2-yl)ethanol hydrochloride | $^1$H-NMR(400 MHz, CDCl$_3$) δ 13.60(s, 1H), 13.35(s, 1H), 10.45(s, 1H), 10.41(s, 1H), 7.61(s, 1H), 7.48(s, 1H), 7.34-7.21(m, 4H), 7.00(m, 2H), 6.23(s, 1H), 5.92(s, 1H), 5.24(br, 1H), 4.88(d, 1H), 4.45(br, 1H), 3.82-3.75(m, 2H), 3.58(br, 1H), 3.47(br, 1H), 3.24(t, 1H), 2.95(t, 1H), 2.62(m, 4H), 2.47(s, 6H), 2.33(br, 2H), 2.08(br, 2H), 1.85(m, 16H), 1.50(br, 2H), 0.95(m, 6H) |
| 134 | 2-{1-[2-(1-ethyl-1H-indol-6-ylamino)-6-propylpyrimidin-4-yl]piperidin-2-yl}ethanol | $^1$H-NMR(400 MHz, CDCl$_3$) δ 7.89(brs, 1H), 7.50(d, 1H), 7.04-7.00(m, 2H), 6.42(m, 1H), 5.93(s, 1H), 4.92(br, 1H), 4.14(m, 2H), 3.50(m, 1H), 3.33(br, 1H), 2.97(m, 1H), 2.52(m, 2H), 2.09-2.04(m, 2H), 1.82-1.71(m, 8H), 1.55(t, 3H), 1.28(t, 3H) |
| 135 | 2-{1-[2-(1H-indol-5-ylamino)-6-propylpyrimidin-4-yl]piperidin-2-yl}ethanol | $^1$H-NMR(400 MHz, CDCl$_3$) δ 8.59(s, 1H), 7.68(s, 1H), 7.22(m, 2H), 7.20-6.98(br, 1H), 6.99(s, 1H), 6.40(s, 1H), 5.87(s, 1H), 4.98(br, 1H), 3.42(m, 1H), 3.23(m, 1H), 2.93(m, 1H), 2.47(m, 2H), 2.02(m, 1H), 1.82-1.62(m, 8H), 1.56(m, 2H), 1.01(t, 3H) |
| 136 | 2-(1-{6-propyl-2-[2-(trifluoromethyl)-1H-benzo[d]imidazol-6-ylamino]pyrimidin-4-yl}piperidin-2-yl)ethanol | $^1$H-NMR(400 MHz, CDCl$_3$) δ 8.09(br, 1H), 7.51(d, 1H), 7.45(br, 1H), 7.13(d, 1H), 6.81(brs, 1H), 6.75(d, 1H), 5.87(s, 1H), 5.08(br, 1H), 3.81(br, 2H), 3.67-3.51(m, 2H), 3.03(m, 1H), 2.33(m, 2H), 2.06(m, 1H), 1.75-1.61(m, 7H), 1.52(m, 1H), 0.93(t, 3H) |
| 137 | 2-{1-[2-(4-methoxyphenylamino)-6-propylpyrimidin-4-yl]piperidin-2-yl}ethanol | $^1$H-NMR(400 MHz, CDCl$_3$) δ 7.43(d, 2H), 6.87(d, 2H), 5.97(br, 1H), 4.87(br, 1H), 3.80(s, 3H), 3.57(br, 1H), 3.38(m, 1H), 2.99(m, 1H), 2.53(m, 2H), 2.05(m, 1H), 1.80-1.70(m, 8H), 1.53(m, 1H), 1.00(t, 3H) |
| 138 | 2-{1-[2-(3-methoxyphenylamino)-6-propylpyrimidin-4-yl]piperidin-2-yl}ethanol | $^1$H-NMR(400 MHz, CDCl$_3$) δ 7.42(s, 1H), 7.17(t, 1H), 6.95(d, 1H), 6.89(br, 1H), 6.54(d, 1H), 5.93(s, 1H), 4.97(br, 1H), 3.95(br, 1H), 3.90(s, 3H), 3.56(m, 1H), 3.35(m, 1H), 2.95(m, 1H), 2.47(m, 2H), 2.06(m, 1H), 1.79-1.63(m, 8H), 1.54(m, 1H), 1.00(t, 3H) |

TABLE 1-15

| Example | Compound | NMR Spectrum |
|---|---|---|
| 139 | 2-{1-[2-(5-methoxy-2-methylphenylamino)-6-propylpyrimidin-4-yl]piperidin-2-yl}ethanol | $^1$H-NMR(400 MHz, CDCl$_3$) δ 7.70(s, 1H), 7.05(d, 1H), 6.55(d, 1H), 5.94(s, 1H), 4.94(br, 1H), 4.09(br, 1H), 3.79(s, 3H), 3.52(m, 1H), 3.34(m, 1H), 2.96(t, 1H), 2.49(m, 2H), 2.26(s, 3H), 2.04(m, 1H), 1.80-1.64(m, 8H), 1.52(m, 1H), 1.01(t, 3H) |
| 140 | 2-{1-[2-(3-chloro-4-methylphenylamino)-6-propylpyrimidin-4-yl]piperidin-2-yl}ethanol | $^1$H-NMR(400 MHz, CDCl$_3$) δ 7.77(s, 1H), 7.20(d, 1H), 7.10(d, 1H), 5.95(s, 1H), 4.91(br, 1H), 3.96(br, 1H), 3.58(m, 1H), 3.38(m, 1H), 2.97(t, 1H), 2.48(m, 2H), 2.30(s, 3H), 2.07(m, 1H), 1.77-1.71(m, 8H), 1.52(m, 1H), 0.98(t, 3H) |
| 141 | 2-{1-[2-(3-nitrophenylamino)-6-propylpyrimidin-4-yl]piperidin-2-yl}ethanol | $^1$H-NMR(400 MHz, CDCl$_3$) δ 8.96(s, 1H), 7.77(d, 1H), 7.54(d, 1H), 7.37(m, 2H), 6.02(s, 1H), 4.99(br, 1H), 3.96(br, 1H), 3.60(m, 1H), 3.42(m, 1H), 2.93(t, 1H), 2.50(m, 2H), 2.07(m, 1H), 1.81-1.68(m, 8H), 1.54(m, 1H), 0.99(t, 3H) |
| 142 | 2-{1-[2-(4-fluoro-3-nitrophenylamino)-6-propylpyrimidin-4-yl]piperidin-2-yl}ethanol | $^1$H-NMR(400 MHz, CDCl$_3$) δ 8.80(d, 1H), 7.76(br, 1H), 7.52(m, 1H), 7.15(t, 1H), 6.03(s, 1H), 4.97(br, 1H), 3.97(br, 1H), 3.60(m, 1H), 3.41(m, 1H), 2.99(t, 1H), 2.50(m, 2H), 2.09(m, 1H), 1.80-1.71(m, 8H), 1.52(m, 1H), 0.99(t, 3H) |
| 143 | 2-{1-[2-(2,3-dimethylbenzofuran-5-ylamino)-6-propylpyrimidin-4-yl]piperidin-2-yl}ethanol | $^1$H-NMR(400 MHz, CDCl$_3$) δ 7.74(s, 1H), 7.26(d, 1H), 7.15(d, 1H), 6.78(br, 1H), 5.89(s, 1H), 4.99(br, 1H), 3.86(br, 1H), 3.47(m, 1H), 3.28(m, 1H), 2.94(m, 1H), 2.47(m, 2H), 2.35(s, 3H), 2.19(s, 3H), 2.11-2.05(br, 1H), 1.82-1.57(m, 9H), 1.00(t, 3H) |

TABLE 1-15-continued

| Example | Compound | NMR Spectrum |
| --- | --- | --- |
| 144 | 2-{1-[6-propyl-2-(quinolin-6-ylamino)pyrimidin-4-yl]piperidin-2-yl}ethanol | $^1$H-NMR(400 MHz, CDCl$_3$) δ 8.75(d, 1H), 8.28(d, 1H), 8.04(d, 1H), 8.00(d, 1H), 7.70(dd, 1H), 7.33(m, 1H), 7.07(br, 1H), 6.00(s, 1H), 5.01(br, 1H), 3.95(br, 1H), 3.59(m, 1H), 3.40(m, 1H), 2.96(t, 1H), 2.53(m, 2H), 2.07(m, 1H), 1.84-1.68(m, 8H), 1.57(m, 1H), 1.01(t, 3H) |
| 145 | 2-{1-[2-(3-chlorophenylamino)-6-propylpyrimidin-4-yl]piperidin-2-yl}ethanol | $^1$H-NMR(400 MHz, CDCl$_3$) δ 7.85(s, 1H), 7.27(d, 1H), 7.18(t, 1H), 6.94(d, 1H), 6.89(br, 1H), 5.95(s, 1H), 4.93(br, 1H), 3.90(br, 1H), 3.61(m, 1H), 3.39(t, 1H), 2.96(t, 1H), 2.48(m, 2H), 2.07(m, 1H), 1.79-1.65(m, 8H), 1.52(m, 1H), 0.97(t, 3H) |
| 146 | 7-{4-[2-(2-hydroxyethyl)piperidin-1-yl]-6-propylpyrimidin-2-ylamino}-4-methyl-2H-chromen-2-one | $^1$H-NMR(400 MHz, CDCl$_3$) δ 8.01(s, 1H), 7.85(br, 1H), 7.46(d, 1H), 7.22(m, 1H), 6.12(s, 1H), 6.02(s, 1H), 4.95(br, 1H), 3.95(br, 1H), 3.63(m, 1H), 3.44(m, 1H), 2.97(t, 1H), 2.53(m, 2H), 2.39(s, 3H), 2.08(m, 1H), 1.79-1.69(m, 8H), 1.56(m, 1H), 0.99(t, 3H) |
| 147 | 2-{1-[6-propyl-2-(3-trifluoromethylphenylamino)pyrimidin-4-yl]piperidin-2-yl}ethanol | $^1$H-NMR(400 MHz, CDCl$_3$) δ 8.20(s, 1H), 7.45(d, 1H), 7.36(t, 1H), 7.21(d, 1H), 6.97(br, 1H), 5.97(s, 1H), 4.94(br, 1H), 4.13(br, 1H), 3.56(m, 1H), 3.38(m, 1H), 2.99(m, 1H), 2.50(t, 1H), 2.08(m, 2H), 1.80-1.63(m, 8H), 1.54(m, 1H), 0.99(t, 3H) |

TABLE 1-16

| Example | Compound | NMR Spectrum |
| --- | --- | --- |
| 148 | 2-{1-[6-propyl-2-(quinolin-3-ylamino)pyrimidin-4-yl]piperidin-2-yl}ethanol | $^1$H-NMR(400 MHz, CDCl$_3$) δ 8.96(s, 1H), 8.58(d, 1H), 8.00(d, 1H), 7.71(d, 1H), 7.55-7.51(m, 2H), 7.47(br, 1H), 6.02(s, 1H), 5.00(br, 1H), 3.95(br, 1H), 3.63(m, 1H), 3.48(m, 1H), 2.97(t, 1H), 2.52(m, 2H), 2.08(m, 1H), 1.81-1.65(m, 8H), 1.54(m, 1H), 1.99(t, 3H) |
| 149 | 3-{4-[2-(2-hydroxyethyl)piperidin-1-yl]-6-propylpyrimidin-2-ylamino}benzonitrile hydrochloride | $^1$H-NMR(400 MHz, CDCl$_3$) δ 13.60(br, 1H), 11.06(d, 1H), 8.16(br, 2H), 7.70(m, 2H), 7.43(m, 4H), 6.03(s, 2H), 5.27(m, 1H), 4.82(m, 1H), 4.29(m, 1H), 4.08(m, 2H), 3.97(m, 2H), 3.87(m, 1H), 3.31(m, 1H), 3.06(m, 1H), 2.65(m, 4H), 2.19(m, 2H), 2.00-1.57(m, 16H), 1.52(m, 2H), 1.00(m, 6H) |
| 150 | (S)-5-[4-(3-aminopiperidin-1-yl)-6-propylpyrimidin-2-ylamino]-2-methylbenzonitrile dihydrochloride | $^1$H-NMR(400 MHz, CD$_3$OD) δ 7.92-7.83(d, 1H), 7.72-7.64(d, 1H), 7.49(m, 1H), 6.59(m, 1H), 4.59-3.99(br, 2H), 3.65-3.60(m, 3H), 2.68(m, 2H), 2.53(s, 3H), 2.20(m, 1H), 1.95(br, 1H), 1.80(m, 4H), 1.06(t, 3H) |
| 151 | (S)-4-(3-aminopiperidin-1-yl)-N-(3-nitrophenyl)-6-propylpyrimidin-2-amine dihydrochloride | $^1$H-NMR(400 MHz, CD$_3$OD) δ 8.80(s, 1H), 8.07(d, 1H), 7.75(d, 1H), 7.67(m, 1H), 6.64(br, 1H), 4.47-4.03(br, 2H), 3.50(m, 3H), 2.70(m, 2H), 2.22(m, 1H), 1.99(m, 1H), 1.82(m, 4H), 1.07(t, 3H) |
| 152 | (S)-3-[4-(3-aminopiperidin-1-yl)-6-propylpyrimidin-2-ylamino]benzonitrile dihydrochloride | $^1$H-NMR(400 MHz, CD$_3$OD) δ 7.99-7.94(br, 1H), 7.81(br, 1H), 7.57(m, 2H), 6.62(br, 1H), 4.82-4.18(br, 2H), 3.57(m, 2H), 3.48(br, 1H), 2.69(m, 2H), 2.20(br, 1H), 1.96(br, 1H), 1.79(m, 4H), 1.06(t, 3H) |
| 153 | (R)-5-[4-(3-aminopiperidin-1-yl)-6-propylpyrimidin-2-ylamino]-2-methylbenzonitrile | $^1$H-NMR(400 MHz, CDCl$_3$) δ 8.25(d, 1H), 7.42(d, H), 7.40(br, 1H), 7.17(d, 1H), 5.96(s, 1H), 4.25(m, 1H), 4.05(m, 1H), 3.05(m, 1H), 2.87(m, 1H), 2.78(m, 1H), 2.47-2.45(m, 5H), 2.02(br, 3H), 1.84(m, 1H), 1.74(m, 2H), 1.68(m, 1H), 1.38(m, 1H), 1.00(t, 3H) |
| 154 | (S)-5-{4-[3-(butylamino)piperidin-1-yl]-6-propylpyrimidin-2-ylamino}-2-methylbenzonitrile | $^1$H-NMR(400 MHz, CDCl$_3$) δ 8.11(s, 1H), 7.51(d, 1H), 7.18(d, 1H), 6.94(br, 1H), 5.96(s, 1H), 4.29(br, 1H), 4.05(br, 1H), 3.05(t, 1H), 2.87(m, 1H), 2.69(m, 3H), 2.49-2.45(m, 3 + 2H), 2.01(m, 1H), 1.81(m, 1H), 1.73(m, 2H), 1.60(m, 3H), 1.46(m, 2H), 1.35(m, 2H), 0.95(t, 3H), 0.85(t, 3H) |
| 155 | (S)-5-{4-[3-(pentylamino)piperidin-1-yl]-6-propylpyrimidin-2-ylamino}-2-methylbenzonitrile | $^1$H-NMR(400 MHz, CDCl$_3$) δ 8.11(s, 1H), 7.53(dd, 1H), 7.18(d, 1H), 7.00(br, 1H), 5.96(s, 1H), 4.25(m, 1H), 4.05(m, 1H), 2.90(m, 1H), 2.72(m, 1H), 2.68(m, 3H), 2.48(m, 5H), 2.01(m, 1H), 1.83(m, 1H), 1.77(m, 3H), 1.69(m, 2H), 1.53(m, 3H), 1.31(m, 4H), 0.98(t, 3H), 0.87(t, 3H) |

TABLE 1-16-continued

| Example | Compound | NMR Spectrum |
| --- | --- | --- |
| 156 | (S)-5-{4-[3-(isobutylamino)piperidin-1-yl]-6-propylpyrimidin-2-ylamino}-2-methylbenzonitrile | $^1$H-NMR(400 MHz, CDCl$_3$) δ 8.09(s, 1H), 7.53(d, 1H), 7.18(d, 1H), 7.06(br, 1H), 5.96(s, 1H), 4.28(m, 1H), 4.05(m, 1H), 3.07(m, 1H), 2.87(m, 1H), 2.63(m, 1H), 2.59-2.44(m, 7H), 2.02(m, 1H), 1.83(m, 1H), 1.77(m, 5H), 1.55(m, 1H), 1.46(m, 1H), 1.00(t, 3H), 0.90(m, 6H) |

TABLE 1-17

| Example | Compound | NMR Spectrum |
| --- | --- | --- |
| 157 | (S)-5-{4-[3-(isopentylamino)piperidin-1-yl]-6-propylpyrimidin-2-ylamino}-2-methylbenzonitrile | $^1$H-NMR(400 MHz, CDCl$_3$) δ 8.11(d, 1H), 7.51(dd, 1H), 7.18(d, 1H), 7.03(br, 1H), 5.96(s, 1H), 4.27(m, 1H), 4.05(m, 1H), 3.08(m, 1H), 2.91(m, 1H), 2.69(m, 3H), 2.47(m, 5H), 2.02(m, 1H), 1.83(m, 1H), 1.79(m, 4H), 1.58(m, 3H), 1.45(m, 3H), 0.95(t, 3H), 0.85(m, 6H) |
| 158 | (S)-2-methyl-5-{4-[3-(neopentylamino)piperidin-1-yl]-6-propylpyrimidin-2-ylamino}benzonitrile | $^1$H-NMR(400 MHz, CDCl$_3$) δ 8.07(s, 1H), 7.55(d, 1H), 7.18(d, 1H), 6.95(br, 1H), 5.95(s, 1H), 4.24(m, 1H), 4.04(m, 1H), 3.10(m, 1H), 2.86(m, 1H), 2.57(m, 1H), 2.47(m, 5H), 2.01(m, 1H), 1.83(m, 1H), 1.77(m, 2H), 1.67(m, 3H), 1.54(m, 2H), 1.00(t, 3H), 0.90(s, 9H) |
| 159 | (S)-5-(4-{3-[(1H-pyrrol-2-yl)methylamino]piperidin-1-yl}-6-propylpyrimidin-2-ylamino)-2-methylbenzonitrile | $^1$H-NMR(400 MHz, CDCl$_3$) δ 8.93(br, 1H), 8.32(s, 1H), 7.33(d, 1H), 7.17(d, 1H), 6.73(s, 1H), 6.11(s, 1H), 6.02(s, 1H), 5.91(s, 1H), 4.32(br, 1H), 3.91(m, 3H), 3.08(m, 1H), 2.96(m, 1H), 2.72(m, 1H), 2.48-2.45(m, 5H), 2.05(m, 1H), 1.83(m, 1H), 1.72(m, 3H), 1.58(m, 1H), 1.46(m, 1H), 0.95(m, 3H) |
| 160 | (S)-2-methyl-5-(4-propyl-6-{3-[(thiophen-2-ylmethyl)amino]piperidin-1-yl}pyrimidin-2-ylamino)benzonitrile | $^1$H-NMR(400 MHz, CDCl$_3$) δ 8.10(s, 1H), 7.51(dd, 1H), 7.20-7.16(m, 2H), 7.00(br, 1H), 6.94-6.91(m, 2H), 5.92(s, 1H), 4.25(m, 1H), 4.07(m, 2H), 4.04(m, 1H), 3.08(m, 1H), 2.99(m, 1H), 2.72(m, 1H), 2.46(m, 5H), 1.99(m, 1H), 1.80(m, 1H), 1.71(m, 2H), 1.58-1.45(m, 3H), 0.98(t, 3H) |
| 161 | (S)-5-(4-{3-[(4,5-dimethylfuran-2-ylmethyl)amino]piperidin-1-yl}-6-propylpyrimidin-2-ylamino)-2-methylbenzonitrile | $^1$H-NMR(400 MHz, CDCl$_3$) δ 8.09(s, 1H), 7.52(m, 1H), 7.17(d, 1H), 6.97(br, 1H), 5.93(s, 1H), 5.92(s, 1H), 4.20-4.09(m, 2H), 3.77(s, 2H), 3.02(m, 1H), 2.90(m, 1H), 2.66(m, 5H), 2.49(s, 3H), 2.01(m, 1H), 1.89(s, 3H), 1.77(m, 1H), 1.69(m, 3H), 1.55(m, 1H), 1.47(m, 1H), 0.98(t, 3H) |
| 162 | (S)-2-methyl-5-{4-[3-(3-methylthiopropylamino)piperidin-1-yl]-6-propylpyrimidin-2-ylamino}benzonitrile | $^1$H-NMR(400 MHz, CDCl$_3$) δ 8.15(s, 1H), 7.49(d, 1H), 7.18(d, 1H), 6.93(br, 1H), 5.96(s, 1H), 4.30(m, 1H), 4.05(m, 1H), 3.09(m, 1H), 2.81(m, 1H), 2.78(m, 2H), 2.67(m, 1H), 2.55(t, 2H), 2.47(m, 5H), 2.09(s, 3H), 2.01(m, 1H), 1.79(m, 2H), 1.69(m, 3H), 1.61(m, 1H), 1.41(m, 1H), 0.98(t, 3H) |
| 163 | (S)-5-{4-[3-(cyclopropylmethylamino)piperidin-1-yl]-6-propylpyrimidin-2-ylamino}-2-methylbenzonitrile | $^1$H-NMR(400 MHz, CDCl$_3$) δ 8.10(d, 1H), 7.53(dd, 1H), 7.18(d, 1H), 6.90(br, 1H), 5.96(s, 1H), 4.30(m, 1H), 4.01(m, 1H), 3.09(m, 1H), 2.96(m, 1H), 2.72(m, 1H), 2.59(m, 1H), 2.52(m, 1H), 2.49(m, 5H), 2.01(m, 2H), 1.82(m, 1H), 1.75(m, 2H), 1.59(m, 1H), 1.48(m, 1H), 0.98(t, 3H), 0.48(m, 2H), 0.13(m, 2H) |
| 164 | (S)-5-{4-[3-(4-hydroxybenzylamino)piperidin-1-yl]-6-propylpyrimidin-2-ylamino}-2-methylbenzonitrile | $^1$H-NMR(400 MHz, CDCl$_3$) δ 8.02(s, 1H), 7.48(d, 1H), 7.11(d, 1H), 7.00(d, 2H), 6.70(d, 2H), 5.91(s, 1H), 4.24(br, 1H), 3.95(br, 1H), 3.75(m, 2H), 3.16(m, 1H), 3.07(m, 1H), 2.71(m, 1H), 2.49(m, 2H), 2.44(s, 3H), 1.99(m, 1H), 1.79(m, 1H), 1.74(m, 2H), 1.50(m, 3H), 0.97(t, 3H) |

TABLE 1-18

| Example | Compound | NMR Spectrum |
| --- | --- | --- |
| 165 | (S)-5-[4-(3-diethylaminopiperidin-1-yl)-6-propylpyrimidin-2-ylamino]-2-methylbenzonitrile | $^1$H-NMR(400 MHz, CDCl$_3$) δ 8.09(d, 1H), 7.52(dd, 1H), 7.18(d, 1H), 6.87(br, 1H), 5.96(s, 1H), 4.44-4.31(br, 2H), 2.75(m, 2H), 2.65(m, 4H), 2.47(m, 4H), 1.99(m, 1H), 1.84(m, 1H), 1.75(m, 4H), 1.53(m, 2H), 1.05(t, 6H), 0.98(t, 3H) |

TABLE 1-18-continued

| Example | Compound | NMR Spectrum |
|---|---|---|
| 166 | (S)-5-(4-{3-[bis(cyclopropylmethyl)amino]piperidin-1-yl}-6-propylpyrimidin-2-ylamino)-2-methylbenzonitrile | $^1$H-NMR(400 MHz, CDCl$_3$) δ 8.17(d, 1H), 7.55(dd, 1H), 7.24(d, 1H), 6.99(br, 1H), 6.03(s, 1H), 4.49-4.04(br, 2H), 2.99(m, 1H), 2.83(m, 2H), 2.64(m, 3H), 2.53(m, 4H), 2.04(m, 1H), 1.92(m, 1H), 1.79(m, 2H), 1.59(m, 2H), 1.06(t, 3H), 0.93(m, 2H), 0.55(m, 4H), 0.20(m, 4H) |
| 167 | (R)-5-(4-{3-[bis(cyclopropylmethyl)amino]piperidin-1-yl}-6-propylpyrimidin-2-ylamino)-2-methylbenzonitrile | $^1$H-NMR(400 MHz, CDCl$_3$) δ 8.17(d, 1H), 7.55(dd, 1H), 7.39(br, 1H), 7.24(d, 1H), 6.03(s, 1H), 4.49-4.04(br, 2H), 2.99(m, 1H), 2.83(m, 2H), 2.64(m, 3H), 2.53(m, 4H), 2.04(m, 1H), 1.92(m, 1H), 1.79(m, 2H), 1.59(m, 2H), 1.06(t, 3H), 0.93(m, 2H), 0.55(m, 4H), 0.20(m, 4H) |
| 168 | 4-ethyl-N-(4-fluorophenyl)-6-(piperidin-1-yl)pyrimidin-2-amine | $^1$H-NMR(400 MHz, CDCl$_3$) δ 7.34(m, 2H), 7.17(m, 2H), 6.10(s, 1H), 3.61(m, 4H), 2.58(m, 2H), 1.61(m, 6H), 1.21(m, 3H) |
| 169 | 4-ethyl-N-(4-fluorophenyl)-6-(octahydroquinolin-1(2H)-yl)pyrimidin-2-amine | $^1$H-NMR(400 MHz, CD$_3$OD) δ 7.43(m, 2H), 7.17(m, 2H), 6.24(s, 1H), 4.15(m, 1H), 3.38(m, 1H), 2.58(m, 2H), 2.10(m, 1H), 1.91-1.66(m, 7H), 1.39(m, 3H), 1.27-1.13(m, 6H) |
| 170 | 4-ethyl-6-(2-ethylpiperidin-1-yl)-N-(4-fluorophenyl)pyrimidin-2-amine | $^1$H-NMR(400 MHz, CD$_3$OD) δ 7.42(m, 2H), 7.18(m, 2H), 6.38(s, 1H), 4.51-4.27(m, 2H), 3.08(m, 1H), 2.58(m, 2H), 1.88-1.66(m, 7H), 1.51(m, 1H), 1.25(m, 3H), 0.99(m, 3H) |
| 171 | 2-{1-[6-ethyl-2-(4-fluorophenylamino)pyrimidin-4-yl]piperidin-2-yl}ethanol | $^1$H-NMR(400 MHz, CD$_3$OD) δ 7.43(m, 2H), 7.17(m, 2H), 6.41(s, 1H), 3.59-3.49(m, 2H), 3.12(m, 1H), 2.58(m, 2H), 2.05(m, 1H), 1.86-1.69(m, 8H), 1.53(m, 1H), 1.23(m, 3H) |
| 172 | 4-ethyl-N-(4-fluorophenyl)-6-morpholinopyrimidin-2-amine | $^1$H-NMR(400 MHz, CD$_3$OD) δ 7.43(m, 2H), 7.22(t, 2H), 6.43(s, 1H), 3.76-3.70(m, 8H), 2.62(q, 2H), 1.25(t, 3H) |
| 173 | N-[4-(piperidin-1-yl)-6-propylpyrimidin-2-yl]-1H-indol-6-amine hydrochloride | $^1$H-NMR(400 MHz, CDCl$_3$) δ 13.20(s, 1H), 10.26(s, 1H), 8.78(s, 1H), 7.68(s, 1H), 7.52(d, 1H), 7.29(d, 1H), 7.22(s, 1H), 6.49(s, 1H), 5.77(s, 1H), 3.88(m, 2H), 3.48(m, 2H), 2.55(t, 2H), 1.82(m, 2H), 1.73(m, 2H), 1.66(m, 4H), 1.00(t, 3H) |
| 174 | 2-{1-[2-(4-methyl-3-nitrophenylamino)-6-propylpyrimidin-4-yl]piperidin-2-yl}ethanol | $^1$H-NMR(400 MHz, CDCl$_3$) δ 8.73(s, 1H), 7.70(brs, NH), 7.38(d, 1H), 7.19(d, 1H), 6.01(s, 1H), 5.08(brs, 1H), 3.99(brs, 1H), 3.48(m, 1H), 3.37(m, 1H), 2.96(m, 1H), 2.54-2.47(m, 5H), 2.08(m, 1H), 1.80-1.70(m, 8H), 1.54(m, 1H), 0.99(t, 3H) |

TABLE 1-19

| Example | Compound | NMR Spectrum |
|---|---|---|
| 175 | 2-{1-[2-(4-amino-3-trifluoromethylphenylamino)-6-propylpyrimidin-4-yl]piperidin-2-yl}ethanol | $^1$H-NMR(400 MHz, CDCl$_3$) δ 7.87(s, 1H), 7.27(d, 1H), 6.71(d, 1H), 5.93(s, 1H), 4.87(brs, 1H), 4.04(s, 3H), 3.53(m, 1H), 3.33(m, 1H), 2.95(m, 1H), 2.47(t, 2H), 2.05(m, 1H), 1.73(m, 8H), 1.51(m, 1H), 0.85(t, 3H) |
| 176 | 2-{1-[2-(4-amino-3-nitrophenylamino)-6-propylpyrimidin-4-yl]piperidin-2-yl}ethanol | $^1$H-NMR(400 MHz, CDCl$_3$) δ 8.67(s, 1H), 7.26(d, 1H), 6.85(brs, 1H), 6.74(d, 1H), 5.93(s, 1H + 2H), 5.08(brs, 1H), 3.89(brs, 1H), 3.56(m, 1H), 3.33(m, 1H), 2.94(m, 1H), 2.46(t, 2H), 2.04(m, 1H), 1.82-1.66(m, 8H), 1.54(m, 1H), 0.99(t, 3H) |
| 177 | 5-{4-[2-(2-hydroxyethyl)piperidin-1-yl]-6-propylpyrimidin-2-ylamino}-2-methylbenzonitrile | $^1$H-NMR(400 MHz, CDCl$_3$) δ 8.10(s, 1H), 7.45(d, 1H), 7.18(d, 1H), 7.07(brs, 1H), 5.97(s, 1H), 4.93(brs, 1H), 3.90(brs, 1H), 3.59(m, 1H), 3.35(m, 1H), 2.97(m, 1H), 2.47(m, 3H + 2H), 2.07(m, 1H), 1.74-1.69(m, 8H), 1.51(m, 1H), 0.99(t, 3H) |
| 178 | 2-fluoro-5-{4-[2-(2-hydroxyethyl)piperidin-1-yl]-6-propylpyrimidin-2-ylamino}benzonitrile | $^1$H-NMR(400 MHz, CDCl$_3$) δ 8.14(m, 1H), 7.66(m, 1H), 7.12(m, 1H), 6.05(s, 1H), 4.92(brs, 1H), 4.00(brs, 1H), 3.67(m, 1H), 3.48(m, 1H), 3.03(m, 1H), 2.53(t, 2H), 2.07(m, 1H), 1.73(m, 8H), 1.53(m, 1H), 1.00(t, 3H) |
| 179 | 2-amino-5-{4-[2-(2-hydroxyethyl)piperidin-1-yl]-6-propylpyrimidin-2-ylamino}benzonitrile | $^1$H-NMR(400 MHz, CDCl$_3$) δ 7.77(s, 1H), 7.32(d, 1H), 7.04(brs, 1H), 6.70(d, 1H), 5.91(s, 1H), 4.89(brs, 1H), 4.24(s, 2H), 3.86(brs, 1H), 3.58(m, 1H), 3.33(m, 1H), 2.95(m, 1H), 2.45(t, 2H), 2.05(m, 1H), 1.72(m, 8H), 1.50(m, 1H), 0.85(t, 3H) |
| 180 | 2-{1-[2-(3-amino-4-methylphenylamino)-6-propylpyrimidin-4-yl]piperidin-2-yl}ethanol | $^1$H-NMR(400 MHz, CDCl$_3$) δ 7.02(s, 1H), 6.94(d, 1H), 6.79(d, 1H), 5.88(s, 1H), 5.00(brs, 1H), 3.84(brs, 1H), 3.55(m, 1H), 3.35(m, 1H), 2.95(m, 1H), 2.46(t, 2H), 2.11(s, 1H), 2.06(m, 2H), 1.71(m, 8H), 1.52(m, 1H), 0.85(t, 3H) |

TABLE 1-19-continued

| Example | Compound | NMR Spectrum |
|---|---|---|
| 181 | 2-{1-[2-(3-amino-4-fluorophenylamino)-6-propylpyrimidin-4-yl]piperidin-2-yl}ethanol | $^1$H-NMR(400 MHz, CDCl$_3$) δ 7.15(d, 1H), 6.98(brs, 1H), 6.89(m, 1H), 6.74(m, 1H), 5.90(s, 1H), 4.96(brs, 1H), 3.83(brs, 1H), 3.74(s, 2H), 3.55(m, 1H), 3.36(m, 1H), 2.96(m, 1H), 2.46(t, 2H), 2.06(m, 1H), 1.71(m, 8H), 1.53(m, 1H), 0.88(t, 3H) |
| 182 | 2-{1-[2-(3-amino-4-chlorophenylamino)-6-propylpyrimidin-4-yl]piperidin-2-yl}ethanol | $^1$H-NMR(400 MHz, CDCl$_3$) δ 7.25(d, 1H), 7.10(d, 1H), 6.85(brs, 1H), 6.76(d, 1H), 5.91(s, 1H), 4.99(brs, 1H), 4.06(s, 2H), 3.84(brs, 1H), 3.58(m, 1H), 3.39(m, 1H), 2.96(m, 1H), 2.46(t, 2H), 2.08(m, 1H), 1.71(m, 8H), 1.51(m, 1H), 0.98(t, 3H) |
| 183 | 2-{1-[2-(indolin-6-ylamino)-6-propylpyrimidin-4-yl]piperidin-2-yl}ethanol | $^1$H-NMR(400 MHz, CDCl$_3$) δ 7.01(m, 3H), 6.76(d, 1H), 5.88(s, 1H), 4.96(brs, 1H), 3.85(brs, 1H), 3.54(m, 3H), 3.35(m, 1H), 2.97(m, 3H), 2.45(t, 2H), 3.01(m, 1H), 1.71(m, 8H), 1.51(m, 1H), 0.98(t, 3H) |
| 184 | (S)-2-{1-[2-(4-chloro-3-nitrophenylamino)-6-propylpyrimidin-4-yl]piperidin-2-yl}ethanol | $^1$H-NMR(400 MHz, CDCl$_3$) δ 8.73(s, 1H), 8.21(brs, 1H), 7.47(d, 1H), 7.36(d, 1H), 6.02(s, 1H), 4.94(brs, 1H), 3.95(s, 1H), 3.65(m, 1H), 3.44(m, 1H), 2.99(t, 1H), 2.49(t, 2H), 2.09(m, 1H), 1.75-1.51(m, 6H), 1.51(m, 1H), 0.98(t, 3H) |

TABLE 1-20

| Example | Compound | NMR Spectrum |
|---|---|---|
| 185 | (S)-2-{1-[2-(4-amino-3-nitrophenylamino)-6-propylpyrimidin-4-yl]piperidin-2-yl}ethanol | $^1$H-NMR(400 MHz, CDCl$_3$) δ 8.70(s, 1H), 7.30(m, 1H), 6.78(d, 1H), 6.15(s, 2H), 6.00(s, 1H), 4.97(brs, 1H), 4.06(brs, 1H), 3.58(m, 1H), 3.43(m, 1H), 3.03(t, 1H), 2.51(t, 2H), 2.08(m, 1H), 1.76(m, 6H), 1.54(m, 1H), 0.99(t, 3H) |
| 186 | (R)-2-{1-[2-(4-amino-3-nitrophenylamino)-6-propylpyrimidin-4-yl]piperidin-2-yl}ethanol | $^1$H-NMR(400 MHz, CDCl$_3$) δ 8.71(s, 1H), 7.32(m, 1H), 6.76(d, 1H), 6.04(s, 2H), 5.96(s, 1H), 5.00(brs, 1H), 3.74(m, 1H), 3.55(m, 1H), 3.39(m, 1H), 3.01(t, 1H), 2.49(t, 2H), 2.09(m, 1H), 1.73(m, 6H), 1.55(m, 1H), 0.99(t, 3H) |
| 187 | 3-[4-(octahydroquinolin-1(2H)-yl)-6-propylpyrimidin-2-ylamino]benzonitrile | $^1$H-NMR(400 MHz, CD$_3$OD) δ 8.26(s, 1H), 7.78(d, 1H), 7.40(t, 1H), 7.23(d, 1H), 5.99(s, 1H), 4.21(m, 1H), 3.38(t, 1H), 3.26(m, 1H), 2.47(m, 2H), 2.15(m, 1H), 1.86-1.58(m, 10H), 1.40-1.19(m, 2H), 1.17-1.12(m, 2H), 0.99(t, 3H) |
| 188 | N-(3-nitrophenyl)-4-(octahydroquinolin-1(2H)-yl)-6-propylpyrimidin-2-amine | $^1$H-NMR(400 MHz, CDCl$_3$) δ 8.97(s, 1H), 8.40(brs, NH), 7.83(d, 1H), 7.64(d, 1H), 7.42(t, 1H), 5.83(s, 1H), 4.45(m, 1H), 3.26(m, 2H), 2.53(m, 2H), 2.11(m, 1H), 1.93-1.68(m, 8H), 1.40-1.18(m, 6H), 1.01(t, 3H) |
| 189 | N-(4-fluoro-3-nitrophenyl)-4-(octahydroquinolin-1(2H)-yl)-6-propylpyrimidin-2-amine | $^1$H-NMR(400 MHz, CDCl$_3$) δ 8.80(s, 1H), 7.90(brs, NH), 7.55(m, 1H), 7.15(m, 1H), 5.81(s, 1H), 4.39(m, 1H), 3.21(m, 2H), 2.50(m, 2H), 2.10(m, 1H), 1.78(m, 8H), 1.42-1.14(m, 6H), 1.00(t, 3H) |
| 190 | N-(4-chloro-3-nitrophenyl)-4-(octahydroquinolin-1(2H)-yl)-6-propylpyrimidin-2-amine | $^1$H-NMR(400 MHz, CDCl$_3$) δ 8.69(s, 1H), 8.52(brs, NH), 7.47(d, 1H), 7.40(d, 1H), 5.83(s, 1H), 4.37(m, 1H), 3.23(m, 2H), 2.51(m, 2H), 2.10(m, 1H), 1.79(m, 8H), 1.41-1.13(m, 6H), 1.00(t, 3H) |
| 191 | N-(3-methoxyphenyl)-4-(octahydroquinolin-1(2H)-yl)-6-propylpyrimidin-2-amine | $^1$H-NMR(400 MHz, CDCl$_3$) δ 8.87(brs, NH), 7.30(m, 1H), 7.18(m, 2H), 6.59(m, 1H), 5.77(s, 1H), 4.30(m, 1H), 3.80(s, 3H), 3.33(m, 1H), 3.20(m, 1H), 2.54(m, 2H), 2.15(m, 1H), 1.87-1.66(m, 8H), 1.51(m, 1H), 1.38-1.28(m, 5H), 1.26(t, 3H) |
| 192 | N-(5-methoxy-2-methylphenyl)-4-(octahydroquinolin-1(2H)-yl)-6-propylpyrimidin-2-amine | $^1$H-NMR(400 MHz, CDCl$_3$) δ 7.71(brs, 1H), 7.06(d, 1H), 6.54(m, 1H), 5.75(s, 1H), 4.36(m, 1H), 3.78(s, 3H), 3.18(m, 2H), 2.54(t, 2H), 2.30(s, 3H), 2.04(m, 1H), 1.82-1.67(m, 8H), 1.42-1.26(m, 6H), 1.01(t, 3H) |
| 193 | N-(4-methoxyphenyl)-4-(octahydroquinolin-1(2H)-yl)-6-propylpyrimidin-2-amine | $^1$H-NMR(400 MHz, CDCl$_3$) δ 9.22(brs, NH), 7.52(d, 2H), 6.86(d, 2H), 5.75(s, 1H), 4.13(m, 1H), 3.80(s, 3H), 3.36(m, 1H), 3.20(m, 1H), 2.55(t, 2H), 1.82(m, 1H), 1.84-1.66(m, 8H), 1.37-1.14(m, 6H), 1.01(t, 3H) |
| 194 | 4-(octahydroquinolin-1(2H)-yl)-6-propyl-N-(3-trifluoromethylphenyl)pyrimidin-2-amine | $^1$H-NMR(400 MHz, CDCl$_3$) δ 8.24(brs, NH), 8.19(s, 1H), 7.58(d, 1H), 7.37(t, 1H), 7.22(d, 1H), 5.78(s, 1H), 4.38(m, 1H), 3.22(m, 2H), 2.52(t, 2H), 2.10(m, 1H), 1.86-1.66(m, 8H), 1.45-1.12(m, 6H), 1.00(t, 3H) |

TABLE 1-21

| Example | Compound | NMR Spectrum |
|---|---|---|
| 195 | N-(3-chlorophenyl)-4-(octahydroquinolin-1(2H)-yl)-6-propylpyrimidin-2-amine | $^1$H-NMR(400 MHz, CDCl$_3$) δ 8.33(brs, NH), 7.86(s, 1H), 7.36(d, 1H), 7.82(t, 1H), 6.97(d, 1H), 5.80(s, 1H), 4.20(m, 1H), 3.34(m, 1H), 3.22(m, 1H), 2.51(t, 2H), 2.12(m, 1H), 1.86-1.63(m, 8H), 1.53-1.16(m, 6H), 1.00(t, 3H) |
| 196 | N-(5-chloro-2-methylphenyl)-4-(octahydroquinolin-1(2H)-yl)-6-propylpyrimidin-2-amine | $^1$H-NMR(400 MHz, CDCl$_3$) δ 8.29(s, 1H), 7.07(d, 1H), 6.90(d, 1H), 5.78(s, 1H), 4.29(m, 1H), 3.21(m, 2H), 2.50(m, 2H), 2.31(s, 3H), 2.04(m, 1H), 1.89-1.64(m, 8H), 1.51-1.12(m, 6H), 1.02(t, 3H) |
| 197 | N-(3-chloro-4-methylphenyl)-4-(octahydroquinolin-1(2H)-yl)-6-propylpyrimidin-2-amine | $^1$H-NMR(400 MHz, CDCl$_3$) δ 8.90(brs, NH), 7.81(s, 1H), 7.31(d, 1H), 7.13(d, 1H), 5.79(s, 1H), 4.20(m, 1H), 3.35(m, 1H), 3.24(m, 1H), 2.54(m, 2H), 2.32(s, 3H), 2.11(m, 1H), 1.87-1.64(m, 8H), 1.55-1.14(m, 6H), 1.01(t, 3H) |
| 198 | N-(3-methylthiophenyl)-4-(octahydroquinolin-1(2H)-yl)-6-propylpyrimidin-2-amine | $^1$H-NMR(400 MHz, CDCl$_3$) δ 8.38(brs, NH), 7.59(s, 1H), 7.39(d, 1H), 7.20(m, 1H), 6.89(d, 1H), 5.77(s, 1H), 4.29(m, 1H), 3.32-3.21(m, 2H), 2.48(m, 2H + 3H), 2.14(m, 1H), 1.86-1.65(m, 8H), 1.49-1.15(m, 6H), 1.00(t, 3H) |
| 199 | N-[4-(octahydroquinolin-1(2H)-yl)-6-propylpyrimidin-2-yl]-1H-indol-5-amine | $^1$H-NMR(400 MHz, CDCl$_3$) δ 9.03(brs, NH), 8.37(s, NH), 7.92(s, 1H), 7.31(m, 2H), 7.19(s, 1H), 6.47(s, 1H), 5.74(s, 1H), 4.13(m, 1H), 3.39-3.21(m, 2H), 2.56(m, 2H), 2.19(m, 1H), 1.85-1.62(m, 8H), 1.68-1.25(m, 6H), 1.01(t, 3H) |
| 200 | N-[4-(octahydroquinolin-1(2H)-yl)-6-propylpyrimidin-2-yl]-2-(trifluoromethyl)-1H-benzo[d]imidazol-5-amine | $^1$H-NMR(400 MHz, CDCl$_3$) δ 9.12(brs, NH), 7.98(s, 1H), 7.63(d, 1H), 7.40(d, 1H), 5.76(s, 1H), 4.24(m, 1H), 3.26-3.13(m, 2H), 2.53(m, 2H), 2.05(m, 1H), 1.83-1.62(m, 8H), 1.35-1.10(m, 6H), 0.99(t, 3H) |
| 201 | N-[4-(octahydroquinolin-1(2H)-yl)-6-propylpyrimidin-2-yl]quinolin-6-amine | $^1$H-NMR(400 MHz, CDCl$_3$) δ 8.76(s, 1H), 8.16(s, 1H), 8.04-7.93(m, 3H), 7.35(m, 1H), 5.81(s, 1H), 4.28(m, 1H), 3.35-3.25(m, 2H), 2.54(m, 2H), 2.27(m, 1H), 1.79-1.75(m, 8H), 1.25(m, 6H), 1.02(m, 3H) |
| 202 | 4-methyl-7-[4-(octahydroquinolin-1(2H)-yl)-6-propylpyrimidin-2-amino]-2H-chromen-2-one | $^1$H-NMR(400 MHz, CD$_3$OD) δ 8.11(s, 1H), 7.61(d, 1H), 7.44(d, 1H), 6.13(s, 1H), 6.01(s, 1H), 4.37(m, 1H), 3.40(m, 1H), 3.24(m, 1H), 2.51(t, 2H), 2.47(s, 3H), 2.16(m, 1H), 1.86-1.67(m, 8H), 1.44-1.15(m, 6H), 1.13(t, 3H) |
| 203 | N-[4-(octahydroquinolin-1(2H)-yl)-6-propylpyrimidin-2-yl]quinolin-3-amine | $^1$H-NMR(400 MHz, CDCl$_3$) δ 8.99(s, 1H), 8.61(s, 1H), 8.03(m, 1H), 7.73(m, 1H), 7.56-7.49(m, 2H), 5.83(s, 1H), 4.40(m, 1H), 3.25(m, 2H), 2.51(m, 2H), 2.13(m, 1H), 1.87-1.35(m, 8H), 1.26-1.02(m, 6H), 0.84(m, 3H) |
| 204 | N-[4-(octahydroquinolin-1(2H)-yl)-6-propylpyrimidin-2-yl]-1H-indol-6-amine hydrochloride | $^1$H-NMR(400 MHz, CD$_3$OD) δ 7.56(d, 1H), 7.48(s, 1H), 7.26(s, 1H), 7.06(m, 1H), 6.45(s, 1H), 6.26(s, 1H), 4.40-4.10(brs, 1H), 3.40(m, 2H), 2.58(m, 2H), 2.04(m, 1H), 1.82-1.72(m, 8H), 1.34-1.23(m, 6H), 1.03(m, 3H) |

TABLE 1-22

| Example | Compound | NMR Spectrum |
|---|---|---|
| 205 | (R)-5-{4-[3-(ethylamino)piperidin-1-yl]-6-propylpyrimidin-2-ylamino}-2-methylbenzonitrile | $^1$H-NMR(400 MHz, CDCl$_3$) δ 8.15(s, 1H), 7.60(br, 1H), 7.48(d, 1H), 7.18(d, 1H), 5.95(s, 1H), 4.34(m, 1H), 4.05(m, 1H), 3.12(m, 1H), 2.93(m, 1H), 2.88(m, 2H), 2.48(m, 5H), 2.06(m, 3H), 1.82(m, 1H), 1.77(m, 2H), 1.56(m, 1H), 1.43(m, 1H), 1.15(t, 3H), 0.98(t, 3H) |
| 206 | (R)-5-{4-[3-(propylamino)piperidin-1-yl]-6-propylpyrimidin-2-ylamino}-2-methylbenzonitrile | $^1$H-NMR(400 MHz, CDCl$_3$) δ 8.12(s, 1H), 7.59(d, 1H), 7.21(d, 1H), 5.97(s, 1H), 4.47(m, 1H), 4.13(br, 1H), 3.27(m, 1H), 3.17(m, 1H), 2.92(m, 1H), 2.77(m, 2H), 2.51(m, 2H), 2.49(s, 3H), 2.16(m, 1H), 1.94(m, 1H), 1.76-1.57(m, 5H), 1.26(m, 2H), 1.01(t, 3H), 0.92(t, 3H) |
| 207 | (R)-5-{4-[3-(butylamino)piperidin-1-yl]-6-propylpyrimidin-2-ylamino}-2-methylbenzonitrile | $^1$H-NMR(400 MHz, CDCl$_3$) δ 8.11(s, 1H), 7.55(d, 1H), 7.49(br, 1H), 7.20(d, 1H), 5.96(s, 1H), 4.40(m, 1H), 4.05(m, 1H), 3.08(m, 1H), 3.00(m, 1H), 2.74(m, 3H), 2.51(m, 5H), 2.09(m, 1H), 1.85(m, 1H), 1.74(m, 2H), 1.56(m, 4H), 1.35(m, 2H), 1.00(t, 3H), 0.92(t, 3H) |

TABLE 1-22-continued

| Example | Compound | NMR Spectrum |
|---|---|---|
| 208 | (R)-2-methyl-5-{4-[3-(pentylamino)piperidin-1-yl]-6-propylpyrimidin-2-ylamino}benzonitrile | $^1$H-NMR(400 MHz, CDCl$_3$) δ 8.11(s, 1H), 7.53(dd, 1H), 7.48(br, 1H), 7.18(d, 1H), 5.96(s, 1H), 4.37(m, 1H), 4.05(m, 1H), 3.10(m, 1H), 3.01(m, 1H), 2.73(m, 3H), 2.49(m, 5H), 2.09(m, 1H), 1.83(m, 1H), 1.74(m, 3H), 1.55(m, 2H), 1.53(m, 3H), 1.30(m, 4H), 0.98(t, 3H), 0.87(t, 3H) |
| 209 | (R)-5-{4-[3-(isobutylamino)piperidin-1-yl]-6-propylpyrimidin-2-ylamino}-2-methylbenzonitrile | $^1$H-NMR(400 MHz, CDCl$_3$) δ 8.09(s, 1H), 7.53(d, 1H), 7.50(br, 1H), 7.18(d, 1H), 5.95(s, 1H), 4.28(m, 1H), 4.05(m, 1H), 3.10(m, 1H), 2.94(m, 1H), 2.63(m, 1H), 2.59-2.44(m, 7H), 2.05(m, 2H), 1.83(m, 1H), 1.72(m, 3H), 1.58(m, 1H), 1.46(m, 1H), 1.00(t, 3H), 0.90(m, 6H) |
| 210 | (R)-5-{4-[3-(isopentylamino)piperidin-1-yl]-6-propylpyrimidin-2-ylamino}-2-methylbenzonitrile | $^1$H-NMR(400 MHz, CDCl$_3$) δ 8.55(br, 1H), 8.09(s, 1H), 7.58(d, 1H), 7.20(d, 1H), 6.00(s, 1H), 4.60(m, 1H), 4.01(m, 1H), 3.22(m, 1H), 3.07(m, 1H), 2.92(m, 1H), 2.87(m, 2H), 2.52(m, 2H), 2.48(s, 3H), 2.24(m, 1H), 1.89(m, 1H), 1.62(m, 1H), 1.59(m, 3H), 1.55(m, 4H), 0.98(t, 3H), 0.85(m, 6H) |
| 211 | (R)-2-methyl-5-{4-[3-(neopentylamino)piperidin-1-yl]-6-propylpyrimidin-2-ylamino}benzonitrile | $^1$H-NMR(400 MHz, CDCl$_3$) δ 8.07(s, 1H), 7.56(d, 1H), 7.19(d, 1H), 7.13(br, 1H), 5.95(s, 1H), 4.26(m, 1H), 4.06(m, 1H), 3.11(m, 1H), 2.91(m, 1H), 2.56(m, 1H), 2.47(m, 5H), 2.02(m, 1H), 1.83(m, 1H), 1.79(m, 2H), 1.69(m, 3H), 1.57(m, 2H), 1.00(t, 3H), 0.90(s, 9H) |
| 212 | (R)-5-{4-[3-(isopropylamino)piperidin-1-yl]-6-propylpyrimidin-2-ylamino}-2-methylbenzonitrile | $^1$H-NMR(400 MHz, CDCl$_3$) δ 8.11(s, 1H), 7.55(d, 1H), 7.20(d, 1H), 5.96(s, 1H), 4.57(m, 1H), 4.09(m, 1H), 3.27-3.14(m, 3H), 2.98(m, 1H), 2.53-2.49(s, 5H), 2.16(m, 1H), 1.88(m, 1H), 1.71(m, 3H), 1.60(m, 2H), 1.24(m, 6H), 0.99(t, 3H) |

TABLE 1-23

| Example | Compound | NMR Spectrum |
|---|---|---|
| 213 | (R)-5-(4-{3-[(1H-pyrrol-2-yl)methylamino]piperidin-1-yl}-6-propylpyrimidin-2-ylamino)-2-methylbenzonitrile | $^1$H-NMR(400 MHz, CDCl$_3$) δ 9.12(br, 1H), 8.32(s, 1H), 7.46(d, 1H), 7.20(d, 1H), 6.75(s, 1H), 6.11(s, 1H), 6.02(s, 1H), 5.86(s, 1H), 4.32(br, 1H), 3.92(m, 3H), 3.08 (m, 1H), 2.96(m, 1H), 2.75(m, 1H), 2.52-2.48(m, 5H), 2.05(m, 1H), 1.83(m, 1H), 1.72(m, 3H), 1.58(m, 1H), 1.46(m, 1H), 0.97(m, 3H) |
| 214 | (R)-2-methyl-5-(4-propyl-6-{3-[(thiophen-2-ylmethyl)amino]piperidin-1-yl}pyrimidin-2-ylamino)benzonitrile | $^1$H-NMR(400 MHz, CDCl$_3$) δ 8.12(s, 1H), 7.51(dd, 1H), 7.20-7.16(m, 2H), 7.11(br, 1H), 6.94-6.91(m, 2H), 5.92(s, 1H), 4.25(m, 1H), 4.07(m, 2H), 4.04(m, 1H), 3.08(m, 1H), 2.99(m, 1H), 2.72(m, 1H), 2.46(m, 5H), 1.99(m, 1H), 1.80(m, 1H), 1.71(m, 2H), 1.58-1.45(m, 3H), 0.98(t, 3H) |
| 215 | (R)-5-(4-{3-[(4,5-dimethylfuran-2-ylmethyl)amino]piperidin-1-yl}-6-propylpyrimidin-2-ylamino)-2-methylbenzonitrile | $^1$H-NMR(400 MHz, CDCl$_3$) δ 8.10(s, 1H), 7.55(m, 1H), 7.44(br, 1H), 7.18(d, 1H), 5.92(s, 1H), 4.13-4.09(m, 2H), 3.76(s, 2H), 3.02(m, 1H), 2.90(m, 1H), 2.66(m, 5H), 2.49(s, 3H), 2.01(m, 1H), 1.89(s, 3H), 1.77(m, 1H), 1.69(m, 3H), 1.55(m, 1H), 1.47(m, 1H), 0.98(t, 3H) |
| 216 | (R)-2-methyl-5-{4-[3-(3-methylthiopropylamino)piperidin-1-yl]-6-propylpyrimidin-2-ylamino}benzonitrile | $^1$H-NMR(400 MHz, CDCl$_3$) δ 8.15(s, 1H), 7.58(br, 1H), 7.49(d, 1H), 7.18(d, 1H), 5.96(s, 1H), 4.30(m, 1H), 4.05(m, 1H), 3.09(m, 1H), 2.81(m, 1H), 2.78(m, 2H), 2.67(m, 1H), 2.55(t, 2H), 2.47(m, 5H), 2.09(s, 3H), 2.01(m, 1H), 1.79(m, 2H), 1.69(m, 3H), 1.61(m, 1H), 1.41(m, 1H), 0.98(t, 3H) |
| 217 | (R)-5-{4-[3-(cyclopropylmethylamino)piperidin-1-yl]-6-propylpyrimidin-2-ylamino}-2-methylbenzonitrile | $^1$H-NMR(400 MHz, CDCl$_3$) δ 8.10(d, 1H), 7.53(dd, 1H), 7.30(br, 1H), 7.18(d, 1H), 5.96(s, 1H), 4.30(m, 1H), 4.01(m, 1H), 3.09(m, 1H), 2.96(m, 1H), 2.72(m, 1H), 2.59(m, 1H), 2.52(m, 1H), 2.49(m, 5H), 2.01(m, 2H), 1.82(m, 1H), 1.75(m, 2H), 1.59(m, 1H), 1.48(m, 1H), 0.98(t, 3H), 0.49(m, 2H), 0.15(m, 2H) |
| 218 | (R)-5-{4-[3-(cyclopentylmethylamino)piperidin-1-yl]-6-propylpyrimidin-2-ylamino}-2-methylbenzonitrile | $^1$H-NMR(400 MHz, CDCl$_3$) δ 8.08(s, 1H), 7.57(d, 1H), 7.47(br, 1H), 7.18(d, 1H), 5.96(s, 1H), 4.36(m, 1H), 4.06(m, 1H), 3.07(m, 1H), 2.96(m, 1H), 2.72-2.62(m, 3H), 2.51-2.48(s, 5H), 2.07(m, 2H), 1.81(m, 4H), 1.57(m, 6H), 1.18(m, 2H), 1.00(t, 3H) |
| 219 | (R)-5-{4-[3-(4-hydroxybenzylamino)piperidin-1-yl]-6-propylpyrimidin-2-ylamino}-2-methylbenzonitrile | $^1$H-NMR(400 MHz, CDCl$_3$) δ 8.04(s, 1H), 7.68(br, 1H), 7.49(d, 1H), 7.16(d, 1H), 7.09(d, 2H), 6.70(d, 2H), 5.90(s, 1H), 4.24(br, 1H), 3.95(br, 1H), 3.75(m, 2H), 3.16(m, 1H), 3.07(m, 1H), 2.71(m, 1H), 2.49(m, 2H), 2.44(s, 3H), 1.99(m, 1H), 1.79(m, 1H), 1.74(m, 2H), 1.50(m, 3H), 0.99(t, 3H) |

TABLE 1-23-continued

| Example | Compound | NMR Spectrum |
| --- | --- | --- |
| 220 | (R)-N-{1-[2-(3-cyano-4-methylphenylamino)-6-propylpyrimidin-4-yl]piperidin-3-yl}acetamide hydrochloride | $^1$H-NMR(400 MHz, CD$_3$OD) δ 7.92(m, 1H), 7.64(m, 1H), 7.44(m, 1H), 6.54-6.43(m, 1H), 4.63-4.22(m, 1H), 4.01(m, 1H), 3.85(m, 1H), 3.54-3.13(m, 1H), 3.43(m, 1H), 2.64(m, 2H), 2.52(s, 3H), 2.01(m, 1H), 1.99(d, 4H), 1.77(m, 2H), 1.66(m, 2H), 1.05(t, 3H) |
| 221 | (R)-3-[4-(3-aminopiperidin-1-yl)-6-propylpyrimidin-2-ylamino]benzonitrile dihydrochloride | $^1$H-NMR(400 MHz, CD$_3$OD) δ 7.96(s, 1H), 7.80(m, 1H), 7.62-7.59(m, 2H), 6.60(s, 1H), 4.09(m, 1H), 3.59-3.42(m, 3H), 2.69(m, 2H), 2.20(m, 1H), 1.95(m, 1H), 1.82-1.77(m, 4H), 1.25(m, 1H), 1.04(t, 3H) |

TABLE 1-24

| Example | Compound | NMR Spectrum |
| --- | --- | --- |
| 222 | (R)-5-[4-(3-aminopiperidin-1-yl)-6-propylpyrimidin-2-ylamino]-2-fluorobenzonitrile dihydrochloride | $^1$H-NMR(400 MHz, CD$_3$OD) δ 7.95(s, 1H), 7.83(m, 1H), 7.45(m, 1H), 6.59(s, 1H), 4.45(brs, 1H), 4.11(brs, 1H), 3.55-3.40(m, 3H), 2.67(m, 2H), 2.19(m, 1H), 1.96(m, 1H), 1.81-1.76(m, 4H), 1.06(t, 3H) |
| 223 | (R)-3-{4-[3-(propylamino)piperidin-1-yl]-6-propylpyrimidin-2-ylamino}benzonitrile | $^1$H-NMR(400 MHz, CDCl$_3$) δ 8.20(s, 1H), 7.64(m, 1H), 7.33(m, 1H), 7.21(m, 2H), 5.99(s, 1H), 4.33(m, 1H), 4.05(m, 1H), 3.07(t, 1H), 2.88(t, 1H), 2.67(m, 3H), 2.48(m, 2H), 1.73(m, 3H), 1.53-1.41(m, 4H), 1.26(m, 1H), 0.98(m, 3H), 0.92(m, 3H) |
| 224 | (R)-3-{4-[3-(cyclopropylmethylamino)piperidin-1-yl]-6-propylpyrimidin-2-ylamino}benzonitrile dihydrochloride | $^1$H-NMR(400 MHz, CD$_3$OD) δ 7.97(s, 1H), 7.78(m, 1H), 7.61(m, 2H), 6.64(s, 1H), 4.57(m, 1H), 4.50(brs, 1H), 3.61-3.40(m, 3H), 2.86(m, 2H), 2.68(t, 2H), 2.28(m, 1H), 1.97(m, 1H), 1.87-1.73(m, 4H), 1.06(t, 4H), 0.69(m, 2H), 0.35(m, 2H) |
| 225 | (R)-2-fluoro-5-{4-[3-(propylamino)piperidin-1-yl]-6-propylpyrimidin-2-ylamino}benzonitrile | $^1$H-NMR(400 MHz, CDCl$_3$) δ 8.14(s, 1H), 7.61(m, 1H), 7.23(brs, 1H), 7.09(m, 1H), 5.98(s, 1H), 4.30(m, 1H), 4.10(m, 1H), 3.09(t, 1H), 2.89(t, 1H), 2.67(m, 3H), 2.46(m, 2H), 1.80-1.69(m, 3H), 1.55-1.26(m, 4H), 1.26(m, 1H), 1.00-0.91(m, 6H) |
| 226 | (R)-5-{4-[3-(cyclopropylmethylamino)piperidin-1-yl]-6-propylpyrimidin-2-ylamino}-2-fluorobenzonitrile dihydrochloride | $^1$H-NMR(400 MHz, CD$_3$OD) δ 7.97(s, 1H), 7.82(m, 1H), 7.46(m, 1H), 6.61(s, 1H), 4.55(m, 1H), 4.20-4.04(brs, 1H), 3.55(m, 2H), 3.38(m, 1H), 2.87(m, 2H), 2.67(t, 2H), 2.26(m, 1H), 1.96(m, 1H), 1.79(m, 2H), 1.72(m, 2H), 1.06(t, 4H), 0.71(m, 2H), 0.37(m, 2H) |
| 227 | (R)-N$^1$-{4-[3-(cyclopropylmethylamino)piperidin-1-yl]-6-propylpyrimidin-2-yl}-4-fluorobenzene-1,3-diamine | $^1$H-NMR(400 MHz, CDCl$_3$) δ 7.11(d, 1H), 6.88-6.84(m, 2H), 5.92(s, 1H), 4.55(m, 1H), 3.95-3.89(m, 3H), 3.14(t, 2H), 2.90(m, 1H), 2.67(m, 2H), 2.51(t, 2H), 2.12(m, 1H), 1.89(m, 1H), 1.78-1.55(m, 4H), 1.00-1.97(m, 4H), 0.53(m, 2H), 0.21(m, 2H) |
| 228 | (R)-N$^1$-{4-[3-(cyclopropylmethylamino)piperidin-1-yl]-6-propylpyrimidin-2-yl}-3-nitrobenzene-1,4-diamine | $^1$H-NMR(400 MHz, CDCl$_3$) δ 8.81(s, 1H), 7.97(brs, 1H), 7.34(d, 1H), 6.77(d, 1H), 5.97(s, 2H), 4.40(m, 1H), 4.11(m, 1H), 3.16(m, 2H), 2.82(m, 2H), 2.58-2.50(m, 4H), 2.10(m, 1H), 1.88(m, 1H), 1.76(m, 2H), 1.59(m, 2H), 0.99(m, 4H), 0.50(m, 2H), 0.14(m, 2H) |
| 229 | (R)-3-amino-5-{4-[3-(cyclopropylmethylamino)piperidin-1-yl]-6-propylpyrimidin-2-ylamino}benzonitrile | $^1$H-NMR(400 MHz, CDCl$_3$) δ 7.66(brs, 1H), 7.36(s, 1H), 7.20(s, 1H), 6.53(s, 1H), 5.98(s, 1H), 4.45(m, 1H), 4.00(m, 3H), 3.12(m, 1H), 2.91(m, 1H), 2.68(m, 2H), 2.49(m, 2H), 2.11(m, 2H), 1.83(m, 1H), 1.74-1.48(m, 4H), 0.98(m, 4H), 0.52(m, 2H), 0.21(m, 2H) |
| 230 | (R)-N$^1$-{4-[3-(cyclopropylmethylamino)piperidin-1-yl]-6-propylpyrimidin-2-yl}-3-(trifluoromethyl)benzene-1,4-diamine | $^1$H-NMR(400 MHz, CDCl$_3$) δ 7.82(s, 1H), 7.67(brs, 1H), 7.15(d, 1H), 6.58(d, 1H), 5.79(s, 1H), 4.17(m, 1H), 3.89(m, 3H), 2.98-2.91(m, 2H), 2.63(m, 1H), 2.42-2.37(m, 4H), 1.95(m, 1H), 1.69-1.62(m, 3H), 1.42(m, 2H), 0.86(m, 4H), 0.36(m, 2H), 0.00(m, 2H) |
| 231 | (R)-N$^1$-{4-[3-(cyclopropylmethylamino)piperidin-1-yl]-6-propylpyrimidin-2-yl}-5-(trifluoromethyl)benzene-1,3-diamine | $^1$H-NMR(400 MHz, CDCl$_3$) δ 8.08(brs, 1H), 7.45(s, 1H), 7.00(s, 1H), 6.54(s, 1H), 5.98(s, 1H), 4.02(m, 1H), 4.00(m, 3H), 3.24-3.13(m, 3H), 2.93(m, 1H), 2.67(m, 2H), 2.50(m, 2H), 2.14(m, 1H), 1.89(m, 1H), 1.60(m, 4H), 0.98(m, 4H), 0.53(m, 2H), 0.20(m, 2H) |

TABLE 1-25

| Example | Compound | NMR Spectrum |
|---|---|---|
| 232 | (R)-N-{1-[2-(4-amino-3-nitrophenylamino)-6-butylpyrimidin-4-yl]piperidin-3-yl}acetamide hydrochloride | $^1$H-NMR(400 MHz, CD$_3$OD) δ 8.41(s, 1H), 7.41(d, 1H), 6.99(d, 1H), 6.51(s, 1H), 4.09(brs, 2H), 3.83(m, 1H), 3.30(m, 2H), 2.63(t, 2H), 2.01(m, 1H), 1.94(s, 3H + 1H), 1.68(m, 4H), 1.44(m, 2H), 1.00(t, 3H) |
| 233 | (R)-N-{1-[6-butyl-2-(4-methyl-3-nitrophenylamino)pyrimidin-4-yl]piperidin-3-yl}acetamide hydrochloride | $^1$H-NMR(400 MHz, CD$_3$OD) δ 8.51(s, 1H), 7.57(d, 1H), 7.46(d, 1H), 6.53(m, 1H), 4.75-4.06(m, 2H), 3.84(m, 1H), 3.59-3.13(m, 2H), 2.69(t, 2H), 2.55(s, 3H), 2.10(m, 1H), 1.95(s, 3H + 1H), 1.71(m, 4H), 1.45(m, 2H), 1.00(t, 3H) |
| 234 | (R)-N-{1-[6-butyl-2-(4-fluoro-3-nitrophenylamino)pyrimidin-4-yl]piperidin-3-yl}acetamide hydrochloride | $^1$H-NMR(400 MHz, CD$_3$OD) δ 8.60(s, 1H), 7.74(m, 1H), 7.46(t, 1H), 6.53(s, 1H), 4.78-3.97(m, 2H), 3.81(m, 1H), 3.50-3.08(m, 2H), 2.68(m, 2H), 2.03(m, 1H), 1.93(s, 3H + 1H), 1.69(m, 4H), 1.47(m, 2H), 1.00(t, 3H) |
| 235 | (R)-N-{1-[6-butyl-2-(4-chloro-3-nitrophenylamino)pyrimidin-4-yl]piperidin-3-yl}acetamide hydrochloride | $^1$H-NMR(400 MHz, CD$_3$OD) δ 8.46(s, 1H), 7.66(s, 2H), 6.56(s, 1H), 4.80-4.12(m, 2H), 3.82(m, 1H), 3.50-3.07(m, 2H), 2.68(t, 2H), 2.02(m, 1H), 1.95(s, 3H + 1H), 1.70(m, 4H), 1.44(m, 2H), 1.00(t, 3H) |
| 236 | (R)-N-{1-[2-(3-amino-5-cyanophenylamino)-6-butylpyrimidin-4-yl]piperidin-3-yl}acetamide hydrochloride | $^1$H-NMR(400 MHz, CD$_3$OD) δ 7.21-6.97(m, 2H), 6.73(s, 1H), 6.48(s, 1H), 4.10(m, 2H), 3.85(m, 1H), 3.50-3.13(m, 2H), 2.65(t, 2H), 2.04(m, 1H), 1.96(s, 3H + 1H), 1.69(m, 4H), 1.44(m, 2H), 1.00(t, 3H) |
| 237 | (R)-N-{1-[2-(3-amino-5-trifluoromethylphenylamino)-6-butylpyrimidin-4-yl]piperidin-3-yl}acetamide hydrochloride | $^1$H-NMR(400 MHz, CD$_3$OD) δ 7.20-6.93(m, 2H), 6.73(s, 1H), 6.46(s, 1H), 4.73-4.07(m, 2H), 3.86(m, 1H), 3.13(m, 2H), 2.65(t, 2H), 2.03(m, 1H), 1.95(s, 3H + 1H), 1.69(m, 4H), 1.44(m, 2H), 0.98(t, 3H) |
| 238 | (R)-N-{1-[2-(4-amino-3-trifluoromethylphenylamino)-6-butylpyrimidin-4-yl]piperidin-3-yl}acetamide hydrochloride | $^1$H-NMR(400 MHz, CD$_3$OD) δ 7.58(s, 1H), 7.31(m, 1H), 6.86(d, 1H), 6.37(s, 1H), 4.48-4.11(m, 2H), 3.82(m, 1H), 3.50(m, 2H), 2.62(t, 2H), 2.01-1.89(m, 1H + 3H + 1H), 1.67(m, 4H), 1.43(m, 2H), 0.99(t, 3H) |
| 239 | (R)-N-{1-[6-butyl-2-(4-fluoro-3-trifluoromethylphenylamino)pyrimidin-4-yl]piperidin-3-yl}acetamide hydrochloride | $^1$H-NMR(400 MHz, CD$_3$OD) δ 8.06-7.70(m, 1H), 7.38(t, 1H), 6.54-6.44(m, 1H), 4.57-4.02(m, 2H), 3.83(m, 1H), 3.48-3.13(m, 2H), 2.67(t, 2H), 2.01(m, 1H), 1.94(s, 1H + 3H), 1.74-1.65(m, 4H), 1.45(m, 2H), 1.00(t, 3H) |
| 240 | (R)-N-{1-[6-butyl-2-(3-cyano-4-fluorophenylamino)pyrimidin-4-yl]piperidin-3-yl}acetamide hydrochloride | $^1$H-NMR(400 MHz, CD$_3$OD) δ 7.98(s, 1H), 7.82(s, 1H), 7.41(t, 1H), 6.52(brs, 1H), 4.63-4.07(m, 2H), 3.82(m, 1H), 3.50-3.10(m, 2H), 2.67(t, 2H), 2.01(m, 1H), 1.96(s, 1H + 3H), 1.68(m, 4H), 1.47(m, 2H), 1.00(t, 3H) |
| 241 | (R)-N-{1-[2-(3-amino-4-fluorophenylamino)-6-butylpyrimidin-4-yl]piperidin-3-yl}acetamide hydrochloride | $^1$H-NMR(400 MHz, CD$_3$OD) δ 7.15(brs, 1H), 6.95(t, 1H), 6.65(m, 1H), 6.41(m, 1H), 4.70-3.85(m, 3H), 3.56-3.20(m, 2H), 2.62(t, 2H), 2.02(m, 1H), 1.96(s, 1H + 3H), 1.68(m, 4H), 1.45(m, 2H), 0.99(t, 3H) |

TABLE 1-26

| Example | Compound | NMR Spectrum |
|---|---|---|
| 242 | (R)-N-{1-[2-(3-amino-4-chlorophenylamino)-6-butylpyrimidin-4-yl]piperidin-3-yl}acetamide hydrochloride | $^1$H-NMR(400 MHz, CD$_3$OD) δ 7.18-7.16(m, 2H), 6.68(m, 1H), 6.43(s, 1H), 4.71-3.86(m, 3H), 3.50-3.10(m, 2H), 2.63(t, 2H), 2.02(m, 1H), 1.97(s, 1H + 3H), 1.70(m, 4H), 1.43(m, 2H), 0.99(t, 3H) |
| 243 | (R)-N-{1-[2-(4-amino-3-cyanophenylamino)-6-butylpyrimidin-4-yl]piperidin-3-yl}acetamide hydrochloride | $^1$H-NMR(400 MHz, CD$_3$OD) δ 7.48(s, 1H), 7.35(m, 1H), 6.84(d, 1H), 6.39(brs, 1H), 4.56-4.02(m, 2H), 3.82(m, 1H), 3.50-3.13(m, 2H), 2.62(t, 2H), 2.01-1.89(m, 1H + 3H + 1H), 1.66(m, 4H), 1.43(m, 2H), 0.99(t, 3H) |
| 244 | (R)-N-{1-[2-(3-cyano-4-methylphenylamino)-6-propylpyrimidin-4-yl]piperidin-3-yl}-2-hydroxyacetamide | $^1$H-NMR(400 MHz, CDCl$_3$) δ 8.47(s, NH), 7.20-7.15(m, 2H), 6.80(m, 1H), 5.98(s, 1H), 4.45(m, 1H), 4.17(m, 1H), 4.02(d, 2H), 3.85(m, 1H), 3.17(m, 1H), 3.07(m, 1H), 2.45(m, 5H), 2.13(m, 1H), 1.81(m, 1H), 1.71(m, 2H), 1.55(m, 2H), 0.97(t, 3H) |
| 245 | (R)-N-{1-[2-(3-cyanophenylamino)-6-propylpyrimidin-4-yl]piperidin-3-yl}-2-hydroxyacetamide | $^1$H-NMR(400 MHz, CDCl$_3$) δ 8.60(brs, NH), 7.36-7.31(m, 2H), 7.22-7.16(m, 2H), 6.75(m, 1H), 6.01(s, 1H), 4.50(m, 1H), 4.14(m, 1H), 4.02(d, 2H), 3.84(m, 1H), 3.15(m, 1H), 3.07(m, 1H), 2.48(m, 5H), 2.16(m, 1H), 1.81(m, 1H), 1.73(m, 2H), 1.56(m, 2H), 0.98(t, 3H) |
| 246 | (R)-N-{1-[2-(3-cyano-4-fluorophenylamino)-6-propylpyrimidin-4-yl]piperidin-3-yl}-2-hydroxyacetamide | $^1$H-NMR(400 MHz, CD$_3$OD) δ 7.99(s, 1H), 7.83(m, 1H), 7.37(m, 1H), 6.46(s, 1H), 4.42(m, 1H), 4.15-3.90(m, 4H), 3.34(m, 1H), 3.15(m, 1H), 2.61(m, 2H), 2.00(m, 1H), 1.88(m, 1H), 1.75(m, 3H), 1.63(m, 1H), 1.04(t, 3H) |

TABLE 1-26-continued

| Example | Compound | NMR Spectrum |
|---|---|---|
| 247 | (R)-N-(1-{2-[3-amino-5-(trifluoromethyl)phenylamino]-6-propylpyrimidin-4-yl}piperidin-3-yl)-2-hydroxyacetamide | $^1$H-NMR(400 MHz, CDCl$_3$) δ 7.26(s, 1H), 6.68(m, 1H), 6.49(m, 1H), 5.94(s, 1H), 4.17(m, 1H), 4.06(s, 2H), 3.65(m, 1H), 3.42(m, 2H), 2.45(m, 2H), 2.00(m, 1H), 1.79(m, 1H), 1.70(m, 4H), 0.97(t, 3H) |
| 248 | (R)-N-(1-{2-[4-amino-3-(trifluoromethyl)phenylamino]-6-propylpyrimidin-4-yl}piperidin-3-yl)-2-hydroxyacetamide | $^1$H-NMR(400 MHz, CDCl$_3$) δ 8.01(s, 1H), 6.72(m, 1H), 6.63(m, 1H), 5.94(s, 1H), 4.04(m, 3H), 3.86-3.58(m, 4H), 2.47(m, 2H), 2.02(m, 1H), 1.75-1.67(m, 5H), 0.98(t, 3H) |
| 249 | (R)-N-(1-{2-[4-fluoro-3-(trifluoromethyl)phenylamino]-6-propylpyrimidin-4-yl}piperidin-3-yl)-2-hydroxyacetamide | $^1$H-NMR(400 MHz, CDCl$_3$) δ 8.26(s, NH), 7.45(m, 1H), 7.11(t, 1H), 6.55(m, 1H), 6.01(s, 1H), 4.09(m, 3H), 3.99(m, 1H), 3.78(m, 1H), 3.42(m, 2H), 2.49(m, 2H), 2.01(m, 1H), 1.76-1.62(m, 5H), 0.98(t, 3H) |
| 250 | (R)-N-{1-[2-(3-amino-4-fluorophenylamino)-6-propylpyrimidin-4-yl]piperidin-3-yl}-2-hydroxyacetamide | $^1$H-NMR(400 MHz, CDCl$_3$) δ 7.48(m, NH), 6.86(t, 1H), 6.71(m, 1H), 6.48(m, 1H), 5.89(s, 1H), 4.24-4.15(m, 2H), 4.08(s, 2H), 3.60(m, 1H), 3.40(m, 2H), 2.45(m, 2H), 2.00(m, 1H), 1.80-1.67(m, 5H), 0.97(t, 3H) |
| 251 | (R)-N-{1-[2-(3-amino-4-chlorophenylamino)-6-propylpyrimidin-4-yl]piperidin-3-yl}-2-hydroxyacetamide | $^1$H-NMR(400 MHz, CDCl$_3$) δ 7.52(s, NH), 7.07(d, 1H), 6.70(m, 1H), 6.47(m, 1H), 5.89(s, 1H), 4.53(s, 2NH), 4.30(m, 1H), 4.09(m, 3H), 3.61(m, 1H), 3.32(m, 2H), 2.46(m, 2H), 2.01(m, 1H), 1.80-1.68(m, 5H), 0.97(t, 3H) |

TABLE 1-27

| Example | Compound | NMR Spectrum |
|---|---|---|
| 252 | (R)-N-{1-[2-(3-amino-4-methylphenylamino)-6-propylpyrimidin-4-yl]piperidin-3-yl}-2-hydroxyacetamide | $^1$H-NMR(400 MHz, CDCl$_3$) δ 7.38(s, NH), 7.07(s, NH), 6.90(m, 1H), 6.80(d, 1H), 6.54(m, 1H), 5.80(s, 1H), 4.26(m, 1H), 4.04(m, 3H), 3.56(m, 1H), 3.26(m, 1H), 3.15(m, 1H), 2.41(m, 2H), 2.09(s, 3H), 1.88(m, 1H), 1.67(m, 2H), 1.59-1.46(m, 3H), 0.96(t, 3H) |
| 253 | (R)-N-{1-[2-(3-chloro-4-methylphenylamino)-6-propylpyrimidin-4-yl]piperidin-3-yl}-2-hydroxyacetamide | $^1$H-NMR(400 MHz, CDCl$_3$) δ 7.81(s, NH), 7.19(m, 1H), 7.10(m, 1H), 6.67(m, 1H), 5.96(s, 1H), 4.26(m, 1H), 4.09(m, 3H), 3.82(m, 1H), 3.65-3.61(m, 3H), 2.47(m, 2H), 2.31(s, 3H), 1.96(m, 1H), 1.75-1.69(m, 5H), 0.98(t, 3H) |
| 254 | (R)-2-hydroxy-N-(1-{2-[4-methyl-3-(trifluoromethyl)phenylamino]-6-propylpyrimidin-4-yl}piperidin-3-yl)acetamide | $^1$H-NMR(400 MHz, CDCl$_3$) δ 8.26(s, NH), 7.34(d, 1H), 7.17(m, 1H), 7.00(brs, NH), 6.63(m, 1H), 5.98(s, 1H), 4.04(m, 3H), 3.85(m, 1H), 3.70(m, 1H), 3.52(m, 2H), 2.48(m, 2H), 2.41(s, 3H), 1.96(m, 1H), 1.74-1.69(m, 5H), 0.97(t, 3H) |
| 255 | (R)-N-{1-[2-(3-amino-5-cyanophenylamino)-6-propylpyrimidin-4-yl]piperidin-3-yl}-2-hydroxyacetamide hydrochloride | $^1$H-NMR(400 MHz, CDCl$_3$) δ 7.33(s, NH), 7.14(s, 1H), 7.13(brs, NH), 6.78(m, 1H), 6.46(s, 1H), 5.95(s, 1H), 4.52(s, 1H), 4.23-4.03(m, 5H), 3.76(m, 1H), 3.15(m, 2H), 2.47(m, 2H), 2.17(m, 1H), 1.81(m, 1H), 1.70-1.57(m, 4H), 0.97(t, 3H) |
| 256 | (R)-N$^1$-[4-(3-aminopiperidin-1-yl)-6-propylpyrimidin-2-yl]-5-(trifluoromethyl)benzene-1,3-diamine dihydrochloride | $^1$H-NMR(400 MHz, CD$_3$OD) δ 7.90-7.70(m, 1H), 7.65-7.45(m, 1H), 7.26(s, 1H), 6.62(brs, 1H), 4.50-3.90(m, 2H), 3.70-3.40(m, 3H), 2.69(t, 2H), 2.30-2.15(m, 1H), 2.05-1.90(m, 1H), 1.90-1.60(m, 4H), 1.06(t, 3H) |
| 257 | (R)-N$^1$-[4-(3-aminopiperidin-1-yl)-6-propylpyrimidin-2-yl]-3-(trifluoromethyl)benzene-1,4-diamine dihydrochloride | $^1$H-NMR(400 MHz, CD$_3$OD) δ 7.70-7.25(m, 2H), 7.00-6.85(m, 1H), 6.48(d, 1H), 4.60-3.85(m, 2H), 3.60-3.30(m, 3H), 2.70-2.50(m, 2H), 2.20-2.10(m, 1H), 2.05-1.60(m, 4H), 1.04(t, 3H) |
| 258 | (R)-4-(3-aminopiperidin-1-yl)-N-(3-fluoro-4-methylphenyl)-6-propylpyrimidin-2-amine dihydrochloride | $^1$H-NMR(400 MHz, CD$_3$OD) δ 7.40-7.10(m, 3H), 6.70-6.45(m, 1H), 4.70-3.90(m, 2H), 3.65-3.30(m, 3H), 2.85-2.65(m, 2H), 2.27(s, 3H), 2.25-2.10(m, 1H), 2.05-1.90(m, 1H), 1.90-1.50(m, 4H), 1.03(t, 3H) |
| 259 | (R)-N$^1$-[4-(3-aminopiperidin-1-yl)-6-propylpyrimidin-2-yl]-4-fluorobenzene-1,3-diamine dihydrochloride | $^1$H-NMR(400 MHz, CD$_3$OD) δ 7.33(d, 1H), 7.10(t, 1H), 6.87(d, 1H), 6.63(d, 1H), 4.70-3.90(m, 2H), 3.65-3.30(m, 3H), 2.67(t, 2H), 2.25-2.15(m, 1H), 2.05-1.90(m, 1H), 1.90-1.60(m, 4H), 1.05(t, 3H) |
| 260 | (R)-3-amino-5-{[4-(3-aminopiperidin-1-yl)-6-propylpyrimidin-2-yl]amino}benzonitrile dihydrochloride | $^1$H-NMR(400 MHz, CD$_3$OD) δ 8.05(d, 1H), 7.82(brs, 1H), 7.46(s, 1H), 6.75-6.60(m, 1H), 4.80-3.90(m, 2H), 3.75-3.40(m, 3H), 2.70(t, 2H), 2.30-2.15(m, 1H), 2.10-1.95(m, 1H), 1.95-1.70(m, 4H), 1.06(t, 3H) |

TABLE 1-27-continued

| Example | Compound | NMR Spectrum |
| --- | --- | --- |
| 261 | (R)-2-amino-5-{[4-(3-aminopiperidin-1-yl)-6-propylpyrimidin-2-yl]amino}benzonitrile dihydrochloride | $^1$H-NMR(400 MHz, CD$_3$OD) δ 7.47(d, 1H), 7.37(s, 1H), 6.89(brs, 1H), 6.50(d, 1H), 4.70-3.90(m, 2H), 3.65-3.30(m, 3H), 2.63(t, 2H), 2.25-2.15(m, 1H), 2.05-1.60(m, 5H), 1.04(t, 3H) |

TABLE 1-28

| Example | Compound | NMR Spectrum |
| --- | --- | --- |
| 262 | (R)-N$^1$-[4-(3-aminopiperidin-1-yl)-6-propylpyrimidin-2-yl]-4-chlorobenzene-1,3-diamine dihydrochloride | $^1$H-NMR(400 MHz, CD$_3$OD) δ 7.40-7.20(m, 1H), 7.04(brs, 1H), 6.80(s, 1H), 7.65-7.50(m, 1H), 4.75-3.90(m, 2H), 3.65-3.30(m, 3H), 2.65(t, 2H), 2.25-2.15(m, 1H), 2.05-1.90(m, 1H), 1.90-1.65(m, 4H), 1.05(t, 3H) |
| 263 | (R)-4-(3-aminopiperidin-1-yl)-N-[4-methyl-3-(trifluoromethyl)phenyl]-6-propylpyrimidin-2-amine dihydrochloride | $^1$H-NMR(400 MHz, CD$_3$OD) δ 7.90(d, 1H), 7.59(d, 1H), 7.44(brs, 1H), 6.57(d, 1H), 4.70-3.90(m, 2H), 3.70-3.30(m, 3H), 2.67(t, 2H), 2.48(s, 3H), 2.25-2.15(m, 1H), 2.05-1.65(m, 5H), 1.06(t, 3H) |
| 264 | (R)-N-[4-(3-aminopiperidin-1-yl)-6-propylpyrimidin-2-yl]-1H-indol-6-amine dihydrochloride | $^1$H-NMR(400 MHz, CD$_3$OD) δ 7.80-7.30(m, 4H), 7.10-6.85(m, 1H), 6.54(brs, 1H), 4.70-3.90(m, 2H), 3.70-3.30(m, 3H), 2.75-2.55(m, 2H), 2.25-2.15(m, 1H), 2.05-1.60(m, 5H), 1.04(t, 3H) |
| 265 | (R)-4-(3-aminopiperidin-1-yl)-N-(4-methyl-3-nitrophenyl)-6-propylpyrimidin-2-amine dihydrochloride | $^1$H-NMR(400 MHz, CD$_3$OD) δ 8.52(s, 1H), 7.65-7.45(m, 2H), 6.61(brs, 1H), 4.60-3.90(m, 2H), 3.60-3.30(m, 3H), 2.68(t, 2H), 2.59(s, 3H), 2.30-2.15(m, 1H), 2.10-1.90(m, 1H), 1.90-1.60(m, 4H), 1.06(t, 3H) |
| 266 | (R)-N$^1$-[4-(3-aminopiperidin-1-yl)-6-propylpyrimidin-2-yl]-3-nitrobenzene-1,4-diamine dihydrochloride | $^1$H-NMR(400 MHz, CD$_3$OD) δ 8.49(s, 1H), 7.36(d, 1H), 7.04(d, 1H), 6.52(brs, 1H), 4.60-3.90(m, 2H), 3.60-3.30(m, 3H), 2.65(t, 2H), 2.25-2.15(m, 1H), 2.05-1.90(m, 1H), 1.90-1.60(m, 4H), 1.05(t, 3H) |
| 267 | (R)-5-{4-[3-(cyclopropylmethylamino)piperidin-1-yl]-6-propylpyrimidin-2-ylamino}-2-methylbenzonitrile dihydrochloride | $^1$H-NMR(400 MHz, CD$_3$OD) δ 7.87(d, 1H), 7.66(d, 1H), 7.49(d, 1H), 6.62(s, 1H), 4.53(br, 1H), 4.11(br, 1H), 3.63(br, 2H), 3.40(br, 1H), 2.83(br, 1H), 2.67(t, 2H), 2.55(s, 3H), 2.01(br, 1H), 1.99(m, 1H), 1.88(m, 1H), 1.80(m, 2H), 1.76(m, 1H), 1.08(t, 3H), 0.68(m, 2H), 0.32(m, 2H) |
| 268 | (R)-N-{1-[2-(3-cyano-4-fluorophenylamino)-6-propylpyrimidin-4-yl]piperidin-3-yl}acetamide hydrochloride | $^1$H-NMR(400 MHz, CD$_3$OD) δ 7.97(m, 1H), 7.80(m, 1H), 7.43(m, 1H), 6.55-6.44(m, 1H), 4.65-4.18(m, 1H), 4.06(m, 1H), 3.82(m, 1H), 3.48-3.09(m, 1H), 3.40(m, 1H), 2.67(m, 2H), 2.01(br, 1H), 1.97(d + m, 4H), 1.77(m, 2H), 1.66(m, 2H), 1.05(t, 3H) |
| 269 | (R)-5-[4-(3-diethylaminopiperidin-1-yl)-6-propylpyrimidin-2-ylamino]-2-methylbenzonitrile | $^1$H-NMR(400 MHz, CDCl$_3$) δ 8.10(s, 1H), 7.75(br, 1H), 7.52(d, 1H), 7.18(d, 1H), 5.96(s, 1H), 4.50-4.27(m, 2H), 2.84(m, 2H), 2.70(m, 4H), 2.48(s + m, 3 + 2H), 2.04(m, 1H), 1.88(m, 1H), 1.73(m, 3H), 1.61(m, 2H), 1.10(t, 6H), 1.08(t, 3H) |
| 270 | (R)-5-[4-(3-diethylaminopiperidin-1-yl)-6-propylpyrimidin-2-ylamino]-2-fluorobenzonitrile dihydrochloride | $^1$H-NMR(400 MHz, CDCl$_3$) δ 8.13(s, 1H), 7.90(br, 1H), 7.64(m, 1H), 7.10(m, 1H), 5.97(s, 1H), 4.46-4.27(m, 2H), 2.82(t, 2H), 2.68(m, 4H), 2.48(t, 2H), 2.05(m, 1H), 1.88(m, 1H), 1.71(m, 2H), 1.56(m, 2H), 1.07(t, 6H), 0.98(t, 3H) |
| 271 | (R)-5-[4-(3-ethylaminopiperidin-1-yl)-6-propylpyrimidin-2-ylamino]-2-fluorobenzonitrile | $^1$H-NMR(400 MHz, CDCl$_3$) δ 8.17(s, 1H), 7.59(m, 1H), 7.35(br, 1H), 7.10(m, 1H), 5.98(s, 1H), 4.33(br, 1H), 4.03(br, 1H), 3.07(m, 1H), 2.90(m, 1H), 2.79-2.70(m, 3H), 2.47(m, 2H), 2.07(m, 1H), 1.81(m, 1H), 1.71(m, 2H), 1.56(m, 1H), 1.44(m, 1H), 1.16(t, 3H), 0.98(t, 3H) |

TABLE 1-29

| Example | Compound | NMR Spectrum |
| --- | --- | --- |
| 272 | (R)-N-{1-[6-butyl-2-(3-cyanophenylamino)pyrimidin-4-yl]piperidin-3-yl}acetamide hydrochloride | $^1$H-NMR(400 MHz, CD$_3$OD) δ 8.13(m, 1H), 8.00(s, 1H), 7.77(brs, 1H), 7.56(m, 2H), 6.53(brs, 1H), 4.67-4.20(m, 1H), 4.09(m, 1H), 3.85(brs, 1H), 3.48(m, 1H), 3.13(m, 1H), 2.67(m, 2H), 1.97(m, 1H), 1.74-1.67(s + m, 4H), 1.48(m, 4H), 1.24(m, 2H), 1.00(t, 3H) |

TABLE 1-29-continued

| Example | Compound | NMR Spectrum |
| --- | --- | --- |
| 273 | (R)-N-{1-[2-(3-cyanophenylamino)-6-propylpyrimidin-4-yl]piperidin-3-yl}acetamide hydrochloride | $^1$H-NMR(400 MHz, CD$_3$OD) δ 8.15(m, 1H), 8.01(s, 1H), 7.79(m, 1H), 7.56(m, 2H), 6.51(s, 1H), 4.86(br, 1H), 4.10(m, 1H), 3.85(brs, 1H), 3.48(m, 1H), 3.23(m, 1H), 2.65(m, 2H), 2.01-1.85(m, 2H), 1.96(s, 3H), 1.80(m, 2H), 1.69(m, 2H), 1.05(t, 3H) |
| 274 | (R)-N-{1-[2-(3-amino-5-cyanophenylamino)-6-propylpyrimidin-4-yl]piperidin-3-yl}acetamide hydrochloride | $^1$H-NMR(400 MHz, CD$_3$OD) δ 8.20-7.22(m, 1H), 7.11(m, 1H), 6.59(s, 1H), 6.47(brs, 1H), 4.78(br, 1H), 4.08(m, 1H), 3.85(m, 1H), 3.48(m, 1H), 3.12(m, 1H), 2.62(m, 2H), 2.04-1.85(m, 2H), 1.97(s, 3H), 1.76(m, 2H), 1.68(m, 2H), 1.04(t, 3H) |
| 275 | N-{1-[2-(4-amino-3-nitrophenylamino)-6-propylpyrimidin-4-yl]piperidin-3-yl}acetamide hydrochloride | $^1$H-NMR(400 MHz, CD$_3$OD) δ 8.41-8.22(m, 1H), 7.39(m, 1H), 6.99(m, 1H), 6.41(brs, 1H), 4.72-4.25(m, 1H), 4.22(m, 1H), 4.17(m, 1H), 3.40(m, 1H), 3.30(m, 1H), 2.60(m, 2H), 2.01-1.90(m, 2H), 1.95(s, 3H), 1.74(m, 2H), 1.65(m, 2H), 1.04(t, 3H) |
| 276 | N-{1-[2-(3-amino-4-fluorophenylamino)-6-propylpyrimidin-4-yl]piperidin-3-yl}acetamide hydrochloride | $^1$H-NMR(400 MHz, CD$_3$OD) δ 8.19(br, 1H), 7.98(br, 1H), 7.76(br, 1H), 7.39(m, 1H), 6.50(brs, 1H), 4.59(m, 1H), 4.32-4.13(m, 1H), 3.82(br, 1H), 3.46(m, 1H), 3.13(m, 1H), 2.63(m, 2H), 2.01-1.90(m, 2H), 1.94(s, 3H), 1.77(m, 2H), 1.65(m, 2H), 1.05(t, 3H) |
| 277 | (R)-N-{1-[2-(4-fluoro-3-trifluoromethylphenylamino)-6-propylpyrimidin-4-yl]piperidin-3-yl}acetamide hydrochloride | $^1$H-NMR(400 MHz, CD$_3$OD) δ 8.22-7.18(br, 1H), 6.95(br, 1H), 6.60(br, 1H), 6.43(br, 1H), 4.71-4.23(br, 1H), 4.07(br, 1H), 3.85(br, 1H), 3.53-3.47(br, 1H), 3.15(br, 1H), 2.59(m, 2H), 2.01(br, 2H), 1.96(s, 3H), 1.73(m, 2H), 1.66(m, 2H), 1.03(t, 3H) |
| 278 | (R)-N-(1-{2-[3-amino-5-(trifluoromethyl)phenylamino]-6-propylpyrimidin-4-yl}piperidin-3-yl)acetamide hydrochloride | $^1$H-NMR(400 MHz, CD$_3$OD) δ 8.34(s, 1H), 7.71(s, 1H), 7.49(s, 1H), 6.62(s, 1H), 4.10(m, 1H), 3.82(m, 1H), 3.48-3.39(m, 2H), 3.10(m, 1H), 2.68(m, 2H), 2.10-1.95(m, 2H), 2.02(s, 3H), 1.79(m, 2H), 1.72(m, 2H), 1.05(m, 3H) |
| 279 | (R)-N-(1-{2-[4-amino-3-(trifluoromethyl)phenylamino]-6-propylpyrimidin-4-yl}piperidin-3-yl)acetamide hydrochloride | $^1$H-NMR(400 MHz, CD$_3$OD) δ 8.13-8.00(m, 1H), 7.93-7.66(m, 1H), 7.53-7.41(m, 1H), 6.57-6.44(m, 1H), 4.57-4.40(m, 1H), 4.09(m, 1H), 3.86(br, 1H), 3.57-3.41(m, 1H), 3.22(m, 1H), 2.66(m, 2H), 2.01-1.94(m, 2H), 1.95(d, 3H), 1.78(m, 2H), 1.67(m, 2H), 1.05(m, 3H) |
| 280 | (R)-5-[4-(3-ethylaminopiperidin-1-yl)-6-propylpyrimidin-2-ylamino]-2-methylbenzonitrile dihydrochloride | $^1$H-NMR(400 MHz, CD$_3$OD) δ 7.90(s, 1H), 7.63(m, 1H), 7.48(m, 1H), 6.61(s, 1H), 4.53(br, 1H), 4.09(br, 1H), 3.60(br, 2H), 3.43(br, 1H), 3.03(m, 2H), 2.66(m, 2H), 2.54(s, 3H), 2.24(m, 1H), 2.00(m, 1H), 1.80(m, 4H), 1.24(m, 3H), 1.06(t, 3H) |

TABLE 1-30

| Example | Compound | NMR Spectrum |
| --- | --- | --- |
| 281 | (R)-5-[4-(3-ethylaminopiperidin-1-yl)-6-propylpyrimidin-2-ylamino]-2-fluorobenzonitrile dihydrochloride | $^1$H-NMR(400 MHz, CD$_3$OD) δ 8.00(m, 1H), 7.82(m, 1H), 7.47(m, 1H), 6.64(s, 1H), 4.52(m, 1H), 4.11(m, 1H), 3.59(m, 1H), 3.48(m, 1H), 3.38(m, 1H), 3.07(m, 2H), 2.68(m, 2H), 2.25(m, 1H), 1.99(m, 1H), 1.79(m, 4H), 1.25(m, 3H), 1.06(t, 3H) |
| 282 | (R)-2-fluoro-5-[4-(3-methylaminopiperidin-1-yl)-6-propylpyrimidin-2-ylamino]benzonitrile dihydrochloride | $^1$H-NMR(400 MHz, CD$_3$OD) δ 8.14-7.90(m, 1H), 7.72(m, 1H), 7.40(m, 1H), 6.73-6.62(m, 1H), 4.39(m, 1H), 3.99-3.86(m, 1H), 3.70-3.60(m, 2H), 3.47(m, 1H), 2.82(m, 1H), 2.82(m, 2H), 2.60(m, 1H), 2.26(br, 1H), 1.96-1.89(m, 2H), 1.81(m, 3H), 1.08(t, 3H) |
| 283 | (R)-2-methyl-5-[4-(3-methylaminopiperidin-1-yl)-6-propylpyrimidin-2-ylamino]benzonitrile dihydrochloride | $^1$H-NMR(400 MHz, CD$_3$OD) δ 7.88(s, 1H), 7.64(d, 1H), 7.48(d, 1H), 6.62(s, 1H), 4.41(m, 1H), 3.91(m, 1H), 3.76(m, 1H), 3.60(m, 1H), 3.34(m, 1H), 2.77(s, 2H), 2.67(m, 3H), 2.50(s, 3H), 2.24(br, 1H), 1.90(m, 2H), 1.77(m, 3H), 1.04(t, 3H) |
| 284 | (R)-N$^1$-[4-(3-methylaminopiperidin-1-yl)-6-propylpyrimidin-2-yl]-5-(trifluoromethyl)benzene-1,3-diamine dihydrochloride | $^1$H-NMR(400 MHz, CD$_3$OD) δ 7.62-7.49(m, 2H), 7.22(m, 1H), 6.69-6.60(m, 1H), 4.35(m, 1H), 4.10-4.01(m, 1H), 3.83(br, 1H), 3.39(br, 1H), 2.87(m, 1H), 2.68(m, 2H), 2.59(m, 2H), 2.24(br, 1H), 2.01-1.91(m, 2H), 1.80(m, 3H), 1.06(t, 3H) |
| 285 | (R)-N$^1$-[4-(3-methylaminopiperidin-1-yl)-6-propylpyrimidin-2-yl]-3-(trifluoromethyl)benzene-1,4-diamine dihydrochloride | $^1$H-NMR(400 MHz, CD$_3$OD) δ 7.51-7.45(m, 1H), 7.29-7.13(m, 1H), 7.06-6.94(m, 1H), 6.62-6.53(m, 1H), 4.32-4.20(m, 1H), 3.99-3.65(m, 1H), 3.74(m, 1H), 3.48-3.31(m, 1H), 2.80(m, 1H), 2.65(m, 2H), 2.51(s, 2H), 2.20(m, 1H), 1.89(m, 2H), 1.77(m, 3H), 1.04(t, 3H) |

TABLE 1-30-continued

| Example | Compound | NMR Spectrum |
|---|---|---|
| 286 | (R)-3-amino-5-[4-(3-methylaminopiperidin-1-yl)-6-propylpyrimidin-2-ylamino]benzonitrile dihydrochloride | $^1$H-NMR(400 MHz, CD$_3$OD) δ 7.50(m, 1H), 7.18(m, 1H), 6.90(m, 1H), 6.65(m, 1H), 4.52-4.34(m, 1H), 3.92-3.84(m, 1H), 3.62(br, 1H), 3.45(m, 1H), 2.81(m, 1H), 2.68(s, 4H), 2.25(br, 1H), 2.00(br, 1H), 1.89-1.79(m, 4H), 1.06(t, 3H) |
| 287 | (R)-(4-fluoro-3-trifluoromethylphenyl)-[4-(3-methylaminopiperidin-1-yl)-6-propylpyrimidin-2-yl]amine dihydrochloride | $^1$H-NMR(400 MHz, CD$_3$OD) δ 8.00-7.65(m, 2H), 7.45(m, 1H), 6.12(m, 1H), 4.29(m, 1H), 4.10(m, 1H), 3.91(m, 1H), 3.78(m, 1H), 3.45(m, 1H), 2.86-2.77(m, 2H), 2.68(m, 2H), 2.54(br, 1H), 2.23(br, 1H), 1.84-1.78(m, 5H), 1.04(t, 3H) |
| 288 | (R)-N$^1$-[4-(3-ethylaminopiperidin-1-yl)-6-propylpyrimidin-2-yl]-3-nitrobenzene-1,4-diamine dihydrochloride | $^1$H-NMR(400 MHz, CD$_3$OD) δ 8.34-8.12(m, 1H), 7.39(m, 1H), 7.14-7.05(m, 1H), 6.48(m, 1H), 4.57(m, 1H), 4.12-4.09(m, 1H), 3.63(m, 1H), 3.54(m, 1H), 3.21(br, 1H), 2.96(m, 1H), 2.65(m, 2H), 2.25(br, 1H), 1.99(m, 1H), 1.78(m, 4H), 1.24(m, 3H), 1.05(t, 3H) |
| 289 | (R)-N$^1$-[4-(3-ethylaminopiperidin-1-yl)-6-propylpyrimidin-2-yl]-4-fluorobenzene-1,3-diamine dihydrochloride | $^1$H-NMR(400 MHz, CD$_3$OD) δ 7.73-7.60(m, 1H), 7.45-7.30(m, 1H), 6.91-6.86(m, 1H), 6.73-6.61(m, 1H), 4.52(m, 1H), 3.91-3.83(m, 1H), 3.74(m, 1H), 3.62(m, 2H), 3.22(m, 1H), 2.96(m, 1H), 2.68(m, 2H), 2.30(br, 1H), 1.99(m, 1H), 1.81(m, 4H), 1.25(m, 3H), 1.06(t, 3H) |

TABLE 1-31

| Example | Compound | NMR Spectrum |
|---|---|---|
| 290 | (R)-N$^1$-[4-(3-ethylaminopiperidin-1-yl)-6-propylpyrimidin-2-yl]-5-(trifluoromethyl)benzene-1,3-diamine dihydrochloride | $^1$H-NMR(400 MHz, CD$_3$OD) δ 7.60(m, 1H), 7.39-7.29(m, 1H), 7.20-6.97(m, 1H), 6.78-6.55(m, 1H), 4.43(m, 1H), 3.84-3.79(m, 1H), 3.64(m, 1H), 3.40(m, 1H), 3.22(m, 1H), 2.83(m, 1H), 2.67(m, 2H), 2.20(m, 1H), 1.91-1.70(m, 1 + 4H), 1.23(m, 3H), 1.03(t, 3H) |
| 291 | (R)-N$^1$-[4-(3-ethylaminopiperidin-1-yl)-6-propylpyrimidin-2-yl]-3-(trifluoromethyl)benzene-1,4-diamine dihydrochloride | $^1$H-NMR(400 MHz, CD$_3$OD) δ 7.90-7.63(m, 2H), 7.36-7.29(m, 1H), 6.73-6.65(m, 1H), 4.70-4.43(m, 1H), 4.01(m, 1H), 3.62(m, 1H), 3.52(m, 1H), 3.42(m, 1H), 3.22-3.07(m, 1H), 2.69(m, 2H), 2.26(br, 1H), 2.00(m, 1H), 1.81(m, 4H), 1.75-1.24(m, 3H), 1.06(t, 3H) |
| 292 | (R)-3-amino-5-[4-(3-ethylaminopiperidin-1-yl)-6-propylpyrimidin-2-ylamino]benzonitrile dihydrochloride | $^1$H-NMR(400 MHz, CD$_3$OD) δ 7.34(m, 1H), 7.24(m, 1H), 7.06(m, 1H), 6.68-6.55(m, 1H), 4.51-4.38(m, 1H), 3.89-3.76(m, 1H), 3.59(br, 1H), 3.41(br, 1H), 3.20(m, 1H), 2.98(m, 1H), 2.67(m, 2H), 2.24(m, 1H), 1.98(m, 1H), 1.80(m, 4H), 1.23-1.17(m, 3H), 1.05(t, 3H) |
| 293 | (R)-5-[4-(3-aminopiperidin-1-yl)-6-butylpyrimidin-2-ylamino]-2-methylbenzonitrile | $^1$H-NMR(400 MHz, CD$_3$OD) δ 8.17(s, 1H), 7.67(d, 1H), 7.30(d, 1H), 6.22(s, 1H), 4.25(d, 1H), 3.96(m, 1H), 3.59-3.31(m, 2H), 2.55(m, 2H), 2.45(s, 3H), 2.14(m, 1H), 1.86(m, 1H), 1.75(m, 4H), 1.39(m, 2H), 0.98(t, 3H) |
| 294 | (R)-5-[4-(3-aminopiperidin-1-yl)-6-butylpyrimidin-2-ylamino]-2-fluorobenzonitrile | $^1$H-NMR(400 MHz, CD$_3$OD) δ 8.23(s, 1H), 7.80(m, 1H), 7.26(m, 1H), 6.23(s, 1H), 4.27(m, 1H), 4.09(m, 1H), 3.47-3.30(m, 2H), 2.50(m, 3H), 2.13(br, 1H), 1.77(br, 1H), 1.70(m, 5H), 1.40(m, 2H), 0.97(t, 3H) |
| 295 | (R)-N-{1-[6-butyl-2-(3-cyano-4-methylphenylamino)pyrimidin-4-yl]piperidin-3-yl}acetamide hydrochloride | $^1$H-NMR(400 MHz, CD$_3$OD) δ 7.98-7.92(d, 1H), 7.65(m, 1H), 7.43(m, 1H), 6.56-6.43(d, 1H), 4.63-4.25(m, 1H), 4.05(m, 1H), 3.94(m, 1H), 3.65-3.21(m, 2H), 2.68(m, 2H), 2.51(d, 3H), 2.10(s, 3H), 2.06-1.94(m, 2H), 1.76(m, 4H), 1.48(m, 2H), 0.96(t, 3H) |
| 296 | (S)-5-[4-(3-ethylaminopiperidin-1-yl)-6-propylpyrimidin-2-ylamino]-2-methylbenzonitrile dihydrochloride | $^1$H-NMR(400 MHz, CD$_3$OD) δ 7.90(s, 1H), 7.63(m, 1H), 7.48(m, 1H), 6.61(s, 1H), 4.53(br, 1H), 4.09(br, 1H), 3.60(br, 1H), 3.03(m, 2H), 2.66(m, 2H), 2.54(s, 3H), 2.24(m, 1H), 2.00(m, 1H), 1.80(m, 4H), 1.24(m, 3H), 1.06(t, 3H) |
| 297 | 5-[4-(3-ethylaminopiperidin-1-yl)-6-propylpyrimidin-2-ylamino]-2-methylbenzonitrile dihydrochloride | $^1$H-NMR(400 MHz, CD$_3$OD) δ 7.90(s, 1H), 7.62(m, 1H), 7.48(m, 1H), 6.60(s, 1H), 4.51(br, 1H), 4.33-4.01(m, 1H), 3.68(m, 1H), 3.56(m, 1H), 3.36(m, 1H), 3.05(m, 2H), 2.67(m, 2H), 2.54(s, 3H), 2.38(m, 1H), 1.95(m, 1H), 1.78(m, 4H), 1.26(m, 3H), 1.07(t, 3H) |

TABLE 1-31-continued

| Example | Compound | NMR Spectrum |
| --- | --- | --- |
| 298 | N-{1-[6-butyl-2-(3-cyano-4-methylphenylamino)pyrimidin-4-yl]piperidin-3-yl}acetamide hydrochloride | $^1$H-NMR(400 MHz, CDCl$_3$) δ 8.15(s, 1H), 7.46(d, 1H), 7.18(d, 1H), 6.99(s, 1H), 6.00(s, 1H), 5.70(m, 1H), 4.00-3.93(m, 2H), 3.73(m, 1H), 3.47(m, 1H), 3.35(m, 1H), 2.50(m, 5H), 1.96(s, 4H), 1.76(m, 1H), 1.65(m, 4H), 1.39(m, 2H), 0.94(t, 3H) |

TABLE 1-32

| Example | Compound | NMR Spectrum |
| --- | --- | --- |
| 299 | (R)-5-({4-butyl-6-[3-(ethylamino)piperidin-1-yl]pyrimidin-2-yl}amino)-2-methylbenzonitrile | $^1$H-NMR(400 MHz, CDCl$_3$) δ 8.15(s, 1H), 7.47(d, 1H), 7.17(d, 1H), 7.10(brs, 1H), 5.96(s, 1H), 4.32(m, 1H), 4.06(m, 1H), 3.06(m, 1H), 2.89(m, 1H), 2.73(m, 2H), 2.66(m, 1H), 2.49(s + m, 3 + 2H), 2.04(m, 2H), 1.82(m, 2H), 1.63(m, 2H), 1.56(m, 1H), 1.39(m, 3H), 1.13(t, 3H), 0.95(t, 3H) |
| 300 | (R)-5-({4-butyl-6-[3-(butylamino)piperidin-1-yl]pyrimidin-2-yl}amino)-2-methylbenzonitrile | $^1$H-NMR(400 MHz, CDCl$_3$) δ 8.11(s, 1H), 7.52(d, 1H), 7.17(d, 1H), 7.07(brs, 1H), 5.95(s, 1H), 4.35(m, 1H), 4.13(m, 1H), 3.09(m, 1H), 2.85(m, 1H), 2.71-2.47(m, 3H), 2.52-2.48(s + m, 3 + 2H), 2.04(m, 2H), 1.69(m, 4H), 1.67(m, 1H), 1.65(m, 1H), 1.49-1.26(m, 7H), 0.95(t, 3H), 0.91(t, 3H) |
| 301 | (R)-5-({4-butyl-6-[3-(pentylamino)piperidin-1-yl]pyrimidin-2-yl}amino)-2-methylbenzonitrile | $^1$H-NMR(400 MHz, CDCl$_3$) δ 8.10(s, 1H), 7.53(d, 1H), 7.19(d, 1H), 7.17(brs, 1H), 5.95(s, 1H), 4.35(m, 1H), 4.11(m, 1H), 3.07(m, 1H), 2.88(m, 1H), 2.72-2.62(m, 3H), 2.52-2.47(s + m, 3 + 2H), 2.00(m, 2H), 1.79(m, 2H), 1.68(m, 3H), 1.51(m, 3H), 1.45(m, 3H), 1.29(m, 5H), 0.95(t, 3H), 0.89(t, 3H) |
| 302 | (R)-5-({4-butyl-6-[3-(isobutylamino)piperidin-1-yl]pyrimidin-2-yl}amino)-2-methylbenzonitrile | $^1$H-NMR(400 MHz, CDCl$_3$) δ 8.10(s, 1H), 7.53(d, 1H), 7.45(br, 1H), 7.18(d, 1H), 5.95(s, 1H), 4.28(m, 1H), 4.01(m, 1H), 3.10(m, 1H), 2.97(m, 1H), 2.65(m, 1H), 2.54-2.48(m, 7H), 2.30(br, 3H), 2.09(m, 2H), 1.83(m, 1H), 1.73(m, 3H), 1.71(m, 1H), 1.46(m, 3H), 1.00(t, 3H), 0.91(m, 6H) |
| 303 | (R)-5-({4-butyl-6-[3-(isopentylamino)piperidin-1-yl]pyrimidin-2-yl}amino)-2-methylbenzonitrile | $^1$H-NMR(400 MHz, CDCl$_3$) δ 8.11(s, 1H), 7.51(m, 1H), 7.18(d, 1H), 7.08(br, 1H), 5.95(s, 1H), 4.25(m, 1H), 4.11(m, 1H), 3.08(m, 1H), 2.90(m, 1H), 2.72-2.62(m, 3H), 2.52-2.47(m, 5H), 2.00(m, 2H), 1.82(m, 1H), 1.71-1.58(m, 6H), 1.39(m, 5H), 1.00(t, 3H), 0.90(m, 6H) |
| 304 | (R)-5-({4-butyl-6-[3-(neopentylamino)piperidin-1-yl]pyrimidin-2-yl}amino)-2-methylbenzonitrile | $^1$H-NMR(400 MHz, CDCl$_3$) δ 8.07(s, 1H), 7.57(d, 1H), 7.45(br, 1H), 7.18(d, 1H), 5.94(s, 1H), 4.30(m, 1H), 4.15(m, 1H), 3.09(m, 1H), 2.89(m, 1H), 2.55(m, 1H), 2.54-2.43(m, 6H), 2.09(m, 2H), 1.81(m, 1H), 1.67(m, 2H), 1.56(m, 1H), 1.43(m, 3H), 0.95(t, 3H), 0.89(s, 9H) |
| 305 | (R)-5-{[4-butyl-6-(3-{[3-(methylthio)propyl]amino}piperidin-1-yl)pyrimidin-2-yl]amino}-2-methylbenzonitrile | $^1$H-NMR(400 MHz, CDCl$_3$) δ 8.16(s, 1H), 7.54(br, 1H), 7.48(d, 1H), 7.18(d, 1H), 5.95(s, 1H), 4.35(m, 1H), 4.00(m, 1H), 3.55(m, 1H), 2.95(m, 1H), 2.79(m, 2H), 2.65(m, 1H), 2.53(m, 2H), 2.50(m, 5H), 2.09(s, 3H), 2.00(m, 2H), 1.80(m, 4H), 1.65(m, 2H), 1.59(m, 1H), 1.44(m, 3H), 0.95(t, 3H) |
| 306 | (R)-4-fluoro-N$^1$-{4-[3-(methylamino)piperidin-1-yl]-6-propylpyrimidin-2-yl}benzene-1,3-diamine dihydrochloride | $^1$H-NMR (400 MHz, CD$_3$OD) δ 7.88-7.81(m, 1H), 7.64(m, 1H), 7.48(m, 1H), 6.71-6.61(m, 1H), 4.43-4.39(m, 1H), 3.97-3.85(m, 1H), 3.68(m, 1H), 3.43(m, 1H), 2.80(m, 1H), 2.70(m, 2H), 2.61(s, 2H), 2.25(m, 1H), 1.99(m, 2H), 1.81(m, 3H), 1.05(t, 3H) |
| 307 | (R)-4-chloro-N$^1$-{4-[3-(methylamino)piperidin-1-yl]-6-propylpyrimidin-2-yl}benzene-1,3-diamine dihydrochloride | $^1$H-NMR (400 MHz, CD$_3$OD) δ 7.59-7.52(m, 2H), 7.38(m,1H), 6.68-6.60(m, 1H), 4.43-4.29(m, 1H), 3.94-3.85(m, 1H), 3.67(m,1H), 3.39(m, 1H), 2.81(s, 1H), 2.68(m, 2H), 2.62(s, 2H), 2.24(m, 1H), 1.99(m, 2H), 1.79(m, 3H), 1.06(t, 3H) |

TABLE 1-33

| Example | Compound | NMR Spectrum |
| --- | --- | --- |
| 308 | (R)-2-amino-5-({4-[3-(methylamino)piperidin-1-yl]-6-propylpyrimidin-2-yl}amino)benzonitrile dihydrochloride | $^1$H-NMR (400 MHz, CD$_3$OD) δ 7.64-7.55(m, 1H), 7.46-7.30(m, 1H), 7.02-6.92(m, 1H), 6.61-6.53(m, 1H), 4.33(m, 1H), 3.87(m, 1H), 3.65(m, 1H), 3.50(m, 1H), 2.80(s, 1H), 2.66-2.61(m, 4H), 2.22(m, 1H), 2.00(m, 2H), 1.77(m, 3H), 1.04(t, 3H) |

TABLE 1-33-continued

| Example | Compound | NMR Spectrum |
| --- | --- | --- |
| 309 | (R)-N-(3-methoxy-4-methylphenyl)-4-[3-(methylamino)piperidin-1-yl]-6-propylpyrimidin-2-amine dihydrochloride | $^1$H-NMR (400 MHz, CD$_3$OD) δ 7.19-7.11(m, 1H), 6.98-6.90(m, 2H), 6.59-6.53(m, 1H), 4.44-4.41(m, 1H), 4.29-4.04(m, 1H), 3.84(s, 3H), 3.75-3.50(m, 1H), 2.80(s, 1H), 2.63(m, 2H), 2.51(s, 2H), 2.19(s + m, 3 + 1H), 1.89(m, 2H), 1.76(m, 3H), 1.05(t, 3H) |
| 310 | (R)-4-methyl-N$^1$-{4-[3-(methylamino)piperidin-1-yl]-6-propylpyrimidin-2-yl}benzene-1,3-diamine dihydrochloride | $^1$H-NMR (400 MHz, CD$_3$OD) δ 7.66-7.60(m, 1H), 7.56-7.51(m, 2H), 7.47(m, 1H), 7.38(m, 1H), 6.67-6.59(m, 1H), 4.38(m, 1H), 4.00-3.95(m, 1H), 3.82(m, 1H), 3.40(m, 1H), 2.80(m, 1H), 2.68(m, 2H), 2.58(s, 2H), 2.44(m, 5H), 2.23(m, 1H), 1.92(m, 2H), 1.79(m, 3H), 1.06(t, 3H) |
| 311 | (R)-5-({4-butyl-6-[3-(methylamino)piperidin-1-yl]pyrimidin-2-yl}amino)-2-methylbenzonitrile dihydrochloride | $^1$H-NMR (400 MHz, CD$_3$OD) δ 7.88(s, 1H), 7.65(m, 1H), 7.48(m, 1H), 6.61(s, 1H), 4.41(m, 1H), 3.88(m, 1H), 3.61(m, 1H), 2.79-2.63(m, 5H), 2.54(s, 3H), 2.23(m, 1H), 1.98-1.94(m, 2H), 1.74(m, 3H), 1.48(m, 2H), 1.00(t, 3H) |
| 312 | (R)-5-({4-butyl-6-[3-(methylamino)piperidin-1-yl]pyrimidin-2-yl}amino)-2-fluorobenzonitrile dihydrochloride | $^1$H-NMR (400 MHz, CD$_3$OD) δ 7.97(m, 1H), 7.82(m, 1H), 7.67(m, 1H), 7.51(m, 1H), 6.62(m, 1H), 4.44-4.31(m, 1H), 3.88(m, 1H), 3.76(m, 1H), 3.61(m, 1H), 2.78(s, 1H), 2.70(m, 2H), 2.64(s, 2H), 2.23(m, 1H), 1.98-1.90(m, 2H), 1.74(m, 3H), 1.48(m, 2H), 1.00(t, 3H) |
| 313 | (R)-N$^1$-{4-butyl-6-[3-(methylamino)piperidin-1-yl]pyrimidin-2-yl}-5-(trifluoromethyl)benzene-1,3-diamine dihydrochloride | 1H-NMR (400 MHz, CD$_3$OD) δ 8.07-7.71(m, 1H), 7.62(m, 1H), 7.30(m, 1H), 6.66(m, 1H), 4.37(m, 1H), 4.12-4.07(m, 1H), 4.00-3.96(m, 1H), 3.59(m, 1H), 2.81-2.73(m, 3H), 2.59(m, 2H), 2.26(m, 1H), 1.99(m, 2H), 1.76(m, 3H), 1.49(m, 2H), 1.01(t, 3H) |
| 314 | (R)-N$^1$-{4-butyl-6-[3-(methylamino)piperidin-1-yl]pyrimidin-2-yl}-3-(trifluoromethyl)benzene-1,4-diamine dihydrochloride | $^1$H-NMR (400 MHz, CD$_3$OD) δ 7.99-7.60(m, 1H), 7.58(m, 1H), 7.32-7.19(m, 1H), 6.65(m, 1H), 4.34-4.23(m, 1H), 3.95(m, 1H), 3.77-3.61(m, 2H), 2.80(s, 1H), 2.68(m, 2H), 2.53(s, 2H), 2.21(m, 1H), 1.73(m, 2H), 1.47(m, 3H), 1.47(m, 2H), 1.00(t, 3H) |
| 315 | (R)-3-amino-5-({4-butyl-6-[3-(methylamino)piperidin-1-yl]pyrimidin-2-yl}amino)benzonitrile dihydrochloride | $^1$H-NMR (400 MHz, CD$_3$OD) δ 7.86-7.62(m, 2H), 7.33(m, 1H), 6.93-6.65(m, 1H), 4.56-4.33(m, 1H), 3.93(m, 1H), 3.60(m, 1H), 3.45(m, 1H), 2.81-2.69(m, 5H), 2.25(m, 1H), 2.00-1.86(m, 2H), 1.75(m, 3H), 1.24(m, 2H), 1.01(t, 3H) |
| 316 | (R)-2-amino-5-({4-butyl-6-[3-(methylamino)piperidin-1-yl]pyrimidin-2-yl}amino)benzonitrile dihydrochloride | $^1$H-NMR (400 MHz, CD$_3$OD) δ 7.75-7.62(m, 1H), 7.55(m, 1H), 7.15(m, 1H), 6.65-6.55(m, 1H), 4.36(m, 1H), 3.86(m, 1H), 3.63(m, 1H), 3.50(m, 1H), 2.80(s, 1H), 2.68(m, 2H), 2.62(s, 2H), 2.23(m, 1H), 1.91(m, 2H), 1.72(m, 3H), 1.25(m, 2H), 1.00(t, 3H) |

TABLE 1-34

| Example | Compound | NMR Spectrum |
| --- | --- | --- |
| 317 | (R)-N$^1$-{4-butyl-6-[3-(methylamino)piperidin-1-yl]pyrimidin-2-yl}-4-fluorobenzene-1,3-diamine dihydrochloride | $^1$H-NMR (400 MHz, CD$_3$OD) δ 7.64(m, 1H), 7.46-7.38(m, 2H), 6.65-6.59(m, 1H), 4.39-4.31(m, 1H), 3.95-3.83(m, 1H), 3.68(m, 1H), 3.53-3.38(m, 1H), 2.81(s, 1H), 2.70(m, 2H), 2.60(s, 2H), 2.24(m, 1H), 1.98(m, 2H), 1.74(m, 3H), 1.48(m, 2H), 1.01(t, 3H) |
| 318 | (R)-4-butyl-N-(3-methoxy-4-methylphenyl)-6-[3-(methylamino)piperidin-1-yl]pyrimidin-2-amine dihydrochloride | $^1$H-NMR (400 MHz, CD$_3$OD) δ 7.27-7.18(m, 1H), 6.97-6.85(m, 2H), 6.53(br, 1H), 4.53-4.52(m, 1H), 4.27(m, 1H), 3.95(m, 4H), 3.67(m, 1H), 2.81(m, 1H), 2.69(m, 2H), 2.52(m, 2H), 2.19(m, 4H), 1.91(m, 2H), 1.73(m, 3H), 1.23(m, 2H), 1.01(t, 3H) |
| 319 | (R)-N$^1$-{4-butyl-6-[3-(methylamino)piperidin-1-yl]pyrimidin-2-yl}-4-methylbenzene-1,3-diamine dihydrochloride | $^1$H-NMR (400 MHz, CD$_3$OD) δ 7.65-7.60(m, 1H), 7.54(m, 1H), 7.45(m, 1H), 6.67-6.59(m, 1H), 4.36(m, 1H), 4.10-3.96(m, 1H), 3.82(m, 1H), 3.68-3.45(m, 1H), 2.80(s, 1H), 2.70(m, 2H), 2.58(s, 2H), 2.42(s, 3H), 2.23(m, 1H), 1.98(m, 2H), 1.74(m, 3H), 1.24(m, 2H), 1.00(t, 3H) |
| 320 | (R)-4-butyl-N-[4-fluoro-3-(trifluoromethyl)phenyl]-6-[3-(methylamino)piperidin-1-yl]pyrimidin-2-amine dihydrochloride | $^1$H-NMR (400 MHz, CD$_3$OD) δ 8.06-7.72(m, 2H), 7.45(m, 1H), 6.66-6.61(m, 1H), 4.31(m, 1H), 3.65-3.81(m, 1H), 3.69(m, 1H), 3.49(m, 1H), 2.80(s, 1H), 2.71(m, 2H).2.55(s, 2H), 2.24(m, 1H), 1.92(m, 2H), 1.48(m, 3H), 1.29(m, 2H), 1.00(t, 3H) |
| 321 | (R)-N$^1$-{4-[3-(methylamino)piperidin-1-yl]-6-propylpyrimidin-2-yl}-3-nitrobenzene-1,4-diamine dihydrochloride | $^1$H-NMR(400 MHz, CD$_3$OD) δ 8.38(s, 1H), 7.39(d, 1H), 7.05(d, 1H), 6.56(s, 1H), 4.38(br, 1H), 3.85(br, 1H), 3.86(br, 1H), 2.75-7.65(m, 5H), 2.41(m, 1H), 2.01-1.88(m, 2H), 1.66(m, 3H), 1.05(t, 3H) |

TABLE 1-34-continued

| Example | Compound | NMR Spectrum |
| --- | --- | --- |
| 322 | (R)-N-(3,4-dimethylphenyl)-4-[3-(methylamino)piperidin-1-yl]-6-propylpyrimidin-2-amine dihydrochloride | $^1$H-NMR(400 MHz, CD$_3$OD) δ 7.21-7.17(m, 3H), 6.59-6.51(m, 1H), 4.34-4.05(m, 2H), 3.75(br, 1H), 3.48-3.31(m, 1H), 2.80(s, 1H), 2.64(m, 2H), 2.50(s, 2H), 2.29(d, 6H), 2.20(m, 1H), 1.90(m, 2H), 1.77(m, 3H), 1.05(t, 3H) |
| 323 | (R)-N-(3-fluoro-4-methylphenyl)-4-[3-(methylamino)piperidin-1-yl]-6-propylpyrimidin-2-amine dihydrochloride | $^1$H-NMR(400 MHz, CD$_3$OD) δ 7.33-7.27(m, 2H), 7.15(d, 1H), 6.58(s, 1H), 4.41(br, 1H), 3.86(m, 1H), 3.64(m, 1H), 2.78(m, 1H), 2.64(m, 4H), 2.26(s, 3H), 2.60(br, 1H), 1.81(m, 2H), 1.77(m, 3H), 1.05(t, 3H) |
| 324 | (R)-N-[4-methyl-3-(trifluoromethyl)phenyl]-4-[3-(methylamino)piperidin-1-yl]-6-propylpyrimidin-2-amine dihydrochloride | $^1$H-NMR(400 MHz, CD$_3$OD) δ 8.01-7.77(m, 1H), 7.65-7.43(m, 2H), 6.66-6.59(m, 1H), 4.35-4.26(m, 1H), 4.11-3.98(m, 1H), 3.79-3.64(m, 2H), 2.80(s, 1H), 2.67(m, 2H), 2.51-2.48(m, 5H), 2.23(m, 1H), 1.91(m, 2H), 1.78(m, 3H), 1.06(t, 3H) |
| 325 | (R)-4-methoxy-N$^1$-{4-[3-(methylamino)piperidin-1-yl]-6-propylpyrimidin-2-yl}benzene-1,3-diamine dihydrochloride | $^1$H-NMR(400 MHz, CD$_3$OD) δ 7.67-7.63(m, 1H), 7.56(m, 1H), 7.40-7.30(m, 1H), 6.65-6.56(m, 1H), 4.30(m, 1H), 4.03-4.00(s + m, 3 + 1H), 3.78-3.71(m, 2H), 2.80(s, 1H), 2.67(m, 2H), 2.56(s, 2H), 2.26(m, 1H), 1.90(m, 2H), 1.78(m, 3H), 1.05(t, 3H) |
| 326 | (R)-N-{4-[3-(methylamino)piperidin-1-yl]-6-propylpyrimidin-2-yl}-1H-indazol-6-amine dihydrochloride | $^1$H-NMR(400 MHz, CD$_3$OD) δ 8.43(m, 1H), 7.94(m, 2H), 7.36(m, 1H), 6.70-6.61(m, 1H), 4.40(m, 1H), 4.03(m, 1H), 3.84(m, 1H), 3.72(m, 1H), 3.60(m, 1H), 2.82(s, 1H), 2.69(m, 2H), 2.51(s, 2H), 2.23(m, 1H), 1.98(m, 2H), 1.80(m, 3H), 1.06(t, 3H) |

TABLE 1-35

| Example | Compound | NMR Spectrum |
| --- | --- | --- |
| 327 | (R)-N$^4$-{4-[3-(methylamino)piperidin-1-yl]-6-propylpyrimidin-2-yl}benzene-1,2,4-triamine | $^1$H-NMR(400 MHz, CD$_3$OD) δ 6.89(m, 2H), 6.73(m, 1H), 6.49(s, 1H), 4.28(m, 1H), 3.91(m, 2H), 3.65(m, 1H), 2.63(m, 4H), 2.21(m, 1H), 1.88(m, 2H), 1.76(m, 3H), 1.04(t, 3H) |
| 328 | (R)-N$^1$-{4-butyl-6-[3-(methylamino)piperidin-1-yl]pyrimidin-2-yl}-3-nitrobenzene-1,4-diamine dihydrochloride | $^1$H-NMR(400 MHz, CD$_3$OD) δ 8.38(s, 1H), 7.40(d, 1H), 7.05(d, 1H), 6.55(s, 1H), 4.39(m, 1H), 3.85(m, 2H), 3.65(m, 1H), 2.68(m, 4H), 2.23(m, 1H), 1.90(m, 2H), 1.71(m, 3H), 1.47(m, 2H), 1.00(t, 3H) |
| 329 | (R)-3-({4-butyl-6-[3-(methylamino)piperidin-1-yl]pyrimidin-2-yl}amino)benzonitrile dihydrochloride | $^1$H-NMR(400 MHz, CD$_3$OD) δ 7.98(s, 1H), 7.79(m, 1H), 7.61(m, 2H), 6.64(s, 1H), 4.45(m, 1H), 3.91(m, 1H), 3.78(m, 1H), 3.61(m, 1H), 3.40(m, 1H), 2.79(m, 1H), 2.71(m, 2H), 2.63(m, 2H), 2.24(m, 1H), 1.95-1.86(m, 2H), 1.75(m, 3H), 1.48(m, 2H), 1.01(t, 3H) |
| 330 | (R)-4-butyl-N-(3,4-dimethylphenyl)-6-[3-(methylamino)piperidin-1-yl]pyrimidin-2-amine dihydrochloride | $^1$H-NMR(400 MHz, CD$_3$OD) δ 7.21-7.17(m, 3H), 6.58-6.51(m, 1H), 4.38-4.22(m, 1H), 4.11-4.04(m, 1H), 3.75(m, 1H), 3.61(m, 1H), 2.81(s, 1H), 2.67(m, 2H), 2.51(m, 2H), 2.29(m, 7H), 2.00(m, 2H), 1.72(m, 3H), 1.46(m, 2H), 1.00(t, 3H) |
| 331 | (R)-4-butyl-N-(3-fluoro-4-methylphenyl)-6-[3-(methylamino)piperidin-1-yl]pyrimidin-2-amine dihydrochloride | $^1$H-NMR(400 MHz, CD$_3$OD) δ 7.31(m, 2H), 7.18(m, 1H), 6.64-6.57(m, 1H), 4.45-4.36(m, 1H), 3.88(m, 1H), 3.65(m,1H), 2.80(s, 1H), 2.69(m, 2H), 2.61(m, 2H), 2.26(s + m, 3 + 1H), 1.92(m, 2H), 1.73(m, 3H), 1.46(m, 2H), 1.00(t, 3H) |
| 332 | (R)-4-butyl-N-[4-methyl-3-(trifluoromethyl)phenyl]-6-[3-(methylamino)piperidin-1-yl]pyrimidin-2-amine dihydrochloride | $^1$H-NMR(400 MHz, CD$_3$OD) δ 7.87(brs, 1H), 7.59(m, 1H), 7.46(m, 1H), 6.60(s, 1H), 4.30(m, 1H), 3.86(br, 2H), 3.63(m, 1H), 2.70(m, 2H), 2.48(m, 2H), 2.23(s, 3H), 2.23(m, 1H), 1.89(m, 2H), 1.73(m, 3H), 1.48(m, 2H), 1.00(t, 3H) |
| 333 | (R)-N$^1$-{4-butyl-6-[3-(methylamino)piperidin-1-yl]pyrimidin-2-yl}-4-methoxybenzene-1,3-diamine dihydrochloride | $^1$H-NMR(400 MHz, CD$_3$OD) 7.60-7.53(m, 2H), 7.39(m, 1H), 7.31(m, 1H), 6.65-6.56(m, 1H), 4.31(m, 1H), 4.32(m, 3 + 1H), 3.79-3.71(m, 2H), 2.80(s, 1H), 2.71(m, 2H), 2.56(s, 2H), 2.23(br, 1H), 1.99(m, 2H), 1.74(m, 3H), 1.47(m, 2H), 0.99(t, 3H) |
| 334 | (R)-N-{4-butyl-6-[3-(methylamino)piperidin-1-yl]pyrimidin-2-yl}-1H-indazol-6-amine dihydrochloride | $^1$H-NMR(400 MHz, CD$_3$OD) δ 8.48-8.42(m, 1H), 8.06-7.93(m, 2H), 7.36(m, 1H), 6.71-6.61(m, 1H), 4.41(m, 1H), 4.09(m, 1H), 3.84(m, 1H), 3.71(m, 1H), 3.61-3.39(m, 1H), 2.82(m, 1H), 2.71(m, 2H), 2.54(s, 2H), 2.26(m, 1H), 1.99(m, 2H), 1.76(m, 3H), 1.47(m, 2H), 1.00(t, 3H) |
| 335 | (R)-N$^4$-{4-butyl-6-[3-(methylamino)piperidin-1-yl]pyrimidin-2-yl}benzene-1,2,4-triamine | $^1$H-NMR(400 MHz, CD$_3$OD) δ 6.85(s, 1H), 6.78(d, 1H), 6.66(d, 1H), 6.46(s, 1H), 4.25(d, 1H), 3.89(m, 2H), 3.63(m, 1H), 2.64(m, 5H), 2.20(m, 1H), 1.88(m, 2H), 1.68(m, 3H), 1.45(m, 2H), 0.98(t, 3H) |

TABLE 1-35-continued

| Example | Compound | NMR Spectrum |
| --- | --- | --- |
| 336 | (R)-4-(3-aminopiperidin-1-yl)-6-butyl-N-(3-nitrophenyl)pyrimidin-2-amine dihydrochloride | $^1$H-NMR(400 MHz, CD$_3$OD) δ 8.30(brs, 1H), 8.25(s, 1H), 7.78(m, 2H), 7.06(s, 1H), 4.59(br, 1H), 4.14(br, 1H), 3.74-3.48(br, 3H), 2.74(m, 2H), 2.22(br, 1H), 2.01(br, 1H), 1.87-1.72(m, 4H), 1.46(m, 2H), 0.99(t, 3H) |

TABLE 1-36

| Example | Compound | NMR Spectrum |
| --- | --- | --- |
| 337 | (R)-N$^1$-[4-(3-aminopiperidin-1-yl)-6-butylpyrimidin-2-yl]-3-nitrobenzene-1,4-diamine dihydrochloride | $^1$H-NMR(400 MHz, CD$_3$OD) δ 8.50-8.46(m, 1H), 7.36(d, 1H), 7.05(d, 1H), 6.55-6.47(m, 1H), 4.45-4.22(m, 1H), 4.03(m, 1H), 3.43(m, 3H), 2.68(m, 2H), 2.20(m, 1H), 1.97(m, 1H), 1.72(m, 4H), 1.46(m, 2H), 1.00(t, 3H) |
| 338 | (R)-4-(3-aminopiperidin-1-yl)-6-butyl-N-(4-fluoro-3-nitrophenyl)pyrimidin-2-amine dihydrochloride | $^1$H-NMR(400 MHz, CD$_3$OD) δ 8.61(m, 1H), 7.72(m, 1H), 7.51(t, 1H), 6.62(br, 1H), 4.75-3.92(m, 2H), 3.48(m, 3H), 2.72(t, 2H), 2.21(m, 1H), 1.97(m, 1H), 1.75(m, 4H), 1.48(m, 2H), 0.99(t, 3H) |
| 339 | (R)-4-(3-aminopiperidin-1-yl)-6-butyl-N-(4-methyl-3-nitrophenyl)pyrimidin-2-amine dihydrochloride | $^1$H-NMR(400 MHz, CD$_3$OD) δ 8.52(s, 1H), 7.58(m, 1H), 7.50(m, 1H), 6.36-6.58(m, 1H), 4.46-4.08(m, 2H), 3.64-3.54(m, 3H), 2.72(m, 2H), 2.52(m, 3H), 2.22(m, 1H), 1.98(m, 1H), 1.76(m, 4H), 1.47(m, 2H), 1.01(t, 3H) |
| 340 | (R)-N$^1$-[4-(3-aminopiperidin-1-yl)-6-butylpyrimidin-2-yl]-3-(trifluoromethyl)benzene-1,4-diamine dihydrochloride | $^1$H-NMR(400 MHz, CD$_3$OD) δ 8.10-7.77(m, 1H), 7.83-7.67(m, 1H), 7.49-7.40(m, 1H), 7.32-6.97(m, 1H), 6.59(m, 1H), 4.58-3.93(m, 2H), 3.63-3.35(m, 3H), 2.70(m, 2H), 2.19(m,1H), 1.94(m, 1H), 1.82(m, 4H), 1.46(m, 2H), 1.00(t, 3H) |
| 341 | (R)-N$^1$-[4-(3-aminopiperidin-1-yl)-6-butylpyrimidin-2-yl]-5-(trifluoromethyl)benzene-1,3-diamine dihydrochloride | $^1$H-NMR(400 MHz, CD$_3$OD) δ 8.16(d, 1H), 7.75(d, 1H), 7.46(s, 1H), 6.97-6.92(m, 1H), 6.65(m, 1H), 4.67-3.97(m, 2H), 3.70-3.59(m, 3H), 2.74(m, 2H), 2.20(m, 1H), 1.96(m, 1H), 1.83(m, 4H), 1.48(m, 2H), 1.01(t, 3H) |
| 342 | (R)-3-amino-5-{[4-(3-aminopiperidin-1-yl)-6-butylpyrimidin-2-yl]amino}benzonitrile dihydrochloride | $^1$H-NMR(400 MHz, CD$_3$OD) δ 8.00(m, 1H), 7.77(m, 1H), 7.42(s, 1H), 6.95(m, 1H), 6.67(m, 1H), 4.69-3.98(m, 2H), 3.63-3.48(m, 3H), 2.73(m, 2H), 2.19(m, 1H), 1.98(m, 1H), 1.48(m, 4H), 1.17(m, 2H), 1.01(t, 3H) |
| 343 | (R)-4-(3-aminopiperidin-1-yl)-6-butyl-N-[4-methyl-3-(trifluoromethyl)phenyl]pyrimidin-2-amine dihydrochloride | $^1$H-NMR(400 MHz, CD$_3$OD) δ 8.03-7.77(m, 1H), 7.71-7.43(m, 2H), 6.60(m, 1H), 4.56-3.96(m, 2H), 3.50(m, 3H), 2.71(m, 2H), 2.48(s, 3H), 2.20(m, 1H), 2.00(m, 1H), 1.95-1.75(m, 4H), 1.47(m, 2H), 1.01(t, 3H) |
| 344 | (R)-4-(3-aminopiperidin-1-yl)-6-butyl-N-(3-fluoro-4-methylphenyl)pyrimidin-2-amine dihydrochloride | $^1$H-NMR(400 MHz, CD$_3$OD) δ 7.27(m, 2H), 7.17(m, 1H), 6.55(s, 1H), 4.57-4.10(m, 2H), 3.61-3.48(m, 3H), 2.68(m, 2H), 2.27(s, 3H), 2.19(m, 1H), 1.93(m, 1H), 1.82-1.71(m, 4H), 1.45(m, 2H), 1.00(t, 3H) |
| 345 | (R)-4-(3-aminopiperidin-1-yl)-6-butyl-N-(3-methoxy-4-methylphenyl)pyrimidin-2-amine dihydrochloride | $^1$H-NMR(400 MHz, CD$_3$OD) δ 7.16(d, 1H), 7.05(br, 1H), 6.93(m, 1H), 6.51(s, 1H), 4.46-4.22(m, 2H), 3.59-3.48(m, 3H), 2.67(t, 2H), 2.19(s + m, 3 + 1H), 1.91(m, 1H), 1.81-1.70(m, 4H), 1.45(m, 2H), 1.00(t, 3H) |
| 346 | (R)-N$^1$-[4-(3-aminopiperidin-1-yl)-6-butylpyrimidin-2-yl]-4-methylbenzene-1,3-diamine dihydrochloride | $^1$H-NMR(400 MHz, CD$_3$OD) δ 7.73-7.59(m, 1H), 7.56-7.45(m, 2H), 7.42-7.30(m, 1H), 6.60(m, 1H), 4.64-3.94(m, 2H), 3.65-3.49(m, 3H), 2.71(m, 2H), 2.42(s, 3H), 2.18(m, 1H), 1.94(m, 1H), 1.81(m, 4H), 1.46(m, 2H), 1.00(t, 3H) |

TABLE 1-37

| Example | Compound | NMR Spectrum |
| --- | --- | --- |
| 347 | (R)-4-(3-aminopiperidin-1-yl)-6-butyl-N-(3,4-dimethylphenyl)pyrimidin-2-amine dihydrochloride | $^1$H-NMR(400 MHz, CD$_3$OD) δ 7.20(m, 3H), 6.51(s, 1H), 4.58-3.94(m, 2H), 3.61-3.58(m, 3H), 2.67(t, 2H), 2.29-2.27(s + s, 6H), 2.18(m, 1H), 1.92(m, 1H), 1.82-1.71(m, 4H), 1.46(m, 2H), 1.00(t, 3H) |
| 348 | (R)-4-(3-aminopiperidin-1-yl)-6-butyl-N-[4-fluoro-3-(trifluoromethyl)phenyl]pyrimidin-2-amine dihydrochloride | $^1$H-NMR(400 MHz, CD$_3$OD) δ 7.94(m, 1H), 7.77(m, 1H), 7.43(t, 1H), 6.58(3, 1H), 4.40-4.16(m, 2H), 3.50(m, 3H), 2.70(t, 2H), 2.18(m, 1H), 1.91(m, 1H), 1.76(m, 4H), 1.46(m, 2H), 1.00(t, 3H) |

TABLE 1-37-continued

| Example | Compound | NMR Spectrum |
|---|---|---|
| 349 | (R)-$N^1$-[4-(3-aminopiperidin-1-yl)-6-butylpyrimidin-2-yl]-4-fluorobenzene-1,3-diamine dihydrochloride | $^1$H-NMR(400 MHz, $CD_3OD$) δ 7.74-7.64(m, 1H), 7.51(m, 1H), 7.42(m, 1H), 7.19-6.77(m, 1H), 6.61-6.55(m, 1H), 4.64-3.95(m, 2H), 3.63-3.48(m, 3H), 2.70(m, 2H), 2.18(m, 1H), 1.95(m,1H), 1.80(m, 4H), 1.48(m, 2H), 1.00(t, 3H) |
| 350 | (R)-2-amino-5-{[4-(3-aminopiperidin-1-yl)-6-butylpyrimidin-2-yl]amino}benzonitrile dihydrochloride | $^1$H-NMR(400 MHz, $CD_3OD$) δ 7.71-7.53(m, 1H), 7.38(s, 1H), 7.15(m, 1H), 6.55(m, 1H), 4.59-3.93(m, 2H), 3.61-3.48(m, 3H), 2.68(m, 2H), 2.18(m, 1H), 1.94(m, 1H), 1.73(m, 4H), 1.45(m, 2H), 1.00(t, 3H) |
| 351 | (R)-3-{[4-(3-aminopiperidin-1-yl)-6-butylpyrimidin-2-yl]amino}benzonitrile dihydrochloride | $^1$H-NMR(400 MHz, $CD_3OD$) δ 7.84(m, 1H), 7.75-7.70(m, 3H), 7.04(s, 1H), 4.60-4.13(m, 2H), 3.74-3.53(m, 3H), 2.73(m, 2H), 2.21(m, 1H), 1.99(m, 1H), 1.85-1.72(m, 4H), 1.47(m, 2H), 0.99(t, 3H) |
| 352 | (R)-$N^1$-[4-(3-aminopiperidin-1-yl)-6-butylpyrimidin-2-yl]benzene-1,4-diamine dihydrochloride | $^1$H-NMR(400 MHz, $CD_3OD$) δ 7.23(m, 2H), 7.54(m, 2H), 6.62(br, 1H), 4.64-3.97(m, 2H), 3.63-3.54(m, 3H), 2.72(m, 2H), 2.20(m, 1H), 1.96(m, 1H), 1.85-1.76(m, 4H), 1.46(m, 2H), 1.00(t, 3H) |
| 353 | (R)-4-(3-aminopiperidin-1-yl)-6-butyl-N-(4-chloro-3-nitrophenyl)pyrimidin-2-amine dihydrochloride | $^1$H-NMR(400 MHz, $CD_3OD$) δ 8.46(br, 1H), 7.71(m, 2H), 6.64(br, 1H) 4.42-4.02(m, 2H), 3.65(m, 3H), 2.73(m, 2H), 2.23(m, 1H), 1.99(m, 1H), 1.76(m, 4H), 1.49(m, 2H), 1.01(t, 3H) |
| 354 | (R)-$N^4$-[4-(3-aminopiperidin-1-yl)-6-butylpyrimidin-2-yl]benzene-1,2,4-triamine | $^1$H-NMR(400 MHz, $CD_3OD$) δ 6.93(s, 1H), 6.69(s, 2H), 6.23(s, 1H), 4.39(d, 1H), 3.97(m, 1H), 3.44-3.35(m, 3H), 2.54(m, 2H), 2.14(m, 1H), 1.87(m, 1H), 1.73-1.65(m, 4H), 1.42(m, 2H), 0.97(t, 3H) |

Test Example 1: Evaluation of Agonistic Activity in CHO-K1 Cells Expressing Human 5-$HT_{4(a)}$ As CHO-K1 cells stably expressing human 5-$HT_{4(a)}$, we used the GeneBIAzer HTR4-CRE-bla CHO-K1 cells (Invitrogen Corp.). The cells were cultured, under the condition of 37° C. and 5% $CO_2$, in a DMEM supplemented with 10% fetal bovine serum (FBS), 25 mM HEPES (pH7.4), 600 μg/ml hygromycin B, 0.1 mM non-essential amino acids, 100 unit/ml penicillin and 100 μg/ml streptomycin. Subcultures were performed three times per one week, each being at less than 80% confluence. At the previous day before treating test compounds, the cells were collected using 0.5% trypsin/EDTA and then diluted with a DMEM supplemented with 1% FBS, 25 mM HEPES, and 0.1 mM non-essential amino acids into 3.125×10$^5$ cells/ml. 32 μl of the diluted cells were added into 384-well plate (10$^4$ cells per well) and then incubated overnight. After the overnight culture, 8 μl of the medium having 1% of DMSO was added into the cell-free control well and the non-stimulating control well, respectively. 8 μl of the respective test compound dilutions (which had been prepared by diluting by 100-times with the medium as mentioned in the above) having 1% of DMSO were added to the respective remaining wells. After being cultured in the incubator for 5 hours, the wells of the 384-plate were treated with the substrate solution (8 μl per well) prepared according to the vendor's instruction (i.e., Invitrogen's instruction), and then incubated in the dark room for additional two hours. Agonistic activities on 5-$HT_4$ receptor were evaluated, on the basis of fluorescence values of the cleavage-products by beta-lactamase. After exciting to 410 nm of wavelength using a fluorescence detector (Genios Pro), we measured the fluorescence values at two emission wavelengths (first wavelength: 465 nm, second wavelength: 535 nm). Data were analyzed on the basis of the ratio of fluorescence intensities of each well at the respective wavelengths. Each $EC_{50}$ value was calculated by non-linear regression analysis using the "GraphPad Prism" program, based on the activities according to 8-different concentrations of the test compounds. The results are shown in Table 2-1 and 2-2 below.

TABLE 2-1

| Example | $EC_{50}$(nM) |
|---|---|
| 22 | 0.19 |
| 24 | 0.026 |
| 25 | 0.073 |
| 40 | 0.26 |
| 45 | 0.27 |
| 47 | 0.15 |
| 73 | 0.24 |
| 74 | 0.063 |
| 76 | 0.061 |
| 77 | 0.084 |
| 78 | 0.12 |
| 82 | 0.096 |
| 83 | 0.36 |
| 84 | 0.27 |
| 99 | 0.37 |
| 100 | 0.2 |
| 101 | 0.24 |
| 102 | 0.47 |
| 104 | 0.36 |
| 109 | 0.32 |
| 111 | 0.091 |
| 112 | 0.37 |
| 114 | 0.31 |
| 117 | 0.077 |
| 118 | 0.024 |
| 119 | 0.156 |
| 120 | 0.073 |
| 121 | 0.093 |
| 122 | 0.011 |
| 123 | 0.121 |
| 124 | 0.028 |
| 125 | 0.051 |
| 126 | 0.013 |
| 127 | 0.053 |
| 128 | 0.0049 |
| 129 | 0.0041 |
| 131 | 0.12 |
| 136 | 0.35 |
| 138 | 0.46 |
| 140 | 0.28 |
| 141 | 0.15 |
| 142 | 0.3 |
| 146 | 0.27 |
| 147 | 0.31 |

TABLE 2-1-continued

| Example | EC$_{50}$(nM) |
|---|---|
| 150 | 0.07 |
| 151 | 0.361 |
| 153 | 0.02 |
| 154 | 0.041 |
| 155 | 0.093 |
| 156 | 0.066 |
| 157 | 0.088 |
| 158 | 0.054 |
| 159 | 0.046 |
| 160 | 0.125 |
| 161 | 0.148 |
| 162 | 0.043 |
| 163 | 0.088 |
| 164 | 0.075 |
| 165 | 0.188 |
| 174 | 0.039 |
| 175 | 0.035 |
| 176 | 0.018 |
| 177 | 0.049 |
| 178 | 0.082 |
| 179 | 0.027 |
| 180 | 0.153 |
| 181 | 0.025 |
| 182 | 0.022 |
| 187 | 0.24 |
| 188 | 0.43 |
| 189 | 0.32 |
| 190 | 0.46 |
| 191 | 0.34 |
| 198 | 0.4 |
| 200 | 0.18 |
| 203 | 0.14 |
| 205 | 0.008 |
| 206 | 0.0087 |
| 207 | 0.013 |
| 208 | 0.029 |
| 209 | 0.015 |
| 210 | 0.022 |
| 211 | 0.023 |
| 212 | 0.1 |
| 214 | 0.072 |
| 215 | 0.064 |
| 216 | 0.016 |
| 217 | 0.013 |
| 218 | 0.016 |
| 219 | 0.01 |
| 220 | 0.0082 |
| 221 | 0.122 |
| 222 | 0.056 |
| 223 | 0.045 |
| 224 | 0.07 |
| 225 | 0.021 |
| 226 | 0.071 |
| 227 | 0.017 |
| 228 | 0.0035 |
| 229 | 0.0041 |
| 230 | 0.0046 |
| 231 | 0.0063 |
| 232 | 0.0037 |
| 233 | 0.009 |
| 234 | 0.015 |
| 235 | 0.012 |
| 236 | 0.0088 |
| 237 | 0.014 |
| 238 | 0.0083 |
| 239 | 0.017 |
| 240 | 0.012 |
| 241 | 0.014 |
| 242 | 0.0091 |
| 243 | 0.0094 |
| 244 | 0.02 |
| 245 | 0.047 |
| 246 | 0.06 |
| 247 | 0.023 |
| 248 | 0.018 |
| 249 | 0.025 |
| 250 | 0.027 |
| 251 | 0.016 |
| 252 | 0.094 |
| 253 | 0.057 |
| 254 | 0.038 |
| 255 | 0.016 |
| 256 | 0.012 |
| 257 | 0.042 |
| 259 | 0.084 |
| 260 | 0.0075 |
| 261 | 0.105 |
| 262 | 0.021 |
| 263 | 0.0072 |
| 264 | 0.328 |
| 265 | 0.049 |
| 266 | 0.0096 |
| 267 | 0.088 |
| 268 | 0.025 |
| 269 | 0.016 |
| 270 | 0.148 |
| 271 | 0.026 |
| 272 | 0.011 |
| 273 | 0.046 |
| 274 | 0.006 |

TABLE 2-2

| Example | EC$_{50}$(nM) |
|---|---|
| 275 | 0.0034 |
| 276 | 0.018 |
| 277 | 0.014 |
| 278 | 0.01 |
| 279 | 0.014 |
| 282 | 0.073 |
| 283 | 0.0084 |
| 284 | 0.0032 |
| 285 | 0.005 |
| 286 | 0.0044 |
| 287 | 0.026 |
| 288 | 0.0046 |
| 289 | 0.0065 |
| 290 | 0.0041 |
| 291 | 0.0028 |
| 292 | 0.019 |
| 293 | 0.023 |
| 294 | 0.108 |
| 295 | 0.0086 |
| 296 | 0.015 |
| 297 | 0.0024 |
| 298 | 0.012 |
| 299 | 0.004 |
| 300 | 0.0097 |
| 301 | 0.019 |
| 302 | 0.019 |
| 303 | 0.025 |
| 304 | 0.049 |
| 305 | 0.0091 |
| 306 | 0.015 |
| 307 | 0.004 |
| 308 | 0.013 |
| 309 | 0.011 |
| 310 | 0.047 |
| 311 | 0.0026 |
| 312 | 0.014 |
| 313 | 0.005 |
| 314 | 0.0019 |
| 315 | 0.0012 |
| 316 | 0.0067 |
| 317 | 0.0066 |
| 318 | 0.025 |
| 319 | 0.0047 |
| 320 | 0.018 |
| 321 | 0.0031 |
| 322 | 0.243 |
| 323 | 0.416 |
| 324 | 0.0087 |

TABLE 2-2-continued

| Example | EC$_{50}$(nM) |
|---|---|
| 328 | 0.0029 |
| 329 | 0.054 |
| 330 | 0.086 |
| 331 | 0.218 |
| 332 | 0.017 |
| 333 | 0.132 |
| 337 | 0.006 |
| 338 | 0.014 |
| 339 | 0.017 |
| 340 | 0.112 |
| 342 | 0.0041 |
| 343 | 0.034 |
| 344 | 0.448 |
| 345 | 0.08 |
| 346 | 0.135 |
| 347 | 0.391 |
| 348 | 0.102 |
| 349 | 0.014 |
| 350 | 0.028 |
| 352 | 0.029 |
| 353 | 0.337 |

As shown in Table 2-1 and 2-2, the compounds of the present invention have excellent activities as a 5-HT$_4$ receptor agonist, and therefore they can be usefully applied for preventing or treating the dysfunction in gastrointestinal motility.

The invention claimed is:

1. A compound of Formula 1 or its pharmaceutically acceptable salt:

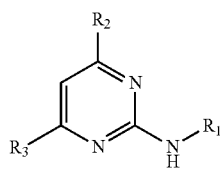

<Formula 1> wherein,

R$_1$ is a phenyl group substituted with one or more substituents selected from the group consisting of amino, halogen, cyano, nitro, C$_{1-3}$ alkyl (where the C$_{1-3}$ alkyl is optionally substituted with halogen), C$_{1-5}$ alkoxy, C$_{1-5}$ alkylthio, and aminocarbonyl; or a heteroaryl group selected from the group consisting of quinolinyl, chromenonyl, benzofuranyl, indolyl, indolinyl, benzimidazol-5-yl, benzimidazol-6-yl, and indazolyl, wherein the heteroaryl group is optionally substituted with one or more C$_{1-5}$ alkyl (where the C$_{1-5}$ alkyl is optionally substituted with halogen), R$_2$ is a nitrogen-containing cyclic group of the following Formula B (where * in Formula B represents the position attached to the compound of Formula 1),

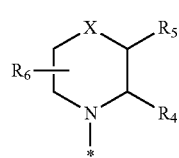

B

R$_3$ is a C$_{2-5}$ alkyl group,

R$_4$ is hydrogen; a C$_{1-5}$ alkyl group optionally substituted with hydroxy; or a C$_{1-5}$ alkoxycarbonyl group, R$_5$ is hydrogen; a hydroxyl group; a benzyloxy group; a C$_{1-5}$ alkyl group; or a group selected from the group consisting of the following Formulas E and I (where * in Formulas E and I represents the position attached to the compound of Formula B),

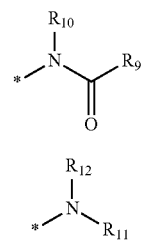

E

I

R$_6$ is hydrogen,

X is —CH(R$_7$)—; —N(R$_8$)—; or —O—,

R$_7$ is hydrogen,

R$_4$ and R$_5$ are optionally joined to each other to form a pentagonal or hexagonal ring, R$_8$ is a C$_{1-5}$ alkyl group, R$_9$ is a C$_{1-10}$ alkyl group optionally substituted with hydroxy, R$_{10}$ is hydrogen, R$_{11}$ and R$_{12}$ are, independently each other, hydrogen; or a C$_{1-10}$ alkyl group optionally substituted with a substituent selected from the group consisting of C$_{1-5}$ alkylthio, C$_{3-10}$ cycloalkyl, phenyl (where the phenyl is optionally substituted with hydroxy), thiophenyl, pyrrolyl, and furanyl (where the furanyl is optionally substituted with mono- or di-C$_{1-5}$ alkyl).

2. The compound or its pharmaceutically acceptable salt of claim 1, which is selected from the group consisting of:
N-(4-fluorophenyl)-4-(piperidin-1-yl)-6-propylpyrimidin-2-amine;
N-(4-fluorophenyl)-4-morpholino-6-propylpyrimidin-2-amine;
N-(4-fluorophenyl)-4-(2-methylpiperidin-1-yl)-6-propylpyrimidin-2-amine;
N-(4-fluorophenyl)-4-(3-methylpiperidin-1-yl)-6-propylpyrimidin-2-amine;
N-(4-fluorophenyl)-4-(decahydroquinolin-1(2H)-yl)-6-propylpyrimidin-2-amine;
N-(4-fluorophenyl)-4-(piperazin-1-yl)-6-propylpyrimidin-2-amine;
4-(2-ethylpiperidin-1-yl)-N-(4-fluorophenyl)-6-propylpyrimidin-2-amine;
2-{1-[2-(4-fluorophenylamino)-6-propylpyrimidin-4-yl]piperidin-2-yl}ethanol;
ethyl 1-[2-(4-fluorophenylamino)-6-propylpyrimidin-4-yl]piperidin-2-carboxylate;
4-butyl-N-(4-fluorophenyl)-6-(piperidin-1-yl)pyrimidin-2-amine;
4-butyl-6-(2-ethylpiperidin-1-yl)-N-(4-fluorophenyl)pyrimidin-2-amine;
2-{1-[6-butyl-2-(4-fluorophenylamino)pyrimidin-4-yl]piperidin-2-yl}ethanol;
4-butyl-N-(4-fluorophenyl)-6-morpholinopyrimidin-2-amine;
2-{1-[2-(4-chloro-3-nitrophenylamino)-6-propylpyrimidin-4-yl]piperidin-2-yl}ethanol;

2-(1-{2-[3-(methylthio)phenylamino]-6-propylpyrimidin-4-yl}piperidin-2-yl)ethanol;
N-{1-[2-(4-fluorophenylamino)-6-propylpyrimidin-4-yl]piperidin-3-yl}acetamide;
4-[3-(benzyloxy)piperidin-1-yl]-N-(4-fluorophenyl)-6-propylpyrimidin-2-amine;
N-[4-(piperidin-1-yl)-6-propylpyrimidin-2-yl]-1H-indol-5-amine;
N-(3-chloro-4-methylphenyl)-4-(piperidin-1-yl)-6-propylpyrimidin-2-amine;
N-[4-(piperidin-1-yl)-6-propylpyrimidin-2-yl]quinolin-6-amine;
4-(piperidin-1-yl)-6-propyl-N-[3-(trifluoromethyl)phenyl]pyrimidin-2-amine;
N-[4-(piperidin-1-yl)-6-propylpyrimidin-2-yl]-2-(trifluoromethyl)-1H-benzo[d]imidazol-5-amine;
N-[3-(methylthio)phenyl]-4-(piperidin-1-yl)-6-propylpyrimidin-2-amine;
N-(5-methoxy-2-methylphenyl)-4-(piperidin-1-yl)-6-propylpyrimidin-2-amine;
N-(5-chloro-2-methylphenyl)-4-(piperidin-1-yl)-6-propylpyrimidin-2-amine;
N-(4-fluoro-3-nitrophenyl)-4-(piperidin-1-yl)-6-propylpyrimidin-2-amine;
N-(4-methoxyphenyl)-4-(piperidin-1-yl)-6-propylpyrimidin-2-amine;
N-(3-methoxyphenyl)-4-(piperidin-1-yl)-6-propylpyrimidin-2-amine;
N-(3-chlorophenyl)-4-(piperidin-1-yl)-6-propylpyrimidin-2-amine;
N-(3-nitrophenyl)-4-(piperidin-1-yl)-6-propylpyrimidin-2-amine;
N-(4-chloro-3-nitrophenyl)-4-(piperidin-1-yl)-6-propylpyrimidin-2-amine;
3-[4-(piperidin-1-yl)-6-propylpyrimidin-2-ylamino]benzonitrile;
N-(4-methyl-3-nitrophenyl)-4-(piperidin-1-yl)-6-propylpyrimidin-2-amine;
N-[4-(octahydroquinolin-1(2H)-yl)-6-propylpyrimidin-2-yl]-1H-indol-6-amine;
2-{1-[2-(1H-indol-6-ylamino)-6-propylpyrimidin-4-yl]piperidin-2-yl}ethanol;
N-[4-(piperidin-1-yl)-6-propylpyrimidin-2-yl]-1H-indol-6-amine;
N-(4-morpholino-6-propylpyrimidin-2-yl)-1H-indol-6-amine;
N-[4-(2-ethylpiperidin-1-yl)-6-propylpyrimidin-2-yl]-1H-indol-6-amine;
(R)-3-[4-(3-ethylmorpholino)-6-propylpyrimidin-2-ylamino]benzonitrile;
(R)-3-[4-(2-methylpiperazin-1-yl)-6-propylpyrimidin-2-ylamino]benzonitrile;
4-morpholino-N-(3-nitrophenyl)-6-propylpyrimidin-2-amine;
N-(4-fluoro-3-nitrophenyl)-4-morpholino-6-propylpyrimidin-2-amine;
N-(4-chloro-3-nitrophenyl)-4-morpholino-6-propylpyrimidin-2-amine;
N-(3-methoxyphenyl)-4-morpholino-6-propylpyrimidin-2-amine;
N-(4-methoxyphenyl)-4-morpholino-6-propylpyrimidin-2-amine;
N-[3-(methylthio)phenyl]-4-morpholino-6-propylpyrimidin-2-amine;
N-(3-chlorophenyl)-4-morpholino-6-propylpyrimidin-2-amine;
N-(3-chloro-4-methylphenyl)-4-morpholino-6-propylpyrimidin-2-amine;
4-morpholino-6-propyl-N-[3-(trifluoromethyl)phenyl]pyrimidin-2-amine;
N-(4-morpholino-6-propylpyrimidin-2-yl)-1H-indol-5-amine;
N-(4-morpholino-6-propylpyrimidin-2-yl)-2-(trifluoromethyl)-1H-benzo[d]imidazol-6-amine;
N-(4-morpholino-6-propylpyrimidin-2-yl)quinolin-6-amine;
3-(4-morpholino-6-propylpyrimidin-2-ylamino)benzonitrile;
N-(5-methoxy-2-methylphenyl)-4-morpholino-6-propylpyrimidin-2-amine;
N-(5-chloro-2-methylphenyl)-4-morpholino-6-propylpyrimidin-2-amine;
N-(4-morpholino-6-propylpyrimidin-2-yl)quinolin-3-amine;
4-(2-ethylpiperidin-1-yl)-N-(3-nitrophenyl)-6-propylpyrimidin-2-amine;
4-(2-ethylpiperidin-1-yl)-N-(4-fluoro-3-nitrophenyl)-6-propylpyrimidin-2-amine;
N-(4-chloro-3-nitrophenyl)-4-(2-ethylpiperidin-1-yl)-6-propylpyrimidin-2-amine;
4-(2-ethylpiperidin-1-yl)-N-(3-methoxyphenyl)-6-propylpyrimidin-2-amine;
4-(2-ethylpiperidin-1-yl)-N-(4-methoxyphenyl)-6-propylpyrimidin-2-amine;
4-(2-ethylpiperidin-1-yl)-N-[3-(methylthio)phenyl]-6-propylpyrimidin-2-amine;
N-(3-chlorophenyl)-4-(2-ethylpiperidin-1-yl)-6-propylpyrimidin-2-amine;
N-(3-chloro-4-methylphenyl)-4-(2-ethylpiperidin-1-yl)-6-propylpyrimidin-2-amine;
4-(2-ethylpiperidin-1-yl)-6-propyl-N-[3-(trifluoromethyl)phenyl]pyrimidin-2-amine;
N-[4-(2-ethylpiperidin-1-yl)-6-propylpyrimidin-2-yl]-1H-indol-5-amine;
N-[4-(2-ethylpiperidin-1-yl)-6-propylpyrimidin-2-yl]-2-(trifluoromethyl)-1H-benzo[d]imidazol-6-amine;
N-[4-(2-ethylpiperidin-1-yl)-6-propylpyrimidin-2-yl]quinolin-6-amine;
3-[4-(2-ethylpiperidin-1-yl)-6-propylpyrimidin-2-ylamino]benzonitrile;
4-(2-ethylpiperidin-1-yl)-N-(5-methoxy-2-methyl phenyl)-6-propylpyrimidin-2-amine;
N-(5-chloro-2-methylphenyl)-4-(2-ethylpiperidin-1-yl)-6-propylpyrimidin-2-amine;
N-[4-(2-ethylpiperidin-1-yl)-6-propylpyrimidin-2-yl]quinolin-3-amine;
(R)—N-(4-chloro-3-nitrophenyl)-4-(2-methyl piperazin-1-yl)-6-propylpyrimidin-2-amine;
(R)—N-[4-(2-methylpiperazin-1-yl)-6-propylpyrimidin-2-yl]-1H-indol-6-amine;
(R)—N-(2-methylpiperazin-1-yl)-6-propyl-N-[3-(trifluoromethyl)phenyl]pyrimidin-2-amine;
(R)—N-(2-methylpiperazin-1-yl)-N-(3-nitrophenyl)-6-propylpyrimidin-2-amine;
(R)—N-(4-fluoro-3-nitrophenyl)-4-(2-methyl piperazin-1-yl)-6-propylpyrimidin-2-amine;
(R)—N-(4-methyl-3-nitrophenyl)-4-(2-methyl piperazin-1-yl)-6-propylpyrimidin-2-amine;
(R)-4-fluoro-$N^1$-[4-(2-methylpiperazin-1-yl)-6-propylpyrimidin-2-yl]benzene-1,3-diamine;
(R)—$N^1$-[4-(2-methylpiperazin-1-yl)-6-propylpyrimidin-2-yl]-3-(trifluoromethyl)benzene-1,4-diamine;

(R)-2-fluoro-5-[4-(2-methylpiperazin-1-yl)-6-propylpyrimidin-2-ylamino]benzonitrile;
(R)-2-methyl-5-[4-(2-methylpiperazin-1-yl)-6-propylpyrimidin-2-ylamino]benzonitrile;
(R)-2-amino-5-[4-(2-methylpiperazin-1-yl)-6-propylpyrimidin-2-ylamino]benzonitrile;
(R)—N$^1$-[4-(2-methylpiperazin-1-yl)-6-propylpyrimidin-2-yl]-3-nitrobenzene-1,4-diamine;
(R)-3-amino-5-[4-(2-methylpiperazin-1-yl)-6-propylpyrimidin-2-ylamino]benzonitrile;
(R)-3-[4-(2-methylpiperazin-1-yl)-6-propylpyrimidin-2-ylamino]benzamide;
3-{4-[2-(2-hydroxyethyl)piperidin-1-yl]-6-propylpyrimidin-2-ylamino}benzonitrile;
2-{1-[2-(1-ethyl-1H-indol-6-ylamino)-6-propyl pyrimidin-4-yl]piperidin-2-yl}ethanol;
2-{1-[2-(1H-indol-5-ylamino)-6-propylpyrimidin-4-yl]piperidin-2-yl}ethanol;
2-(1-{6-propyl-2-[2-(trifluoromethyl)-1H-benzo[d]imidazol-6-ylamino]pyrimidin-4-yl}piperidin-2-yl)ethanol;
2-{1-[2-(4-methoxyphenylamino)-6-propylpyrimidin-4-yl]piperidin-2-yl}ethanol;
2-{1-[2-(3-methoxyphenylamino)-6-propylpyrimidin-4-yl]piperidin-2-yl}ethanol;
2-{1-[2-(5-methoxy-2-methylphenylamino)-6-propylpyrimidin-4-yl]piperidin-2-yl}ethanol;
2-{1-[2-(3-chloro-4-methylphenylamino)-6-propylpyrimidin-4-yl]piperidin-2-yl}ethanol;
2-{1-[2-(3-nitrophenylamino)-6-propylpyrimidin-4-yl]piperidin-2-yl}ethanol;
2-{1-[2-(4-fluoro-3-nitrophenylamino)-6-propylpyrimidin-4-yl]piperidin-2-yl}ethanol;
2-{1-[2-(2,3-dimethylbenzofuran-5-ylamino)-6-propylpyrimidin-4-yl]piperidin-2-yl}ethanol;
2-{1-[6-propyl-2-(quinolin-6-ylamino)pyrimidin-4-yl]piperidin-2-yl}ethanol;
2-{1-[2-(3-chlorophenylamino)-6-propylpyrimidin-4-yl]piperidin-2-yl}ethanol;
7-{4-[2-(2-hydroxyethyl)piperidin-1-yl]-6-propylpyrimidin-2-ylamino}-4-methyl-2H-chromen-2-one;
2-{1-[6-propyl-2-(3-trifluoromethylphenylamino)pyrimidin-4-yl]piperidin-2-yl}ethanol;
2-{1-[6-propyl-2-(quinolin-3-ylamino)pyrimidin-4-yl]piperidin-2-yl}ethanol;
(S)-5-[4-(3-aminopiperidin-1-yl)-6-propylpyrimidin-2-ylamino]-2-methylbenzonitrile;
(S)-4-(3-aminopiperidin-1-yl)-N-(3-nitrophenyl)-6-propylpyrimidin-2-amine;
(S)-3-[4-(3-aminopiperidin-1-yl)-6-propylpyrimidin-2-ylamino]benzonitrile;
(R)-5-[4-(3-aminopiperidin-1-yl)-6-propylpyrimidin-2-ylamino]-2-methylbenzonitrile;
(S)-5-{4-[3-(butylamino)piperidin-1-yl]-6-propylpyrimidin-2-ylamino}-2-methylbenzonitrile;
(S)-5-{4-[3-(pentylamino)piperidin-1-yl]-6-propylpyrimidin-2-ylamino}-2-methylbenzonitrile;
(S)-5-{4-[3-(isobutylamino)piperidin-1-yl]-6-propylpyrimidin-2-ylamino}-2-methylbenzonitrile;
(S)-5-{4-[3-(isopentylamino)piperidin-1-yl]-6-propylpyrimidin-2-ylamino}-2-methylbenzonitrile;
(S)-2-methyl-5-{4-[3-(neopentylamino)piperidin-1-yl]-6-propylpyrimidin-2-ylamino}benzonitrile;
(S)-5-(4-{3-[(1H-pyrrol-2-yl)methylamino]piperidin-1-yl}-6-propylpyrimidin-2-ylamino)-2-methyl benzonitrile;
(S)-2-methyl-5-(4-propyl-6-{3-[(thiophen-2-ylmethyl)amino]piperidin-1-yl}pyrimidin-2-ylamino)benzonitrile;
(S)-5-(4-{3-[(4,5-dimethylfuran-2-ylmethyl)amino]piperidin-1-yl}-6-propylpyrimidin-2-ylamino)-2-methylbenzonitrile;
(S)-2-methyl-5-{4-[3-(3-methylthiopropylamino)piperidin-1-yl]-6-propylpyrimidin-2-ylamino}benzonitrile;
(S)-5-{4-[3-(cyclopropylmethylamino)piperidin-1-yl]-6-propylpyrimidin-2-ylamino}-2-methylbenzonitrile;
(S)-5-{4-[3-(4-hydroxybenzylamino)piperid in-1-yl]-6-propylpyrimidin-2-ylamino}-2-methylbenzonitrile;
(S)-5-[4-(3-diethylaminopiperidin-1-yl)-6-propylpyrimidin-2-ylamino]-2-methylbenzonitrile;
(S)-5-(4-{3-[bis(cyclopropylmethyl)amino]piperidin-1-yl}-6-propylpyrimidin-2-ylamino)-2-methyl benzonitrile;
(R)-5-(4-{3-[bis(cyclopropylmethyl)amino]piperidin-1-yl}-6-propylpyrimidin-2-ylamino)-2-methyl benzonitrile;
4-ethyl-N-(4-fluorophenyl)-6-(piperidin-1-yl)pyrimidin-2-amine;
4-ethyl-N-(4-fluorophenyl)-6-(octahydroquinolin-1(2H)-yl)pyrimidin-2-amine;
4-ethyl-6-(2-ethylpiperidin-1-yl)-N-(4-fluorophenyl)pyrimidin-2-amine;
2-{1-[6-ethyl-2-(4-fluorophenylamino)pyrimidin-4-yl]piperidin-2-yl}ethanol;
4-ethyl-N-(4-fluorophenyl)-6-morpholinopyrimidin-2-amine;
2-{1-[2-(4-methyl-3-nitrophenylamino)-6-propylpyrimidin-4-yl]piperidin-2-yl}ethanol;
2-{1-[2-(4-amino-3-trifluoromethylphenylamino)-6-propylpyrimidin-4-yl]piperidin-2-yl}ethanol;
2-{1-[2-(4-amino-3-nitrophenylamino)-6-propylpyrimidin-4-yl]piperidin-2-yl}ethanol;
5-{4-[2-(2-hydroxyethyl)piperidin-1-yl]-6-propylpyrimidin-2-ylamino}-2-methylbenzonitrile;
2-fluoro-5-{4-[2-(2-hydroxyethyl)piperidin-1-yl]-6-propylpyrimidin-2-ylamino}benzonitrile;
2-amino-5-{4-[2-(2-hydroxyethyl)piperidin-1-yl]-6-propylpyrimidin-2-ylamino}benzonitrile;
2-{1-[2-(3-amino-4-methylphenylamino)-6-propylpyrimidin-4-yl]piperidin-2-yl}ethanol;
2-{1-[2-(3-amino-4-fluorophenylamino)-6-propylpyrimidin-4-yl]piperidin-2-yl}ethanol;
2-{1-[2-(3-amino-4-chlorophenylamino)-6-propylpyrimidin-4-yl]piperidin-2-yl}ethanol;
2-{1-[2-(indolin-6-ylamino)-6-propylpyrimidin-4-yl]piperidin-2-yl}ethanol;
(S)-2-{1-[2-(4-chloro-3-nitrophenylamino)-6-propylpyrimidin-4-yl]piperidin-2-yl}ethanol;
(S)-2-{1-[2-(4-amino-3-nitrophenylamino)-6-propylpyrimidin-4-yl]piperidin-2-yl}ethanol;
(R)-2-{1-[2-(4-amino-3-nitrophenylamino)-6-propylpyrimidin-4-yl]piperidin-2-yl}ethanol;
3-[4-(octahydroquinolin-1(2H)-yl)-6-propylpyrimidin-2-ylamino]benzonitrile;
N-(3-nitrophenyl)-4-(octahydroquinolin-1(2H)-yl)-6-propylpyrimidin-2-amine;
N-(4-fluoro-3-nitrophenyl)-4-(octahydroquinolin-1(2H)-yl)-6-propylpyrimidin-2-amine;
N-(4-chloro-3-nitrophenyl)-4-(octahydroquinolin-1(2H)-yl)-6-propylpyrimidin-2-amine;
N-(3-methoxyphenyl)-4-(octahydroquinolin-1(2H)-yl)-6-propylpyrimidin-2-amine;

N-(5-methoxy-2-methylphenyl)-4-(octahydroquinolin-1 (2H)-yl)-6-propylpyrimidin-2-amine;
N-(4-methoxyphenyl)-4-(octahydroquinolin-1(2H)-yl)-6-propylpyrimidin-2-amine;
4-(octahydroquinolin-1(2H)-yl)-6-propyl-N-(3-trifluoromethylphenyl)pyrimidin-2-amine;
N-(3-chlorophenyl)-4-(octahydroquinolin-1(2H)-yl)-6-propylpyrimidin-2-amine;
N-(5-chloro-2-methyl phenyl)-4-(octahydroquinolin-1 (2H)-yl)-6-propylpyrimidin-2-amine;
N-(3-chloro-4-methyl phenyl)-4-(octahydroquinolin-1 (2H)-yl)-6-propylpyrimidin-2-amine;
N-(3-methylthiophenyl)-4-(octahydroquinolin-1(2H)-yl)-6-propylpyrimidin-2-amine;
N-[4-(octahydroquinolin-1(2H)-yl)-6-propylpyrimidin-2-yl]-1H-indol-5-amine;
N-[4-(octahydroquinolin-1(2H)-yl)-6-propylpyrimidin-2-yl]-2-(trifluoromethyl)-1H-benzo[d]imidazol-5-amine;
N-[4-(octahydroquinolin-1(2H)-yl)-6-propylpyrimidin-2-yl]quinolin-6-amine;
4-methyl-7-[4-(octahydroquinolin1(2H)-yl)-6-propylpyrimidin-2-amino]-2H-chromen-2-one;
N-[4-(octahydroquinolin-1(2H)-yl)-6-propylpyrimidin-2-yl]quinolin-3-amine;
(R)-5-{4-[3-(ethylamino)piperidin-1-yl]-6-propylpyrimidin-2-ylamino}-2-methylbenzonitrile;
(R)-5-{4-[3-(propylamino)piperidin-1-yl]-6-propylpyrimidin-2-ylamino}-2-methylbenzonitrile;
(R)-5-{4-[3-(butylamino)piperidin-1-yl]-6-propylpyrimidin-2-ylamino}-2-methylbenzonitrile;
(R)-2-methyl-5-{4-[3-(pentylamino)piperidin-1-yl]-6-propylpyrimidin-2-ylamino}benzonitrile;
(R)-5-{4-[3-(isobutylamino)piperidin-1-yl]-6-propylpyrimidin-2-ylamino}-2-methylbenzonitrile;
(R)-5-{4-[3-(isopentylamino)piperidin-1-yl]-6-propylpyrimidin-2-ylamino}-2-methylbenzonitrile;
(R)-2-methyl-5-{4-[3-(neopentylamino)piperidin-1-yl]-6-propylpyrimidin-2-ylamino}benzonitrile;
(R)-5-{4-[3-(isopropylamino)piperidin-1-yl]-6-propylpyrimidin-2-ylamino}-2-methylbenzonitrile;
(R)-5-(4-{3-[(1H-pyrrol-2-yl)methylamino]piperidin-1-yl}-6-propylpyrimidin-2-ylamino)-2-methyl benzonitrile;
(R)-2-methyl-5-(4-propyl-6-{3-[(thiophen-2-ylmethyl)amino]piperidin-1-yl}pyrimidin-2-ylamino)benzonitrile;
(R)-5-(4-{3-[(4,5-dimethylfuran-2-ylmethyl)amino]piperidin-1-yl}-6-propylpyrimidin-2-ylamino)-2-methylbenzonitrile;
(R)-2-methyl-5-{4-[3-(3-methylthiopropylamino)piperidin-1-yl]-6-propylpyrimidin-2-ylamino}benzonitrile;
(R)-5-{4-[3-(cyclopropylmethylamino)piperidin-1-yl]-6-propylpyrimidin-2-ylamino}-2-methylbenzonitrile;
(R)-5-{4-[3-(cyclopentylmethylamino)piperidin-1-yl]-6-propylpyrimidin-2-ylamino}-2-methylbenzonitrile;
(R)-5-{4-[3-(4-hydroxybenzylamino)piperidin-1-yl]-6-propylpyrimidin-2-ylamino}-2-methylbenzonitrile;
(R)—N-{1-[2-(3-cyano-4-methylphenylamino)-6-propylpyrimidin-4-yl]piperidin-3-yl}acetamide;
(R)-3-[4-(3-aminopiperidin-1-yl)-6-propylpyrimidin-2-ylamino]benzonitrile;
(R)-5-[4-(3-aminopiperidin-1-yl)-6-propylpyrimidin-2-ylamino]-2-fluorobenzonitrile;
(R)-3-{4-[3-(propylamino)piperidin-1-yl]-6-propylpyrimidin-2-ylamino}benzonitrile;
(R)-3-{4-[3-(cyclopropylmethylamino)piperidin-1-yl]-6-propylpyrimidin-2-ylamino}benzonitrile;
(R)-2-fluoro-5-{4-[3-(propylamino)piperidin-1-yl]-6-propylpyrimidin-2-ylamino}benzonitrile;
(R)-5-{4-[3-(cyclopropylmethylamino)piperidin-1-yl]-6-propylpyrimidin-2-ylamino}-2-fluorobenzonitrile;
(R)—N¹-{4-[3-(cyclopropylmethylamino)piperidin-1-yl]-6-propylpyrimidin-2-yl}-4-fluorobenzene-1,3-diamine;
(R)—N¹-{4-[3-(cyclopropylmethylamino)piperidin-1-yl]-6-propylpyrimidin-2-yl}-3-nitrobenzene-1,4-diamine;
(R)-3-amino-5-{4-[3-(cyclopropylmethylamino)piperidin-1-yl]-6-propylpyrimidin-2-ylamino}benzonitrile;
(R)—N¹-{4-[3-(cyclopropylmethylamino)piperidin-1-yl]-6-propylpyrimidin-2-yl}-3-(trifluoromethyl)benzene-1,4-diamine;
(R)—N¹-{4-[3-(cyclopropylmethylamino)piperidin-1-yl]-6-propylpyrimidin-2-yl}-5-(trifluoromethyl)benzene-1,3-diamine;
(R)—N-{1-[2-(4-amino-3-nitrophenylamino)-6-butylpyrimidin-4-yl]piperidin-3-yl}acetamide;
(R)—N-{1-[6-butyl-2-(4-methyl-3-nitrophenylamino)pyrimidin-4-yl]piperidin-3-yl}acetamide;
(R)—N-{1-[6-butyl-2-(4-fluoro-3-nitrophenylamino)pyrimidin-4-yl]piperidin-3-yl}acetamide;
(R)—N-{1-[6-butyl-2-(4-chloro-3-nitrophenylamino)pyrimidin-4-yl]piperidin-3-yl}acetamide;
(R)—N-{1-[2-(3-amino-5-cyanophenylamino)-6-butylpyrimidin-4-yl]piperidin-3-yl}acetamide;
(R)—N-{1-[2-(3-amino-5-trifluoromethylphenylamino)-6-butylpyrimidin-4-yl]piperidin-3-yl}acetamide;
(R)—N-{1-[2-(4-amino-3-trifluoromethylphenylamino)-6-butylpyrimidin-4-yl]piperidin-3-yl}acetamide;
(R)—N-{1-[6-butyl-2-(4-fluoro-3-trifluoromethylphenylamino)pyrimidin-4-yl]piperidin-3-yl}acetamide;
(R)—N-{1-[6-butyl-2-(3-cyano-4-fluorophenylamino)pyrimidin-4-yl]piperidin-3-yl}acetamide;
(R)—N-{1-[2-(3-amino-4-fluorophenylamino)-6-butylpyrimidin-4-yl]piperidin-3-yl}acetamide;
(R)—N-{1-[2-(3-amino-4-chlorophenylamino)-6-butylpyrimidin-4-yl]piperidin-3-yl}acetamide;
(R)—N-{1-[2-(4-amino-3-cyanophenylamino)-6-butylpyrimidin-4-yl]piperidin-3-yl}acetamide;
(R)—N-{1-[2-(3-cyano-4-methylphenylamino)-6-propylpyrimidin-4-yl]piperidin-3-yl}-2-hydroxyacetamide;
(R)—N-{1-[2-(3-cyanophenylamino)-6-propylpyrimidin-4-yl]piperidin-3-yl}-2-hydroxyacetamide;
(R)—N-{1-[2-(3-cyano-4-fluorophenylamino)-6-propylpyrimidin-4-yl]piperidin-3-yl}-2-hydroxyacetamide;
(R)—N-(1-{2-[3-amino-5-(trifluoromethyl)phenylamino]-6-propylpyrimidin-4-yl}piperidin-3-yl)-2-hydroxyacetamide;
(R)—N-(1-{2-[4-amino-3-(trifluoromethyl)phenylamino]-6-propylpyrimidin-4-yl}piperidin-3-yl)-2-hydroxyacetamide;
(R)—N-(1-{2-[4-fluoro-3-(trifluoromethyl)phenylamino]-6-propylpyrimidin-4-yl}piperidin-3-yl)-2-hydroxyacetamide;
(R)—N-{1-[2-(3-amino-4-fluorophenylamino)-6-propylpyrimidin-4-yl]piperidin-3-yl}-2-hydroxyacetamide;
(R)—N-{1-[2-(3-amino-4-chlorophenylamino)-6-propylpyrimidin-4-yl]piperidin-3-yl}-2-hydroxyacetamide;
(R)—N-{1-[2-(3-amino-4-methylphenylamino)-6-propylpyrimidin-4-yl]piperidin-3-yl}-2-hydroxyacetamide;
(R)—N-{1-[2-(3-chloro-4-methylphenylamino)-6-propylpyrimidin-4-yl]piperidin-3-yl}-2-hydroxyacetamide;

(R)-2-hydroxy-N-(1-{2-[4-methyl-3-(trifluoromethyl)phenylamino]-6-propylpyrimidin-4-yl}piperidin-3-yl)acetamide;
(R)—N-{1-[2-(3-amino-5-cyanophenylamino)-6-propylpyrimidin-4-yl]piperidin-3-yl}-2-hydroxyacetamide;
(R)—$N^1$-[4-(3-aminopiperidin-1-yl)-6-propylpyrimidin-2-yl]-5-(trifluoromethyl)benzene-1,3-diamine;
(R)—$N^1$-[4-(3-aminopiperidin-1-yl)-6-propylpyrimidin-2-yl]-3-(trifluoromethyl)benzene-1,4-diamine;
(R)-4-(3-aminopiperidin-1-yl)-N-(3-fluoro-4-methylphenyl)-6-propylpyrimidin-2-amine;
(R)—$N^1$-[4-(3-aminopiperidin-1-yl)-6-propylpyrimidin-2-yl]-4-fluorobenzene-1,3-diamine;
(R)-3-amino-5-{[4-(3-aminopiperidin-1-yl)-6-propylpyrimidin-2-yl]amino}benzonitrile;
(R)-2-amino-5-{[4-(3-aminopiperidin-1-yl)-6-propylpyrimidin-2-yl]amino}benzonitrile;
(R)—$N^1$-[4-(3-aminopiperidin-1-yl)-6-propylpyrimidin-2-yl]-4-chlorobenzene-1,3-diamine;
(R)-4-(3-aminopiperidin-1-yl)-N-[4-methyl-3-(trifluoromethyl)phenyl]-6-propylpyrimidin-2-amine;
(R)—N-[4-(3-aminopiperidin-1-yl)-6-propylpyrimidin-2-yl]-1H-indol-6-amine;
(R)-4-(3-aminopiperidin-1-yl)-N-(4-methyl-3-nitrophenyl)-6-propylpyrimidin-2-amine;
(R)—$N^1$-[4-(3-aminopiperidin-1-yl)-6-propylpyrimidin-2-yl]-3-nitrobenzene-1,4-diamine;
(R)—N-{1-[2-(3-cyano-4-fluorophenylamino)-6-propylpyrimidin-4-yl]piperidin-3-yl}acetamide;
(R)-5-[4-(3-diethylaminopiperidin-1-yl)-6-propylpyrimidin-2-ylamino]-2-methylbenzonitrile;
(R)-5-[4-(3-diethylaminopiperidin-1-yl)-6-propylpyrimidin-2-ylamino]-2-fluorobenzonitrile;
(R)-5-[4-(3-ethylaminopiperidin-1-yl)-6-propylpyrimidin-2-ylamino]-2-fluorobenzonitrile;
(R)—N-{1-[6-butyl-2-(3-cyanophenylamino)pyrimidin-4-yl]piperidin-3-yl}acetamide;
(R)—N-{1-[2-(3-cyanophenylamino)-6-propylpyrimidin-4-yl]piperidin-3-yl}acetamide;
(R)—N-{1-[2-(3-amino-5-cyanophenylamino)-6-propylpyrimidin-4-yl]piperidin-3-yl}acetamide;
N-{1-[2-(4-amino-3-nitrophenylamino)-6-propylpyrimidin-4-yl]piperidin-3-yl}acetamide;
N-{1-[2-(3-amino-4-fluorophenylamino)-6-propylpyrimidin-4-yl]piperidin-3-yl}acetamide;
(R)—N-{1-[2-(4-fluoro-3-trifluoromethylphenylamino)-6-propylpyrimidin-4-yl]piperidin-3-yl}acetamide;
(R)—N-(1-{2-[3-amino-5-(trifluoromethyl)phenylamino]-6-propylpyrimidin-4-yl}piperidin-3-yl)acetamide;
(R)—N-(1-{2-[4-amino-3-(trifluoromethyl)phenylamino]-6-propylpyrimidin-4-yl}piperidin-3-yl)acetamide;
(R)-5-[4-(3-ethylaminopiperidin-1-yl)-6-propylpyrimidin-2-ylamino]-2-methylbenzonitrile;
(R)-2-fluoro-5-[4-(3-methylaminopiperidin-1-yl)-6-propylpyrimidin-2-ylamino]benzonitrile;
(R)-2-methyl-5-[4-(3-methylaminopiperidin-1-yl)-6-propylpyrimidin-2-ylamino]benzonitrile;
(R)—$N^1$-[4-(3-methylaminopiperidin-1-yl)-6-propylpyrimidin-2-yl]-5-(trifluoromethyl)benzene-1,3-diamine;
(R)—$N^1$-[4-(3-methylaminopiperidin-1-yl)-6-propylpyrimidin-2-yl]-3-(trifluoromethyl)benzene-1,4-diamine;
(R)-3-amino-5-[4-(3-methylaminopiperidin-1-yl)-6-propylpyrimidin-2-ylamino]benzonitrile;
(R)-(4-fluoro-3-trifluoromethylphenyl)-[4-(3-methylaminopiperidin-1-yl)-6-propylpyrimidin-2-yl]amine;
(R)—$N^1$-[4-(3-ethylaminopiperidin-1-yl)-6-propylpyrimidin-2-yl]-3-nitrobenzene-1,4-diamine;
(R)—$N^1$-[4-(3-ethylaminopiperidin-1-yl)-6-propylpyrimidin-2-yl]-4-fluorobenzene-1,3-diamine;
(R)—$N^1$-[4-(3-ethylaminopiperidin-1-yl)-6-propylpyrimidin-2-yl]-5-(trifluoromethyl)benzene-1,3-diamine;
(R)—$N^1$-[4-(3-ethylaminopiperidin-1-yl)-6-propylpyrimidin-2-yl]-3-(trifluoromethyl)benzene-1,4-diamine;
(R)-3-amino-5-[4-(3-ethylaminopiperidin-1-yl)-6-propylpyrimidin-2-ylamino]benzonitrile;
(R)-5-[4-(3-aminopiperidin-1-yl)-6-butylpyrimidin-2-ylamino]-2-methylbenzonitrile;
(R)-5-[4-(3-aminopiperidin-1-yl)-6-butylpyrimidin-2-ylamino]-2-fluorobenzonitrile;
(R)—N-{1-[6-butyl-2-(3-cyano-4-methylphenylamino)pyrimidin-4-yl]piperidin-3-yl}acetamide;
(S)-5-[4-(3-ethylaminopiperidin-1-yl)-6-propylpyrimidin-2-ylamino]-2-methylbenzonitrile;
5-[4-(3-ethylaminopiperidin-1-yl)-6-propylpyrimidin-2-ylamino]-2-methylbenzonitrile;
N-{1-[6-butyl-2-(3-cyano-4-methylphenylamino)pyrimidin-4-yl]piperidin-3-yl}acetamide;
(R)-5-({4-butyl-6-[3-(ethylamino)piperidin-1-yl]pyrimidin-2-yl}amino)-2-methylbenzonitrile;
(R)-5-({4-butyl-6-[3-(butylamino)piperidin-1-yl]pyrimidin-2-yl}amino)-2-methylbenzonitrile;
(R)-5-({4-butyl-6-[3-(pentylamino)piperidin-1-yl]pyrimidin-2-yl}amino)-2-methylbenzonitrile;
(R)-5-({4-butyl-6-[3-(isobutylamino)piperidin-1-yl]pyrimidin-2-yl}amino)-2-methylbenzonitrile;
(R)-5-({4-butyl-6-[3-(isopentylamino)piperidin-1-yl]pyrimidin-2-yl}amino)-2-methylbenzonitrile;
(R)-5-({4-butyl-6-[3-(neopentylamino)piperidin-1-yl]pyrimidin-2-yl}amino)-2-methylbenzonitrile;
(R)-5-{[4-butyl-6-(3-{[3-(methylthio)propyl]amino}piperidin-1-yl)pyrimidin-2-yl]amino}-2-methylbenzonitrile;
(R)-4-fluoro-$N^1$-{4-[3-(methylamino)piperidin-1-yl]-6-propylpyrimidin-2-yl}benzene-1,3-diamine;
(R)-4-chloro-$N^1$-{4-[3-(methylamino)piperidin-1-yl]-6-propylpyrimidin-2-yl}benzene-1,3-diamine;
(R)-2-amino-5-({4-[3-(methylamino)piperidin-1-yl]-6-propylpyrimidin-2-yl}amino)benzonitrile;
(R)—N-(3-methoxy-4-methylphenyl)-4-[3-(methylamino)piperidin-1-yl]-6-propylpyrimidin-2-amine;
(R)-4-methyl-$N^1$-{4-[3-(methylamino)piperidin-1-yl]-6-propylpyrimidin-2-yl}benzene-1,3-diamine;
(R)-5-({4-butyl-6-[3-(methylamino)piperidin-1-yl]pyrimidin-2-yl}amino)-2-methylbenzonitrile;
(R)-5-({4-butyl-6-[3-(methylamino)piperidin-1-yl]pyrimidin-2-yl}amino)-2-fluorobenzonitrile;
(R)—$N^1$-{4-butyl-6-[3-(methylamino)piperidin-1-yl]pyrimidin-2-yl}-5-(trifluoromethyl)benzene-1,3-diamine;
(R)—$N^1$-{4-butyl-6-[3-(methylamino)piperidin-1-yl]pyrimidin-2-yl}-3-(trifluoromethyl)benzene-1,4-diamine;
(R)-3-amino-5-({4-butyl-6-[3-(methylamino)piperidin-1-yl]pyrimidin-2-yl}amino)benzonitrile;
(R)-2-amino-5-({4-butyl-6-[3-(methylamino)piperidin-1-yl]pyrimidin-2-yl}amino)benzonitrile;
(R)—$N^1$-{4-butyl-6-[3-(methylamino)piperidin-1-yl]pyrimidin-2-yl}-4-fluorobenzene-1,3-diamine;
(R)-4-butyl-N-(3-methoxy-4-methylphenyl)-6-[3-(methylamino)piperidin-1-yl]pyrimidin-2-amine;
(R)—$N^1$-{4-butyl-6-[3-(methylamino)piperidin-1-yl]pyrimidin-2-yl}-4-methylbenzene-1,3-diamine;
(R)-4-butyl-N-[4-fluoro-3-(trifluoromethyl)phenyl]-6-[3-(methylamino)piperidin-1-yl]pyrimidin-2-amine;

(R)—N¹-{4-[3-(methylamino)piperidin-1-yl]-6-propylpyrimidin-2-yl}-3-nitrobenzene-1,4-diamine;
(R)—N-(3,4-dimethylphenyl)-4-[3-(methylamino)piperidin-1-yl]-6-propylpyrimidin-2-amine;
(R)—N-(3-fluoro-4-methylphenyl)-4-[3-(methylamino)piperidin-1-yl]-6-propylpyrimidin-2-amine;
(R)—N-[4-methyl-3-(trifluoromethyl)phenyl]-4-[3-(methylamino)piperidin-1-yl]-6-propylpyrimidin-2-amine;
(R)-4-methoxy-N¹-{4-[3-(methylamino)piperidin-1-yl]-6-propylpyrimidin-2-yl}benzene-1,3-diamine;
(R)—N-{4-[3-(methylamino)piperidin-1-yl]-6-propylpyrimidin-2-yl}-1H-indazol-6-amine;
(R)—N⁴-{4-[3-(methylamino)piperidin-1-yl]-6-propylpyrimidin-2-yl}benzene-1,2,4-triamine;
(R)—N¹-{4-butyl-6-[3-(methylamino)piperidin-1-yl]pyrimidin-2-yl}-3-nitrobenzene-1,4-diamine;
(R)-3-({4-butyl-6-[3-(methylamino)piperidin-1-yl]pyrimidin-2-yl}amino)benzonitrile;
(R)-4-butyl-N-(3,4-dimethylphenyl)-6-[3-(methylamino)piperidin-1-yl]pyrimidin-2-amine;
(R)-4-butyl-N-(3-fluoro-4-methylphenyl)-6-[3-(methylamino)piperidin-1-yl]pyrimidin-2-amine;
(R)-4-butyl-N-[4-methyl-3-(trifluoromethyl)phenyl]-6-[3-(methylamino)piperidin-1-yl]pyrimidin-2-amine;
(R)—N¹-{4-butyl-6-[3-(methylamino)piperidin-1-yl]pyrimidin-2-yl}-4-methoxybenzene-1,3-diamine;
(R)—N-{4-butyl-6-[3-(methylamino)piperidin-1-yl]pyrimidin-2-yl}-1H-indazol-6-amine;
(R)—N⁴-{4-butyl-6-[3-(methylamino)piperidin-1-yl]pyrimidin-2-yl}benzene-1,2,4-triamine;
(R)-4-(3-aminopiperidin-1-yl)-6-butyl-N-(3-nitrophenyl)pyrimidin-2-amine;
(R)—N¹-[4-(3-aminopiperidin-1-yl)-6-butylpyrimidin-2-yl]-3-nitrobenzene-1,4-diamine;
(R)-4-(3-aminopiperidin-1-yl)-6-butyl-N-(4-fluoro-3-nitrophenyl)pyrimidin-2-amine;
(R)-4-(3-aminopiperidin-1-yl)-6-butyl-N-(4-methyl-3-nitrophenyl)pyrimidin-2-amine;
(R)—N¹-[4-(3-aminopiperidin-1-yl)-6-butylpyrimidin-2-yl]-3-(trifluoromethyl)benzene-1,4-diamine;
(R)—N¹-[4-(3-aminopiperidin-1-yl)-6-butylpyrimidin-2-yl]-5-(trifluoromethyl)benzene-1,3-diamine;
(R)-3-amino-5-{[4-(3-aminopiperidin-1-yl)-6-butylpyrimidin-2-yl]amino}benzonitrile;
(R)-4-(3-aminopiperidin-1-yl)-6-butyl-N-[4-methyl-3-(trifluoromethyl)phenyl]pyrimidin-2-amine;
(R)-4-(3-aminopiperidin-1-yl)-6-butyl-N-(3-fluoro-4-methylphenyl)pyrimidin-2-amine;
(R)-4-(3-aminopiperidin-1-yl)-6-butyl-N-(3-methoxy-4-methylphenyl)pyrimidin-2-amine;
(R)—N¹-[4-(3-aminopiperidin-1-yl)-6-butylpyrimidin-2-yl]-4-methylbenzene-1,3-diamine;
(R)-4-(3-aminopiperidin-1-yl)-6-butyl-N-(3,4-dimethylphenyl)pyrimidin-2-amine;
(R)-4-(3-aminopiperidin-1-yl)-6-butyl-N-[4-fluoro-3-(trifluoromethyl)phenyl]pyrimidin-2-amine;
(R)—N¹-[4-(3-aminopiperidin-1-yl)-6-butylpyrimidin-2-yl]-4-fluorobenzene-1,3-diamine;
(R)-2-amino-5-{[4-(3-aminopiperidin-1-yl)-6-butylpyrimidin-2-yl]amino}benzonitrile;
(R)-3-{[4-(3-aminopiperidin-1-yl)-6-butylpyrimidin-2-yl]amino}benzonitrile;
(R)—N¹-[4-(3-aminopiperidin-1-yl)-6-butylpyrimidin-2-yl]benzene-1,4-diamine;
(R)-4-(3-aminopiperidin-1-yl)-6-butyl-N-(4-chloro-3-nitrophenyl)pyrimidin-2-amine; and
(R)—N⁴-[4-(3-aminopiperidin-1-yl)-6-butylpyrimidin-2-yl]benzene-1,2,4-triamine.

3. A pharmaceutical composition for agonizing a 5-HT₄ receptor, comprising a therapeutically effective amount of a compound of Formula 1 or its pharmaceutically acceptable salt; and a pharmaceutically acceptable carrier:

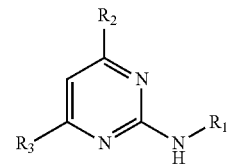

<Formula 1> wherein, $R_1$ is a phenyl group substituted with one or more substituents selected from the group consisting of amino, halogen, cyano, nitro, $C_{1-3}$ alkyl (where the $C_{1-3}$ alkyl is optionally substituted with halogen), $C_{1-5}$ alkoxy, $C_{1-5}$ alkylthio, and aminocarbonyl, or a heteroaryl group selected from the group consisting of, quinolinyl, chromenonyl, benzofuranyl, indolyl, indolinyl, benzimidazol-5-yl, benzimidazol-6-yl, and indazolyl, wherein the heteroaryl group is optionally substituted with one or more $C_{1-5}$ alkyl (where the $C_{1-5}$ alkyl is optionally substituted with halogen), $R_2$ is a nitrogen-containing cyclic group of the following Formula B (where * in Formula B represents the position attached to the compound of Formula 1),

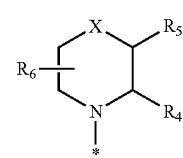

B $R_3$ is a $C_{2-5}$ alkyl group,
$R_4$ is hydrogen; a $C_{1-5}$ alkyl group optionally substituted with hydroxy; or a $C_{1-5}$ alkoxycarbonyl group,
$R_5$ is hydrogen; a hydroxyl group; a benzyloxy group; a $C_{1-5}$ alkyl group; or a group selected from the group consisting of the following Formulas E and I (where * in Formulas E and I represents the position attached to the compound of Formula B),

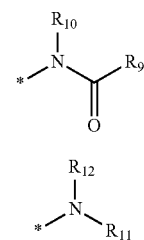

E

I $R_6$ is hydrogen,
X is —CH($R_7$)—; —N($R_8$)—; or —O,
$R_7$ is hydrogen,
$R_4$ and $R_5$, are optionally joined to each other to form a pentagonal or hexagonal ring, $R_8$ is a $C_{1-5}$ alkyl group, $R_9$ is a $C_{1-10}$ alkyl group optionally substituted with hydroxy, $R_{10}$ is hydrogen, $R_{11}$ and $R_{12}$ are, independently each other, hydrogen; or a $C_{1-10}$ alkyl group optionally substituted with a substituent selected from the group consisting of $C_{1-5}$ alkylthio, $C_{3-10}$ cycloalkyl, phenyl (where the phenyl is optionally substituted with hydroxy, thiophenyl, pyrrolyl, and furanyl (where the furanyl is optionally substituted with mono- or di-$C_{1-5}$ alkyl), wherein the agonizing a 5-HT$_4$ receptor effects to treat a dysfunction in gastrointestinal motility in a disease selected from the group consisting of gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, and diabetic gastric atony.

* * * * *